(12) United States Patent
Duan et al.

(10) Patent No.: US 8,304,539 B2
(45) Date of Patent: *Nov. 6, 2012

(54) FUSED HETEROARYL MODULATORS OF GLUCOCORTICOID RECEPTOR, AP-1, AND/OR NF-κB ACTIVITY AND USE THEREOF

(75) Inventors: Jingwu Duan, Yardley, PA (US); David S. Weinstein, East Windsor, NJ (US); Bin Jiang, Norristown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 193 days.

This patent is subject to a terminal disclaimer.

(21) Appl. No.: 12/866,270

(22) PCT Filed: Feb. 5, 2009

(86) PCT No.: PCT/US2009/033134
§ 371 (c)(1),
(2), (4) Date: Aug. 5, 2010

(87) PCT Pub. No.: WO2009/100171
PCT Pub. Date: Aug. 13, 2009

(65) Prior Publication Data
US 2011/0002952 A1     Jan. 6, 2011

Related U.S. Application Data

(60) Provisional application No. 61/026,816, filed on Feb. 7, 2008.

(51) Int. Cl.
*C07D 491/147* (2006.01)
*C07D 413/00* (2006.01)

(52) U.S. Cl. .......................................... 544/126; 546/83

(58) Field of Classification Search .................. None
See application file for complete search history.

(56) References Cited

U.S. PATENT DOCUMENTS 8,034,940 B2 * 10/2011 Weinstein et al. .............. 546/80

FOREIGN PATENT DOCUMENTS

| WO | WO 2004/054505 | 7/2004 |
| WO | WO 2005/072732 | 8/2005 |
| WO | WO 2008/021926 | 2/2008 |

OTHER PUBLICATIONS

Mohler, M.L. et al., "Non-steroidal glucocorticoid receptor antagonists: the race to replace RU-486 for anti-glucocorticoid therapy", Expert Opinion Ther. Patents, vol. 17, No. 1, pp. 59-81 (2007).

* cited by examiner

Primary Examiner — Janet Andres
Assistant Examiner — Timothy R Rozof
(74) Attorney, Agent, or Firm — Burton Rodney; Laurelee A. Duncan

(57) ABSTRACT

Novel non-steroidal compounds are provided which are useful in treating diseases or disorders associated with modulation of the glucocorticoid receptor, AP-1, and/or NF-κB activity, including metabolic and inflammatory and immune diseases or disorders, having the structure of formula (I): an enantiomer, diastereomer, or tautomer thereof, or a prodrug ester thereof, or a pharmaceutically-acceptable salt thereof, in which: Z is heterocyclo or heteroaryl; •A is a S- to 8-membered carbocyclic ring or a S- to 8-membered heterocyclic ring; $B_1$ and $B_2$ rings are pyridyl rings, wherein the $B_1$ and $B_2$ rings are each fused to the A ring and the $B_1$ ring is optionally substituted by one to three groups which are the same or different and are independently selected from $R_1$, $R_2$, and $R_4$, and the $B_2$ ring is optionally substituted by one to three groups which are the same or different and are independently selected from $R_5$, $R_7$, and $R_3$ $J_1$, $J_2$, and $J_3$ are at each occurrence the same or different and are independently -$A_1QA_2$-; Q is a bond, O, S, S(O), or $S(O)_2$; $A_1$ and $A_2$ are the same or different and are at each occurrence independently selected from a bond, $C_{1-3}$ alkylene, substituted $C_{1-3}$ alkylene, $C_{2-4}$ alkenylene, and substituted $C_{2-4}$ alkenylene, provided that $A_1$ and $A_2$ are chosen so that ring A is a 5- to 8-membered carbocyclic or heterocyclic ring; $R_1$ to $R_{11}$ are as defined herein.

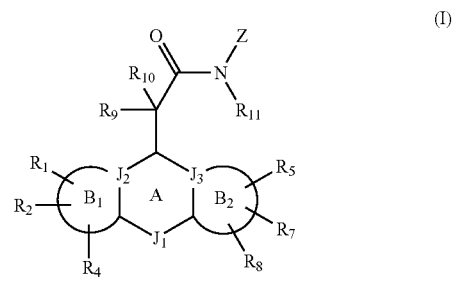

(I)

19 Claims, No Drawings

FUSED HETEROARYL MODULATORS OF GLUCOCORTICOID RECEPTOR, AP-1, AND/OR NF-κB ACTIVITY AND USE THEREOF

FIELD OF THE INVENTION

The present invention relates to new non-steroidal compounds which are effective modulators of the glucocorticoid receptor, AP-1, and/or NF-κB activity and thus are useful in treating diseases or disorders including metabolic and inflammatory or immune associated diseases or disorders. The present invention also provides compositions thereof and methods for using such compounds and compositions to treat these and related diseases or disorders.

BACKGROUND OF THE INVENTION

The transcription factors NF-κB and AP-1 are involved in regulating the expression of a number of genes involved in mediating inflammatory and immune responses. NF-κB regulates the transcription of genes including TNF-α, IL-1, IL-2, IL-6, adhesion molecules (such as E-selectin) and chemokines (such as Rantes), among others. AP-1 regulates the production of the cytokines TNF-α, IL-1, IL-2, as well as, matrix metalloproteases. Drug therapies targeting TNF-α, a gene whose expression is regulated by both NF-κB and AP-1, have been shown to be highly efficacious in several inflammatory human diseases including rheumatoid arthritis and Crohn's disease. Accordingly, NF-κB and AP-1 play key roles in the initiation and perpetuation of inflammatory and immunological disorders. See Baldwin, A. S., *Journal of Clin. Investigation,* 107, 3 (2001); Firestein, G. S., and Manning, A. M., *Arthritis and Rheumatism,* 42, 609 (1999); and Peltz, G., *Curr. Opin. in Biotech.* 8, 467 (1997).

There are many signaling molecules (kinases and phosphatases) upstream of AP-1 and NF-κB which are potential therapeutic drug targets. The kinase JNK plays an essential role in regulating the phosphorylation and subsequent activation of c-jun, one of the subunits which constitute the AP-1 complex (fos/c-jun). Compounds which inhibit JNK have been shown to be efficacious in animal models of inflammatory disease. See Manning, A. M. and Davis, R. J., *Nature Rev. Drug Disc.,* V. 2, 554 (2003). A kinase critical to the activation of NF-κB is the IκB kinase (IKK). This kinase plays a key role in the phosphorylation of IκB. Once IκB is phosphorylated it undergoes degradation leading to the release of NF-κB which can translocate into the nucleus and activate the transcription of the genes described above. An inhibitor of IKK, BMS-345541, has been shown to be efficacious in animal models of inflammatory disease. See Burke, J. R., *Curr. Opin. Drug Discov. Devel.*, September; 6 (5), 720-8, (2003).

In addition to inhibiting signaling cascades involved in the activation of NF-κB and AP-1, the glucocorticoid receptor has been shown to inhibit the activity of NF-κB and AP-1 via direct physical interactions. The glucocorticoid receptor (GR) is a member of the nuclear hormone receptor family of transcription factors, and a member of the steroid hormone family of transcription factors. Affinity labeling of the glucocorticoid receptor protein allowed the production of antibodies against the receptor which facilitated cloning the glucocorticoid receptors. For results in humans see Weinberger et al., *Science,* 228, 740-742 (1985); Weinberger et al., *Nature,* 318, 670-672 (1986) and for results in rats see Miesfeld, R., *Nature,* 312, 779-781 (1985).

Glucocorticoids which interact with GR have been used for over 50 years to treat inflammatory diseases. It has been clearly shown that glucocorticoids exert their anti-inflammatory activity via the inhibition by GR of the transcription factors NF-κB and AP-1. This inhibition is termed transrepression. It has been shown that the primary mechanism for inhibition of these transcription factors by GR is via a direct physical interaction. This interaction alters the transcription factor complex and inhibits the ability of NF-κB and AP-1 to stimulate transcription. See Jonat, C. et al., *Cell,* 62, 1189 (1990); Yang-Yen, H. F. et al., *Cell,* 62, 1205 (1990); Diamond, M. I. et al., *Science* 249, 1266 (1990); and Caldenhoven, E. et al., *Mol. Endocrinol.,* 9, 401 (1995). Other mechanisms such as sequestration of co-activators by GR have also been proposed. See Kamei, Y. et al., *Cell,* 85, 403 (1996); and Chakravarti, D. et al., *Nature,* 383, 99 (1996).

In addition to causing transrepression, the interaction of a glucocorticoid with GR can cause GR to induce transcription of certain genes. This induction of transcription is termed transactivation. Transactivation requires dimerization of GR and binding to a glucocorticoid response element (GRE).

Recent studies using a transgenic GR dimerization defective mouse which cannot bind DNA have shown that the transactivation (DNA binding) activities of GR could be separated from the transrepressive (non-DNA binding) effect of GR. These studies also indicate that many of the side effects of glucocorticoid therapy are due to the ability of GR to induce transcription of various genes involved in metabolism, whereas, transrepression, which does not require DNA binding leads to suppression of inflammation. See Reichardt, H. M. et al., *Cell,* 93, 531 (1998) and Reichardt, H. M., *EMBO J.,* 20, 7168 (2001).

Compounds that modulate AP-1 and NF-κB activity would be in the treatment of inflammatory and immune diseases and disorders such as osteoarthritis, rheumatoid arthritis, multiple sclerosis, asthma, inflammatory bowel disease, transplant rejection and graft vs. host disease.

Also, with respect to the glucocorticoid receptor pathway, it is known that glucocorticoids are potent anti-inflammatory agents, however their systemic use is limited by side effects. Compounds that retain the anti-inflammatory efficacy of glucocorticoids while minimizing the side effects such as diabetes, osteoporosis and glaucoma would be of great benefit to a very large number of patients with inflammatory diseases.

Additionally concerning GR, the art is in need of compounds that antagonize transactivation. Such compounds may be useful in treating metabolic diseases associated with increased levels of glucocorticoid, such as diabetes, osteoporosis and glaucoma.

Additionally concerning GR, the art is in need of compounds that cause transactivation. Such compounds may be useful in treating metabolic diseases associated with a deficiency in glucocorticoid. Such diseases include Addison's disease.

DESCRIPTION OF THE INVENTION

The present invention relates to new non-steroidal compounds which are effective modulators of the glucocorticoid receptor, AP-1, and/or NF-κB activity and thus are useful in treating diseases or disorders including metabolic and inflammatory or immune associated diseases or disorders. The present invention also provides compositions and combinations thereof and methods for using such compounds, combinations and compositions to treat these and related diseases or disorders.

In accordance with one aspect of the invention (Embodiment 1), compounds are provided having the structure of formula I

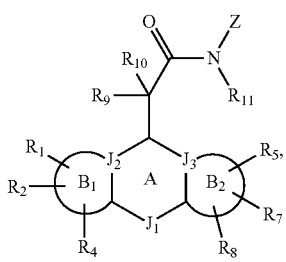

an enantiomer, diastereomer, tautomer, or a pharmaceutically-acceptable salt thereof, wherein:

Z is selected from heterocyclo, heteroaryl, and cyano;

A is selected from a 5- to 8-membered carbocyclic ring and a 5- to 8-membered heterocyclic ring;

$B_1$ and $B_2$ rings are pyridyl rings, wherein the $B_1$ and $B_2$ rings are each fused to the A ring and the $B_1$ ring is optionally substituted by one to three groups which are the same or different and are independently selected from $R_1$, $R_2$, and $R_4$, and the $B_2$ ring is optionally substituted by one to three groups which are the same or different and are independently selected from $R_5$, $R_7$, and $R_8$ $J_1$, $J_2$, and $J_3$ are the same or different and at each occurrence are independently $-A_1QA_2-$;

Q is independently at each occurrence selected from a bond, O, S, S(O), and $S(O)_2$;

$A_1$ and $A_2$ are the same or different and at each occurrence are independently selected from a bond, $C_{1-3}$alkylene, substituted $C_{1-3}$alkylene, $C_{2-4}$alkenylene, and substituted $C_{2-4}$alkenylene, provided that $A_1$ and $A_2$ are chosen so that ring A is a 5- to 8-membered carbocyclic ring or a 5- to 8-membered heterocyclic ring;

$R_1$, $R_2$, $R_4$, $R_5$, $R_7$, and $R_8$ are the same or different and at each occurrence are independently selected from (i) hydrogen, halogen, alkyl, substituted alkyl, alkenyl, substituted alkenyl, alkynyl, substituted alkynyl, alkoxy, substituted alkoxy, nitro, cyano, $OR_{12}$, $-NR_{12}R_{13}$, $-C(=O)R_{12}$, $-CO_2R_{12}$, $-C(=O)NR_{12}R_{13}$, $-OC(=O)NR_{12}, R_{13}$,

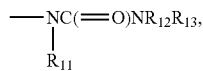

$-OC(=O)R_{12}$, $-NR_{12}C(=O)R_{13}$, $-NR_{12}C(O)OR_{13}$, $-NR_{12}C(S)OR_{13}$, $-S(O)_pR_{16}$, $NR_{12}SO_2R_{16}$, dialkylaminoalkoxy, alkoxyalkyloxyalkyloxy, $SO_2NR_{12}R_{13}$, cycloalkyl, cycloalkenyl, cycloalkynyl, heterocyclo, aryl, and heteroaryl; and/or (ii) where possible, together with the atoms to which they are attached, each one of $R_1$, $R_2$, $R_4$, $R_5$, $R_7$, and $R_8$ is taken together with any one of $R_1$, $R_2$, $R_4$, $R_5$, $R_7$, and $R_8$ located on an adjacent atom to form a fused ring;

$R_9$ and $R_{10}$ are the same or different and at each occurrence are independently selected from (i) hydrogen, halogen, alkyl, substituted alkyl, alkenyl, substituted alkenyl, alkynyl, substituted alkynyl, nitro, cyano, $OR_{14}$, $NR_{14}R_{15}$, $C(=O)R_{14}$, $CO_2R_{14}$, $C(=O)NR_{14}R_{15}$, $-O-C(=O)R_{14}$, $NR_{14}C(=O)R_{15}$, $NR_{14}C(=O)OR_{15}$, $NR_{14}C(=S)OR_{15}$, $S(O)_pR_{17}$, $NR_{14}SO_2R_{17}$, $SO_2NR_{14}R_{15}$, cycloalkyl, cycloalkenyl, heterocyclo, aryl, and heteroaryl; or (ii) together with the atom to which the are attached, $R_9$ and $R_{10}$ are taken together to form a carbonyl, alkenyl, substituted alkenyl, cycloalkyl, cycloalkenyl, or heterocyclo group;

$R_{11}$ at each occurrence is independently selected from hydrogen, alkyl, substituted alkyl, aryl, heteroaryl, heterocyclo, and cycloalkyl;

$R_{12}$, $R_{13}$, $R_{14}$, and $R_{15}$, are the same or different and at each occurrence are independently selected from (i) hydrogen, alkyl, substituted alkyl, alkenyl, substituted alkenyl, alkynyl, substituted alkynyl, cycloalkyl, cycloalkenyl, aryl, heteroaryl, and heterocyclo; or (ii) where possible $R_{12}$ is taken together with $R_{13}$, and/or where possible $R_{14}$ is taken together with $R_{15}$ to form a heteroaryl or heterocyclo ring;

$R_{16}$ and $R_{17}$, are the same or different and at each occurrence are independently selected from alkyl, substituted alkyl, alkenyl, substituted alkenyl, alkynyl, substituted alkynyl, cycloalkyl, cycloalkenyl, aryl, heteroaryl, and heterocyclo; and p is 0, 1 or 2.

Other Embodiments of the present invention are as described below.

Embodiment 2: a compound as defined in Embodiment 1, or an enantiomer, diastereomer, tautomer, or a pharmaceutically-acceptable salt thereof, wherein:

$J_1$ is a bond, O, S, SO, $SO_2$, $CH_2$, or $CH_2CH_2$ (especially compounds where $J_1$ is O, S, SO or $SO_2$, more especially where $J_1$ is O); and $J_2$ and $J_3$ are each a bond.

Embodiment 3: a compound as defined in Embodiments 1-2, or an enantiomer, diastereomer, tautomer, or a pharmaceutically-acceptable salt thereof, wherein the tricyclic moiety:

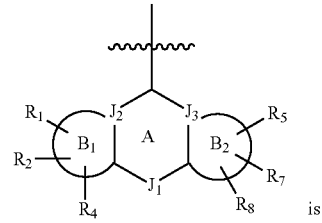

is

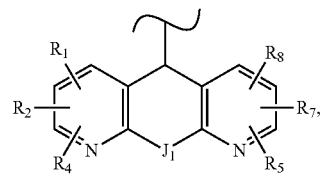

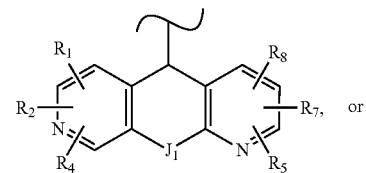

or

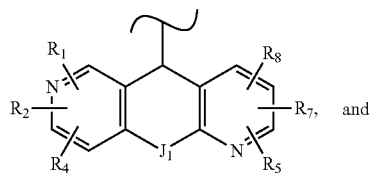

and especially compounds where

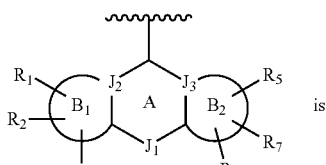 is

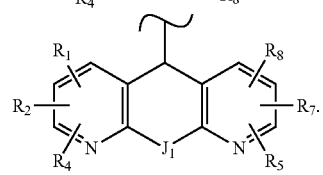

Embodiment 4: a compound as defined in Embodiments 1-3, or an enantiomer, diastereomer, tautomer, or a pharmaceutically-acceptable salt thereof, wherein $R_1$, $R_2$, $R_7$ and $R_8$ are each hydrogen.

Embodiment 5: the compound as defined in Embodiments 1-4, or an enantiomer, diastereomer, tautomer, or a pharmaceutically-acceptable salt, thereof, wherein $R_4$ is selected from hydrogen, alkyl, alkenyl, alkylthio, substituted alkylthio, aryl, substituted aryl, cyano, $CF_3$, alkoxy, halogen, hydroxyl, dialkylamino, monoalkylamino, dialkylaminoalkoxy, alkoxyalkoxyalkoxy, and a 4- to 7-membered heterocyclo having one to three heteroatoms selected from O, S and N. Preferred compounds are those where $R_4$ is hydrogen, $C_{1-6}$alkyl, halogen, cyano, —$SC_{1-6}$alkyl, $C_{2-6}$alkenyl, (un)substituted phenyl, $(C_{1-6}alkyl)_{1-2}$amino, and a 5- to 6-membered heterocyclo having one to three heteroatoms selected from O, S, and N. Especially preferred compounds are those where $R_4$ is hydrogen, methyl, chloro, iso-propylthio, ethenyl, phenyl, cyano, dimethylamino, N-pyrollidinyl, or N-morpholinyl. Embodiment 6: a compound as defined in Embodiments 1-5, or an enantiomer, diastereomer, tautomer, or a pharmaceutically-acceptable salt thereof, wherein $R_5$ is selected from hydrogen, haloalkyl, alkoxy, haloalkoxy, halogen, amino, dialkylamino, heterocyclo, phenyl, halophenyl, alkyl(halo)$_{0-1}$aryl, heterocyclocarbonyl(halo)$_{0-1}$aryl, alkoxy(halo)$_{0-1}$aryl, carboxy(halo)$_{0-1}$aryl, alkylaminocarbonyl(halo)$_{0-1}$aryl, dialkylaminocarbonyl(halo)$_{0-1}$aryl, alkylamino, hydroxyl, dialkylaminoalkoxy, arylalkylamino, alkoxyarylalkylamino, alkylheterocyclo, arylalkyl, heterocycloalkoxy, arylheterocyclo, arylalkyl(alkyl)amino, haloaryl, dialkylamino(halo)$_{0-1}$ aryl, alkoxyalkoxyalkoxyl, alkylcarbonylamino, heteroaryl, dialkyl(halo)$_{0-1}$aryl, alkyl(halo)$_{0-1}$aryl, hydroxy(halo)$_{0-1}$aryl, alkoxycarbonyl(halo)$_{0-1}$aryl, alkylcarbonylamino(halo)$_{0-1}$aryl, dialkylaminosulfonyl(halo)$_{0-1}$aryl, alkylsulfonylamino(halo)$_{0-1}$aryl, alkylthio(halo)$_{0-1}$aryl, amino(halo)$_{0-1}$aryl, alkylcarbonylaryl, alkylcarbonyl(halo)aryl, aryloxy(halo)$_{0-1}$aryl, alkylsulfonylaryl, alkylsulfinylaryl, thioxyaryl, cycloalkoxyaryl, cycloalkylaminocarbonyl, and cyano(halo)$_{0-1}$aryl. Preferable compounds are those in which $R_5$ is a halogen, $(C_{1-6})_{1-2}$alkylamino, morpholinylcarbonyl(halo)$_{0-1}$phenyl, (halo)$_{0-2}$pyrrolidinylcarbonyl(halo)$_{0-1}$phenyl, aziridinylcarbonyl(halo)$_{0-1}$phenyl, $C_{1-6}$alkylcarbonyl(halo)$_{0-1}$phenyl, phenoxy(halo)$_{0-1}$phenyl, $C_{1-6}$alkoxy(halo)$_{0-1}$phenyl, trifluoromethyoxy(halo)$_{0-1}$phenyl, $(C_{1-6})_{1-2}$alkylaminosulfonyl(halo)$_{0-1}$phenyl, alkylthio(halo)$_{0-1}$phenyl, $C_{1-6}$alkylsulfinyl(halo)$_{0-1}$phenyl, and $C_{1-6}$alkylsulfonyl(halo)$_{0-1}$phenyl, Especially preferred are compounds in which:

$R_5$ is chloro, dimethylamino,

[structures with $X_a$, $X_b$], or $X_a$ is hydrogen or fluoro, and
$X_b$ is selected from $(Me)_2NC(O)$—,

[morpholinyl carbonyl structure], $(Et)(Me)NC(O)$—,

[pyrrolidinyl carbonyl structure], $MeC(O)$—, —O(phenyl), —$OCF_3$, —$SO_2N(Me)_2$, (t-Bu)NHC(O)—, —S(iPr), —S(Me), —O(iPr), —S(O)Me, —$S(O)_2Me$,

[azetidinyl carbonyl and difluoropyrrolidinyl carbonyl structures], $S(O)(iPr)$, $S(O)_2(iPr)$, $S(O)Et$, iBu, —O(t-Bu), —S(Et), iBu, iPr, —O(cyclopentyl), $EtC(O)$—,

[t-butanol structure], and —C(O)N(Me)(cyclopropyl).

Embodiment 7: a compound as defined in Embodiments 1-6, or an enantiomer, diastereomer, tautomer, or a pharmaceutically-acceptable salt thereof, wherein

[structure]  is

-continued

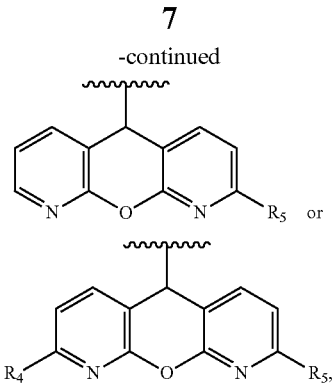

wherein:

$R_4$ is hydrogen, methyl, chloro, iso-propylthio, ethenyl, phenyl, cyano, dimethylamino, N-pyrollidinyl, or N-morpholinyl; and $R_5$ is chloro, dimethlamino,

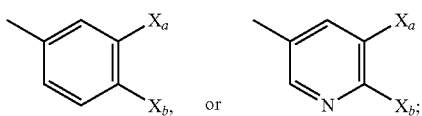

$X_a$ is hydrogen or fluoro, and

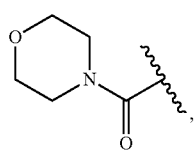

$X_b$ is selected from $(Me)_2NC(O)$—, $(Et)(Me)NC(O)$—

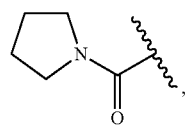

MeC(O)—, —O(phenyl), —OCF$_3$, —SO$_2$N(Me)$_2$, (t-Bu) NHC(O)—, —S(iPr), —S(Me), —O(iPr), —S(O)Me, —S(O)$_2$Me,

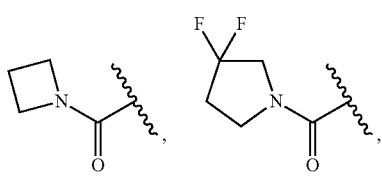

S(O)(iPr), S(O)$_2$(iPr), S(O)Et, iBu, —O(t-Bu), —S(Et), iBu, iPr, —O(cyclopentyl), EtC(O)—,

and —C(O)N(Me)(cyclopropyl).

Embodiment 8: a compound as defined in Embodiments 1-7, or an enantiomer, diastereomer, tautomer, or a pharmaceutically-acceptable salt thereof, wherein:

$R_9$ and $R_{10}$ are (i) the same or different and independently selected from hydrogen, alkyl, and substituted alkyl; or (ii) $R_9$ and $R_{10}$ taken together with the atom to which they are attached combine to form $C_{3-6}$cycloalkyl; and $R_{11}$ is hydrogen.

Embodiment 9: a compound as defined in Embodiments 1-8, or an enantiomer, diastereomer, tautomer, or a pharmaceutically-acceptable salt thereof, wherein $R_9$ and $R_{10}$ are each independently selected from methyl, or combined with the carbon they are attached to form cyclopropyl, cyclobutyl, and cyclopentyl, and especially wherein $R_9$ and $R_{10}$ are each methyl.

Embodiment 10: a compound as defined in Embodiments 1-9, or an enantiomer, diastereomer, tautomer, or a pharmaceutically-acceptable salt thereof, wherein:

Z is a 5- to 6-membered heteroaryl or heterocyclo group, each group substituted with one, two or three groups, $R^m$, $R^n$, and/or $R^o$, which are the same or different and are independently selected from hydrogen, halogen, alkyl, substituted alkyl, alkenyl, substituted alkenyl, alkynyl, substituted alkynyl, nitro, cyano, $OR^c$, $NR^aR^b$, $C(=O)R^a$, $CO_2R^a$, $C(=O)NR^aR^b$, —O—$C(=O)R^a$, $NR^aC(=O)R^b$, $NR^aC(=O)OR^b$, $NR^aC(=S)OR^b$, $S(O)_pR^c$, $NR^aSO_2R^c$, $SO_2NR^aR^b$, cycloalkyl, cycloalkenyl, heterocyclo, aryl, and heteroaryl, wherein p is 0, 1 or 2;

$R^a$ and $R^b$ are the same or different and at each occurrence are independently selected from (i) hydrogen, alkyl, substituted alkyl, alkenyl, substituted alkenyl, alkynyl, substituted alkynyl, cycloalkyl, cycloalkenyl, aryl, heteroaryl, and heterocyclo; or (ii) where possible together with the atoms to which they are attached $R^a$ is taken together with $R^b$ to form a heteroaryl or heterocyclo ring; and $R^c$ at each occurrence is independently selected from alkyl, substituted alkyl, substituted alkenyl, alkynyl, substituted alkynyl, cycloalkyl, cycloalkenyl, aryl, heteroaryl, and heterocyclo.

Embodiment 11: a compound as defined in Embodiments 1-10, or an enantiomer, diastereomer, tautomer, or a pharmaceutically-acceptable salt thereof, wherein Z is

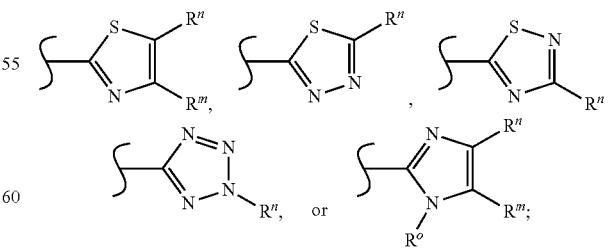

$R^m$ and $R^n$ are the same or different and at each occurrence are independently selected from hydrogen, —$CO_2R^a$, —$C(O)NR^aR^b$, $C_{1-6}$alkyl, —$CF_3$, —$CH_2OH$, —$SR^c$, —$NR^aR^b$, —$CH_2F$, cyano, and $C_{3-6}$cycloalkyl (especially compounds where R''' is hydrogen; and R'' is hydrogen, —C(O)NH(cyclopropyl), —C(O)NH(Me), —C(O)N(Me)₂, —C(O)NH(Et), methyl, —C(O)OEt, —C(O)NH(cyclobutyl), or

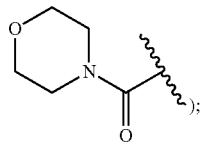
);

R° is hydrogen or C₁₋₆alkyl;

Rᵃ and Rᵇ are (i) the same or different and at each occurrence are independently selected from hydrogen, C₁₋₆alkyl, substituted C₁₋₆alkyl, 4- to 7-membered heterocyclo having 1-3 heteroatoms selected from O, S, or N, and C₃₋₆cycloalkyl; or (ii) Rᵃ is taken together with Rᵇ to form a 4- to 7-membered heterocyclo having 1-3 heteroatoms selected from O, S, or N; and Rᶜ is selected from C₁₋₆alkyl, and C₃₋₆cycloalkyl.

Embodiment 12: a compound as defined in Embodiments 1-11, or an enantiomer, diastereomer, tautomer, or a pharmaceutically-acceptable salt thereof, wherein:

Z is

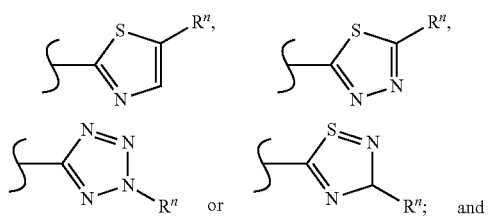

R" is hydrogen, —C(O)NH(cyclopropyl), —C(O)NH(Me), —C(O)N(Me)₂, —C(O)NH(Et), methyl, —C(O)OEt, —C(O)NH(cyclobutyl), —C(O)NH(CH₂)₂OH, —C(O)NH(iPr)—C(O)NHCH₂(CF₃),

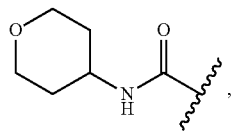

cyclopropyl, or

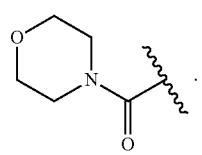

Embodiment 13: a compound as defined in Embodiments 1-12, or an enantiomer, diastereomer, tautomer, or a pharmaceutically-acceptable salt thereof, having the structure:

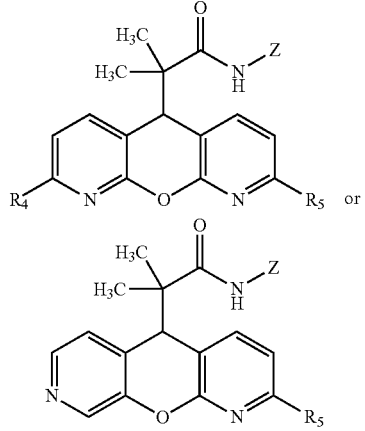

or

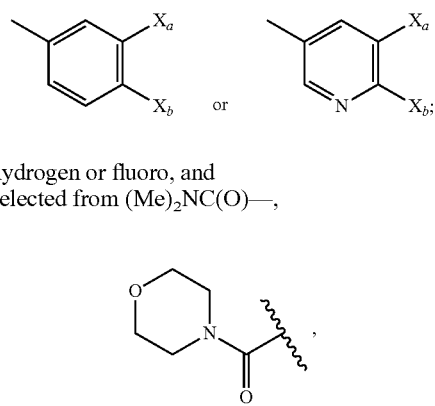

wherein:

R₄ is hydrogen, methyl, chloro, iso-propylthio, ethenyl, phenyl, cyano, dimethylamino, N-pyrollidinyl, or N-morpholinyl; and R₅ is chloro, dimethylamino,

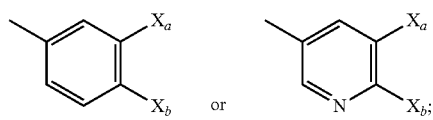

Xₐ is hydrogen or fluoro, and

Xᵦ is selected from (Me)₂NC(O)—,

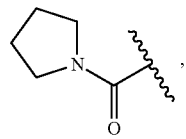

(Et)(Me)NC(O)—,

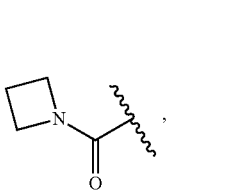

MeC(O)—, —O(phenyl), —OCF₃, —SO₂N(Me)₂, (t-Bu)NHC(O)—, —S(iPr), —S(Me), —O(iPr), —S(O)Me, —S(O)₂Me,

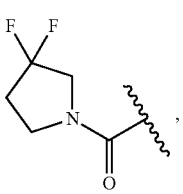

S(O)(iPr), S(O)₂(iPr), S(O)Et, iBu, —O(t-Bu), —S(Et), iBu, iPr, —O(cyclopentyl), EtC(O)—,

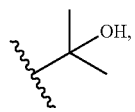

and —C(O)N(Me)(cyclopropyl).

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements (including individual variable definitions) of an embodiment are meant to be combined with any and all other elements from any of the embodiments to describe additional embodiments. The present invention also provides a pharmaceutical composition comprising a compound of formula I, or an enantiomer, diastereomer, or a pharmaceutically-acceptable salt, and a pharmaceutically acceptable carrier therefore.

Other embodiments of the present invention are 1) a method of treating a disease or disorder comprising administering to a patient in need of treatment a therapeutically effective amount of a compound of formula I, 2) a compound of formula I for use in treating a disease or disorder, and 3) use of a compound of formula I in the manufacture of a medicament for treating a disease or disorder, wherein the disease or disorder is selected from an endocrine disorder, rheumatic disorder, collagen disease, dermatologic disease, allergic disease, ophthalmic disease, respiratory disease, hematologic disease, gastrointestinal disease, inflammatory disease, immune disease, neoplastic disease and metabolic disease.

In still another embodiment, the present invention provides a method of treating endocrine disorder, rheumatic disorder, collagen disease, dermatologic disease, allergic disease, ophthalmic disease, respiratory disease, hematologic disease, gastrointestinal disease, inflammatory disease, immune disease, neoplastic disease and metabolic disease, a disease associated with the expression product of a gene whose transcription is stimulated or repressed by glucocorticoid receptors, or a disease associated with AP-1- and/or NFκB-induced transcription, or a disease associated with AP-1 and/or NFκB dependent gene expression, wherein the disease is associated with the expression of a gene under the regulatory control of AP-1 and/or NF-κB (particularly AP-1), including inflammatory and immune diseases and disorders as described hereinafter, which includes the step of administering a therapeutically effective amount of a compound of formula I of the invention to a patient.

Other embodiments of the present invention are 1) a method of treating a disease or disorder comprising administering to a patient in need of treatment a therapeutically effective amount of a compound of formula I, 2) a compound of formula I for use in treating a disease or disorder, and 3) use of a compound of formula I in the manufacture of a medicament for treating a disease or disorder wherein the disease or disorder is selected from a metabolic disease or an inflammatory or immune disease comprising the administration to a patient in need of treatment, a therapeutically effective amount of a compound of formula I.

A more preferred embodiment of the present invention provides 1) a method of treating a disease or disorder comprising administering to a patient in need of treatment a therapeutically effective amount of a compound of formula I, 2) a compound of formula I for use in treating a disease or disorder, and 3) use of a compound of formula I in the manufacture of a medicament for treating a disease or disorder wherein the disease or disorder is selected from a metabolic disease wherein the disease is a metabolic disease selected from Type I diabetes, Type II diabetes, juvenile diabetes, and obesity.

Other preferred embodiments of the present invention are 1) a method of treating a disease or disorder comprising administering to a patient in need of treatment a therapeutically effective amount of a compound of formula I, 2) a compound of formula I for use in treating a disease or disorder, and 3) use of a compound of formula I in the manufacture of a medicament for treating a disease or disorder, wherein the disease or disorder is an inflammatory or immune disease selected from transplant rejection of kidney, liver, heart, lung, pancreas, bone marrow, cornea, small bowel, skin allografts, skin homografts, heart valve xenograft, serum sickness, and graft vs. host disease, rheumatoid arthritis, psoriatic arthritis, multiple sclerosis, asthma, inflammatory bowel disease, Crohn's disease, ulcerative colitis, pyoderma gangrenum, systemic lupus erythematosis, myasthenia gravis, psoriasis, dermatitis, dermatomyositis, eczema, seborrhoea, pulmonary inflammation, eye uveitis, hepatitis, Graves' disease, Hashimoto's thyroiditis, autoimmune thyroiditis, Behcet's or Sjorgen's syndrome, pernicious or immunohaemolytic anaemia, atherosclerosis, Addison's disease, idiopathic adrenal insufficiency, autoimmune polyglandular disease, glomerulonephritis, scleroderma, morphea, lichen planus, vitiligo, alopecia areata, autoimmune alopecia, autoimmune hypopituitarism, Guillain-Barre syndrome, alveolitis, contact hypersensitivity, delayed-type hypersensitivity, contact dermatitis, uticaria, skin allergies, respiratory allergies, hayfever, gluten-sensitive enteropathy, osteoarthritis, acute pancreatis, chronic pancreatitis, acute respiratory distress syndrome, Sezary's syndrome, restenosis, stenosis, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetitformis, severe erythema multiforme, exfoliative dermatitis, seborrheic dermatitis, seasonal or perennial allergic rhinitis, bronchial asthma, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, regional enteritis, autoimmune vasculitis, sepsis, and chronic obstructive pulmonary disease.

Especially preferred embodiments are 1) a method of treating a disease or disorder comprising administering to a patient in need of treatment a therapeutically effective amount of a compound of formula I, 2) a compound of formula I for use in treating a disease or disorder, and 3) use of a compound of formula I in the manufacture of a medicament for treating a disease or disorder where the disease or disorder is selected from transplant rejection, rheumatoid arthritis, psoriatic arthritis, multiple sclerosis, asthma, inflammatory bowel disease, systemic lupus erythematosis, and psoriasis.

Another embodiment of the present invention involves a method for treating a disease or disorder associated with the expression product of a gene whose transcription is stimulated or repressed by glucocorticoid receptors, or a method of treating a disease or disorder associated with AP-1- and/or NF-κB- (particularly AP-1-) induced transcription, or a method for treating a disease or disorder associated with AP-1 and/or NF-κB (particularly AP-1) dependent gene expression, wherein the disease is associated with the expression of a gene under the regulatory control of AP-1 and/or NF-κβ (particularly AP-1), such as inflammatory and immune disorders, cancer and tumor disorders, such as solid tumors, lymphomas and leukemia, and fungal infections such as mycosis fungoides.

In still another embodiment, the present invention provides a pharmaceutical combination comprising one or more compounds of Formula I and an immunosuppressant, an anticancer agent, an anti-viral agent, an anti-inflammatory agent, an anti-fungal agent, an anti-biotic, an anti-vascular hyperproliferation agent, an anti-depressant agent, a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the lipid lowering agent is an MTP inhibitor, an HMG CoA reductase inhibitor, a squalene synthetase inhibitor, a fabric acid derivative, an upregulator of LDL receptor activity, a lipoxygenase inhibitor, or an ACAT inhibitor, wherein the antihypertensive agent is an ACE inhibitor, angiotensin II receptor antagonist, NEP/ACE inhibitor, calcium channel blocker and/or β-adrenergic blocker.

Even more preferred combinations are those wherein the antidiabetic agent is 1, 2, 3 or more of metformin, glyburide, glimepiride, glipyride, glipizide, chlorpropamide, gliclazide, acarbose, miglitol, pioglitazone, troglitazone, rosiglitazone, insulin, G1-262570, isaglitazone, JTT-501, N,N-2344, L895645, YM-440, R-119702, AJ9677, repaglinide, nateglinide, KAD1129, AR-HO39242, GW-409544, KRP297, AC2993, LY315902, P32/98 and/or NVP-DPP-728A, wherein the anti-obesity agent is orlistat, ATL-962, AJ9677, L750355, CP331648, sibutramine, topiramate, axokine, dexamphetamine, phentermine, phenylpropanolamine, and/or mazindol, wherein the lipid lowering agent is pravastatin, lovastatin, simvastatin, atorvastatin, cerivastatin, fluvastatin, itavastatin, visastatin, fenofibrate, gemfibrozil, clofibrate, avasimibe, TS-962, MD-700, cholestagel, niacin and/or LY295427, wherein the antihypertensive agent is an ACE inhibitor which is captopril, fosinopril, enalapril, lisinopril, quinapril, benazepril, fentiapril, ramipril or moexipril; an NEP/ACE inhibitor which is omapatrilat, [S[(R*,R*)]-hexahydro-6-[(2-mercapto-1-oxo-3-phenylpropyl)amino]-2,2-dimethyl-7-oxo-1H-azepine-1-acetic acid (gemopatrilat) or CGS 30440;

an angiotensin II receptor antagonist which is irbesartan, losartan or valsartan;

amlodipine besylate, prazosin HCl, verapamil, nifedipine, nadolol, propranolol, carvedilol, or clonidine HCl, wherein the platelet aggregation inhibitor is aspirin, clopidogrel, ticlopidine, dipyridamole or ifetroban;

the immunosuppressant is a cyclosporin, mycophenolate, interferon-beta, deoxyspergolin, FK-506 or Ant.-IL-2;

the anti-cancer agent is azathiprine, 5-fluorouracel, cyclophosphamide, cisplatin, methotrexate, thiotepa, or carboplatin;

the anti-viral agent is abacavir, aciclovir, ganciclovir, zidanocin, or vidarabine; and the antiinflammatory drug is ibuprofen, celecoxib, rofecoxib, aspirin, naproxen, ketoprofen, diclofenac sodium, indomethacin, piroxicam, prednisone, dexamethasone, hydrocortisone, or triamcinolone diacetate.

The term "disease associated with GR transactivation," as used herein, refers to a disease associated with the transcription product of a gene whose transcription is transactivated by a GR. Such diseases include, but are not limited to: osteoporosis, diabetes, glaucoma, muscle loss, facial swelling, personality changes, hypertension, obesity, depression, and AIDS, the condition of wound healing, primary or secondary andrenocortical insufficiency, and Addison's disease.

The term "treat", "treating", or "treatment," in all grammatical forms, as used herein refers to the prevention, reduction, or amelioration, partial or complete alleviation, or cure of a disease, disorder, or condition, wherein prevention indicates treatment of a person at risk for developing such a disease, disorder or condition.

The terms "glucocorticoid receptor" and "GR," as used herein, refer either to a member of the nuclear hormone receptor ("NHR") family of transcription factors which bind glucocorticoids and either stimulate or repress transcription, or to GR-beta.

These terms, as used herein, refer to glucocorticoid receptor from any source, including but not limited to: human glucocorticoid receptor as disclosed in Weinberger, et al., *Science*, 228:740-742 (1985), and in Weinberger, et al., *Nature*, 318:670-672 (1986); rat glucocorticoid receptor as disclosed in Miesfeld, R., *Nature*, 312:779-781 (1985); mouse glucocorticoid receptor as disclosed in Danielson, M. et al., *EMBO J.*, 5:2513; sheep glucocorticoid receptor as disclosed in Yang, K. et al., *J. Mol. Endocrinol.*, 8:173-180 (1992); marmoset glucocorticoid receptor as disclosed in Brandon, D. D. et al., *J. Mol. Endocrinol.* 7:89-96 (1991); and human GR-beta as disclosed in Hollenberg, S. M. et al., *Nature*, 318:635 (1985); Bamberger, C. M. et al., *J. Clin Invest.*, 95:2435 (1995).

The term, "disease or disorder associated with AP-1 and/or NF-κB" as used herein, refers to a disease associated with the expression product of a gene under the regulatory control of AP-1 and/or NF-κB. Such diseases include, but are not limited to: inflammatory and immune diseases and disorders; cancer and tumor disorders, such as solid tumors, lymphomas and leukemia; and fungal infections such as mycosis fungoides.

The term "inflammatory or immune associated diseases or disorders" is used herein to encompass any condition, disease, or disorder that has an inflammatory or immune component, including, but not limited to, each of the following conditions: transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, Type I and Type II diabetes, juvenile diabetes, obesity, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Graves' disease, Hashimoto's thyroiditis, autoimmune thyroiditis, Behcet's or Sjorgen's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, viteligo (depigmentation of the skin), alopecia areata, autoimmune alopecia, autoimmune hypopituatarism, Guillain-Barre syndrome, and alveolitis; T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); inflammatory diseases such as osteoarthritis, acute pancreatitis, chronic pancreatitis, acute respiratory distress syndrome, Sezary's syndrome and vascular diseases which have an inflammatory and or a proliferatory component such as restenosis, stenosis and artherosclerosis. Inflammatory or immune associated diseases or disorders also includes, but is not limited to: endocrine disorders, rheumatic disorders, collagen diseases, dermatologic disease, allergic disease, ophthalmic disease, respiratory disease, hematologic disease, gastrointestinal disease, inflammatory disease, autoimmune disease, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis.

Synthesis

Methods of Preparation

Compounds of the present invention may be synthesized by many methods known to those skilled in the art of organic chemistry. Accordingly, the synthetic schemes described below are illustrative only as additional methods of preparing compounds of the present invention will be evident to those skilled in the art. Likewise, it will be apparent to one of skill in the art that various steps in the synthetic schemes may be performed in an alternate sequence to give the desired compound or compounds. Exemplified compounds are typically prepared according to synthetic schemes 1-6 as racemic mixtures. Homochiral compounds may be prepared by techniques known to one skilled in the art, for example, by the separation of racemic products by chiral phase preparative HPLC. Enantiomerically enriched compounds may be prepared by known methods including, but not limited to, the incorporation of chiral auxiliary functionalities into racemic intermediates providing enantio-enriched products upon cleavage of the chiral auxiliary.

Scheme 1 illustrates the preparation of title compounds of the invention (1) from intermediate carboxylic acids 2. The amides 1 (1a and 1b) may be prepared from 2 by many methods, including dehydrative condensation of carboxylic acids and amines For example, the condensation of acid 2 with amine 3 (NHR$_{11}$Z, where R$_{11}$=H, alkyl, cycloalkyl, alkoxy, dialkylamino, aryl or heteroaryl) may be effected by treatment of 2 with an activating reagent, such as a water-soluble carbodiimide (EDC), in the presence of an N-hydroxy triazole (HOAt or HOBt, or the like) and amine in the presence of base (preferably triethylamine, diisopropylethylamine, or the like) in an appropriate polar aprotic solvent (N,N-dimethylformamide, acetonitrile, dichloromethane, or the like). The carboxylic acid 2 may also be converted to an acid chloride by treatment with an appropriate chlorinating agent (thionyl chloride, oxalyl chloride, or the like). Similarly, 2 may be converted to an acyl fluoride upon exposure to a fluorinating agent (such as cyanuric fluoride). Condensation of the acyl halide (chloride or fluoride) with the amine 3 (typically carried out in the presence of a base such as pyridine or triethylamine in an aprotic solvent) may then provide the amide 1. In cases where R$_{11}$=H (i.e., 3=NH$_2$Z), the product of the condensation of 2 and 3 (1a, R$_{11}$=H) may be converted to 1b (R$_{11}$=alkyl) by treatment of 1a with an alkylating agent (alkyl halide, alkyl sulfonate, or the like) in the presence of a base (cesium carbonate, sodium hydride, or the like). Alternatively, 1a (R$_{11}$=H) may be converted to 1b (R$_{11}$=C(O)alkyl, CO$_2$alkyl) by treatment with a strong base (sodium hydride, lithium diisopropylamide, or the like) followed by acylation with an appropriate acylating reagent (an acid chloride, chloroformate, or the like). Similarly, sulfonylation may be effected by treatment with a base and sulfonyl halide to provide 1b (R$_{11}$=SO$_2$aryl or SO$_2$alkyl). Arylation of 1a to give 1b (R$_{11}$=aryl) may also be effected by palladium-catalyzed N-arylation of amides (see, for example, Yin, J.; Buchwald S. Org. Lett. 2000, 2, 1101-1104 and references cited therein) or the copper-promoted arylation of amides with aryl boronic acids or arylsiloxanes (see, for example, Lam, P. et al. Synlett 2000, 674-676).

SCHEME 1
Condensation of carboxylic acid 2 with amine 3 to form product 1

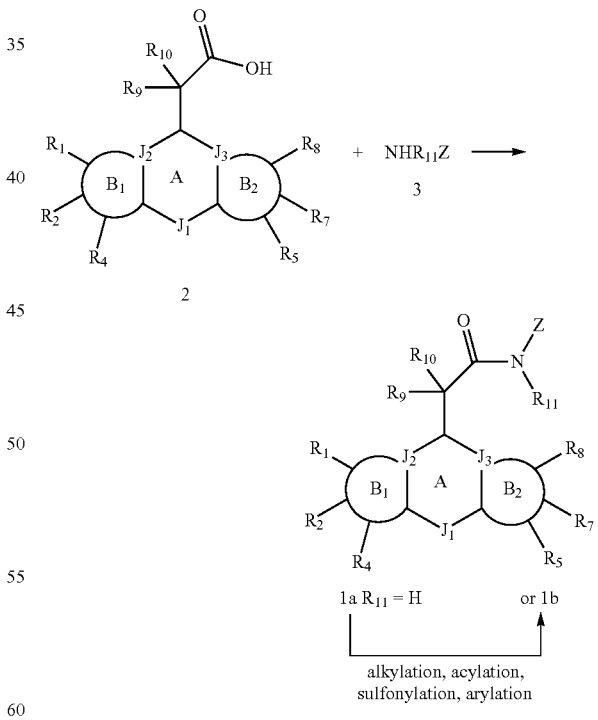

Scheme 2 illustrates various methods for the preparation of the intermediate carboxylic acid 2. The intermediate ketone 4 may be reduced to alcohol 5 by treatment with a reducing agent (typically a metal hydride such as sodium borohydride in methanol or lithium aluminum hydride in diethyl ether or THF). In one mode of preparation, the alcohol may be condensed with malonic acid to give, after decarboxylation of a putative intermediate dicarboxylic acid, the desired intermediate 2 (Jones et al. *J. Am. Chem. Soc.* 1948, 70, 2843; Beylin et al. *Tetrahedron Lett.* 1993, 34, 953-956). The alcohol 5 may also be treated with a silyl ketene acetal, represented by 6. Alternatively, alcohol 5 may be acylated with anhydride or acyl halide in the presence of a suitable base (triethylamine, pyridine or DMAP) to give 5a, which may also react with a silyl ketene acetal 6. In cases where $R_9=R_{10}=R_{50}=R_{51}=Me$, 6 may be obtained from commercial sources. The condensation of 5 ($J_2=J_3$=bond) with 6 to give ester 7 generally requires the presence of a Lewis acid, such as boron trifluoride etherate, titanium tetrachloride, or the like and is best carried out in a polar, aprotic solvent such as dichloromethane. Saponification of ester 7 to 2 may be carried out with sodium hydroxide or potassium hydroxide in water in the presence of co-solvents such as methanol, THF, and/or DMSO. In cases where $R_9=R_{10}$=alkyl, the hydrolysis of ester 7 is best carried out at elevated temperature (generally 80° C.) for prolonged times (>5 h).

The ketone 4 may also be condensed with an enolate derived from ester 9 ($R_{51}$=alkyl), prepared by treatment of 9 with an appropriate base (lithium diisopropyl amide, lithium or potassium hexamethyldisilizane or the like) at low temperature (−78° C. to 0° C.), to give ester 10. An intermediate carboxylic acid 10 ($R_{51}$=H) may also be prepared by first treating a carboxylic acid 9 ($R_{51}$=H) with at least two equivalents of a strong base (preferably lithium diisopropyl amide or lithium diethyl amide) to generate an enediolate dianion. Generation of the enediolate is preferably carried out at 0° C. to 55° C. Condensation of the in situ prepared enediolate with ketone 4 may then give the hydroxy acid 10 ($R_{51}$=H). In cases where one or both of $J_2$ and/or $J_3$ are an alkylene group, the intermediate alcohol 10 may readily dehydrate to give the unsaturated intermediates 11 and/or 12. The dehydration may occur spontaneously by exposure of 10 ($J_2$, $J_3$=alkylene) to acidic conditions, such as aqueous acid or Lewis acid (boron trifluoride, titanium tetrachloride, or the like). The intermediate olefins 11 and 12 may be reduced to give ester 7 ($R_{51}$=alkyl) via catalytic hydrogenation (typically palladium on carbon in the presence of hydrogen gas), which may be saponified as described above to prepare carboxylic acid 2. Alternatively, in cases where olefins 11 and 12 are carboxylic acids ($R_{51}$=H), catalytic hydrogenation (typically palladium on carbon in the presence of hydrogen gas) may directly provide the carboxylic acid 2. In cases where dehydration of alcohol 10 to 11 and/or 12 does not spontaneously occur, 10 ($R_{51}$=H) may be reduced to 2. Such a reduction may be performed by treating acid 10 ($R_{51}$=H) with a silane (typically triethylsilane) in the presence of a protic acid (typically trifluoroacetic acid). The ester 10 ($R_{51}$=alkyl) may also be reduced to ester 7 under the same conditions employed for conversion of 10 to 2. Ester 7 may be hydrolyzed to acid 2 under conditions described above.

The ketone 4 may also be treated with silyl ketene acetal 6 to provide the hydroxy ester 10 ($R_{51}$=alkyl). The condensation is best carried out in the presence of a Lewis acid (boron trifluoride etherate, or the like) in dichloromethane at 0° C. Hydroxy ester 10 may be isolated, or, alternatively, in situ reduction to ester 7 may be carried out. In cases where any one or more of $R_1$, $R_2$, $R_4$=OH, addition of triethylsilane to the reaction mixture containing the unisolated hydroxy ester 10 may give the ester 7. Alternatively, addition of a strong protic acid (typically trifluoroacetic acid) and triethylsilane to the reaction mixture containing unisolated hydroxy ester 10 may provide ester 7. Conversion of ester 7 to carboxylic acid 2 may then be carried out as described above.

SCHEME 2
Preparation of carboxylic acid 2 from ketone 3

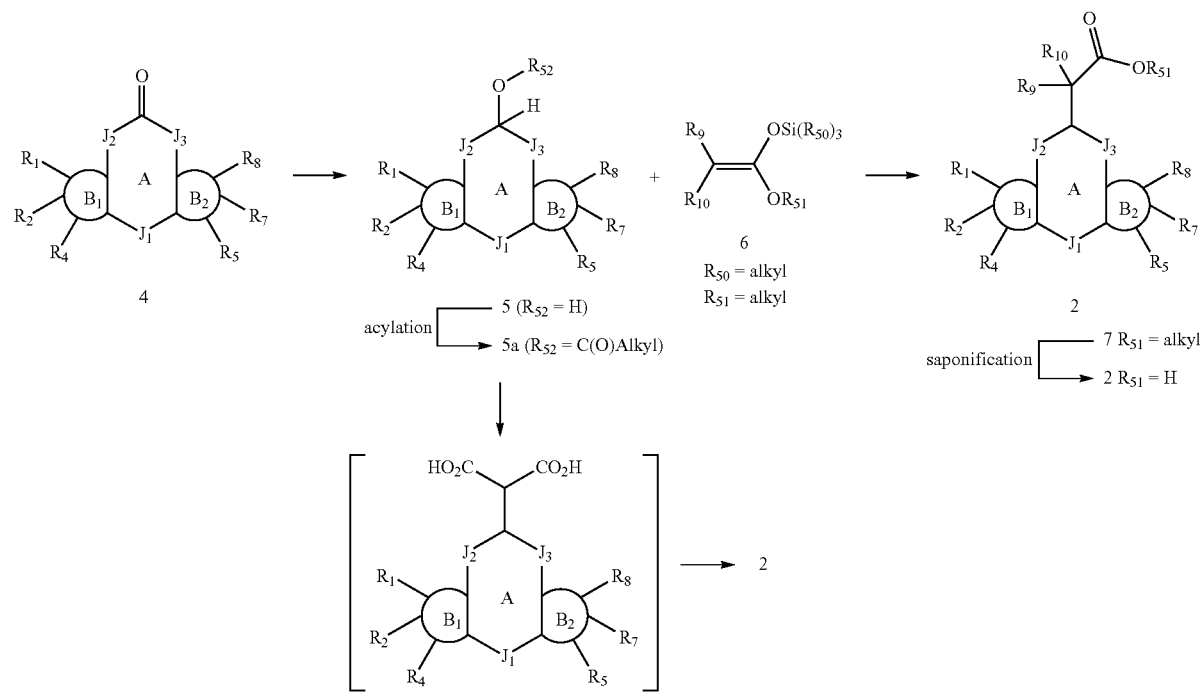

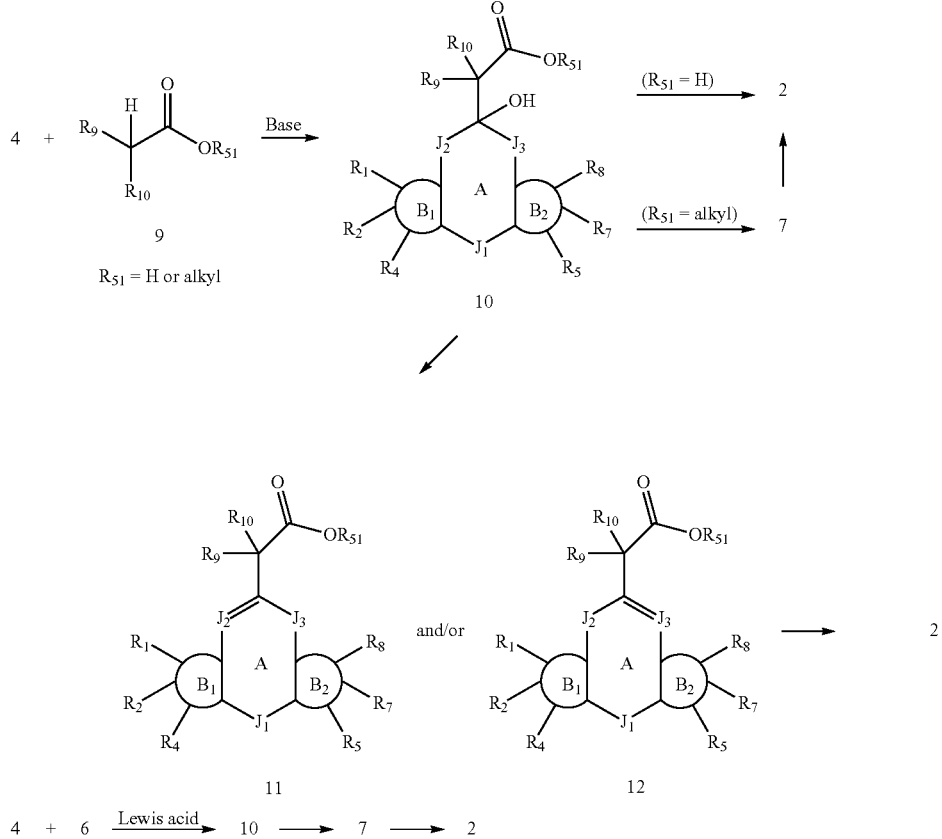

Scheme 3 illustrates methods for the preparation of the intermediate ketone 4. In one route, 2-chloropyridine 14 can be treated with strong base such as lithium diisopropylamide (LDA) in solvent such as tetrahydrofuran at low temperature (−78° C.) to generate a 3-lithiated pyridine regioselectively (Trecourt et al. *J. Chem. Soc. Perkin Trans.* 11990, 2409-2415). The pyridinyl lithium intermediate can react in situ with ortho-chloro-substituted pyridine aldehyde 13 via nucleophilic addition to give alcohol 15. Oxidation of 15 to ketone 16 can be achieved under various conditions well known in the literature, such as Dess-Martin Periodinane or Swern oxidation in dichloromethane. The halogens in 16 can be displaced with methoxy groups using conditions such as sodium methoxide in methanol at reflux. The resulting dimethoxy derivative 17 could undergo cyclization upon treatment with pyridine hydrochloride at elevated temperature to give diazaxanthone 4a (Trecourt et al. *J. Chem. Soc. Perkin Trans.* 11990, 2409-2415). In an alternative route, 2-methoxypyridine or 2,6-dimethoxypyridine (19, Z=H or OMe) can be treated with strong base such as mesityllithium in tetrahydrofuran to effect regioselective deprotonation at 3-position of the pyridine (Comins and LaMunyon *Tetrahedron Lett.* 1988, 29, 773-776). Addition of aldehyde 18 to the in situ generated lithiated-pyridine can give alcohol 20. Alcohol 20 can also be prepared from bromopyridine 21 via lithium-bromine exchange with butyllithium and subsequent addition to aldehyde 18 (Trecourt et al. *J. Chem. Res.* 1979, 46-47). Conversion of 20 to ketone 22 can be effected using similar oxidation conditions such as Dess-Martin Periodinane or Swern oxidation. Ketone 22 (Z=H or OMe) can be converted to diazaxanthone 4b (Z=H or OMe) following conditions described previously.

Another synthesis of the diazaxanthone 4c is shown in the bottom section of Scheme 3. Appropriately substituted pyridine carboxylic acid 23 can be converted to the corresponding methyl ester using conditions such as refluxing MeOH in the presence of HCl or $H_2SO_4$, trimethylsilyl diazamethane in tetrahydrofuran and methanol, or iodomethane in the presence of base such as potassium carbonate in polar solvent such as DMF or DMSO. Conversion of ester 24 ($Z_1$=OMe) to cyanoketone 25 can be accomplished by reaction with the anion of acetonitrile, which can be generated with LDA in solvents such as THF (see, for example, Ridge, David N. et al, *J Med Chem* 1979, 1385). Alternatively, cyanoketone 25 can be synthesized by reaction of cyanoacetic acid and butyllithium in THF with acid chloride 24 ($Z_1$=Cl), which can be prepared from acid 23 using well known conditions such as treating with thionyl chloride at an elevated temperature or with oxalyl chloride/DMF/$CH_2Cl_2$. The vinylogous amide 27 is commercially available or can be prepared from ketone 26 by treatment with N,N-dimethylformamide dimethyl acetal, typically by heating a mixture of the two at reflux. Conditions for the condensation of cyanoketone 25 and vinylogous amide 27 was developed based on a literature report for a related but different system (Bondavalli et al *Synthesis,* 1999, 1169-1174). Typically, the reaction can be conducted in hot (typically 100-140° C.) solvent (typically DMF or DMA) under acidic conditions (typically acetic acid) to give ketone 4c. The elaboration of intermediate 4a-c may then be carried out as depicted in Scheme 2 for the conversion of 4 to 2, and further, as depicted in Scheme 1 for the conversion of 2 to 1.

SCHEME 3
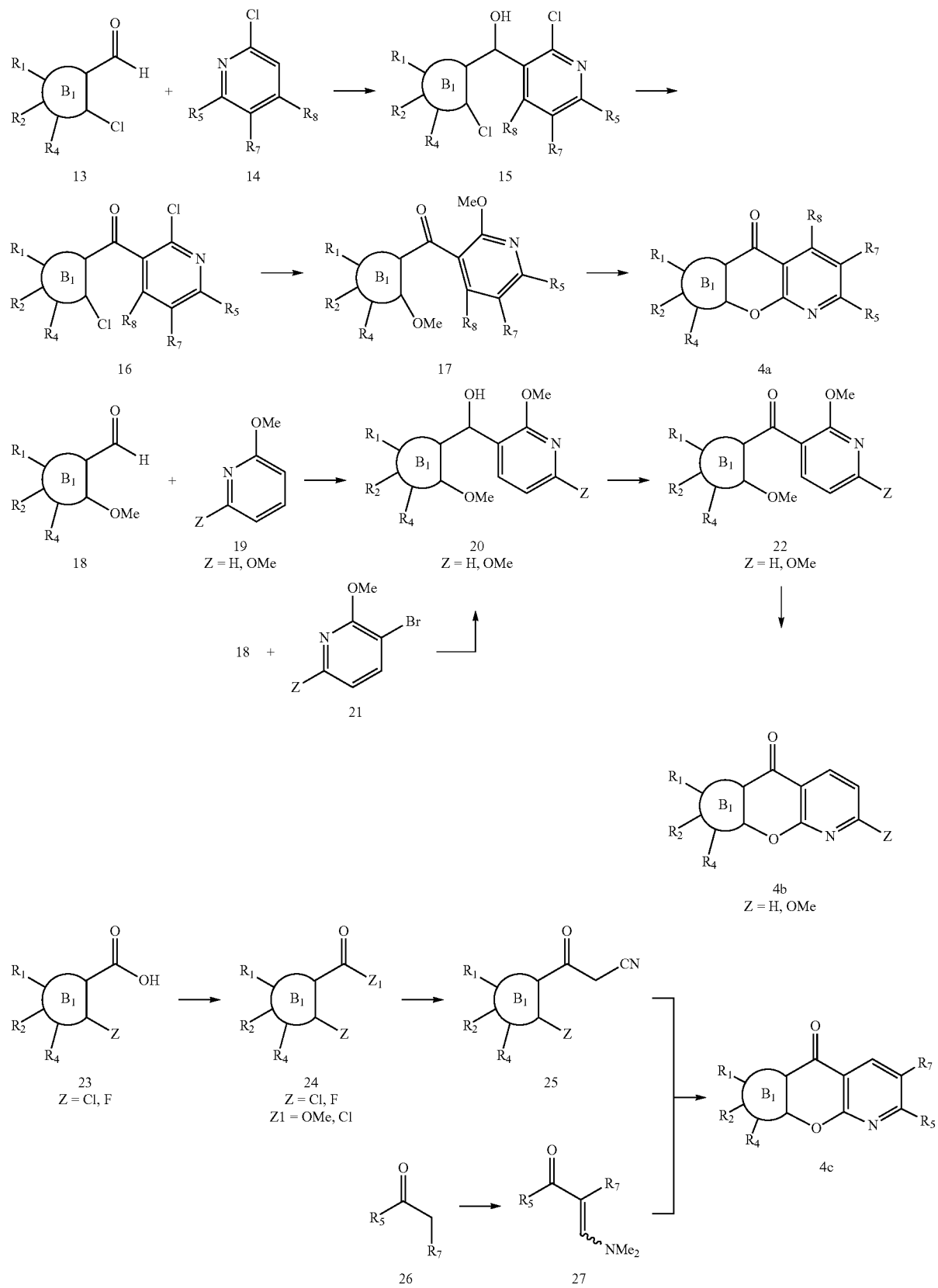

Scheme 4 outlines a synthesis of intermediate ketone 4d. An appropriately functionalized pyridine acyl chloride 24, which may be prepared according to methods described in Scheme 3, can be reacted with an enolate of acetone (derived from acetone and LDA in THF at low temperature, typically −78° C.) to give diketone 29. Conversion to vinylogous amide 30 can be achieved with N,N-dimethylformamide dimethyl acetal in toluene at elevated temperature (typically at reflux). Vinylogous amide 30 can be deprotonated using base such as lithium bis-(trimethylsilyl)amide or LDA in polar solvent such as THF. The resulting enolate could react with acyl chloride 31 via nucleophilic addition followed by Michael addition/retro-Michael elimination to give pyranone 32. The pyranone can be treated with ammonia source such as ammonium acetate in acidic and polar solvents such as a mixture of acetic acid and DMF at elevated temperature to induce formation of pyridone and cyclization to diazaxanthone 4d. Intermediate 4d may be elaborated as depicted in Scheme 2 for the conversion of 4 to 2, and further, as depicted in Scheme 1 for the conversion of 2 to 1.

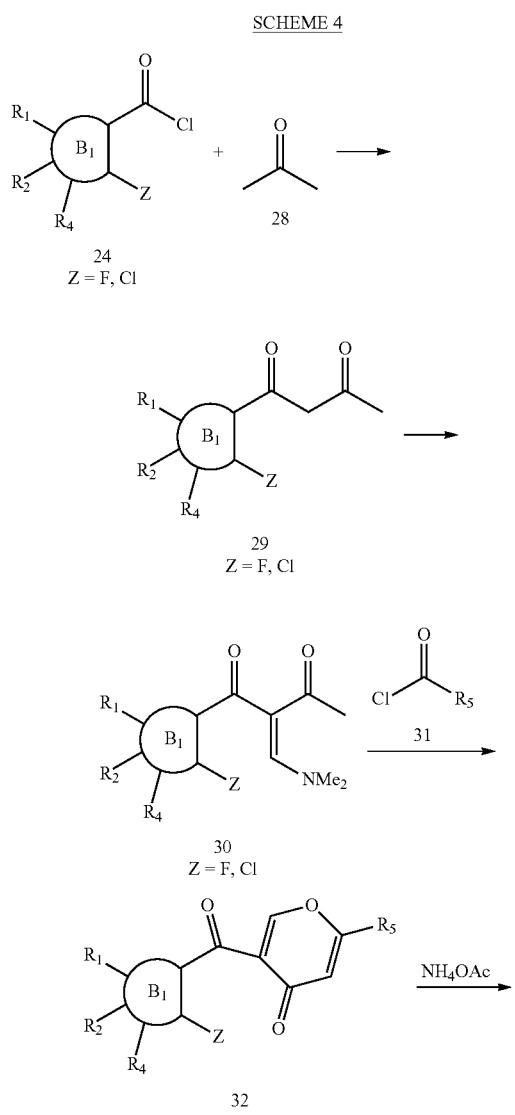

SCHEME 4

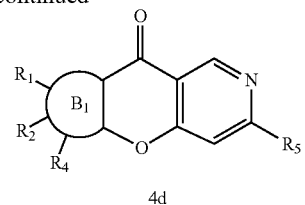

4d

Scheme 5 illustrates the synthesis of a series of chloro-substituted diazaxanthenes and subsequent derivatization. Intermediate 33 can be prepared according to syntheses described above in Scheme 3 and in Scheme 2. Oxidation to N-oxide intermediate 34 may be effected under conditions known for the preparation of pyridine N-oxides, such as mCPBA in dichloromethane or MeReO$_3$ and hydrogen peroxide in dichloromethane (Coperet et al *J. Org. Chem.* 1998, 63, 1740). The N-oxide intermediate 34 may be treated with an appropriate chlorinating reagent (preferably phosphorous oxychloride, POCl$_3$, in the absence of a co-solvent) to give the chlorodiazaxanthene 35. Hydrolysis of 35 to carboxylic acid 36 may be effected under conditions described above for the preparation of 7 from 2, preferably in the absence of DMSO. The carboxylic acid 36 may be converted to amide 37 as described above for the preparation of 1a from 2 and 3.

Displacement of chloro-diazaxanthene 37 with an amine (NHR$_{12}$R$_{13}$) at elevated temperature (typically 130° C.) may provide 39a. Alternatively, 37 may undergo metal-mediated cross-coupling reactions to give 39b. For example, Suzuki coupling may be effected by treatment of 37 with an aryl or heteroaryl boronic acid or boronate ester in the presence of a palladium catalyst (tetrakis triphenylphosphine palladium, or the like) and an aqueous base (potassium carbonate, sodium carbonate, potassium phosphate or the like) in an appropriate solvent or solvent combination (DMF, toluene/ethanol, 1,4-dioxane or the like) at elevated temperature (typically 100° C.). The chloride 37 may also undergo a variety of other metal-mediated cross-coupling reactions known to one skilled in the art (See, for example, de Meijere, A., & Diederich, F. (2004). Metal-Catalyzed Cross-Coupling Reactions. (2nd ed.): John Wiley & Sons). The chloride 37 may also undergo a Sonogashira or Stevens-Castro cross-coupling with an alkyne in the presence of a palladium catalyst (preferably bis(triphenylphosphine)-palladium (II) chloride) using catalytic cuprous iodide in the presence of a hindered secondary amine base (preferably diisopropylamine) to give alkyne 39c. Chloride 37 may also be converted to nitrile 39d under known methods for palladium-catalyzed cyanation of aryl halides (Sundmeier, M. et al, *Eur. J. Inorg. Chem.* 2003, 3513). For example, the treatment of 37 with a cyanide source (typically zinc cyanide) in the presence of a palladium catalyst (typically tetrakis(triphenylphosphine) palladium (0)) in a polar solvent (typically DMF) at elevated temperature (typically 120° C.) provides nitrile 39d. Nitrile 39d may also be converted to amide 39e in a two-step procedure involving initial hydrolysis by hydroxide (typically potassium hydroxide) to give a carboxylic acid (R$_5$=CO$_2$H) which may then be condensed with primary or secondary amines as described for the preparation of 1a from 2 to give carboxamide 39e. Chloride 37 may also be converted to ketone 39f as described by Jean-Yves Legros et al. (*Tetrahedron* 2001, 57, 2507). Similar transformations can be performed on chloro acid 36 to give 38a-f, which may be converted to 39a-f following the conditions described above for the preparation of 1 from 2 and 3. Any of the racemic intermediates 33-38 or example compounds may be separated into purified, single enantiomers by any of the various methods known to one skilled in the art.

SCHEME 5

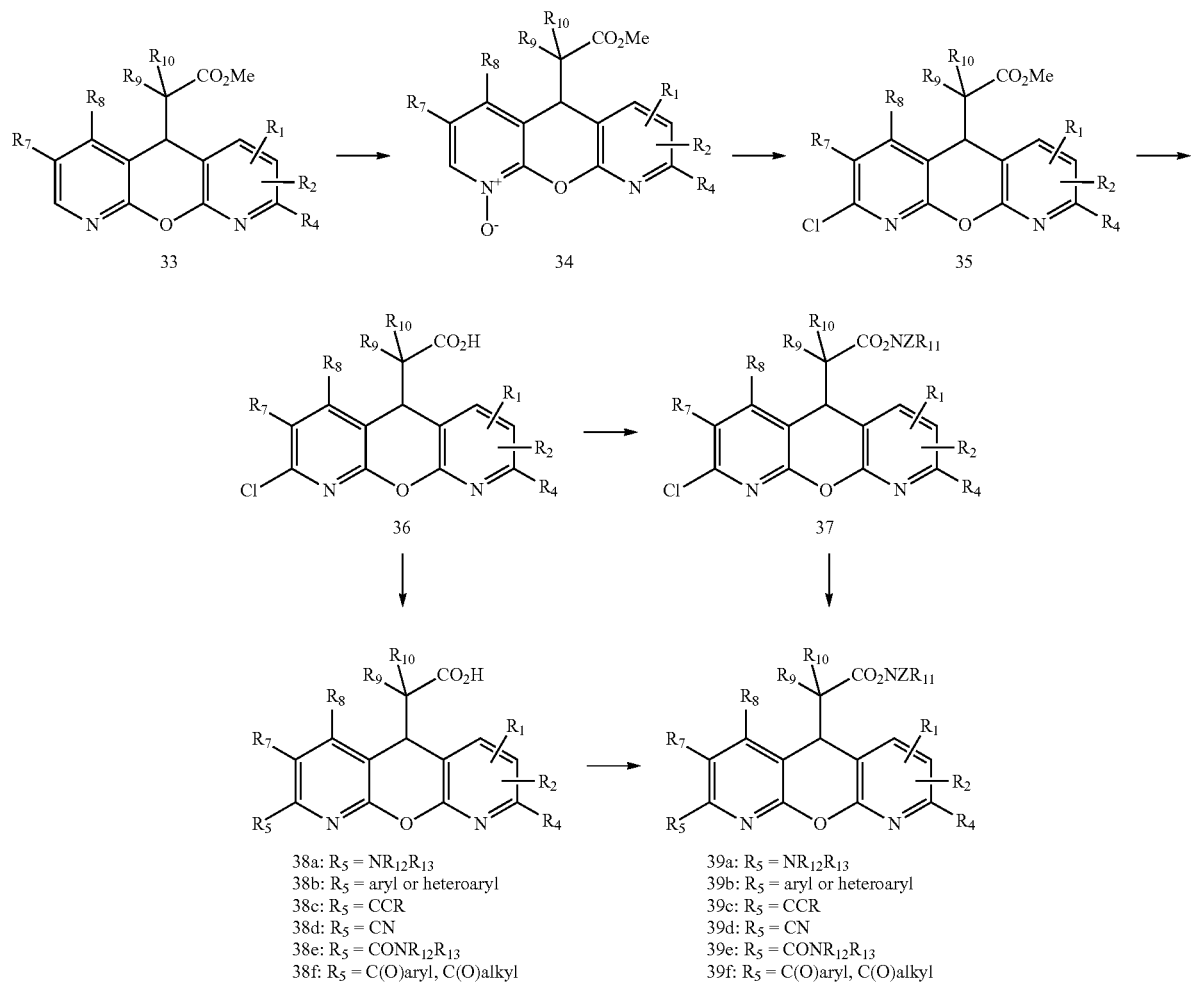

2-(Para-substituted phenyl)-diazaxanthenes may be further elaborated as depicted in Scheme 6. Phenol 40a ($R_x$=OH) may be alkylated under Mitsunobu conditions (*Synthesis* 1, 1981). Thus treatment of 40a with an alcohol ($R_yOH$) in the presence of a phosphine (preferably, triphenylphosphine) and an alkyl azodicarboxylate (preferably diisopropyl azodicarboxylate or diethyl azodicarboxylate) in tetrahydrofuran may provide ether 40b. A thioether (for example, 41a, $R_x$=SMe) may be oxidized to sulfoxide or sulfone 41b by treatment with any of a number of oxidants, including m-chloroperbenzoic acid and Oxone. Carboxylic acid 42a may be converted to benzamide 42b using many of the myriad methods for the conversion of benzoic acids to benzamides. Preferably, treatment of 42a with an activating reagent(s) (typically HOBt in the presence of a carbodiimide such as EDCI) in the presence of a tertiary amine base (typically triethylamine or diisopropylethylamine) and a primary or secondary amine in a polar, aprotic solvent (typically acetonitrile or DMF) gives benzamide 42b. Aldehyde 43a may be converted to alcohol 43b by reduction with an appropriate reducing agent (sodium borohydride, or the like) or by treatment with an organometallic nucleophile (alkyl or aryl lithium, Grignard reagent, or the like). Similarly, ketone 44a may be condensed with an organometallic nucleophile to provide tertiary alcohol 44b.

SCHEME 6
Elaboration of phenyl-substituted 5H-chromeno[2,3-b]pyridines

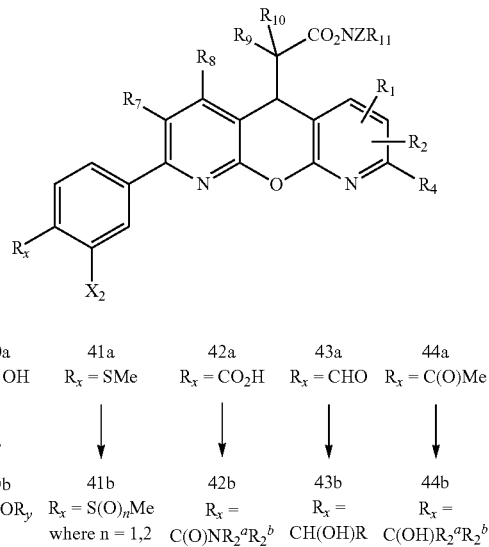

DEFINITIONS

The following are definitions of terms used in this specification and appended claims. The initial definition provided for a group or term herein applies to that group or term throughout the specification and claims, individually or as part of another group, unless otherwise indicated.

The term "alkyl" refers to straight or branched chain hydrocarbon groups having 1 to 12 carbon atoms, preferably 1 to 6 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy($C_{0-2}$)alkyl or ($C_{0-2}$)hydroxyalkyl includes hydroxy, hydroxymethyl and hydroxyethyl.

The term "substituted alkyl" refers to an alkyl group as defined above having one, two, or three substituents selected from the group consisting of halo (e.g., trifluoromethyl), alkenyl, substituted alkenyl, alkynyl, nitro, cyano, oxo (=O), $OR_a$, $SR_a$, (=S), —$NR_aR_b$, —$N(alkyl)_3^+$, —$NR_aSO_2$—, —$NR_aSO_2R_c$, —$SO_2R_c$, —$SO_2NR_aR_b$, —$SO_2NR_aC(=O)$ $R_b$, —$SO_3H$, —$PO(OH)_2$, —$OC(O)R_a$, —$C(=O)R_a$, —$CO_2R_a$, —$C(=O)NR_aR_b$, —$C(=O)(C_{1-4}alkylene)$ $NR_aR_b$, —$C(=O)NR_a(SO_2)R_b$, —$CO_2(C_{1-4}alkylene)$ $NR_aR_b$, —$NR_aC(=O)R_b$, —$NR_aCO_2R_b$, —$NR_a(C_{1-4}alkylene)CO_2R_b$, =N—OH, =N—O-alkyl, aryl, cycloalkyl, heterocyclo, and/or heteroaryl, wherein $R_a$ and $R_b$ are selected from hydrogen, alkyl, alkenyl, $CO_2H$, $CO_2(alkyl)$, $C_{3-7}$cycloalkyl, phenyl, benzyl, phenylethyl, napthyl, a four to seven membered heterocyclo, or a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being selected from the group consisting of $(C_{1-6})$alkyl, $(C_{2-6})$alkenyl, hydroxy, halogen, cyano, nitro, =O (as valence allows), $CF_3$, $O(C_{1-6}alkyl)$, $OCF_3$, $C(=O)H$, $C(=O)(C_{1-6}alkyl)$, $CO_2H$, $CO_2(C_{1-6}alkyl)$, $NHCO_2(C_{1-6}alkyl)$, —$S(C_{1-6}alkyl)$, —$NH_2$, $NH(C_{1-6}alkyl)$, $N(C_{1-6}alkyl)_2$, $N(CH_3)_3^+$, $SO_2(C_{1-6}alkyl)$, $C(=O)(C_{1-4}alkylene)$ $NH_2$, $C(=O)(C_{1-4}alkylene)NH(alkyl)$, $C(=O)(C_{1-4}alkylene)N(C_{1-4}alkyl)_2$, $C_{3-7}$cycloalkyl, phenyl, benzyl, phenylethyl, phenyloxy, benzyloxy, napthyl, a four to seven membered heterocyclo or cycloalkyl, or a five to six membered heteroaryl. When a substituted alkyl is substituted with an aryl (including, for example, phenyl and napthyl), heterocyclo, cycloalkyl, or heteroaryl group, said ringed systems are as defined below and thus may have zero, one, two, or three substituents, also as defined below.

One skilled in the field will understand that, when the designation "$CO_2$" is used herein, this is intended to refer to the group

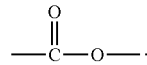

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl $(C_{0-4})$alkyl includes a substituted lower alkyl having at least one aryl substituent and also includes an aryl directly bonded to another group, i.e., aryl($C_0$)alkyl.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., $\{—CH_2—\}_n$, wherein n is 1 to 12, preferably 1-8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substituents as defined above for substituted alkyl groups.

The term "heteroalkylene" is used herein to refer to saturated and unsaturated bivalent straight or branched chain hydrocarbon groups having 2 to 12 carbon atoms, preferably 2 to 8 carbon atoms, wherein one or two carbon atoms in the straight chain are replaced by heteroatom(s) selected from —O—, —S—, —S(=O)—, —$SO_2$—, —NH—, and —$NHSO_2$—. Thus, the term "heteroalkylene" includes bivalent alkoxy, thioalkyl, and aminoalkyl groups, as defined below, as well as alkylene and alkenylene groups having a combination of heteroatoms in the alkyl chain. As an illustration, a "heteroalkylene" herein may comprise groups such as —S—$(CH_2)_{1-5}$NH—$CH_2$—, —O—$(CH_2)_{1-5}$S(=O)—$CH_2$—, —$NHSO_2$—$CH_2$—, —$CH_2$—NH—, and so forth. Preferably, a heteroalkylene does not have two adjacent atoms simultaneously selected from —O— and —S—. When a subscript is used with the term heteroalkylene, e.g., as in $C_{2-3}$heteroalkylene, the subscript refers to the number of carbon atoms in the group in addition to heteroatoms. Thus, for example, a $C_{1-2}$heteroalkylene may include groups such as —NH—$CH_2$—, —$CH_2$—NH—$CH_2$—, —$CH_2$—$CH_2$—NH—, —S—$CH_2$—, —$CH_2$—S—$CH_2$—, —O—$CH_2$—NH—$CH_2$—, $CH_2$—O—$CH_2$ and so forth.

The term "substituted heteroalkylene" refers to a heteroalkylene group as defined above wherein at least one of the nitrogen or carbon atoms in the heteroalkylene chain is bonded to (or substituted with) a group other than hydrogen. Carbon atoms in the heteroalkylene chain may be substituted with a group selected from those recited above for substituted alkyl groups, or with a further alkyl or substituted alkyl group. Nitrogen atoms of the heteroalkylene chain may be substituted with a group selected from alkyl, alkenyl, alkynyl, cyano, or $A_1$-Q-$A_2$-$R_h$, wherein $A_1$ is a bond, $C_{1-2}$alkylene, or $C_{2-3}$alkenylene; Q is a bond, —$C(=O)$—, —$C(=O)NR_d$—, —$C(=S)NR_d$—, —$SO_2$—, —$SO_2NR_d$—, —$CO_2$—, or —$NR_dCO_2$—; $A_2$ is a bond, $C_{1-3}$alkylene, $C_{2-3}$alkenylene, —$C_{1-4}$alkylene-$NR_d$—, —$C_{1-4}$alkylene-$NR_dC(=O)$—, —$C_{1-4}$alkylene-S—, —$C_{1-4}$alkylene-$SO_2$—, or —$C_{1-4}$alkylene-O—, wherein said $A_2$ alkylene groups are branched or straight chain and optionally substituted as defined herein for substituted alkylene; $R_h$ is hydrogen, alkyl, substituted alkyl, alkenyl, substituted alkenyl, aryl, heteroaryl, heterocyclo, or cycloalkyl; and $R_d$ is selected from hydrogen, alkyl, and substituted alkyl, as defined herein, provided, however, that for a substituted heteroalkylene $R_h$ is not hydrogen when $A_1$, Q and $A_2$ are each bonds. When $R_h$ is aryl, heteroaryl, cycloalkyl, or heterocyclo, these rings are, in turn, optionally substituted with one to three groups as defined below in the definitions for these terms.

The term "alkoxy" refers to an oxygen atom substituted by alkyl or substituted alkyl, as defined herein. For example, the term "alkoxy" or includes the group —O—$C_{1-6}$alkyl.

The term "alkylthio" refers to a sulfur atom that is substituted by an alkyl or substituted alkyl group as defined herein. For example, the term "thioalkyl" includes the group —S—$C_{1-6}$alkyl, and so forth.

The term "alkylamino" refers to an amino group substituted with an alkyl group or substituted alkyl group as defined above. For example, the term "alkylamino" includes the group —NR—$C_{1-12}$alkyl. (where R is preferably hydrogen but may include alkyl or substituted alkyl as defined above.)

When a subscript is used with reference to an alkoxy, thioalkyl or aminoalkyl, the subscript refers to the number of carbon atoms that the group may contain in addition to heteroatoms. Thus, for example, monovalent $C_{1-2}$-aminoalkyl includes the groups —$CH_2$—$N(CH_3)_2$, and —$(CH_2)_2$—$NH_2$. A lower aminoalkyl comprises an aminoalkyl having one to four carbon atoms. The term $(C_{1-4}$alkyl$)_{0-2}$amino includes the groups $NH_2$, —$NH(C_{1-4}$alkyl$)$, and —$N(C_{1-4}$alkyl$)_2$. "Amino" used by itself refers to the group $NH_2$. A "substituted amino" refers to an amino group substituted as described above for the nitrogen atom of a heteroalkylene chain and includes, for example, the terms alkylamino and acylamino (—$NR_dC(O)R_e$). Where amino is designated as mono-substituted without further definition, the extra nitrogen valence is hydrogen. For example, the term "alkylaminocarbonyl(halo)$_{0-1}$aryl" describes a group of the general formula:

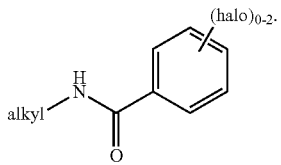

The alkoxy, thioalkyl, or aminoalkyl groups may be monovalent or bivalent. By "monovalent" it is meant that the group has a valency (i.e., ability to combine with another group), of one, and by "bivalent" it is meant that the group has a valency of two. Thus, for example, a monovalent alkoxy includes groups such as —O—$C_{1-12}$alkyl, whereas a bivalent alkoxy includes groups such as —O—$C_{1-12}$alkylene-.

It should be understood that the selections for all groups, including for examples, alkoxy, thioalkyl, and aminoalkyl, will be made by one skilled in the field to provide stable compounds. Thus, for example, in compounds of formula I, when G is attached to a nitrogen atom (N*) of ring A and is selected from an alkoxy or alkylthio group, the alkoxy and alkylthio groups will have at least one carbon atom bonded directly to ring A (at N*), with the oxygen or sulfur atoms being at least one atom away from said nitrogen atom.

The term "carbonyl" refers to a bivalent carbonyl group —C(=O)—. When the term "carbonyl" is used together with another group, such as in "heterocyclocarbonyl", this conjunction defines with more specificity at least one of the substituents that the substituted carbonyl will contain. For example, "heterocyclocarbonyl" refers to a carbonyl group as defined above where at least one of the substituents is an heterocyclo, such as morpholinyl.

The term "acyl" refers to a carbonyl group linked to an organic radical, more particularly, the group C(=O)$R_e$. The group $R_e$ can be selected from alkyl, alkenyl, alkynyl, aminoalkyl, substituted alkyl (i.e. substituted alkylene), substituted alkenyl, substituted alkynyl, cycloalkyl, heterocyclo, aryl, or heteroaryl, as defined herein. When $R_e$ is aryl, heteroaryl, cycloalkyl, or heterocyclo, these rings are, in turn, optionally substituted with one to three groups as defined below in the definitions for these terms.

The term "alkoxycarbonyl" refers to a carboxy group

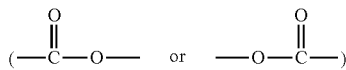

linked to an organic radical ($CO_2R_e$), as well as the bivalent groups —$CO_2$—, —$CO_2R_e$— which are linked to organic radicals in compounds of formula I, wherein $R_e$ is as defined above for acyl. The organic radical to which the carboxy group is attached may be monovalent (e.g., —$CO_2$-alkyl or —OC(=O)alkyl), or bivalent (e.g., —$CO_2$-alkylene, —OC(=O)alkylene, etc.) Accordingly, in compounds of formula I, when it is recited that G can be "alkoxycarbonyl," this is intended to encompass a selection for G of —$CO_2$— and also the groups —$CO_2R_e$— or —$R_eCO_2$—, wherein in this instance, the group $R_e$ will be selected from bivalent groups, e.g., alkylene, alkenylene, alkynylene, bivalent aminoalkyl, substituted alkylene, substituted alkenylene, or substituted alkynylene.

The term "sulfonyl" refers to a sulphoxide group (—S(O)$_2$—) linked to an organic radical in compounds of formula I, more particularly, the monovalent group —S(O)$_2$—$R_e$. Likewise, the term "sulfinyl" refers to a the group (—S(O)—) linked to an organic radical in compounds of formula I, more particularly, the monovalent group —S(O)—$R_e$. Additionally, the sulfonyl or sulfinyl group may be bivalent, in which case $R_e$ is a bond. The group $R_e$ is selected from those recited above for acyl and alkoxycarbonyl groups, with the exception that $R_e$ is not hydrogen.

The term "cycloalkyl" refers to fully saturated and partially unsaturated hydrocarbon rings (and therefore includes hydrocarbon rings also known as "cycloalkenyl rings") of 3 to 9, preferably 3 to 7 carbon atoms. The term "cycloalkyl" includes such rings having zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), OR$_a$, SR$_a$, (=S), —NR$_a$R$_b$, —N(alkyl)$_3^+$, —NR$_a$SO$_2$, —NR$_a$SO$_2$R$_c$, —SO$_2$R$_c$, —SO$_2$NR$_a$R$_b$, —SO$_2$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, =N—OH, =N—O-alkyl, aryl, cycloalkyl, heterocyclo, and/or heteroaryl, wherein R$_a$, R$_b$ and R$_c$ are as defined above for substituted alkyl groups, and are also in turn optionally substituted as recited above in the definition for substituted alkyl groups. The term "cycloalkyl" also includes such rings having a second ring fused thereto (e.g., including benzo, heterocyclo, or heteroaryl rings) or having a carbon-carbon bridge of 3 to 4 carbon atoms. When a cycloalkyl is substituted with a further ring (or has a second ring fused thereto), said ring in turn is optionally substituted with one to two of (C$_{1-4}$)alkyl, ($C_{2-4}$)alkenyl, ($C_{2-4}$)alkynyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, —$S(C_{1-4}alkyl)$, —$NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, $C(=O)(C_{1-4}alkylene)N(C_{1-4}alkyl)_2$ and/or phenyl optionally substituted with any of the preceeding groups. As valence allows, if said further ring is cycloalkyl or heterocyclo it is additionally optionally substituted with =O (oxo).

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems,

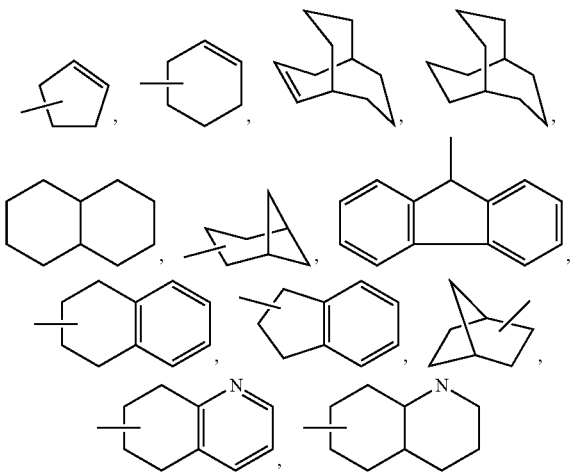

and the like, which optionally may be substituted at any available atoms of the ring(s). Preferred cycloalkyl groups include cyclopropyl, cyclopentyl, cyclohexyl, and

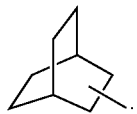

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "aryl" refers to phenyl, biphenyl, fluorenyl, 1-naphthyl and 2-naphthyl. The term "aryl" includes such rings having zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), $SO_3H$, —$NR_aR_b$, —$N(alkyl)_3^+$, —$NR_aSO_2$, —$NR_aSO_2R_c$, —$SO_2R_c$—$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to two of ($C_{1-4}$alkyl, ($C_{2-4}$)alkenyl, ($C_{2-4}$)alkynyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, —$S(C_{1-4}alkyl)$, —$NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, $C(=O)(C_{1-4}alkylene)N(C_{1-4}alkyl)_2$ and/or phenyl optionally substituted with any of the preceeding groups. As valence allows, if said further ring is cycloalkyl or heterocyclo it is additionally optionally substituted with =O (oxo).

Thus, examples of aryl groups include:

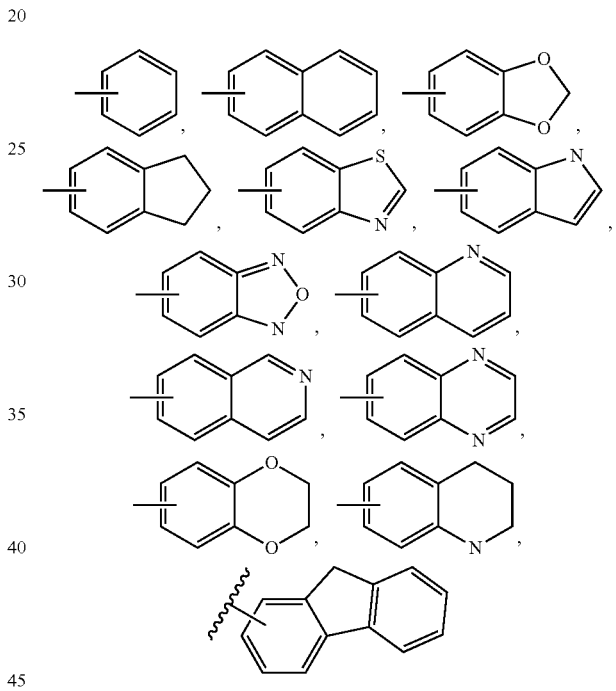

(fluorenyl) and the like, which optionally may be substituted at any available carbon or nitrogen atom. A preferred aryl group is optionally-substituted phenyl.

The terms "heterocycloalkyl", "heterocyclo" or "heterocyclic" may be used interchangeably and refer to substituted and unsubstituted non-aromatic 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The heterocyclo ring may contain zero, one, two or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), $-NR_aR_b$, $-N(alkyl)_3^+$, $-NR_aSO_2$, $-NR_aSO_2R_c$, $-SO_2R_c-SO_2NR_aR_b$, $-SO_2NR_aC(=O)R_b$, $SO_3H$, $-PO(OH)_2$, $-C(=O)R_a$, $-CO_2R_a$, $-C(=O)NR_aR_b$, $-C(=O)(C_{1-4}alkylene)NR_aR_b$, $-C(=O)NR_a(SO_2)R_b$, $-CO_2(C_{1-4}alkylene)NR_aR_b$, $-NR_aC(=O)R_b$, $-NR_aCO_2R_b$, $-NR_a(C_{1-4}alkylene)CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above. When a heterocyclo is substituted with a further ring, said ring in turn is optionally substituted with one to two of $(C_{1-4})$alkyl, $(C_{2-4})$alkenyl, $(C_{2-4})$alkynyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, $-S(C_{1-4}alkyl)$, $-NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, $C(=O)(C_{1-4}alkylene)N(C_{1-4}alkyl)_2$ and/or phenyl optionally substituted with any of the preceeding groups. As valence allows, if said further ring is cycloalkyl or heterocyclo it is additionally optionally substituted with =O (oxo).

Monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

Heterocyclo groups in compounds of formula I include

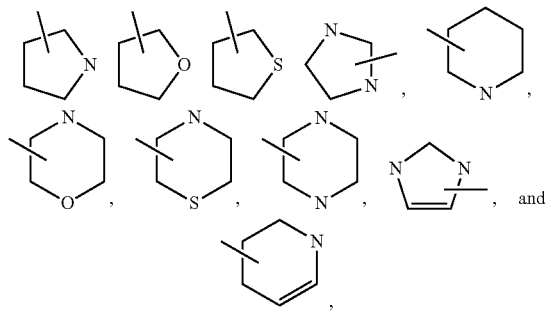

which optionally may be substituted.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), $-NR_aR_b$, $-N(alkyl)_3^+$, $-NR_aSO_2$, $-NR_aSO_2R_c$, $-SO_2R_c-SO_2NR_aR_b$, $-SO_2NR_aC(=O)R_b$, $SO_3H$, $-PO(OH)_2$, $-C(=O)R_a$, $-CO_2R_a$, $-C(=O)NR_aR_b$, $-C(=O)(C_{1-4}alkylene)NR_aR_b$, $-C(=O)NR_a(SO_2)R_b$, $-CO_2(C_{1-4}alkylene)NR_aR_b$, $-NR_aC(=O)R_b$, $-NR_aCO_2R_b$, $-NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. When a heteroaryl is substituted with a further ring, said ring in turn is optionally substituted with one to two of $(C_{1-4})$alkyl, $(C_{2-4})$alkenyl, $(C_{2-4})$alkynyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, $-S(C_{1-4}alkyl)$, $-NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, $C(=O)(C_{1-4}alkylene)N(C_{1-4}alkyl)_2$ and/or phenyl optionally substituted with any of the preceeding groups. As valence allows, if said further ring is cycloalkyl or heterocyclo it is additionally optionally substituted with =O (oxo).

Monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula I, preferred heteroaryl groups include

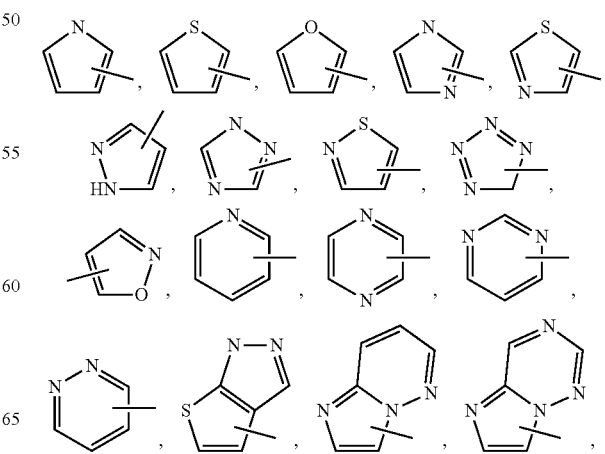

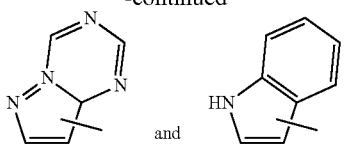

and the like, which optionally may be substituted at any available carbon or nitrogen atom. Aromatic rings may also be designated by an unbroken circle in the ring.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and fury') unless otherwise specifically indicated the reference is intended to include rings having 0 to 3, preferably 0-2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

When the term "optionally substituted" is used herein to refer to a ring or group, the ring or group may be substituted or unsubstituted.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I can form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s) may include zwitterions (inner salts), e.g., when a compound of formula I contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Prodrugs and solvates (e.g. hydrates) of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, Vol. 8, pp. 1-38 (1992), each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization.

Combinations

Where desired, the compounds of structure I may be used in combination with one or more other types of therapeutic agents such as immunosuppressants, anticancer agents, antiviral agents, anti-inflammatory agents, anti-fungal agents, antibiotics, anti-vascular hyperproliferation agents, anti-depressive agents, hypolipidemic agents or lipid-lowering agents or lipid modulating agents, antidiabetic agents, anti-obesity agents, antihypertensive agents, platelet aggregation inhibitors, and/or anti-osteoporosis agents, which may be administered orally in the same dosage form, in a separate oral dosage form or by injection.

The immunosuppressants which may be optionally employed in combination with compounds of formula I of the invention include cyclosporins, for example cyclosporin A, mycophenolate, interferon-beta, deoxyspergolin, FK-506 or Ant.-IL-2.

The anti-cancer agents which may be optionally employed in combination with compounds of formula I of the invention include azathiprine, 5-fluorouracil, cyclophosphamide, cisplatin, methotrexate, thiotepa, carboplatin, and the like.

The anti-viral agents which may be optionally employed in combination with compounds of formula I of the invention include abacavir, aciclovir, ganciclovir, zidanocin, vidarabine, and the like.

The anti-inflammatory agents which may be optionally employed in combination with compounds of formula I of the invention include non-steroidal anti-inflammatory drugs (NSAIDs) such as ibuprofen, cox-2 inhibitors such as celecoxib, rofecoxib, aspirin, naproxen, ketoprofen, diclofenac sodium, indomethacin, piroxicam, steroids such as prednisone, dexamethasone, hydrocortisone, triamcinolone diacetate, gold compounds, such as gold sodium thiomalate, TNF-α inhibitors such as tenidap, anti-TNF antibodies or soluble TNF receptor, and rapamycin (sirolimus or Rapamune) or derivatives thereof, infliximab (Remicade® Centocor, Inc.). CTLA-4Ig, LEA29Y, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins such as etanercept, fusion proteins constructed from CD40 and/or CD154gp39 (e.g. CD40Ig and CD8gp39), inhibitors, such as nuclear translocation inhibitors, of NF-kappa B function, such as deoxyspergualin (DSG).

The anti-fungal agents which may be optionally employed in combination with compounds of formula I of the invention include fluconazole, miconazole, amphotericin B, and the like.

The antibiotics which may be optionally employed in combination with compounds of formula I of the invention include penicillin, tetracycline, amoxicillin, ampicillin, erythromycin, doxycycline, vancomycin, minocycline, clindamycin or cefalexin.

The anti-vascular hyperproliferation agents which may be optionally employed with compounds of formula I of the invention include methotrexate, leflunomide, FK506 (tacrolimus, Prograf), The hypolipidemic agent or lipid-lowering agent or lipid modulating agents which may be optionally employed in combination with the compounds of formula I of the invention may include 1, 2, 3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na$^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-trifluoroethoxy)benzoyl]amino]-1-piperidinyl]butyl]-N-(2,2,2-trifluoroethyl)-9H-fluorene-9-carboxamide

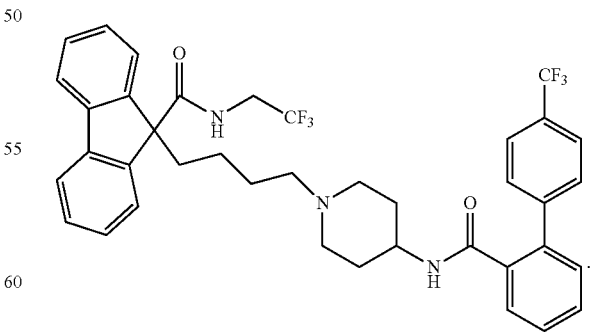

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 642-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propanephosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al., J. Med. Chem., Vol. 31, No. 10, pp. 1869-1871 (1988), including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, Vol. 2, pp. 1-40 (1996).

In addition, other squalene synthetase inhibitors suitable for use herein include the terpenoid pyrophosphates disclosed by P. Ortiz de Montellano et al., J. Med. Chem., 1977, 20, 243-249, the farnesyl diphosphate analog A and presqualene pyrophosphate (PSQ-PP) analogs as disclosed by Corey and Volante, J. Am. Chem. Soc., 98, 1291-1293 (1976), phosphinylphosphonates reported by McClard, R. W. et al., J. Am. Chem. Soc., 1987, 109, 5544 (1987), and cyclopropanes reported by Capson, T. L., PhD dissertation, Dept. Med. Chem. U. of Utah, Abstract, Table of Contents, pp. 16, 17, 40-43, 48-51, Summary (June, 1987).

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, Drugs of the Future, 24, 9-15 (1999), (Avasimibe); "The ACAT inhibitor, C1-1011 is effective in the prevention and regression of aortic fatty streak area in hamsters", Nicolosi et al., Atherosclerosis (Shannon, Irel). 137 (1), 77-85 (1998), "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16 (1), 16-30; "RP 73163: a bioavailable alkylsulfinyl-diphenylimidazole ACAT inhibitor", Smith, C., et al, Bioorg. Med. Chem. Lett. 6 (1), 47-50 (1996); "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways 173-98 (1995), Publisher: CRC, Boca Raton, Fla.; "ACAT inhibitors: potential anti-atherosclerotic agents", Sliskovic et al, Curr. Med. Chem. 1 (3), 204-25 1994); "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. 8 (6), 359-62 (1995), or TS-962 (acetamide, N-[2,6-bis(1-methylethyl)phenyl]-2-(tetradecylthio)-) (Taisho Pharmaceutical Co. Ltd).

The hypolipidemic agent may be an upregulator of LD2 receptor activity such as MD-700 (1(3H)-isobenzofuranone, 3-(13-hydroxy-10-oxotetradecyl)-5,7-dimethoxy) (Taisho Pharmaceutical Co. Ltd) and LY295427 (cholestan-3-ol, 4-(2-propenyl)-, (3a, 4a, 5a)-) (Eli Lilly).

The hypolipidemic agent may be a cholesterol absorption inhibitor preferably Schering-Plough's ezetimibe (SCH58235) and SCH48461 as well as those disclosed in Atherosclerosis 115, 45-63 (1995) and J. Med. Chem. 41, 973 (1998).

The hypolipidemic agent may be an ileal Na+/bile acid cotransporter inhibitor such as disclosed in Drugs of the Future, 24, 425-430 (1999).

The lipid-modulating agent may be a cholesteryl ester transfer protein (CETP) inhibitor such as Pfizer's CP 529,414 (torcetrapib) (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", *Brit. J. Pharmacology* 120, 1199-1206 (1997), and Cornicelli et al, "15-Lipoxygenase and its Inhibition: A Novel Therapeutic Target for Vascular Disease", *Current Pharmaceutical Design,* 5, 11-20 (1999).

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of formula I may be 1, 2, 3 or more antidiabetic agents or antihyperglycemic agents including insulin secretagogues or insulin sensitizers, or other antidiabetic agents preferably having a mechanism of action different from the compounds of formula I of the invention, which may include biguanides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Wellcome's GL-262570 (farglitazar), englitazone (CP-68722, Pfizer) or darglitazone (CP-86325, Pfizer, isaglitazone (MIT/J&J), JTT-501 (reglitazar) (JPNT/P&U), L-895645 (Merck), R-119702 (rivoglitazone) (Sankyo/WL), N,N-2344 (balaglitazone) (Dr. Reddy/NN), or YM-440 ((Z)-1,4-bis-4-[(3,5-dioxo-1,2,4-oxadiazolidin-2-yl-methyl)]-phenoxybut-2-ene) (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (exenatide) (Amylin) and LY-315902 (8-37-glucagon-like peptide I (human), N-[3-(1H-imidazol-4-yl)-1-oxopropyl]-26-L-arginine-34-[N6-(1-oxooctyl)-L-lysine]-) (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

The other antidiabetic agent may also be a PPAR α/γ dual agonist such as AR-HO39242 (tesaglitazar) (Astra/Zeneca), GW-409544 (Glaxo-Wellcome), KRP297 (benzamide, 5-[(2,4-dioxo-5-thiazolidinyl)methyl]-2-methoxy-N-[[4-(trifluoromethyl)phenyl]methyl]-(Kyorin Merck) as well as those disclosed by Murakami et al, "A Novel Insulin Sensitizer Acts As a Coligand for Peroxisome Proliferation-Activated Receptor Alpha (PPAR alpha) and PPAR gamma Effect on PPAR alpha Activation on Abnormal Lipid Metabolism in Liver of Zucker Fatty Rats", *Diabetes* 47, 1841-1847 (1998).

The antidiabetic agent may be an SGLT2 inhibitor such as disclosed in U.S. application Ser. No. 09/679,027, filed Oct. 4, 2000, employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000, employing dosages as set out herein. Preferred are the compounds designated as preferred in the above application.

The antidiabetic agent may be a DP4 inhibitor such as disclosed in U.S. application Ser. No. 09/788,173 filed Feb. 16, 2001, WO99/38501, WO99/46272, WO99/67279 (PROBIODRUG), WO99/67278 (PROBIODRUG), WO99/61431 (PROBIODRUG), saxagliptin (preferred), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, *Biochemistry*, 38 (36), 11597-11603, (1999), TSL-225 (tryptophyl-1,2,3,4-tetrahydro-isoquinoline-3-carboxylic acid (disclosed by Yamada et al, *Bioorg. & Med. Chem. Leu.* 8 1537-1540 (1998), 2-cyanopyrrolidides and 4-cyanopyrrolidides as disclosed by Ashworth et al, *Bioorg. & Med. Chem. Lett.*, Vol. 6, No. 22, pp 1163-1166 and 2745-2748 (1996) employing dosages as set out in the above references.

The meglitinide which may optionally be employed in combination with the compound of formula I of the invention may be repaglinide, nateglinide (Novartis) or KAD1229 (mitiglinide) (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of formula I may be AJ9677 (rafabegron) (Takeda/Dainippon), L750355 (benezenesulfonamide, N-[4-[2-[[(2S)-3-[(6-amino-3-pyridinyl)oxy]-2-hydroxypropyl]amino]ethyl]phenyl]-4-(1-methylethyl)-) (Merck), or CP331684 (4-[2-[[2-(6-aminopyridin-3-yl)-2(R)-hydroxyethyl]-amino]ethoxy]phenyl]acetic acid) (Pfizer) or other known beta 3 agonists as disclosed in U.S. Pat. Nos. 5,541,204, 5,770,615, 5,491,134, 5,776,983 and 5,488,064, with AJ9677, L750,355 (benzenesulfonamide, N-[4-[2-[[(2S)-3-[(6-amino-3-pyridinyl)oxy]-2-hydroxypropyl]amino]ethyl]phenyl]-4-(1-methylethyl)-) and CP331684 being preferred.

The lipase inhibitor which may be optionally employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor agonist which may be optionally employed in combination with a compound of formula I may be a thyroid receptor ligand as disclosed in WO97/21993 (U. Cal SF), WO99/00353 (KaroBio), WO00/039077 (KaroBio), and U.S. Provisional Application 60/183,223 filed Feb. 17, 2000, with compounds of the KaroBio applications and the above U.S. provisional application being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenyl-butyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and *Jap. J. Pharmacol.* 40:373 (1986); Ciba-Geigy's CGS 14824 (3-([1-ethoxy-carbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechsst) disclosed in Euro. Patent No. 79-022 and *Curr. Ther. Res.* 40:74 (1986); Ru 44570 (Hoechst) disclosed in *Arzneimittelforschung* 34:1254 (1985), cilazapril (Hoffman-LaRoche) disclosed in *J. Cardiovasc. Pharmacol.* 9:39 (1987); R 31-2201 (Hoffman-LaRoche) disclosed in *FEBS Lett.* 165:201 (1984); lisinopril (Merck), indalapril (delapril) disclosed in U.S. Pat. No. 4,385,051; indolapril (Schering) disclosed in *J. Cardiovasc. Pharmacol.* 5:643, 655 (1983), spirapril (Schering) disclosed in *Acta. Pharmacol. Toxicol.* 59 (Supp. 5):173 (1986); perindopril (Servier) disclosed in *Eur. J. Clin. Pharmacol.* 31:519 (1987); quinapril (Warner-Lambert) disclosed in U.S. Pat. No. 4,344,949 and CI925 (Warner-Lambert) ([3S-[2[R(*)R(*)]]3R(*)]-2-[2-[[1-(ethoxy-carbonyl)-3-phenylpropyl]amino]-1-oxopropyl]-1,2,3,4-tetrahydro-6,7-dimethoxy-3-isoquinolinecarboxylic acid HCl) disclosed in *Pharmacologist* 26:243, 266 (1984), WY-44221 (Wyeth) disclosed in *J. Med. Chem.* 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, U.S. Pat. No. 5,552,397, U.S. Pat. No. 5,504,080, U.S. Pat. No. 5,612,359, U.S. Pat. No. 5,525,723, European Patent Application 0599444, 0481522, 0599444, 0595610, European Patent Application 0534363A2, 534396 and 534492, and European Patent Application 0629627A2.

Preferred are those NEP/ACE inhibitors and dosages thereof which are designated as preferred in the above patents/applications which U.S. patents are incorporated herein by reference; most preferred are omapatrilat, BMS 189,921 ([S—(R*,R*)]-hexahydro-6-[(2-mercapto-1-oxo-3-phenyl-propyl)amino]-2,2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physician's Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of formula I include hydrochlorothiazide, torasemide, furosemide, spironolactono, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula I of the invention include parathyroid hormone or bisphosphonates, such as MK-217 (alendronate) (Fosamax®).

Dosages employed for the above drugs will be as set out in the Physician's Desk Reference.

Pharmaceutical Formulations

The pharmaceutical composition of the invention includes a pharmaceutically acceptable carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the modulators of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the invention may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds of the invention may, for example, be administered in a form suitable for immediate release or extended release. Immediate release or extended release may be achieved by the use of suitable pharmaceutical compositions including the compounds of the invention, or, particularly in the case of extended release, by the use of devices such as subcutaneous implants or osmotic pumps. The compounds of the invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the compound(s) of the invention with fast dissolving diluents such as mannitol, lactose, sucrose and/or cyclodextrins. Also included in such formulations may be high molecular weight excipients such as celluloses (Avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, or between 0.5 and 2000 mg per day which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The compounds of formula I of the invention are glucocorticoid receptor modulators as shown either by their ability to bind glucocorticoid receptors in GR binding assays, or by their ability to inhibit AP-1 activity as indicated in cellular transrespressional assays, and cause none to minimal transactivation as indicated in cellular transscriptional assays.

Compounds of the invention, including the compounds described in the examples hereof, have been tested in at least one of the assay(s) described below and have glucocorticoid receptor (GR)/Dexamethasone (Dex) inhibition activity (>25% at 10 µM) and/or AP-1 inhibition activity ($EC_{50}$ less than 15 µM).

Identical and/or similar assays are described in U.S. application Ser. No. 10/621,807, filed Jul. 17, 2003 which is incorporated in its entirety herein by reference.

GR Binding Assays

Glucocorticoid Receptor Binding Assay (I)

In order to assess the affinity of test compounds for the human glucocorticoid receptor, a commercially available kit was used (Glucocorticoid Receptor Competitor Assay Kit, Invitrogen Part #2893). Briefly, purified human recombinant full-length glucocorticoid receptor (2 nM) was mixed with fluorescently labeled glucocorticoid (1 nM Fluormone GS Red) in the presence or absence of test compound. After two hour incubation at room temperature in the dark, the fluorescence polarization (FP) of the samples was measured. The FP of a mixture of receptor, fluorescent probe (i.e. Fluormone GS Red) and 5 µM dexamethasone represented background fluorescence or 100% inhibition, whereas, the FP of the mixture without dexamethasone (but in the presence of vehicle) was taken to be 100% binding. The percentage inhibition of test compounds were then compared to the sample with 5 µM dexamethasone and expressed as % relative binding activity with dexamethasone being 100% and no inhibition is 0%. Test compounds were analyzed in the concentration range from 8.5E-05 µM to 5 µM.

Glucocorticoid Receptor Binding Assay (II)

In order to measure the binding of compounds on the glucocorticoid receptor a commercially available kit was used (Glucocorticoid receptor competitor assay kit, PanVera Co., Madison, Wis., P2816). Briefly, a cell lysate containing recombinantly expressed human full-length glucocorticoid receptor was mixed with a fluorescently labeled glucocorticoid (1 nM Fluormone GS1) in the presence or absence of test compound. After one hour at room temperature, the fluorescence polarization (FP) of the samples were measured. The FP of a mixture of receptor, fluorescent probe (i.e. Fluormone GS1) and 1 mM dexamethasone represented background fluorescence or 100% inhibition, whereas, the FP of the mixture without dexamethasone was taken to be 100% binding. The percentage inhibition of test molecules were then compared to the sample with 1 mM dexamethasone and expressed as % relative binding activity with dexamethasone being 100% and no inhibition is 0%. Test molecules were analyzed in the concentration range from 2.4 nM to 40 microMolar.

Site I binding assays for any NHR (Nuclear Hormone Receptor) are conducted similarly to the above. An appropriate cell lysate or purified NHR is used as the source of the NHR. The fluorescent probe and unlabeled competitor are appropriate for the specific NHR, i.e. are ligands for the specific NHR.

Cellular Transrepressional Assay

To measure the ability of test molecules to inhibit AP-1 induced transcriptional activity we utilized an A549 cell which was stably transfected with a plasmid containing 7×AP-1 DNA binding sites (pAP-1-Luc plasmid, Stratagene Co. La Jolla, Calif.) followed by the gene for luciferase. Cells were activated with 10 ng/ml of phorbol myristic acid (PMA) plus or minus test molecules for 7 hours. After 7 hours a luciferase reagent was added to measure luciferase enzymatic activity in the cell. After a 10 minute incubation of luciferase reagent with cells, luminescence was measured in a TopCount luminescence counter. Repression of AP-1 activity was calculated as the percentage decrease in the signal induced by PMA alone. Test molecules were analyzed in the concentration range from 0.1 nM to 40 µM. EC50s were determined by using standard curve fitting methods such as Excel fit (Microsoft Co.). An EC50 is the test molecule concentration at which there is a 50% repression of the maximal inhibition of transcription, i.e. a 50% reduction of AP-1 activity.

Other reporters and cell lines also may be used in a cellular transrepressional assay. A similar assay is performed in which NF-κB activity is measured. A plasmid containing NF-κB DNA binding sites is used, such as pNF-kB-Luc, (Stratagene, LaJolla Calif.), and PMA or another stimulus, such as TNF-α or lipopolysaccharide, is used to activate the NF-κB pathway. NF-κB assays similar to that described in Yamamoto K., et al., *J. Biol. Chem.*, December 29; 270 (52):31315-20 (1995) may be used.

The cellular transrepressional assays described above may be used to measure transrepression by any NHR. One of skill in the art will understand that assays may require the addition of components, such as a stimulus (eg. PMA, lipopolysaccharide, TNF-α, etc) which will induce transcription mediated by AP-1 or NF-κB.

Additionally, AR mediated transrepression may be measured by the assay described in Palvimo J J, et al. *J. Biol. Chem.*, September 27; 271 (39):24151-6 (1996), and PR mediated transrepression may be measured by the assay described in Kalkhoven E., et al. *J. Biol. Chem.*, March 15; 271 (11):6217-24 (1996).

Examples of compounds of the present invention prepared by methods described in the general schemes are given in the preparations and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diaststereoselectivity of transformations, providing enantio-enriched products upon cleavage of the chiral auxiliary.

ABBREVIATIONS

The following abbreviations are employed in the specification as well as the following Preparations and Examples:

| | |
|---|---|
| Ph = | phenyl |
| Bn = | benzyl |
| iBu = | iso butyl |
| t-Bu = | tertiary butyl |
| Me = | methyl |
| Et = | ethyl |
| ACN = | acetonitrile |
| TMS = | trimethylsilyl |
| $TMSN_3$ = | trimethylsilyl azide |
| TBS = | tert-butyldimethylsilyl |
| FMOC = | fluorenylmethoxycarbonyl |
| Boc = | tert-butoxycarbonyl |
| Cbz = | carbobenzyloxy or carbobenzoxy or benzyloxycarbonyl |
| THF = | tetrahydrofuran |
| $Et_2O$ = | diethyl ether |
| hex = | hexanes |
| EtOAc = | ethyl acetate |
| DMF = | dimethyl formamide |
| MeOH = | methanol |
| Et = | ethyl |
| EtOH = | ethanol |
| i-PrOH or iPr = | isopropanol |
| DMSO = | dimethyl sulfoxide |
| DME = | 1,2 dimethoxyethane |
| DCE = | 1,2 dichloroethane |
| HMPA = | hexamethyl phosphoric triamide |
| HOAc or AcOH = | acetic acid |
| TFA = | trifluoroacetic acid |
| TFAA = | trifluoroacetic anhydride |
| i-$Pr_2$NEt = | diisopropylethylamine |
| $Et_3$N = | triethylamine |
| NMM = | N-methyl morpholine |
| DMAP = | 4-dimethylaminopyridine |
| $NaBH_4$ = | sodium borohydride |
| $NaBH(OAc)_3$ = | sodium triacetoxyborohydride |
| DIBALH = | diisobutyl aluminum hydride |
| LAH or $LiAlH_4$ = | lithium aluminum hydride |
| n-BuLi = | n-butyllithium |
| LDA = | lithium diisopropylamide |
| Pd/C = | palladium on carbon |

| | |
|---|---|
| PtO₂ = | platinum oxide |
| KOH = | potassium hydroxide |
| NaOH = | sodium hydroxide |
| LiOH = | lithium hydroxide |
| K₂CO₃ = | potassium carbonate |
| NaHCO₃ = | sodium bicarbonate |
| DBU = | 1,8-diazabicyclo[5.4.0]undec-7-ene |
| EDC (or EDC•HCl) or EDCI (or EDCI•HCl) or EDAC = | 3-ethyl-3'-(dimethylamino)propyl-carbodiimide hydrochloride (or 1-(3-dimethylaminopropyl)-3-ethylcarbodiimide hydrochloride) |
| HOBT or HOBT•H₂O = | 1-hydroxybenzotriazole hydrate |
| HOAT = | 1-Hydroxy-7-azabenzotriazole |
| BOP reagent = | benzotriazol-1-yloxy-tris (dimethylamino) phosphonium hexafluorophosphate |
| NaN(TMS)₂ = | sodium hexamethyldisilazide or sodium bis(trimethylsilyl)amide |
| Ph₃P = | triphenylphosphine |
| Pd(OAc)₂ = | Palladium acetate |
| (Ph₃P)₄Pd° = | tetrakis triphenylphosphine palladium |
| DEAD = | diethyl azodicarboxylate |
| DIAD = | diisopropyl azodicarboxylate |
| Cbz—Cl = | benzyl chloroformate |
| CAN = | ceric ammonium nitrate |
| SAX = | Strong Anion Exchanger |
| SCX = | Strong Cation Exchanger |
| Ar = | argon |
| N₂ = | nitrogen |
| min = | minute(s) |
| h or hr = | hour(s) |
| L = | liter |
| mL = | milliliter |
| μL = | microliter |
| g = | gram(s) |
| mg = | milligram(s) |
| mol = | moles |
| mmol = | millimole(s) |
| meq = | milliequivalent |
| rt or RT = | room temperature |
| sat or sat'd = | saturated |
| aq. = | aqueous |
| TLC = | thin layer chromatography |
| HPLC = | high performance liquid chromatography |
| Reverse phase HPLC = | reverse phase high performance liquid chromatography, using a YMC ODS S5 column and a binary solvent A/solvent B eluents |
| Solvent A = | 10% MeOH - 90% H₂O - 0.1% TFA |
| Solvent B = | 90% MeOH - 10% H₂O - 0.1% TFA; or |
| Solvent A = | H₂O containing 0.1% TFA |
| Solvent B = | ACN containing 0.1% TFA |
| LC/MS = | high performance liquid chromatography/mass spectrometry |
| MS or Mass Spec = | mass spectrometry |
| NMR = | nuclear magnetic resonance |
| NMR spectral data: | s = singlet; d = doublet; m = multiplet; br = broad; t = triplet |
| mp = | melting point |

EXAMPLES

The following Examples illustrate embodiments of the inventive compounds and starting materials, and are not intended to limit the scope of the claims.

Analytical HPLC methods

Method A:

Linear gradient of 0 to 100% solvent B over 4 min, with 1 min hold at 100% B.

UV visualization at 220 nm

Column: YMC CombiScreen ODS-A S5 4.6×50 mm

Flow rate: 4 mL/min

Solvent A: 0.2% phosphoric acid, 90% water, 10% methanol

Solvent B: 0.2% phosphoric acid, 90% methanol, 10% water

Method B:

Linear gradient of 0 to 100% solvent B over 4 min, with 1 min hold at 100% B.

UV visualization at 220 nm

Column. YMC S50DS-A 4.5×50 mm

Flow rate: 4 mL/min

Solvent A: 0.2% phosphoric acid, 90% water, 10% methanol

Solvent B: 0.2% phosphoric acid, 90% methanol, 10% water

Example 1

4-(5-(1,1-dimethyl-2-oxo-2-(1,3,4-thiadiazol-2-ylamino)ethyl)-5H-pyrido[4',3':5,6]pyrano[2,3-b]pyridin-2-yl)-N,N-dimethylbenzamide

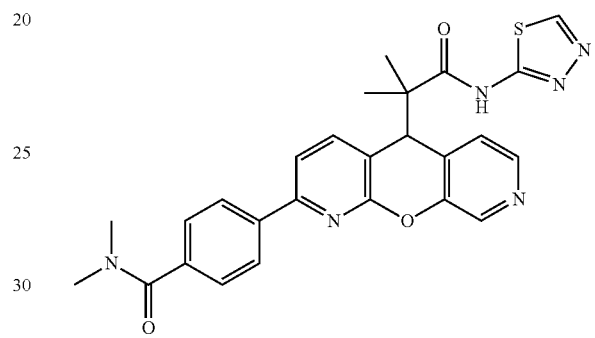

Step 1

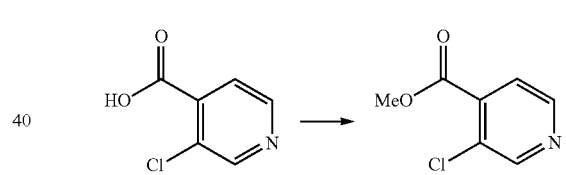

Potassium carbonate (36.3 g, 263 mmol) was added to 3-chloroisonicotinic acid (10.35 g, 65.7 mmol) in DMSO (50 mL). After 30 min, MeI (8.22 mL, 131 mmol) was added. The mixture was stirred at room temperature for 2 h, quenched with saturated NH₄Cl (300 mL) and water (200 mL), and extracted with EtOAc (3×200 mL). The combined extracts were washed with brine (2×50 mL), dried (MgSO₄) and concentrated. Silica gel chromatography, eluting with 10-30% ethyl acetate in hexanes, gave methyl 3-chloroisonicotinate as a colorless liquid (6.275 g, 56% yield). MS (ES+) m/z: 172 (M+H); LC retention time: 2.45 min (analytical HPLC Method A).

Step 2

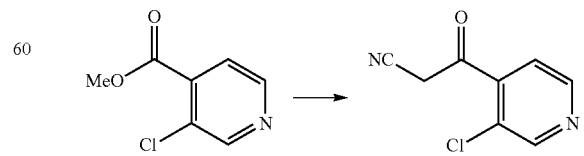

A 2.5 M hexane solution of BuLi (16.79 mL, 42.0 mmol) was added dropwise to a solution of diisopropylamine (6.23 mL, 43.7 mmol) in THF (150 mL) at −78° C. The mixture was stirred at 0° C. for 15 min and cooled to −78° C. Acetonitrile (2.192 mL, 42.0 mmol) was added dropwise. The solution gradually turned to milky white. After 1 h at −78° C., methyl 3-chloroisonicotinate (3.00 g, 17.48 mmol) in THF (10 mL) was added dropwise. The flask was rinsed with THF (2 mL) and added. After 1 h at −78° C., the mixture was quenched with brine (200 mL) and acidified to pH~1. THF was evaporated in vacuo. The aqueous residue was extracted with EtOAc (3×100 mL). The combined extracts were washed with brine (50 mL), dried (MgSO$_4$) and concentrated to give impure 3-(3-chloropyridin-4-yl)-3-oxopropanenitrile as a tan solid (3.12 g, 81% pure, 80% yield). MS (ES+) m/z: 181 (M+H); LC retention time: 1.90 min (analytical HPLC Method A).

Step 3

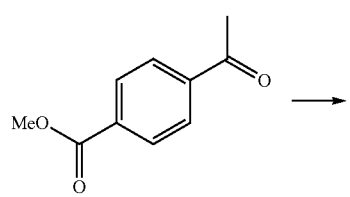

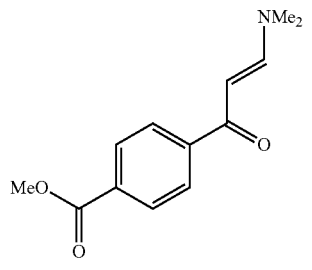

A mixture of methyl 4-acetylbenzoate (25 g, 140 mmol) and N,N-dimethylformamide dimethyl acetal (100 mL) was heated to reflux for 2 days, diluted with MeOH (100 mL) and cooled to 0° C. The precipitate was collected by filtration and washed with MeOH to give (E)-methyl 4-(3-(dimethylamino) acryloyl)benzoate as a brown solid (27.65 g, 84% yield). MS (ES+) m/z: 234 (M+H); LC retention time: 2.91 min (analytical HPLC Method A).

Step 4

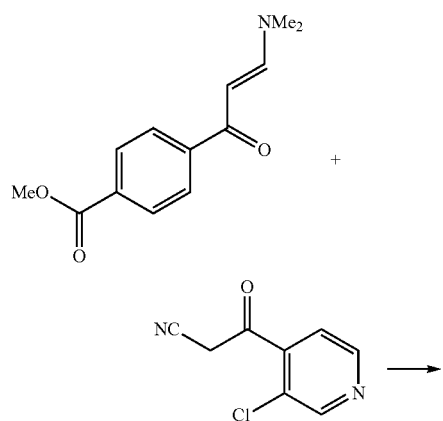

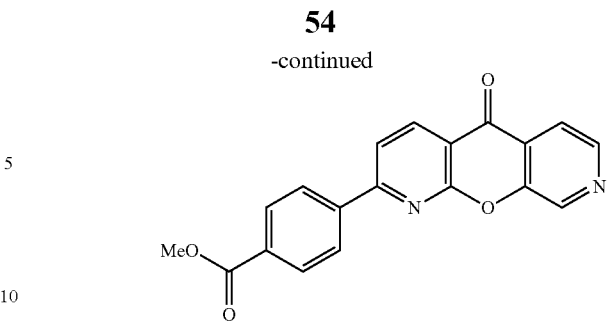

A mixture of (E)-methyl 4-(3-(dimethylamino)acryloyl) benzoate (1.85 g, 7.93 mmol), 3-(3-chloropyridin-4-yl)-3-oxopropanenitrile (2.005 g, 11.10 mmol), acetic acid (2.270 mL, 39.7 mmol) and DMF (20 mL) was heated to 140° C. for 62 h, cooled to room temperature and diluted with MeOH (20 mL). The precipitate was collected by filtration and washed with MeOH twice to give the expected diazaxanthone as a brown powder (932.9 mg, 35% yield). MS (ES+) m/z: 333 (M+H); LC retention time: 4.02 min (analytical HPLC Method A).

Step 5

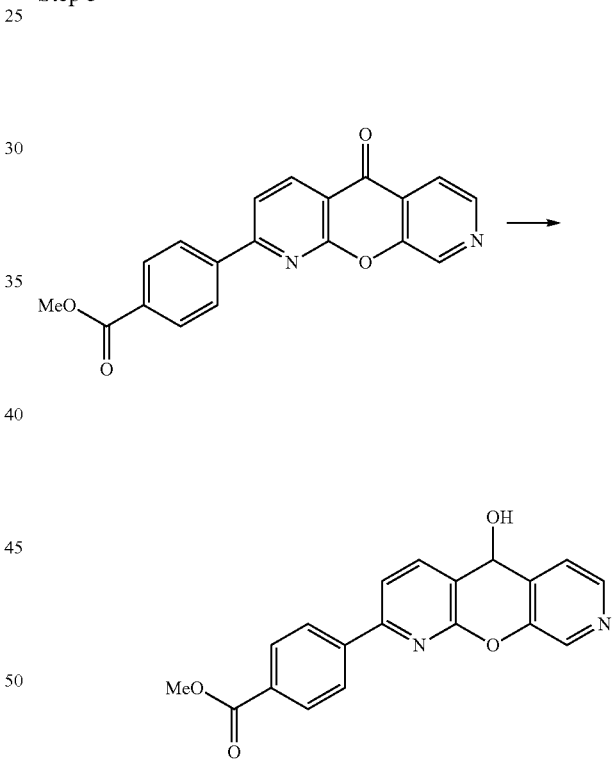

Sodium borohydride (1.062 g, 28.1 mmol) was added to a suspension of the product from Step 4 (932.9 mg, 2.81 mmol) in MeOH (50 mL) and CH$_2$Cl$_2$ (50 mL) at 0° C. After 3 h at 0° C., the mixture was quenched with saturated NH$_4$Cl (100 mL) and water (100 mL). The organic solvents were evaporated in vacuo. The precipitate was collected by filtration and washed with water (2×) and MeOH to give the expected azaxanthene alcohol as off-white solid (759.3 mg, 81% yield). MS (ES+) m/z: 335 (M+H); LC retention time: 3.20 min (analytical HPLC Method A).

Step 6

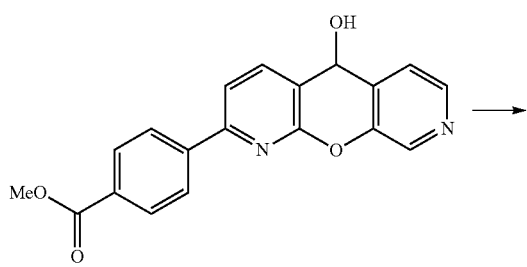

DMAP (963 mg, 7.88 mmol) and Ac₂O (0.279 mL, 2.96 mmol) were added to a suspension of the alcohol from Step 5 (659 mg, 1.971 mmol) in CH₂Cl₂ (25 mL) at 0° C. The mixture gradually turned to a homogeneous solution. After 30 min at room temperature, the mixture was quenched with brine (50 mL). The two phases were separated and the aqueous extracted with CH₂Cl₂ (2×25 mL). The combined dichloromethane extracts were dried (MgSO₄) and concentrated. Silica gel chromatography, eluting with 30-65% EtOAc in hexanes, gave the expected acetate product as a white solid (686.2 mg, 92% yield). MS (ES+) m/z: 377 (M+H); LC retention time: 3.88 min (analytical HPLC Method A).
Step 7

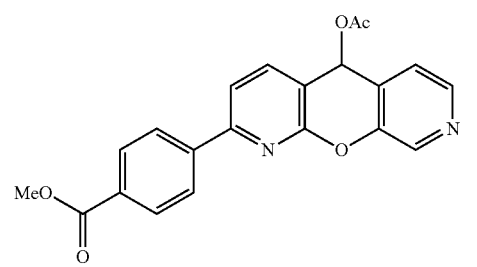

To a solution of the acetate from Step 6 (0.686 g, 1.823 mmol) in CH₂Cl₂ (50 mL) at 0° C. was added a 1 M CH₂Cl₂ solution of titanium(IV) chloride (3.65 mL, 3.65 mmol). The resultant tan colored suspension was stirred at 0° C. for 5 min. Methyl trimethylsilyl dimethylketene acetal (1.148 mL, 5.649 mmol) was added. The mixture was stirred at 0° C. for 1 h, quenched with saturated NaHCO₃ (50 mL), stirred overnight and filtered through a celite pad. The pad was rinsed with CH₂Cl₂. The two phases were separated and the aqueous phase extracted with CH₂Cl₂ (2×50 mL). The combined organic extracts were dried (MgSO₄) and concentrated. Silica gel chromatography, eluting with 30-70% EtOAc in hexanes, gave the expected product as a white solid (350 mg, 46% yield). MS (ES+) m/z: 419 (M+H); LC retention time: 3.83 min (analytical HPLC Meth A).
Step 8

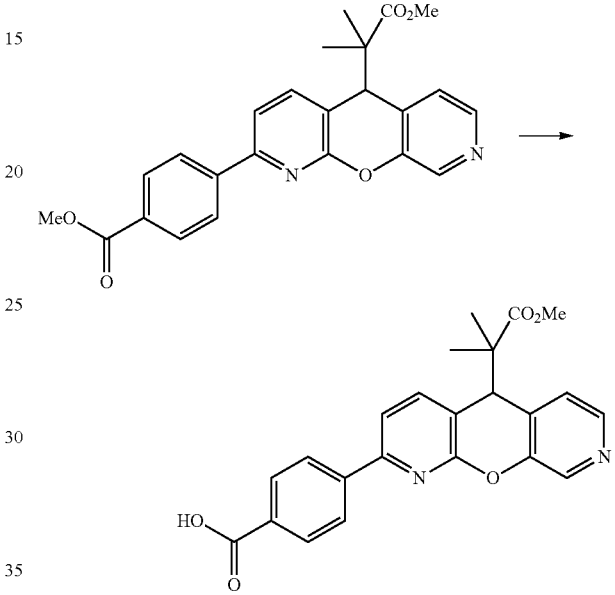

A 1 N aqueous solution of NaOH (20 mL, 20.00 mmol) was added to a solution of the product from Step 7 (350 mg, 0.836 mmol) in MeOH (50 mL), THF (50 mL) and CH₂Cl₂ (25 mL). After 4 h at room temperature, the mixture was quenched with 1 N HCl (21 mL). The organic solvents were evaporated in vacuo. The precipitate was collected by filtration and washed with water to give the expected acid as a white powder (268.3 mg, 79% yield). MS (ES+) m/z: 405 (M+H); LC retention time: 3.45 min (analytical HPLC Method A).
Step 9

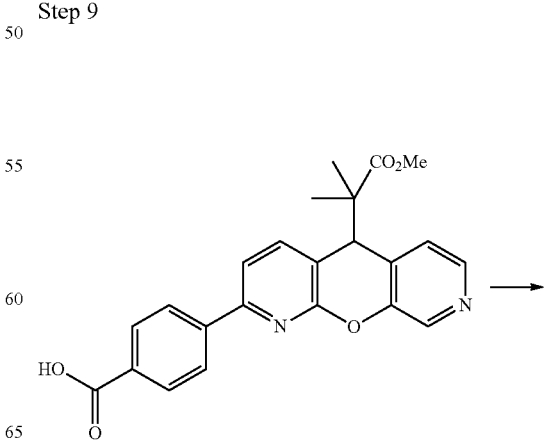

-continued

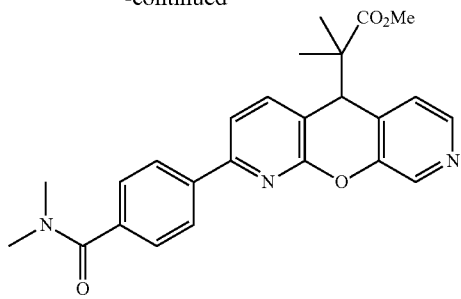

Hunig's base (0.429 mL, 2.458 mmol) was added to a suspension of the acid from Step 8 (165.7 mg, 0.410 mmol), 1-hydroxybenzotriazole hydrate (125 mg, 0.819 mmol) and N-(3-dimethylaminopropyl)-N'-ethylcarbodiimide hydrochloride (157 mg, 0.819 mmol) in DMF (5 mL). After 30 min at room temperature, a 2 M THF solution of dimethylamine (0.615 mL, 1.229 mmol) was added. After 3 h, additional dimethylamine (1 mL) was added. After a total of 24 h, the mixture was concentrated. Purification by reverse-phase HPLC (YMC ODS S5 30×100 mm column, 45 to 65% solvent B gradient) gave the expected product as a viscous oil, assumed as bis-TFA salt (134.5 mg, 50% yield). MS (ES+) m/z: 432 (M+H); LC retention time: 3.15 min (analytical HPLC Method A). Unreacted starting material was also recovered (63.0 mg).

Step 10

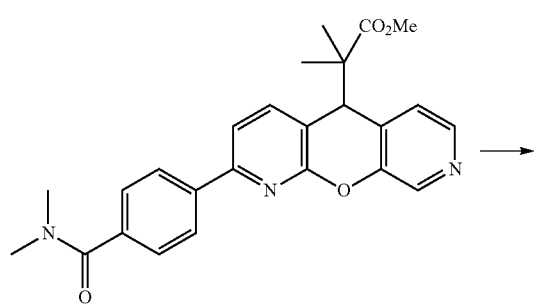

Sodium 2-propanethiolate (400 mg, 4.08 mmol) was added to a solution of the product from Step 9 (134.5 mg, 0.204 mmol) in DMF (5 mL). The mixture was stirred at 50° C. for 1 h, quenched with 1 N HCl (3.84 mL), diluted with saturated NH$_4$Cl (30 mL), adjusted to pH 7-8 with 1 N NaOH, and extracted with CHCl$_3$ (6×25 mL). The combined extracts were dried (MgSO$_4$) and concentrated to give the expected acid as a slightly yellow solid (84.4 mg, 99% yield). MS (ES+) m/z: 418 (M+H); LC retention time: 2.91 min (analytical HPLC Method A).

Step 11

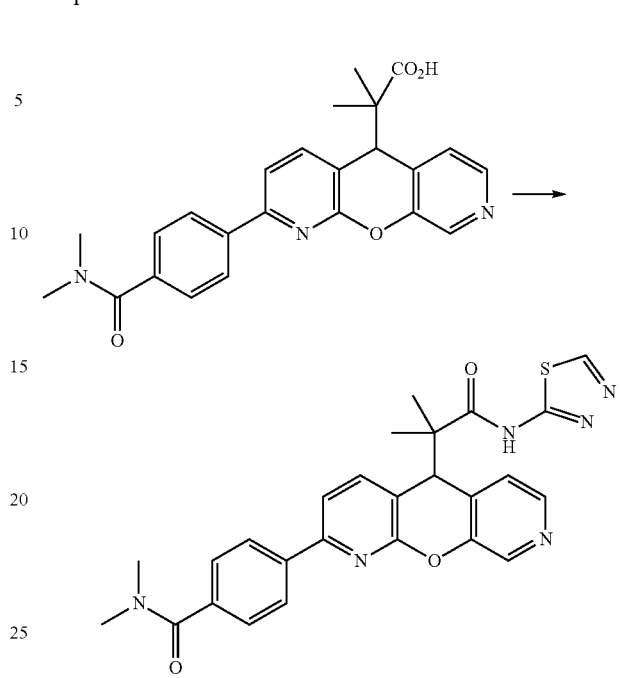

O-(7-Azabenzotriazol-1-yl)-N,N,N',N'-tetramethyluronium hexafluorophosphate (52.6 mg, 0.138 mmol) and Hunig's base (0.081 mL, 0.461 mmol) were added to a solution of the acid from Step 10 (32.1 mg, 0.077 mmol) in DMF (2 mL). The brown solution was stirred at room temperature for 30 min. 1,3,4-Thiadiazol-2-amine (23.33 mg, 0.231 mmol) was added. The mixture was stirred at 80° C. overnight. After 20 h at 80° C., the mixture was concentrated and purified by reverse phase HPLC (Sunfire S10 30×250 mm column, 45 to 65% solvent B gradient) to give Example 1, assumed as bis-TFA salt (26.6 mg, 48% yield). $^1$H NMR (400 MHz, methanol-d4) δ ppm 9.11 (1H, s), 8.81 (1H, s), 8.48 (1H, d, J=4.03 Hz), 8.13 (2H, d, J=8.31 Hz), 7.82 (2H, s), 7.69 (1H, d, J=5.54 Hz), 7.54 (2H, d, J=8.31 Hz), 4.85 (1H, s), 3.12 (3H, s), 3.03 (3H, s), 1.25 (3H, s), 1.24 (3H, s); MS (ES+) m/z: 501 (M+H); LC retention time: 3.08 min (analytical HPLC Method A).

Example 2

2-methyl-2-(2-(4-(4-morpholinylcarbonyl)phenyl)-5H-pyrido[4',3':5,6]pyrano[2,3-b]pyridin-5-yl)-N-1,3,4-thiadiazol-2-ylpropanamide

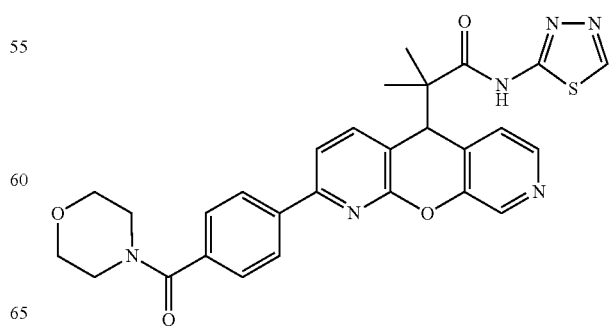

Step 1

1-Hydroxybenzotriazole hydrate (0.048 g, 0.312 mmol), N-(3-dimethylaminopropyl)-N'-ethylcarbodiimide hydrochloride (0.060 g, 0.312 mmol) and Hunig's base (0.163 mL, 0.936 mmol) were added to a solution of the acid from Step 8 of Example 1 (0.063 g, 0.156 mmol) in DMF (5 mL) and CH$_2$Cl$_2$ (10 mL) at room temperature. After 5 min, morpholine (0.054 mL, 0.624 mmol) was added. The mixture was stirred for 13 h, quenched with saturated NH$_4$Cl (25 mL) and extracted with CH$_2$Cl$_2$ (3×10 mL). The combined extracts were dried (MgSO$_4$) and concentrated to give the expected product as a slightly yellow solid. The crude material was taken to next reaction without purification. MS (ES+) m/z: 474 (M+H); LC retention time: 3.13 min (analytical HPLC Method A).

Step 2

A 1 N solution of NaOH (10 mL, 10.00 mmol) was added to a suspension of the crude product from Step 1 in MeOH (10 mL) and THF (10 mL). The mixture was heated to reflux for 1 h. HPLC indicated approximately 1:1 mixture of expected ester hydrolysis product and the mono-acid from selective amide hydrolysis. In addition there were two small peaks corresponding unreacted starting material and di-acid product (each about 25% of the major peaks). The organic solvents were evaporated in vacuo. The aqueous residue was acidified to pH~2 with 1 N HCl and extracted with CH$_2$Cl$_2$ (3×15 mL). There was still product in the aqueous phase. The aqueous phase was saturated with solid NH$_4$Cl and extracted with EtOAc (3×15 mL). The combined extracts were dried (MgSO$_4$) and concentrated to give an off-white solid, which was used in the next reaction without purification.

Step 3

1-Hydroxybenzotriazole hydrate (96 mg, 0.624 mmol), N-(3-dimethylaminopropyl)-N'-ethylcarbodiimide hydrochloride (120 mg, 0.624 mmol) and Hunig's base (0.327 mL, 1.872 mmol) were added to a solution of the crude acid from Step 2 in DMF (5 mL) at room temperature. After 5 min, 1,3,4-thiadiazol-2-amine (95 mg, 0.936 mmol) was added and the mixture was heated to 70° C. for 3 h. DMF was evaporated in vacuo. The residue was diluted with saturated NH$_4$Cl (25 mL) and extracted with CH$_2$Cl$_2$ (3×10 mL). The combined extracts were dried (MgSO$_4$) and concentrated. Reverse phase HPLC (Sunfire S10 30×250 mm column, 50 to 75% solvent B gradient) gave Example 2, assumed as bis-TFA salt (18.1 mg, 15% yield over three steps). $^1$H NMR (400 MHz, methanol-d4) δ ppm 8.99 (1H, s), 8.63 (1H, s), 8.32 (1H, s), 8.02-8.06 (2H, m), 7.70 (2H, s), 7.32-7.54 (3H, m), 4.70 (1H, s), 3.58-3.74 (4H, m), 3.47-3.58 (2H, m), 3.31-3.44 (2H, m), 1.13 (3H, s), 1.11 (3H, s); MS (ES+) m/z: 543 (M+H); LC retention time: 3.07 min (analytical HPLC Method A).

Example 3

4-(5-(1,1-dimethyl-2-oxo-2-(1,3,4-thiadiazol-2-ylamino)ethyl)-5H-pyrido[3',2':5,6]pyrano[2,3-b]pyridin-2-yl)-N,N-dimethylbenzamide

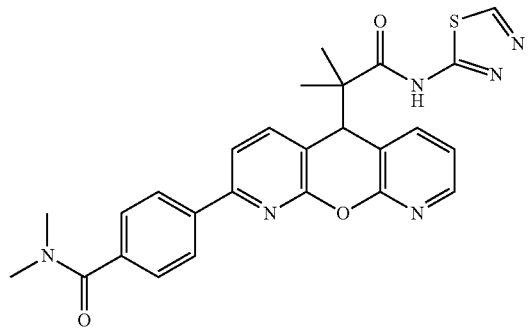

Step 1

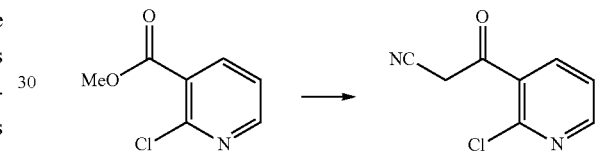

A 1.6 M hexane solution of BuLi (339 mL, 543 mmol) was added to a solution of diisopropylamine (81 mL, 566 mmol) in THF (600 mL) at −78° C. The mixture was stirred at 0° C. for 30 minutes and cooled to −78° C. Acetonitrile (28.4 mL, 543 mmol) was dropwise. After 1 h at −78° C., ethyl 2-chloronicotinate (42 g, 226 mmol) in THF (200 mL) was added dropwise. The resultant mixture was stirred at −78° C. for 1 h, quenched with brine (200 mL), allowed to warm to room temperature and adjusted to pH 1-2 with 1 N HCl. The two phases were separated. The aqueous layer was extracted with ethyl acetate (2×500 mL). The combined organic phase was washed with brine (400 mL), dried (MgSO$_4$) and concentrated. The residue was dissolved in ethyl acetate (200 mL) with heating and cooled to room temperature. The brown solid was collected by filtration to give the expected product (26.6 g, 65% yield). MS (ES+) m/z: 181 (M+H); LC retention time: 1.69 min (analytical HPLC Method A).

Step 2

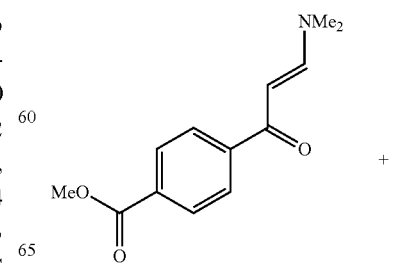

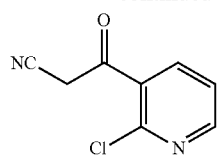

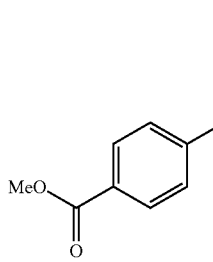

Acetic acid (1.838 mL, 32.1 mmol) was added to a mixture of (E)-methyl 4-(3-(dimethylamino)acryloyl)benzoate (1.498 g, 6.42 mmol) and 3-(2-chloropyridin-3-yl)-3-oxopropanenitrile (1.52 g, 8.42 mmol) in N,N-dimethylacetamide (20 mL). The mixture was stirred at 120° C. for 6 h, cooled to room temperature, diluted with MeOH (20 mL) and stirred at 0° C. for 30 min. The yellow solid was filtered and washed with cold MeOH to give the expected product (1.64 g, 77% yield). MS (ES+) m/z: 333 (M+H); LC retention time: 3.90 min (analytical HPLC Method A).

Step 3

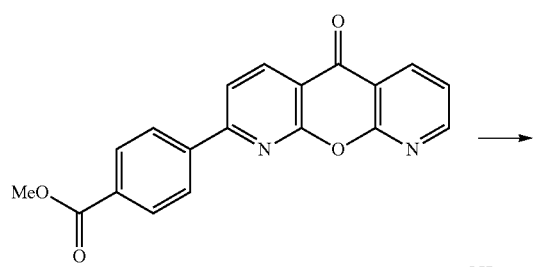

Sodium borohydride (7.29 g, 193 mmol) was added in small portions to a suspension of the ketone from Step 2 (12.8 g, 38.5 mmol) in MeOH (400 mL) and dichloromethane (100 mL) at 0° C. The mixture was stirred at 0° C. for 2 h, at room temperature for 3 h and quenched with saturated NH₄Cl (100 mL) and H₂O (100 mL). After stirring for 20 min, the organic solvents were evaporated in vacuo. The aqueous suspension was filtered and the brown solid washed with H₂O, cold methanol, dichloromethane, and dried under vacuum to provide the expected product (11.7 g, 91% yield). MS (ES+) m/z: 335 (M+H); LC retention time: 3.40 min (analytical HPLC Method A).

Step 4

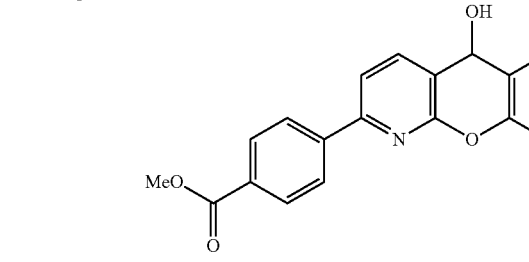

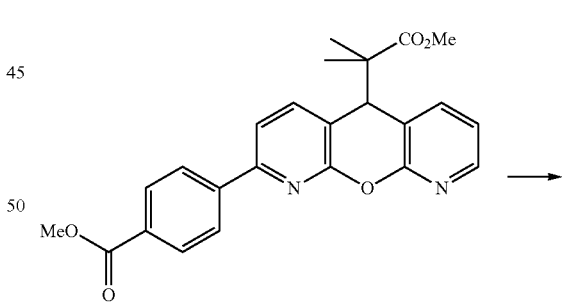

To a suspension of the alcohol from Step 3 (11.7 g, 35.0 mmol) in CH₂Cl₂ (300 mL) at 0° C. was added a 1 M CH₂Cl₂ solution of titanium(IV) chloride (52.5 mL, 52.5 mmol). The resultant tan suspension was stirred for 5 min. Methyl trimethylsilyl dimethylketene acetal (21.33 mL, 105 mmol) was added. The mixture was stirred at 0° C. for 1 h, and quenched with saturated NaHCO₃ (100 mL). The organic layer was separated and the aqueous phase extracted with CH₂Cl₂ (2×100 mL). The combined organic layers were washed with brine (100 mL), dried (MgSO₄) and concentrated to a small volume. A light-yellow solid crashed out during concentration, and was collected by filtration and dried under vacuum to provide the expected product (9.7 g, 66% yield). MS (ES+) m/z: 419 (M+H); LC retention time: 3.36 min (analytical HPLC Method A).

Step 5

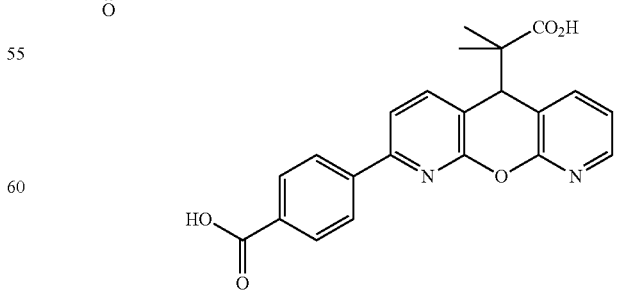

A 1 N aqueous solution of NaOH (30 mL, 30.0 mmol) was added to a suspension of the product from Step 4 (689 mg, 1.647 mmol) in THF (30 mL) and MeOH (30 mL). Upon heating to reflux, the mixture turned to a yellow solution. After 4.5 h at reflux, the organic solvent was evaporated in vacuo. The aqueous residue was cooled to 0° C., and acidified to pH~3 with slow addition of 1 N HCl. The mixture was filtered. The solid was washed with water (2×25 mL) and dried under vacuum to give the expected product (601 mg, 93% yield). MS (ES+) m/z: 391 (M+H); LC retention time: 3.45 min (analytical HPLC Method A).

Step 6

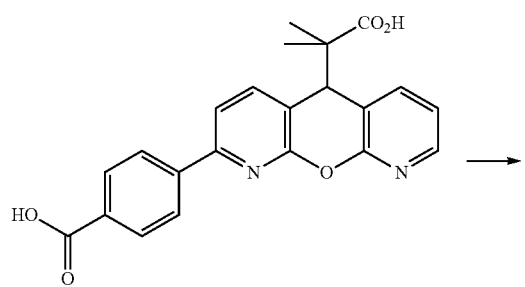

→

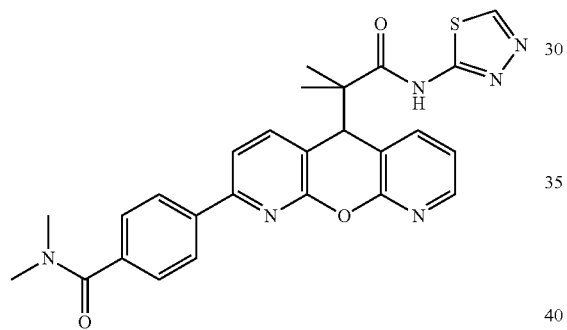

O-(7-Azabenzotriazol-1-yl)-N,N,N',N'-tetramethyluronium hexafluorophosphate (1.086 g, 2.86 mmol) and Hunig's base (1.596 mL, 9.14 mmol) were added to a suspension of the product from Step 5 (446 mg, 1.142 mmol) in acetonitrile (20 mL). The suspension became nearly homogeneous then changed to a thick suspension. After 30 min at room temperature, the mixture was cooled to 0° C. A 2 M THF solution of dimethylamine (0.571 mL, 1.142 mmol) was added. After 2 h at 0° C., 1,3,4-thiadiazol-2-amine (347 mg, 3.43 mmol) was added. The mixture was heated to 60° C. for 7 h, quenched with saturated NH$_4$Cl (100 mL) and extracted with CHCl$_3$ (4×50 mL). The combined extracts were dried (MgSO$_4$), concentrated and purified by reverse phase HPLC, using Sunfire S10 30×250 mm column and eluting with 40 to 70% solvent B, to give Example 3 as a crystalline solid, assumed as bis-TFA salt (316.7 mg, 38% yield). $^1$H NMR (400 MHz, methanol-d4) δ ppm 9.11 (1H, s), 8.28 (1H, dd, J=4.91, 1.64 Hz), 8.15 (2H, d, J=8.56 Hz), 7.70-7.83 (3H, m), 7.54 (2H, d, J=8.31 Hz), 7.25 (1H, dd, J=7.43, 4.91 Hz), 4.69 (1H, s), 3.12 (3H, s), 3.04 (3H, s), 1.19 (6H, s); MS (ES+) m/z: 501 (M+H); LC retention time: 3.29 min (analytical HPLC Method A).

Examples 4-9

Examples 4-7 were prepared from the acid from Step 5 of Example 3 in the manner described above for the preparation of the title compound of Example 3, using commercially available amines except 5-amino-N-cyclopropyl-1,3,4-thiadiazole-2-carboxamide, the synthesis of which is described below the Table. Examples 8-9 were obtained from chiral resolution of Examples 3-4, using SFC Chiralcel OJ-H column (3×25 cm CO$_2$/MeOH 70:30, 120 ml/min, 254 nm, 40° C.), both second peak off the column.

| Ex # | Structure | $^1$H NMR (400 MHz) δ ppm | RT (min) | Obs. MS Ion |
|---|---|---|---|---|
| 4 | 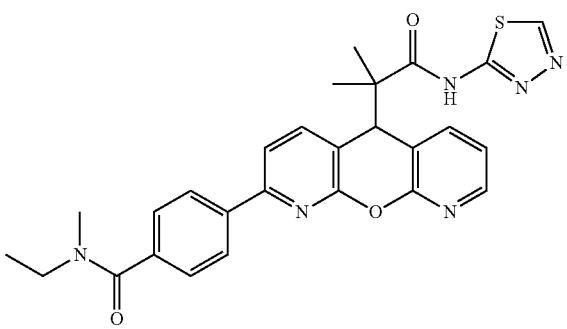 | Methanol-d4: 2 sets of signals for C(O)NEtMe group 9.11 (1 H, s), 8.28 (1 H, dd, J = 4.91, 1.64 Hz), 8.08-8.20 (2 H, m), 7.71-7.81 (3 H, m), 7.51 (2 H, t, J = 7.30 Hz), 7.24 (1 H, dd, J = 7.43, 4.91 Hz), 4.69 (1 H, s), 3.32-3.70 (2 H, m), 2.95-3.15 (3 H, m), 1.04-1.38 (9 H, m) | 3.43 | 515 |

-continued

| Ex # | Structure | ¹H NMR (400 MHz) δ ppm | RT (min) | Obs. MS Ion |
|---|---|---|---|---|
| 5 | 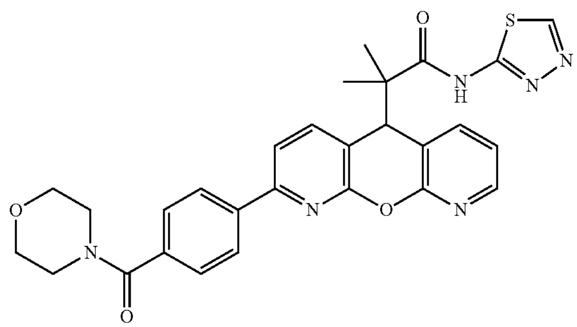 | Methanol-d4: 9.11 (1 H, s), 8.28 (1 H, dd, J = 4.78, 1.76 Hz), 8.16 (2 H, d, J = 8.56 Hz), 7.71-7.82 (3 H, m), 7.55 (2 H, d, J = 8.56 Hz), 7.25 (1 H, dd, J = 7.55, 5.04 Hz), 4.70 (1 H, s), 3.42-3.88 (8 H, m), 1.20 (6 H, s) | 3.25 | 543 |
| 6 | 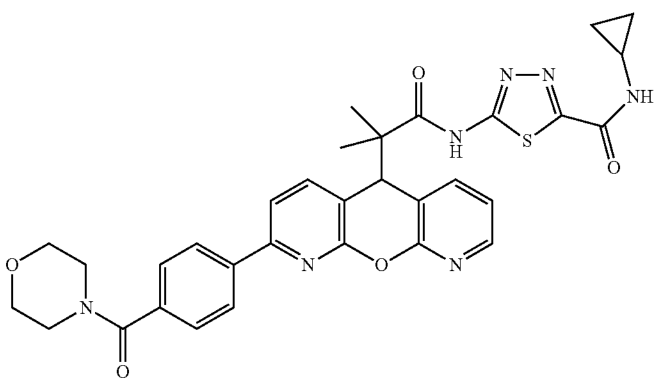 | Methanol-d4: 8.22 (1 H, dd, J = 4.81, 1.79 Hz), 8.10 (2 H, d, J = 8.25 Hz), 7.68-7.79 (2 H, m), 7.49 (2 H, d, J = 8.25 Hz), 7.20 (1 H, dd, J = 7.56, 4.81 Hz), 4.65 (1 H, s), 3.37-3.90 (8 H, m), 2.72-2.90 (1 H, m), 1.13 (6 H, d, J = 7.42 Hz), 0.74-0.83 (2 H, m), 0.54 -0.73 (2 H, m). | 3.29 | 626 |
| 7 | 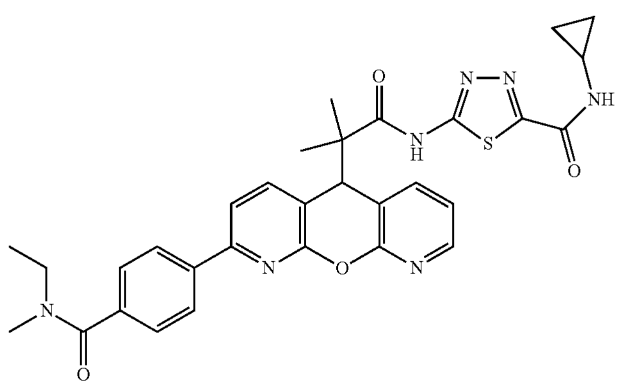 | Methanol-d4: 8.23(1 H, dd, J = 4.95, 1.65 Hz), 8.09 (2 H, d, J = 8.25 Hz), 7.65-7.78 (2 H, m), 7.46 (2 H, dd, J = 9.07 Hz), 7.20 (1 H, dd, J = 7.56, 4.81 Hz), 4.63 (1 H, s), 3.44-3.66 (1 H, m), 3.29-3.40 (1 H, m), 2.93-3.17 (3 H, m), 2.78-2.90 (1 H, m). 1.07-1.23 (9 H, m), 0.74-0.87 (2 H, m), 0.59-0.73 (2 H, m). | 3.45 | 598 |
| 8 | homochiral | Methanol-d4: 9.11 (1 H, s), 8.27(1 H, dd, J = 4.78, 1.76 Hz), 8.08-8.17 (2 H, m), 7.67-7.80 (3 H, m), 7.48-7.56 (2 H, m), 7.23 (1 H, dd, J = 7.43, 4.91 Hz), 4.69 (1 H, s), 3.60 (1 H, s) 3.12 (3H, s),3.04 (3 H, s), 1.18 (6 H, s) | 3.28 | 501 |

| Ex # | Structure | ¹H NMR (400 MHz) δ ppm | RT (min) | Obs. MS Ion |
|---|---|---|---|---|
| 9 | 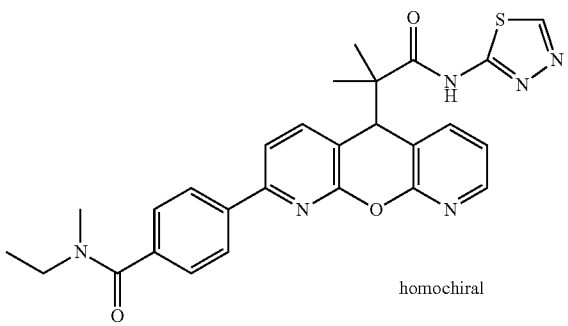 homochiral | Methanol-d4: 2 sets of signals for C(O)NEtMe group 9.11 (1 H, s), 8.28 (1 H, dd, J = 4.91, 1.89 Hz), 8.15 (2 H, d, J = 8.31 Hz), 7.71-7.83 (3 H, m), 7.52 (2 H, t, J = 8.06 Hz), 7.24 (1 H, dd, J = 7.43, 4.91 Hz), 4.70 (1 H, s), 3.31-3.68 (2 H, m), 2.96-3.15 (3 H, m), 1.07-1.35 (9 H, m) | 3.44 | 515 |

Synthesis of 5-amino-N-cyclopropyl-1,3,4-thiadiazole-2-carboxamide

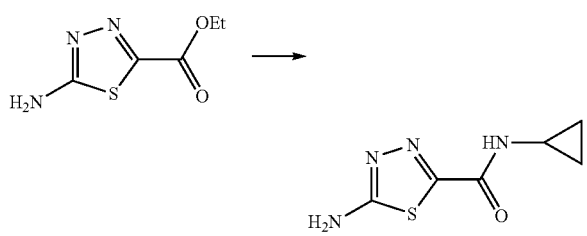

To a suspension of ethyl 5-amino-1,3,4-thiadiazole-2-carboxylate (2 g, 11.55 mmol) in methanol (15 mL) was added cyclopropylamine (1.5 mL, 21.65 mmol). The mixture was stirred at room temperature for 1 h and at 40° C. for 1.5 h. Additional cyclopropylamine (2 mL) was added. After 3 h at 40° C., 1 h at 50° C. and 20 min at 70° C., the mixture was concentrated to half the volume, diluted with water (2.5 mL), heated to boil to give a clear solution and cooled to room temperature. The solid was filtered, washed with cold methanol, and dried to give 5-amino-N-cyclopropyl-1,3,4-thiadiazole-2-carboxamide as yellow crystals (1.52 g, 72% yield). MS (ES+) m/z: 185 (M+H); LC retention time: 0.87 min (analytical HPLC Method A).

Example 10

4-(5-(1,1-dimethyl-2-oxo-2-(1,3,4-thiadiazol-2-ylamino)ethyl)-8-methyl-5H-pyrido[3',2':5,6]pyrano[2,3-b]pyridin-2-yl)-N,N-dimethylbenzamide

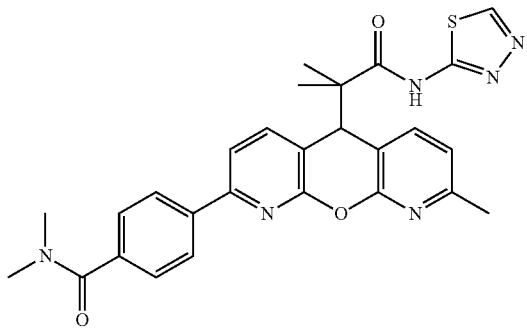

Step 1

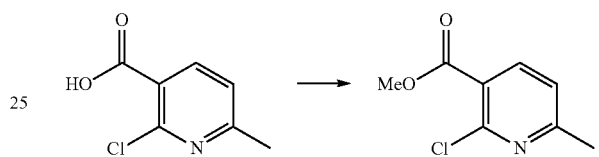

A 2 M ether solution of (trimethylsilyl)diazomethane (30 mL, 60.0 mmol) was added to a solution of 2-chloro-6-methylnicotinic acid (8 g, 45.2 mmol) in THF (100 mL) and MeOH (25 mL) in a room temperature water bath. After 30 min, HOAc (2 mL) was added. The mixture was concentrated and purified by silica gel chromatography, eluting with 0-20% EtOAc in hexanes, to give methyl 2-chloro-6-methylnicotinate as colorless oil (7.77 g, 93% yield). MS (ES+) m/z: 186 (M+H); LC retention time: 2.64 min (analytical HPLC Method A).

Step 2

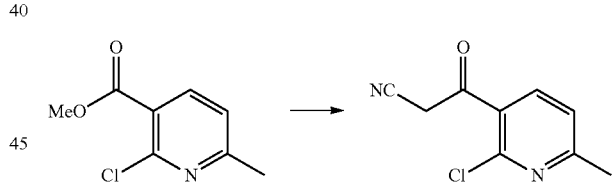

A 2.5 M hexane solution of BuLi (40.2 mL, 100 mmol) was added dropwise to a solution of diisopropylamine (14.92 mL, 105 mmol) in THF (160 mL) at −78° C. The mixture was stirred at 0° C. for 15 min and cooled to −78° C. Acetonitrile (5.25 mL, 100 mmol) was added dropwise. The solution gradually turned to milky white. After 1 h at −78° C., methyl 2-chloro-6-methylnicotinate (7.77 g, 41.9 mmol) in THF (25 mL) was added dropwise. The flask was rinsed with THF (5 mL) and added. After 1 h at −78° C., the mixture was quenched with brine (100 mL) and acidified to pH~1. The aqueous residue was extracted with EtOAc (3×100 mL). The combined extracts were washed with brine (50 mL), dried (MgSO₄) and concentrated to give a brown oil which slowly solidified after standing overnight. The solid was triturated with CH₂Cl₂ and filtered to give the expected product (3.4115 g) as off-white solid. The filtrate was purified by silica gel chromatography, eluting with 10-50% EtOAc in hexanes, to give additional product (3.9584 g). The combined yield is 90%. MS (ES+) m/z: 195 (M+H); LC retention time: 2.09 min (analytical HPLC Method A).

Step 3

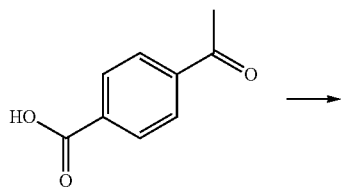

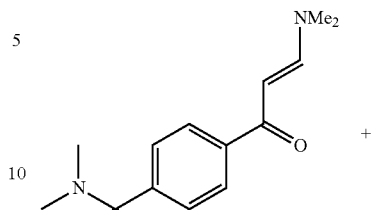

A mixture of 4-acetylbenzoic acid (40 g, 244 mmol), 40% aqueous dimethylamine (33.0 g, 292 mmol), N-(3-dimethylaminopropyl)-N'-ethylcarbodiimide hydrochloride (56.1 g, 292 mmol), 1-hydroxybenzotriazole hydrate (44.8 g, 292 mmol) and N,N-diisopropylethylamine (85 mL, 487 mmol) in $CH_3CN$ (400 mL) was stirred at room temperature for 15 h then concentrated. The residue was dissolved in ethyl acetate (1000 mL), washed with $H_2O$ (2×200 mL), brine (200 mL), dried ($MgSO_4$) and concentrated to provide 4-acetyl-N,N-dimethylbenzamide (24 g). The crude product was taken to the next step without purification.

Step 4

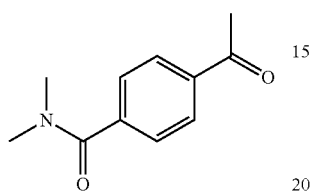

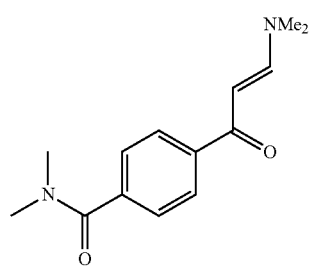

A mixture of crude 4-acetyl-N,N-dimethylbenzamide (24.0 g) and N,N-dimethylformamide dimethyl acetal (100 mL) was heated to reflux for 15 h, cooled to room temperature and concentrated. The residue was washed with ether and dried under vacuum to provide (E)-4-(3-(dimethylamino)acryloyl)-N,N-dimethylbenzamide as brown solid (16 g, 27% yield over 2 steps). MS (ES+) m/z: 247 (M+H).

Step 5

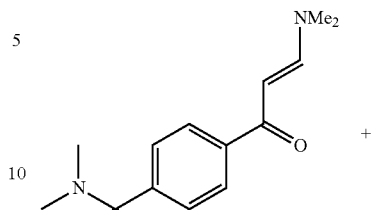

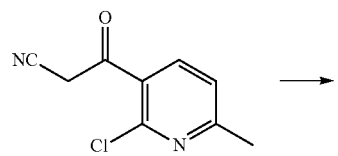

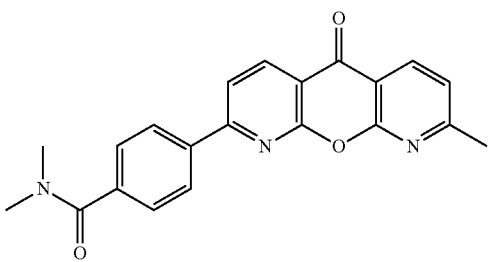

Glacial acetic acid (4.81 mL, 84 mmol) was added to a brown solution of (E)-4-(3-(dimethylamino)acryloyl)-N,N-dimethylbenzamide (4.137 g, 16.80 mmol) and 3-(2-chloro-6-methylpyridin-3-yl)-3-oxopropanenitrile (3.92 g, 20.16 mmol) in DMF (30 mL). The solution was heated to 120° C. for 7 h, cooled to room temperature and diluted with MeOH (30 mL). The precipitate was collected by filtration, washed with MeOH (3×25 mL), dried under vacuum to give the expected product as a slightly pink solid (4.629 g). The filtrate was concentrated and purified by silica gel chromatography, eluting with 3-10% MeOH in $CH_2Cl_2$. The product containing fractions were combined and re-purified with 0-10% MeOH in $CH_2Cl_2$ to give additional product as brown solid (438 mg). The combined yield of the product was 5.067 g (84% yield). MS (ES+) m/z: 360 (M+H); LC retention time: 3.45 min (analytical HPLC Method A).

Step 6

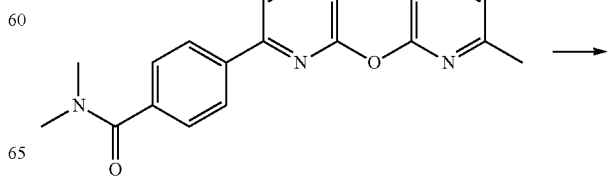

-continued

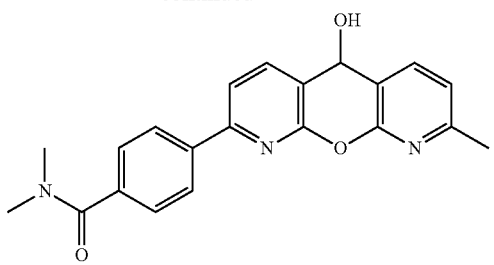

Powder sodium borohydride (3.33 g, 88 mmol) was added in small portions to a solution of the product from Step 5 (7.05 g, 19.62 mmol) in CH$_2$Cl$_2$ (218 mL) and MeOH (218 mL) at 0° C. After 2 h at 0° C., the mixture was quenched with saturated NH$_4$Cl (200 mL) and water (200 mL). The two phases were separated. The aqueous layer was extracted with CH$_2$Cl$_2$ (3×100 mL). The combined CH$_2$Cl$_2$ layer was concentrated and dried under vacuum to give the expected product as a brown powder (7.392 g). The crude material was taken to the next step without purification.

Step 7

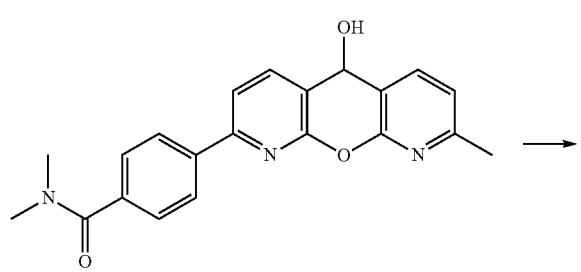

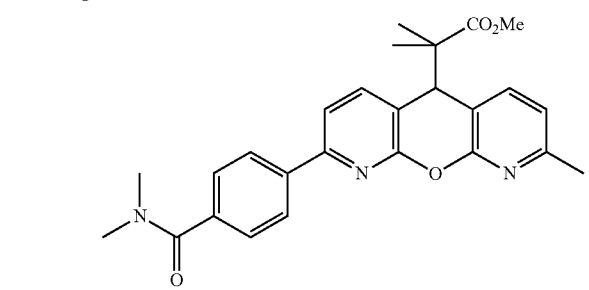

A 1 M CH$_2$Cl$_2$ solution of titanium(IV) chloride (24.54 mL, 24.54 mmol) was added over 10 min to a suspension of the alcohol from Step 6 (7.39 g) in CH$_2$Cl$_2$ (500 mL) at 0° C. The resultant tan suspension was stirred at 0° C. for 10 min. Methyl trimethylsilyl dimethylketene acetal (12.46 mL, 61.3 mmol) was added dropwise. After 1 h at 0° C., the ice bath was removed and the reaction mixture was quenched with saturated NaHCO$_3$ (250 mL, caution CO$_2$ release). The mixture was stirred for 30 min and filtered through a celite pad. The pad was rinsed with CH$_2$Cl$_2$ (250 mL). The biphasic filtrate layers were separated. The aqueous phase was extracted with CH$_2$Cl$_2$ (2×100 mL). The combined CH$_2$Cl$_2$ phase was dried (MgSO$_4$) and concentrated. Silica gel chromatography, loading with CH$_2$Cl$_2$ and eluting with 30% to 100% EtOAc in CH$_2$Cl$_2$-hexane (1:1), gave the expected product as a tan solid (7.78 g, 89% yield for two steps). MS (ES+) m/z: 446 (M+H); LC retention time: 3.54 min (analytical HPLC Method A).

Step 8

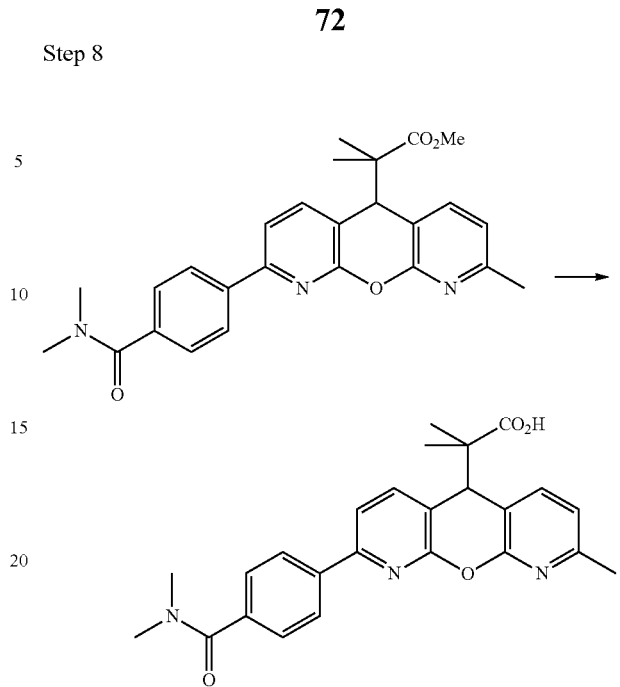

Sodium 2-propanethiolate (15.42 g, 157 mmol) was added to a suspension of the product from Step 7 (7.78 g, 17.46 mmol) in DMF (100 mL) and tetrahydrofuran (100 mL). The resultant dark mixture was heated to 50° C. for 5 h, cooled to 0° C. and quenched with careful addition of 1 N HCl (157 mL). The brown solution was concentrated and dried under vacuum at 50° C. overnight. The residue was taken up in saturated NH$_4$Cl (250 mL), adjusted to pH ~2 with 1 N NaOH and extracted with CHCl$_3$ (5×150 mL). The combined extracts were dried (MgSO$_4$) and concentrated. Silica gel chromatography, loading with CH$_2$Cl$_2$ and eluting with 0-10% MeOH in CH$_2$Cl$_2$, gave the expected product as a brown solid (8.35 g). MS (ES+) m/z: 432 (M+H); LC retention time: 3.37 min (analytical HPLC Method A).

Step 9

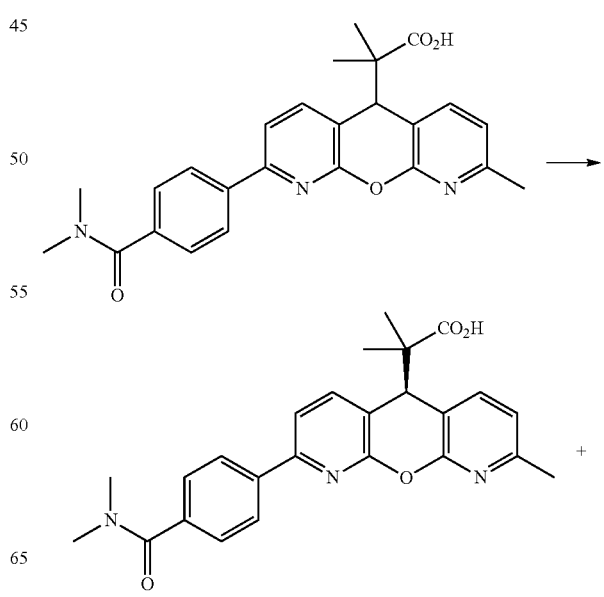

-continued

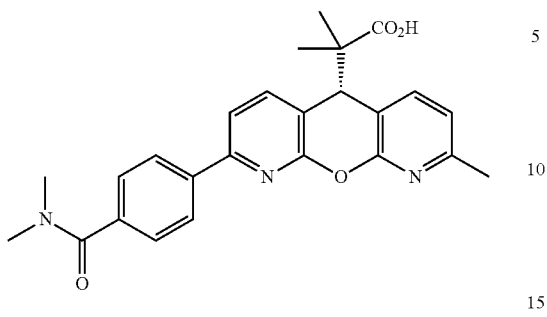

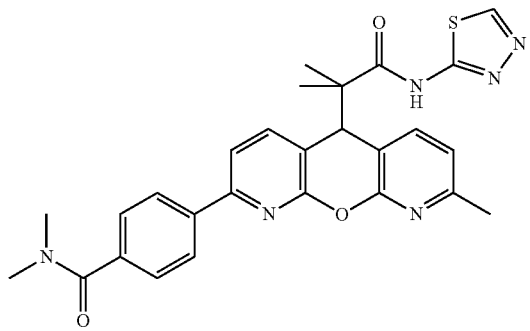

The two enantiomers of the acid from Step 8 (3.0 g) was separated using Chiralpak AD-H column. The first peak from the column was found to be the S enantiomer (1.201 g) and used for subsequent synthesis of analogues. MS (ES+) m/z: 432 (M+H); LC retention time: 3.40 min (analytical HPLC Method A).

Step 10

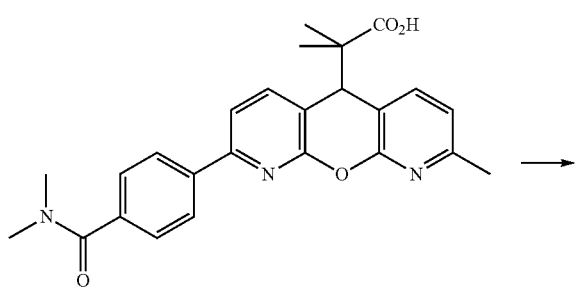

A solution of the acid from Step 8 (26 mg, 0.039 mmol), 1,3,4-thiadiazol-2-amine (22 mg, 0.218 mmol), N,N-diisopropylethylamine (0.034 mL, 0.197 mmol) and O-(7-azabenzotriazol-1-yl)-N,N,N',N'-tetramethyluronium hexafluorophosphate (43.8 mg, 0.115 mmol) in $CH_3CN$ (1.5 mL) was stirred at 60° C. for 17 h. The crude material was purified by reverse phase HPLC (Sunfire S10 30×250 mm column, 55-85% solvent B gradient) to give Example 10 as off-white solid (17.7 mg, 60% yield). $^1$H NMR (400 MHz, chloroform-d) δ ppm 8.90 (1H, s), 8.08 (2H, d, J=8.31 Hz), 7.60-7.69 (1H, m), 7.48-7.60 (4H, m), 7.02 (1H, d, J=7.55 Hz), 4.62 (1H, s), 3.19 (3H, s), 3.05 (3H, s), 2.58 (3H, s), 1.26 (3H, s), 1.25 (3H, s); MS (ES+) m/z: 515 (M+H); LC retention time: 3.45 min (analytical HPLC Method A).

Examples 11-13

Examples 11-13 were prepared from the S-acid from Step 9 of Example 10 in the manner described above for the preparation of the title compound of Example 10, using commercially available amines

| Ex # | Structure | $^1$H NMR (400 MHz) δ ppm | RT (min) | Obs. MS Ion |
|---|---|---|---|---|
| 11 | 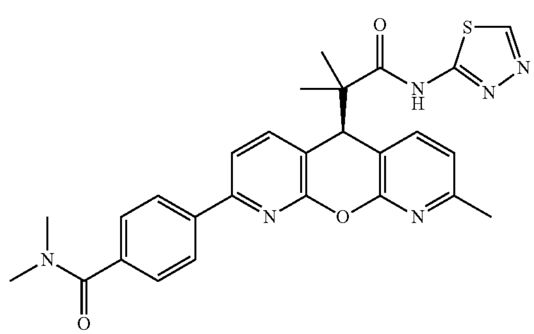 | Methanol-d4: 9.11 (1 H, s), 8.17 (2 H, d, J = 8.31 Hz), 7.77 (2 H, s), 7.62 (1 H, d, J = 7.81 Hz), 7.55 (2 H, d, J = 8.31 Hz), 7.10 (1 H, d, J = 7.55 Hz), 4.65 (1 H, s), 3.13 (3 H, s), 3.05 (3 H, s), 2.51 (3 H, s), 1.18 (6 H, d, J = 3.02 Hz) | 3.44 | 515 |

| Ex # | Structure | $^1$H NMR (400 MHz) δ ppm | RT (min) | Obs. MS Ion |
|---|---|---|---|---|
| 12 | 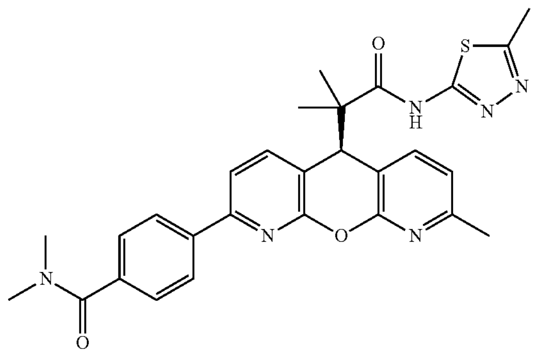 | Chloroform-d: 8.10 (2 H, d, J = 8.31 Hz), 7.61-7.67 (1 H, m), 7.55-7.60 (1 H, m), 7.52 (2 H, d, J = 8.31 Hz), 7.48 (1 H, d, J = 7.81 Hz), 6.99 (1 H, d, J = 7.81 Hz), 4.59 (1 H, s), 3.17 (3 H, s), 3.04 (3 H, s), 2.76 (3 H, s), 2.56 (3 H, s), 1.24 (3 H, s), 1.22 (3 H, s) | 3.60 | 529 |
| 13 | 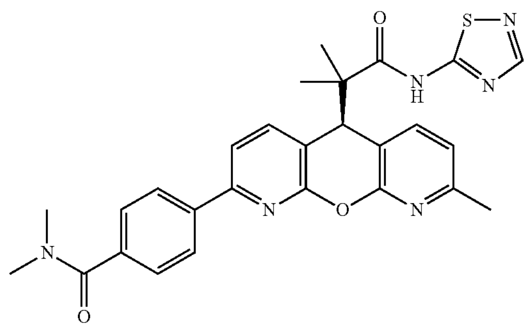 | Chloroform-d: 8.27 (2, 1 H), 8.10 (d, J = 8.31 Hz, 2 H), 7.55-7.64 (m, 2 H), 7.53 (d, J = 8.31 Hz, 2 H), 7.48 (d, J = 7.81 Hz, 2 H), 4.58 (s, 1 H), 3.18 (s, 3 H), 3.05 (s, 3 H), 2.57 (s, 3 H), 1.26 (s, 3 H), 1.25 (s, 3 H) | 3.67 | 515 |

Example 14

4-(5-(1,1-dimethyl-2-oxo-2-(1,3,4-thiadiazol-2-ylamino)ethyl)-8-methyl-5H-pyrido[3',2':5,6]pyrano[2,3-b]pyridin-2-yl)-N-ethyl-N-methylbenzamide

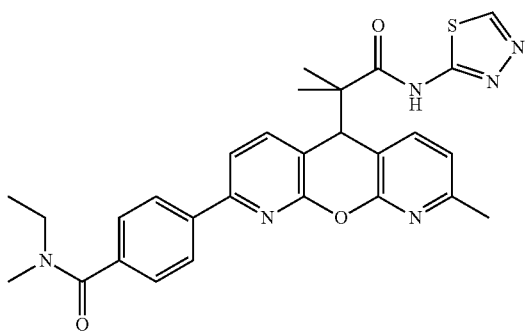

Step 1

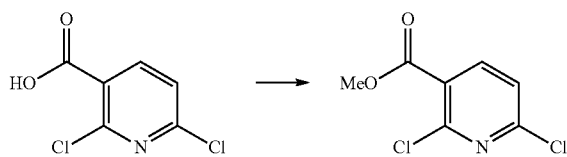

A 2.0 M ether solution of (trimethylsilyl)diazomethane (30 mL, 60.0 mmol) was added dropwise to a solution of 2,6-dichloronicotinic acid (8.00 g, 37.5 mmol) in THF (100 mL) and MeOH (25 mL) in a room temperature water bath. After 1 h, HOAc (4 mL) was added. The mixture was stirred until bubbling stopped and concentrated. The resulting solid was dissolved in minimum amount of ethyl acetate, diluted with hexanes, and partially concentrated in vacuo. A white crystalline solid precipitated out and was collected by filtration. This process was repeated three times to give 4.553 g of the desired product. The mother liquor was concentrated and purified by silica gel chromatography, eluting with 0-20% EtOAc in hexanes, to give additional product (2.48 g). The total amount of the product was 7.033 g (91% yield). MS (ES+) m/z: 206 (M+H); LC retention time: 2.99 min (analytical HPLC Method A).

Step 2

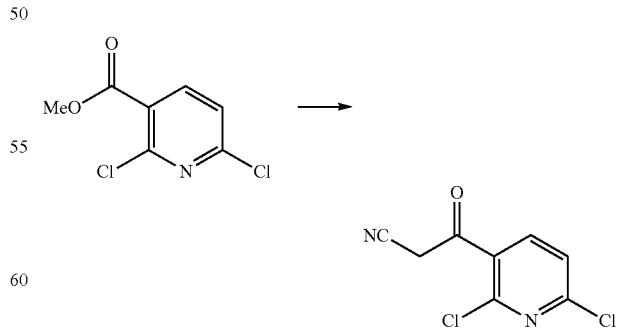

A 2.5 M hexane solution of BuLi (32.6 mL, 82 mmol) was added dropwise to a solution of diisopropylamine (12.11 mL, 85 mmol) in THF (100 mL) at −78° C. The mixture was stirred at 0° C. for 15 min and cooled to −78° C. Acetonitrile (4.26 mL, 82 mmol) was added dropwise. The solution gradually turned to milky white. After 1 h at −78° C., methyl 2,6-dichloronicotinate (7.00 g, 34.0 mmol) in THF (25 mL) was added dropwise. The flask was rinsed with THF (5 mL) and added. After 1 h at −78° C., the mixture was quenched with brine (100 mL), acidified to pH~1 and extracted with EtOAc (3×100 mL). The combined extracts were washed with brine (50 mL), dried (MgSO$_4$) and concentrated. Silica gel chromatography, eluting with 0-5% methanol in CH$_2$Cl$_2$, gave the desired product as yellow solid (4.6374 g, 64% yield). MS (ES+) m/z: 215 (M+H); LC retention time: 2.45 min (analytical HPLC Method A).

Step 3

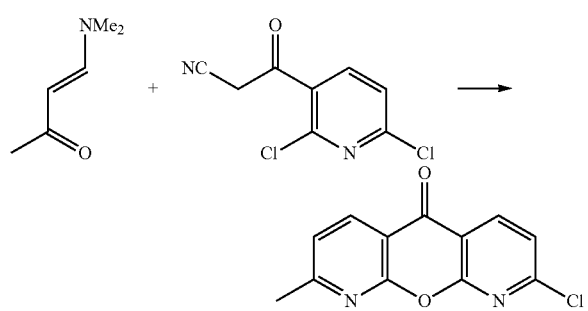

Glacial acetic acid (2.277 mL, 39.8 mmol) was added to a brown solution of (E)-4-(dimethylamino)but-3-en-2-one (0.90 g, 7.95 mmol) and 3-(2,6-dichloropyridin-3-yl)-3-oxo-propanenitrile (2.052 g, 9.54 mmol) in DMF (20 mL). The mixture was heated to 100° C. After 2.5 h at 100° C., heating was stopped. MeOH (40 mL) was added. The mixture was cooled to 0° C. and filtered. The solid from the filtration was washed with MeOH (3×15 mL) to give the expected product as a tan solid (1.239 g). The filtrate was concentrated and purified by silica gel chromatography, eluting with 0-30% EtOAc in CH$_2$Cl$_2$-hex (1:4), to give additional product (0.364 g). The combined amount of the product is 1.603 g (82% yield). MS (ES+) m/z: 247 (M+H); LC retention time: 3.15 min (analytical HPLC Method A).

Step 4

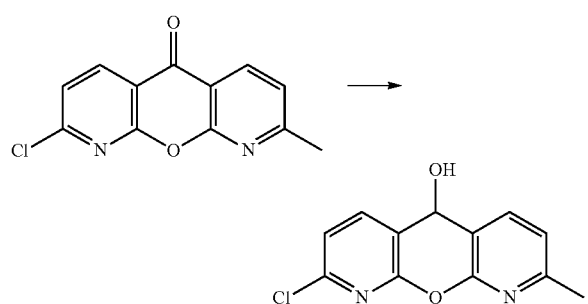

The ketone from Step 3 (1.658 g, 6.72 mmol) was dissolved in dichloromethane (75 mL), diluted with methanol (75 mL) and cooled to 0° C. Granular sodium borohydride (1.272 g, 33.6 mmol) was added in small portions. After 30 min at 0° C., the mixture was quenched with saturated NH$_4$Cl (80 mL) and water (80 mL). The organic solvents were evaporated in vacuo. The precipitate was collected by filtration, washed with water (3×25 mL) and dried under vacuum to give the expected product as yellow solid (1.510 g, 91% yield). MS (ES+) m/z: 249 (M+H); LC retention time: 2.733 min (analytical HPLC Method A).

Step 5

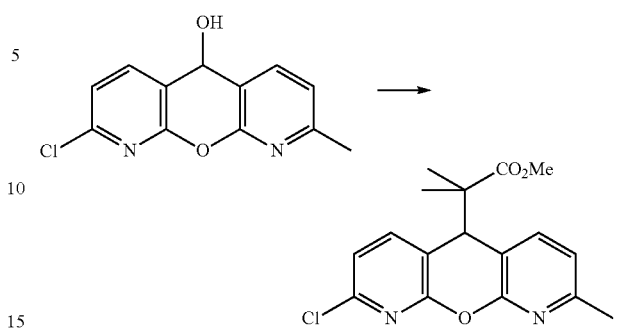

A 1.0 M CH$_2$Cl$_2$ solution of titanium(IV) chloride (6.37 mL, 6.37 mmol) was added dropwise to a suspension of the alcohol from Step 4 (1.320 g, 5.31 mmol) in CH$_2$Cl$_2$ (80 mL) at 0° C. After 10 min at 0° C., methyl trimethylsilyl dimethylketene acetal (2.157 mL, 10.62 mmol) was added dropwise. The suspension gradually became a dark homogeneous solution. After 1 h at 0° C., the mixture was quenched with saturated NaHCO$_3$ (80 mL) and filtered through a celite pad. The celite pad was rinsed with CH$_2$Cl$_2$. The two phases of the filtrate were separated. The aqueous phase was extracted with CH$_2$Cl$_2$ (2×50 mL). The combined CH$_2$Cl$_2$ phase was dried (MgSO$_4$) and concentrated. The solid residue was dissolved in CH$_2$Cl$_2$ (50 mL), concentrated to about 10 mL and diluted with 30% EtOAc in hexane (50 mL). The solid was collected by filtration and washed with 30% EtOAc in hexane (2×20 mL) to give the expected product as a white solid (1.264 g). The filtrate was concentrated and purified by silica gel chromatography, eluting with 10-50% EtOAc in 3:7 mixture of CH$_2$Cl$_2$-hexanes, to give additional product (224 mg). Total amount of the expected product is 1.488 g (84% yield). MS (ES+) m/z: 333 (M+H); LC retention time: 3.40 min (analytical HPLC Method A).

Step 6

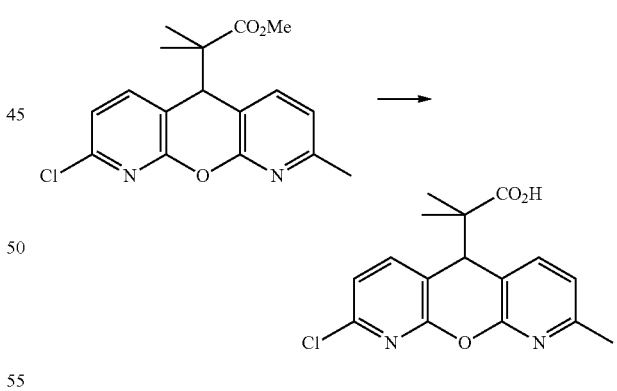

A 1.0 N aqueous NaOH (20 mL, 20.00 mmol) solution was added to a suspension of the product from Step 5 (1.50 g, 4.51 mmol) in MeOH (20 mL) and THF (20 mL) at room temperature. After 6 h at 80° C., heating was stopped. The organic solvents were evaporated in vacuo. The aqueous residue was adjusted with 1 N HCl to pH 1-2 and the solid was collected by filtration. The filtrate was extracted with CH$_2$Cl$_2$ (2×50 mL). The combined extracts were dried (MgSO$_4$) and concentrated to give a solid, which was combined with the solid from the filtration to give the expected product (1.40 g, 97% yield). MS (ES+) m/z: 319 (M+H); LC retention time: 3.11 min (analytical HPLC Method A).

Step 7

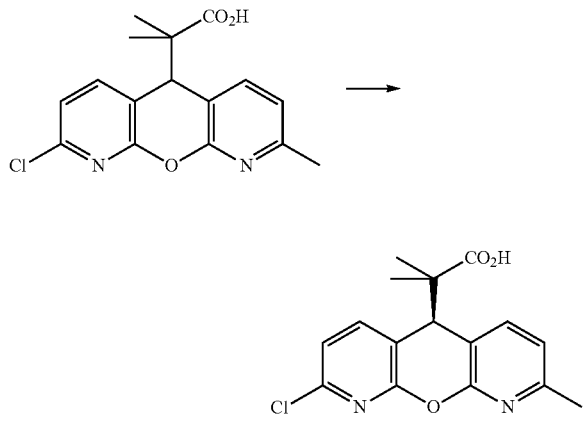

The two enantiomers of the acid from Step 6 (10.7 g) were separated using SFC Chiralpak AD column. The first peak from the column was found to be the S enantiomer (5.54 g), as a Et$_2$NH salt (Et$_2$NH added to make a solution for SFC injection). MS (ES+) m/z: 319 (M+H); LC retention time: 3.26 min (analytical HPLC Method A).

Step 8

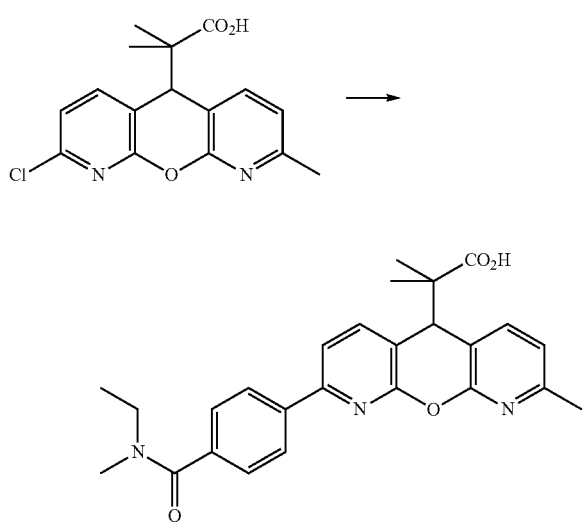

A solution of the acid from Step 6 (30 mg, 0.055 mmol), 4-(ethyl(methyl)carbamoyl)phenylboronic acid (22.7 mg, 0.110 mmol), 2.0 M aqueous potassium phosphate (0.137 mL, 0.274 mmol) and Pd(PPh$_3$)$_4$ (12.68 mg, 0.011 mmol) in DMF (2 mL) was purged with N$_2$. After 4 h at 90° C., the mixture was cooled to room temperature, treated with 1 N NaOH (10 mL), washed with CH$_2$Cl$_2$ (2×5 mL), adjusted pH 1-2 with 1 N HCl and extracted with CH$_2$Cl$_2$ (2×30 mL). The combined extracts were washed with brine (10 mL), dried (MgSO$_4$) and concentrated. Reverse phase HPLC (Sunfire S10 30×250 mm column, 20-100% solvent B gradient) gave the desired product, assumed as bis-TFA salt (31 mg, 84% yield). MS (ES+) m/z: 446 (M+H); LC retention time: 3.35 min (analytical HPLC Method A).

Step 9

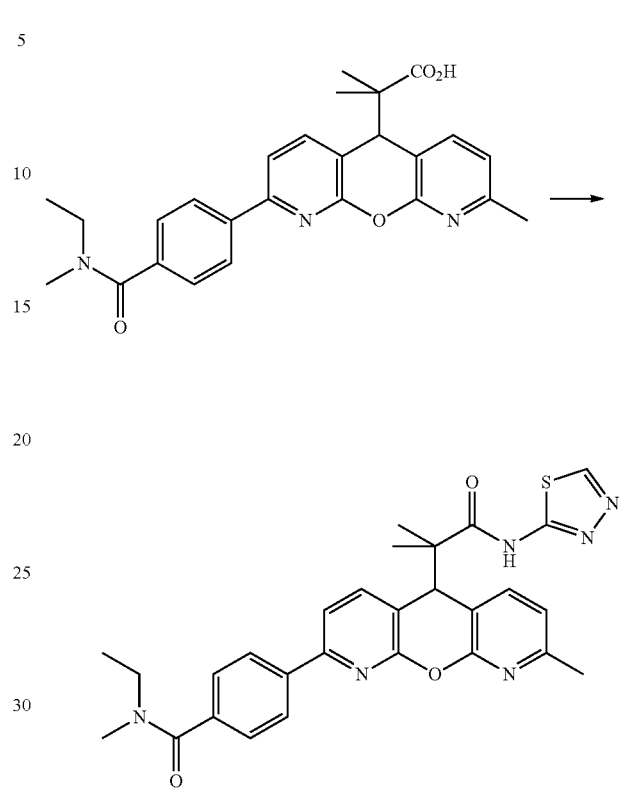

Hunig's base (0.056 mL, 0.322 mmol) was added dropwise to a suspension of O-(7-azabenzotriazol-1-yl)-N,N,N',N'-tetramethyluronium hexafluorophosphate (26.2 mg, 0.069 mmol) and the acid from Step 8 (31 mg, 0.046 mmol) in acetonitrile (2 mL). After 5 min at room temperature, 1,3,4-thiadiazol-2-amine (13.96 mg, 0.138 mmol) was added. After 7 h at 60° C., the mixture was cooled to room temperature, concentrated and purified by reverse phase HPLC (Sunfire S10 30×250 mm column, 20-100% solvent B gradient) to provide the expected product. The impure product was further purified by silica gel chromatography, eluting with 0-10% MeOH in CH$_2$Cl$_2$, to give the expected product, which was converted to bis-TFA salt (18 mg, 52% yield). $^1$H NMR (400 MHz, methanol-d4) δ ppm 9.11 (1H, s), 8.12 (2H, d, J=8.31 Hz), 7.74 (1H, s), 7.68 (1H, d, J=7.55 Hz), 7.49 (2H, t, J=7.93 Hz), 7.14 (1H, d, J=7.81 Hz), 4.64 (1H, s), 3.50-3.71 (1H, m), 3.30-3.40 (1H, m), 2.97-3.14 (3H, m), 2.52 (3H, s), 1.11-1.35 (9H, m); MS (ES+) m/z: 529 (M+H); LC retention time: 3.37 min (analytical HPLC Method A).

Examples 15-19

Examples 15-19 were prepared using the acid from Step 6 of Example 14 in the manner described above for the preparation of the title compound of Example 14, using commercially available boronic acids and 2-amino-1,3,4-thiadiazole. The synthesis of the boronic acid for Example 18 is described below the table.

| Ex # | Structure | ¹H NMR (400 MHz) δ ppm | RT (min) | Obs. MS Ion |
|---|---|---|---|---|
| 15 | 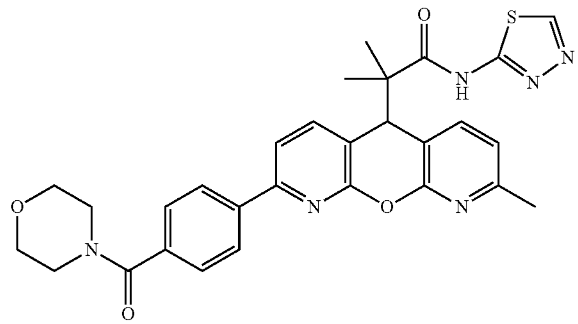 | Methanol-d4: 9.13 (1 H, s), 8.15-8.31 (2 H, m), 8.04-8.17 (2 H, m), 7.74-7.87 (2 H, m), 7.60-7.73 (1 H, m), 6.95-7.24 (1 H, m), 4.67 (1 H, s), 2.67 (3 H, s), 2.54 (3 H, s), 1.20 (6 H, s). | 3.17 | 557 |
| 16 | 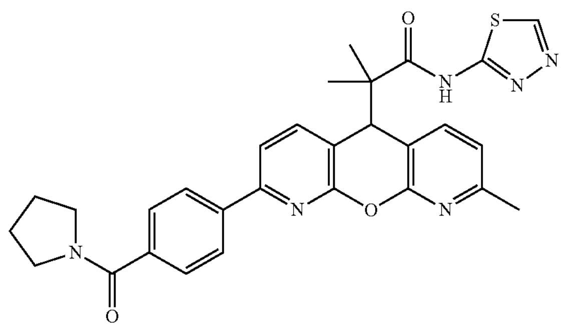 | Methanol-d4: 9.11 (1 H, s), 8.14 (2 H, d, J = 8.31 Hz), 7.76 (2 H, s), 7.56-7.72 (3 H, m), 7.13 (1 H, d, J = 7.55 Hz), 4.65 (1 H, s), 3.60 (2 H, d, J = 7.05 Hz), 3.54-3.70 (2 H, m), 3.44-3.54 (2 H, m), 2.47-2.58 (3 H, m), 1.83-2.14 (4 H, m), 1.18 (6 H, s). | 3.29 | 541 |
| 17 | 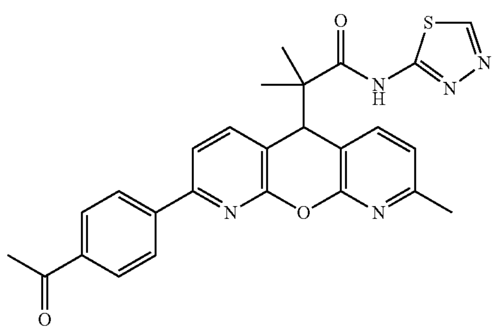 | Methanol-d4: 9.13 (1 H, s), 8.15-8.31 (2 H, m), 8.04-8.17 (2 H, m), 7.74-7.87 (2 H, m), 7.60-7.73 (1 H, m), 6.95-7.24 (1 H, m), 4.67 (1 H, s), 2.67 (3 H, s), 2.54 (3 H, s), 1.20 (6 H, s). | 3.44 | 486 |
| 18 | 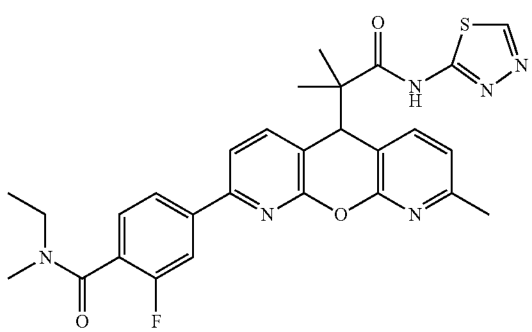 | Methanol-d4: 9.08 (1 H, s), 7.80-8.21 (2 H, m), 7.75 (2 H, s), 7.60 (1 H, d, J = 7.81 Hz), 7.45 (1 H, dd, J = 7.30, 2.77 Hz), 7.09 (1 H, d, J = 7.55 Hz), 4.63 (1 H, s), 3.19-3.78 (2 H, m), 2.81-3.21 (3 H, m), 2.48 (3 H, s), 0.81-1.57 (9 H, m). | 3.45 | 547 |
| 19 | 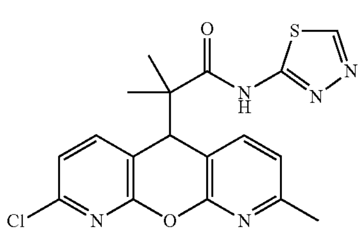 | Methanol-d4: 9.09 (1 H, s), 7.68 (1 H, d, J = 8.06 Hz), 7.59 (1 H, d, J = 7.55 Hz), 7.24 (1 H, d, J = 7.81 Hz), 7.10 (1 H, d, J = 7.55 Hz), 4.60 (1 H, s), 2.48 (3 H, s), 1.00-1.26 (6 H, m). | 3.10 | 402 |

Synthesis of 4-(ethyl(methyl)carbamoyl)-3-fluorophenylboronic acid

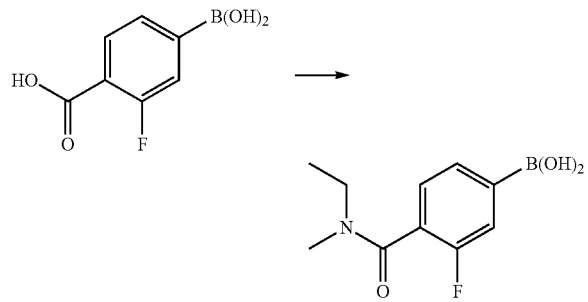

N-Methylethanamine (1.5 mL, 17.46 mmol) was added to a DMF (10 mL) solution (sonicated to help dissolve) of 4-borono-2-fluorobenzoic acid (1.13 g, 6.14 mmol) and O-(7-azabenzotriazol-1-yl)-N,N,N',N'-tetramethyluronium hexafluorophosphate (2.54 g, 6.68 mmol). After 3 h at room temperature, saturated NH₄Cl (50 mL) and water (10 mL) were added. The mixture was acidified to pH 3 with concentrated HCl (~0.5 mL). The mixture was extracted with ethyl acetate (3×50 mL). The combined extracts were washed with brine (5 mL), dried (MgSO₄) and concentrated to give a thick brown oil, which was treated with water (7 mL) and allowed to stand overnight. The white needles were removed by filtration. The filtrate was purified by reverse phase HPLC (Sunfire S10 30×250 mm column, 30-50% solvent B gradient) to give the expected product as white glassy solid (1.1036 g, 80% yield). LC retention time: 2.49 min (analytical HPLC Method A).

Example 20

2-(2-(dimethylamino)-8-methyl-5H-pyrido[3',2':5,6]pyrano[2,3-b]pyridin-5-yl)-2-methyl-N-1,3,4-thiadiazol-2-ylpropanamide

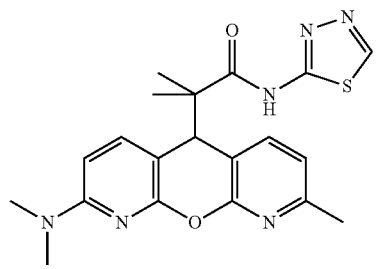

Step 1

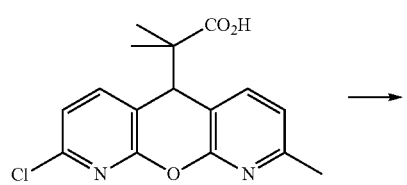

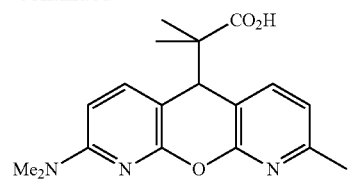

A mixture of the acid from Step 6 of Example 14 (30 mg, 0.094 mmol), 40% aqueous dimethylamine (0.5 mL, 3.99 mmol) in CH₃CN (0.5 mL) and MeOH (0.5 mL) was microwaved at 150° C. for 1 h, cooled to room temperature and concentrated. The residue was purified by reverse phase HPLC (Sunfire S10 30×250 mm column, 20-100% solvent B gradient) to provide the expected product as TFA salt (20 mg, 48% yield). MS (ES+) m/z: 328 (M+H); LC retention time: 3.16 min (analytical HPLC Method A).

Step 2

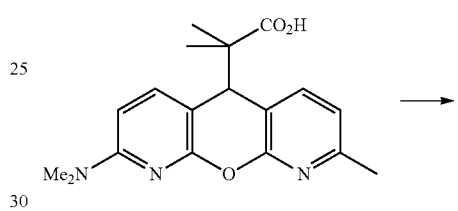

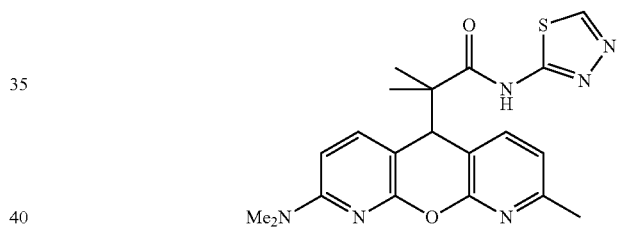

A mixture of the acid from Step 1 (20 mg, 0.045 mmol), 1,3,4-thiadiazol-2-amine (9.16 mg, 0.091 mmol), N-(3-dimethylaminopropyl)-N'-ethylcarbodiimide hydrochloride (17.37 mg, 0.091 mmol), 1-hydroxybenzotriazole hydrate (13.88 mg, 0.091 mmol) and N,N-diisopropylethylamine (0.040 mL, 0.227 mmol) in CH₃CN (2 mL) was heated to 80° C. After 6 h at 80° C., the mixture was concentrated and purified by reverse phase HPLC (Sunfire S10 30×250 mm column, 20-100% solvent B gradient) to provide the expected product, assumed as tris-TFA salt (5 mg, 15% yield). ¹H NMR (400 MHz, methanol-d4) δ ppm 9.09 (1H, s), 7.62 (1H, d, J=7.55 Hz), 7.38 (1H, d, J=8.56 Hz), 7.08 (1H, d, J=7.81 Hz), 6.42 (1H, d, J=8.56 Hz), 4.43 (1H, s), 3.07 (6H, s), 2.50 (3H, s), 1.07-1.20 (6H, m); MS (ES+) m/z: 411 (M+H); LC retention time: 3.30 min (analytical HPLC Method A).

Examples 21-35

Examples 21-35 were prepared using the S-enantiomer from Step 7 of Example 14 in the manner described above for the preparation of the title compound of Example 14, using commercially available boronic acids and amines.

| Ex # | Structure | ¹H NMR (400 MHz) δ ppm | RT (min) | Obs. MS Ion |
|---|---|---|---|---|
| 21 | 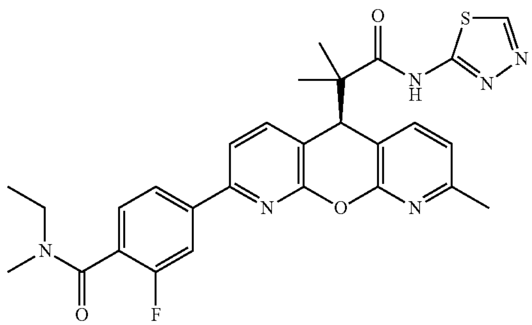 | Chloroform-d: 1:1 mixture of two tautomers 8.89 (s, 2 H), 7.82-7.90 (m, 4 H), 7.61-7.66 (m, 2 H), 7.55 (dd, J = 7.81, 2.52 Hz, 2 H), 7.47-7.51 (m, 2 H), 7.40-7.47 (m, 2 H), 6.97-7.03 (m, 2 H), 4.58 (s, 2 H), 3.65 (q, J = 7.05 Hz, 2 H), 3.29 (q, J = 6.97 Hz, 2 H), 3.14 (s, 3 H), 2.96 (d, J = 1.26 Hz, 3 H), 2.56 (s, 6 H), 1.26-1.31 (m, 3 H), 1.25 (s, 6 H), 1.24 (s, 6 H), 1.14 (t, J = 7.05 Hz, 3 H) | 3.63 | 547 |
| 22 | 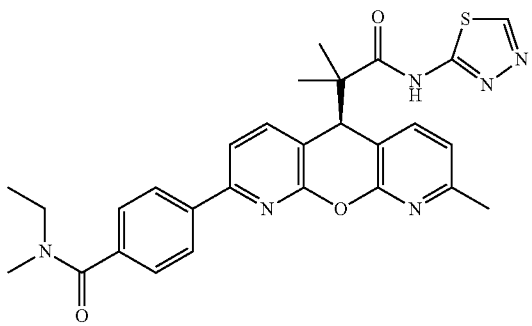 | Methanol-d4: 9.10 (1 H, s), 8.14 (2 H, d, J = 8.31 Hz), 7.74 (2 H, s), 7.59 (2 H, d, J = 7.81 Hz), 7.50 (2 H, t, J = 8.18 Hz), 7.08 (1 H, d, J = 7.81 Hz), 4.63 (1 H, s), 3.30-3.71 (2 H, m), 2.93-3.14 (3 H, m), 2.49 (3 H, s), 1.06-1.33 (9 H, m). | 3.28 | 529 |
| 23 | 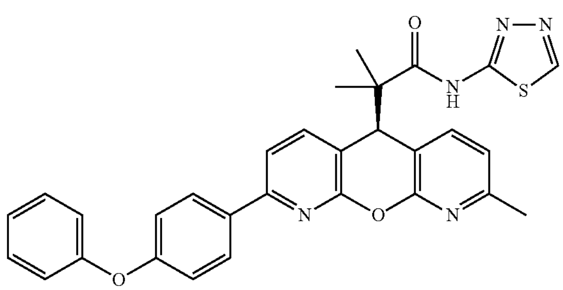 | Chloroform-d: 12.23 (1 H, br. s), 8.89 (1 H, s), 8.01 (2 H, d, J = 8.52 Hz), 7.60 (1 H, d, J = 7.97 Hz), 7.53 (2 H, t, J = 8.52 Hz), 7.37 (2 H, t, J = 7.70 Hz), 7.15 (1 H, t, J = 7.42 Hz), 7.07 (4 H, dd, J = 8.11, 4.54 Hz), 7.01 (1 H, d, J = 7.42 Hz), 4.58 (1 H, s), 2.58 (3 H, s), 1.26 (3 H, s), 1.24 (3 H, s) | 4.26 | 536 |
| 24 | 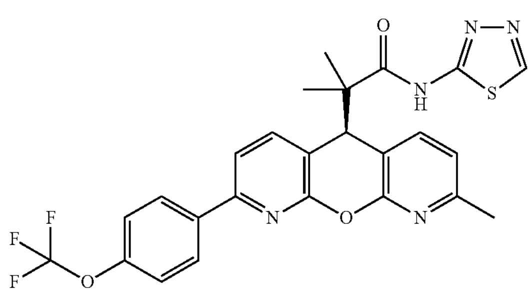 | Chloroform-d: 8.89 (1 H, s), 8.08 (2 H, d), 7.63 (1 H, d, J = 7.97 Hz), 7.52-7.58 (2 H, m), 7.31 (2 H, d, J = 7.97 Hz), 7.02 (1 H, d, J = 7.70 Hz), 4.58 (1 H, s), 2.58 (3 H, s), 1.26 (3 H, s), 1.25 (3 H, s) | 4.21 | 528 |
| 25 | 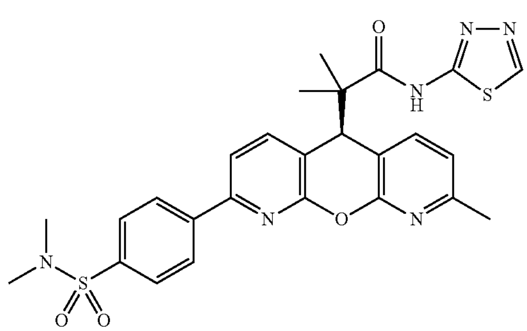 | Chloroform-d: 8.90 (1 H, s), 8.22 (2 H, d, J = 8.52 Hz), 7.87 (2 H, d, J = 8.52 Hz), 7.66-7.72 (1 H, m), 7.60-7.66 (1 H, m), 7.55 (1 H, d, J = 7.70 Hz), 7.03 (1 H, d, J = 7.70 Hz), 4.62 (1 H, s), 2.74 (6 H, s), 2.58 (3 H, s), 1.27 (3 H, s), 1.26 (3 H, s) | 3.57 | 551 |

-continued

| Ex # | Structure | ¹H NMR (400 MHz) δ ppm | RT (min) | Obs. MS Ion |
|---|---|---|---|---|
| 26 | 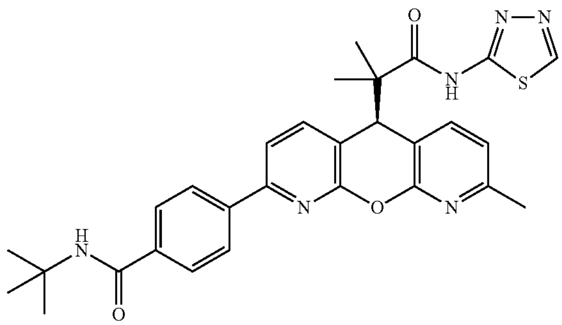 | Chloroform-d: 8.89 (1 H, s), 8.11 (2 H, d, J = 8.25 Hz), 7.79 (2 H, d, J = 8.52 Hz), 7.62-7.67 (1 H, m), 7.57-7.62 (1 H, m), 7.51 (1 H, d, J = 7.70 Hz), 7.00 (1 H, d, J = 7.70 Hz), 6.14 (1 H, s), 4.60 (1 H, s), 2.57 (3 H, s), 1.51 (9 H, s), 1.27 (3 H, s), 1.25 (3 H, s) | 3.83 | 543 |
| 27 | 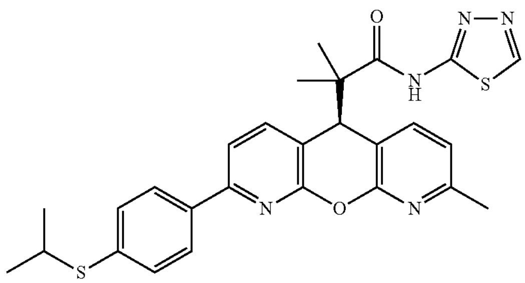 | Chloroform-d: 8.88 (1 H, s), 7.98 (2 H, d, J = 8.25 Hz), 7.57-7.62 (1 H, m), 7.52-7.56 (1 H, m), 7.49 (1 H, d, J = 7.70 Hz), 7.44 (2 H, d, J = 8.52 Hz), 6.99 (1 H, d, J = 7.70 Hz), 4.57 (1 H, s), 3.44-3.53 (1 H, m), 2.57 (3 H, s), 1.34 (6 H, d, J = 6.60 Hz), 1.25 (3 H, s), 1.23 (3 H, s) | 4.37 | 518 |
| 28 | 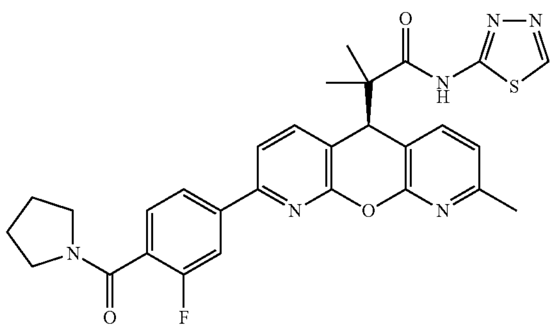 | Methanol-d4: 9.00 (1 H, s), 7.79-8.00 (2 H, m), 7.62-7.73 (2 H, m), 7.51 (1 H, d, J = 7.55 Hz), 7.35-7.47 (1 H, m), 7.00 (1 H, d, J = 7.55 Hz), 4.54 (1 H, s), 3.52 (2 H, t, J = 6.80 Hz), 3.28 (2 H, t, J = 6.55 Hz), 2.40 (3 H, s), 1.76-2.04 (4 H, m), 1.07 (6 H, s). | 3.39 | 559 |
| 29 | 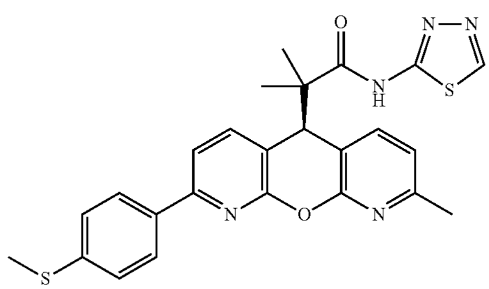 | Methanol-d4: 9.09 (1 H, s), 7.94 (2 H, d, J = 8.80 Hz), 7.51-7.73 (3 H, m), 7.29 (2 H, d, J = 8.52 Hz), 7.05 (1 H, d, J = 7.70 Hz), 4.57 (1 H, s), 2.49 (3 H, s), 2.48 (3 H, s), 1.09-1.17 (6 H, m). | 3.73 | 490 |
| 30 | 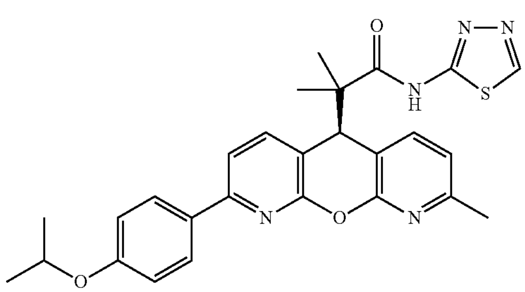 | Methanol-d4: 9.05 (1 H, s), 7.87-7.99 (2 H, m), 7.60-7.67 (1 H, m), 7.54 (2 H, dd, J = 7.70, 4.67 Hz), 7.02 (1 H, d, J = 7.70 Hz), 6.93 (2 H, d, J = 8.80 Hz), 4.57-4.73 (1 H, m), 4.55 (1H, s), 2.44 (3 H, s), 1.29 (6 H, d, J = 6.05 Hz), 1.11 (6 H, d, J = 6.87 Hz). | 3.82 | 502 |

| Ex # | Structure | ¹H NMR (400 MHz) δ ppm | RT (min) | Obs. MS Ion |
|---|---|---|---|---|
| 31 | 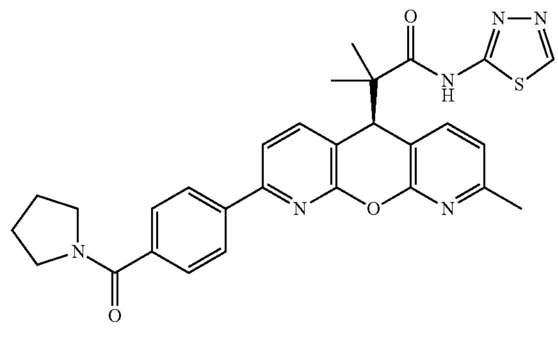 | Methanol-d4: 9.08 (1 H, s), 8.12 (2 H, d, J = 8.56 Hz), 7.73 (2 H, d, J = 1.51 Hz), 7.54-7.67 (3 H, m), 7.07 (1 H, d, J = 7.55 Hz), 4.64 (1 H, s), 3.42-3.70 (4 H, m), 2.49 (3 H, s), 1.78-2.09 (4 H, m), 1.06-1.23 (6 H, m). | 3.41 | 41 |
| 32 | 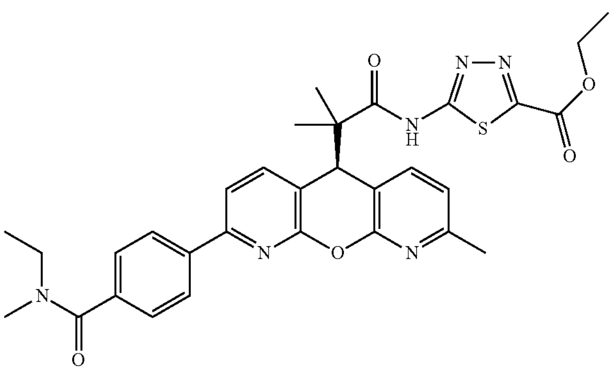 | Methanol-d4: 8.15 (2 H, d, J = 8.25 Hz), 7.75 (2 H, s), 7.61 (1 H, d, J = 7.70 Hz), 7.51 (2 H, t, J = 9.35 Hz), 7.10 (1 H, d, J = 7.15 Hz), 4.64 (1 H, s), 4.40-4.53 (2 H, m), 3.52-3.69 (1 H, m), 3.32-3.43 (1 H, m), 2.97-3.18 (3 H, m), 2.50 (3 H, s), 1.43 (3 H, t, J = 7.15 Hz), 1.08-1.31 (9 H, m). | 3.6 | 601 |
| 33 | 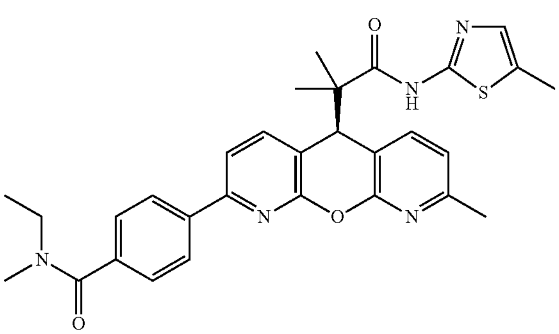 | Chloroform-d: 1:1 mixture of two tautomers 8.07 (4 H, d, J = 8.25 Hz), 7.56-7.67 (6 H, m), 7.46-7.55 (4 H, m), 7.27 (2 H, s), 7.08 (2 H, d, J = 7.70 Hz), 4.67 (2 H, s), 3.65 (2 H, q, J = 6.87 Hz), 3.35 (2 H, q, J = 6.78 Hz), 3.15 (3 H, s), 3.01 (3 H, s), 2.61 (6 H, s), 2.50 (6 H, s), 1.29 (3 H, t, J = 7.01 Hz), 1.20 (6 H, s), 1.19 (6 H, s), 1.17 (3 H, t, J = 7.01 Hz). | 3.95 | 52 |

| Ex # | Structure | $^1$H NMR (400 MHz) δ ppm | RT (min) | Obs. MS Ion |
|---|---|---|---|---|
| 34 | 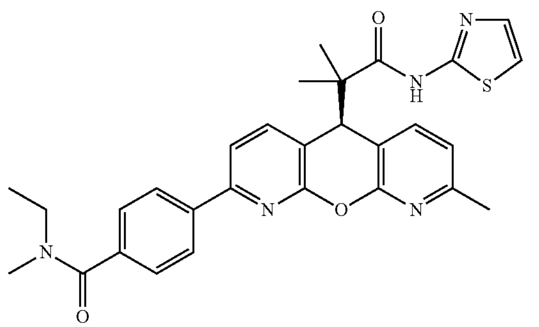 | Chloroform-d: 1:1 mixture of two tautomers 8.08 (4 H, d, J = 8.25 Hz), 7.56-7.66 (8 H, m), 7.45-7.54 (4 H, m), 7.21 (2 H, d, J = 4.40 Hz), 7.07 (2 H, d, J = 7.70 Hz), 4.68 (2 H, s), 3.65 (2 H, q, J = 6.87 Hz), 3.35 (2 H, q, J - 6.87 Hz), 3.15 (3 H, s), 3.01 (3 H, s), 2.61 (6 H, s), 1.29 (3 H, t, J = 7.15 Hz), 1.22 (6 H, br. s.), 1.21 (6 H, br. s.), 1.18 (3 H, t) | 3.79 | 528 |
| 35 | 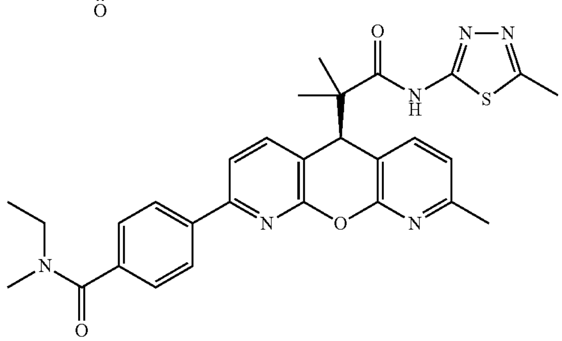 | Chloroform-d: 1:1 mixture of two tautomers 8.08 (d, J = 8.31 Hz, 4 H), 7.54-7.68 (m, 6 H), 7.50 (t, J = 8.06 Hz, 4 H), 7.05 (d, J = 7.81 Hz, 2 H), 4.57 (s, 2 H), 3.65 (q, J = 7.05 Hz, 2 H), 3.35 (q, J = 6.97 Hz, 2 H), 3.15 (s, 3 H), 3.01 (s, 3 H), 2.76 (s, 6 H), 2.59 (s, 6 H), 1.29 (t, J = 7.05 Hz, 3 H), 1.24 (s, 6 H), 1.23 (s, 6 H), 1.18 (t, J = 7.05 Hz, 3 H) | 3.73 | 543 |

Example 36

(4-((5S)-5-(1,1-dimethyl-2-oxo-2-(1,3,4-thiadiazol-2-ylamino)ethyl)-8-methyl-5H-pyrido[3',2':5,6]pyrano[2,3-b]pyridin-2-yl)phenyl)(methyl)sulfoniumolate A solution of oxone (37.7 mg, 0.061 mmol) in water (1 mL) was added dropwise to a solution of Example 29 (30 mg, 0.061 mmol) in MeOH (1 mL) at 0° C. After 1 h, the mixture was quench with saturated Na$_2$SO$_3$ (1 mL), diluted with EtOAc (60 mL), washed with saturated NaHCO$_3$ (2×5 mL), brine (5 mL), dried (MgSO$_4$) and concentrated to give Example 36 as white solid (29 mg, 94% yield). $^1$H NMR (400 MHz, methanol-d4) δ ppm 9.02 (1H, s), 8.24 (2H, d, J=8.56 Hz), 7.69-7.87 (4H, m), 7.58 (1H, d, J=7.55 Hz), 7.05 (1H, d, J=7.55 Hz), 4.63 (1H, s), 2.81 (3H, s), 2.46 (3H, s), 1.12 (6H, s); MS (ES+) m/z: 506 (M+H); LC retention time: 3.09 min (analytical HPLC Method A).

Example 37

2-methyl-2-((5S)-2-methyl-8-(4-(methylsulfonyl)phenyl)-5H-pyrido[3',2':5,6]pyrano[2,3-b]pyridin-5-yl)-N-1,3,4-thiadiazol-2-ylpropanamide

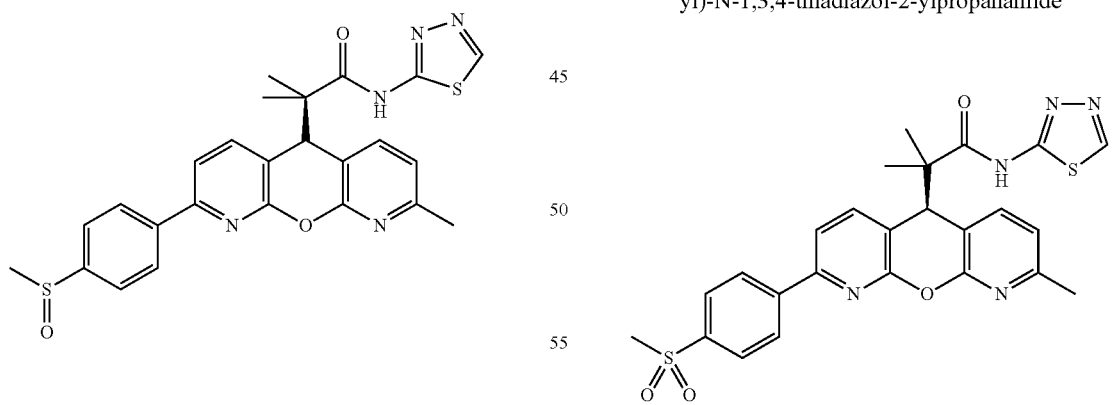

A solution of oxone (43.8 mg, 0.071 mmol) in water (1 mL) was added dropwise to a solution of Example 36 (18 mg, 0.036 mmol) in MeOH (1 mL) at room temperature. After 3 h, the mixture was quench with saturated Na$_2$SO$_3$ (1 mL), diluted with EtOAc (60 mL), washed with saturated NaHCO$_3$ (2×5 mL), brine (5 mL), dried (MgSO$_4$) and concentrated to give Example 37 as white solid (17 mg, 92% yield). $^1$H NMR (400 MHz, methanol-d4) δ ppm 9.10 (1H, s), 8.26 (2H, d, J=8.56 Hz), 8.01 (2H, d, J=8.56 Hz), 7.69-7.83 (2H, m, J=5.79 Hz), 7.59 (1H, d, J=7.81 Hz), 7.08 (1H, d, J=7.55 Hz), 4.62 (1H, s), 3.17 (3H, s), 2.49 (3H, s), 1.16 (6H, d, J=3.02 Hz); MS (ES+) m/z: 522 (M+H); LC retention time: 3.12 min (analytical HPLC Method A).

Examples 38-42

Examples 38-42 were prepared using the S-enantiomer from Step 7 of Example 14 in the manner described above for the preparation of the title compound of Example 14. Synthesis of the prerequisite boronic acids were described below the table.

| Ex # | Structure | $^1$H NMR (400 MHz) δ ppm | RT (min) | Obs. MS Ion |
|---|---|---|---|---|
| 38 | 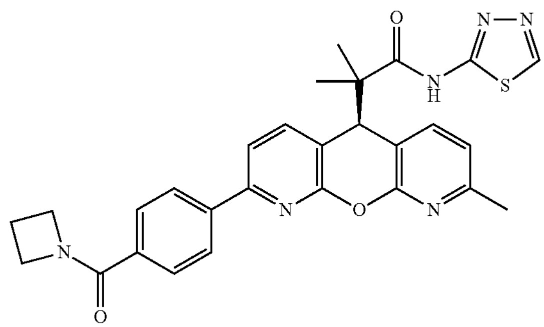 | Chloroform-d: 8.91 (1 H, s), 8.10 (2 H, d, J = 8.52 Hz), 7.71 (2 H, d, J = 8.25 Hz), 7.68 (1 H, d, J = 7.97 Hz), 7.59 (1 H, d, J = 7.97 Hz), 7.54 (1 H, d, J = 7.70 Hz), 7.00 (1 H, d, J = 7.42 Hz), 4.69 (1 H, s), 4.40 (2 H, t, J = 6.87 Hz), 4.30 (2 H, t, J = 7.15 Hz), 2.56 (3 H, s), 2.40 (2 H, quin, J = 7.84 Hz), 1.27 (3 H, s), 1.26 (3 H, s) | 3.53 | 527 |
| 39 | 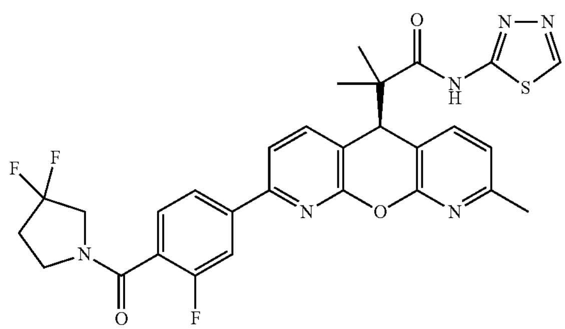 | Methanol-d4: 9.10 (1 H, s), 7.89-8.28 (2 H, m), 7.71-7.83 (2 H, m), 7.44-7.68 (2 H, m), 7.09 (1 H, d, J = 7.81 Hz), 4.63 (1 H, s), 3.59-4.18 (4 H, m), 2.39-2.60 (5 H, m), 1.16 (6 H, s). | 3.18 | 595 |
| 40 | 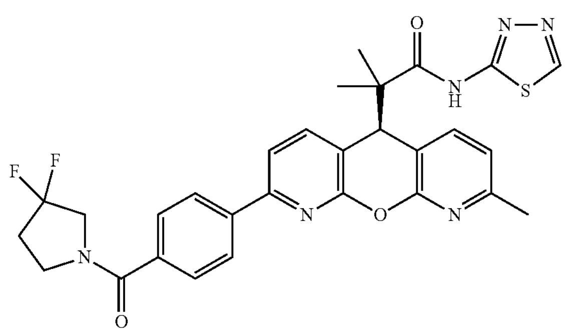 | Methanol-d4: 9.10 (1 H, s), 8.13 (2 H, d, J = 7.81 Hz), 7.72 (2 H, s), 7.52-7.68 (3 H, m), 7.07 (1 H, d, J = 7.55 Hz), 4.62 (1 H, s), 3.64-4.07 (4 H, m), 2.46-2.60 (3 H, m), 2.34-2.50 (2 H, m), 1.16 (6 H, s). | 3.37 | 577 |
| 41 | 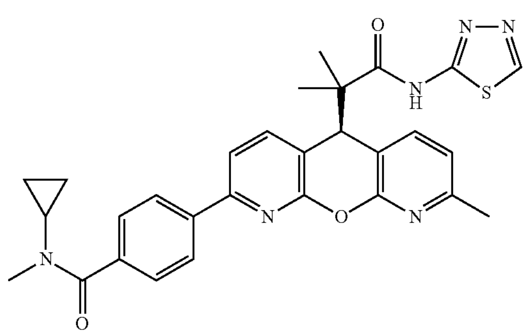 | Chloroform-d: 8.90 (s, 1 H), 8.09 (d, J = 8.31 Hz, 2 H), 7.56-7.64 (m, 4 H), 7.50 (d, J = 7.81 Hz, 1 H), 7.00 (d, J = 7.55 Hz, 1 H), 4.59 (s, 1 H), 3.16 (br s, 3 H), 2.82-2.94 (m, 1 H), 2.56 (s, 3 H), 1.25 (s, 3 H), 1.23 (s, 3 H), 0.64 (br s, 2 H), 0.48 (br s, 2 H) | 3.65 | 541 |

| Ex # | Structure | ¹H NMR (400 MHz) δ ppm | RT (min) | Obs. MS Ion |
|---|---|---|---|---|
| 42 | 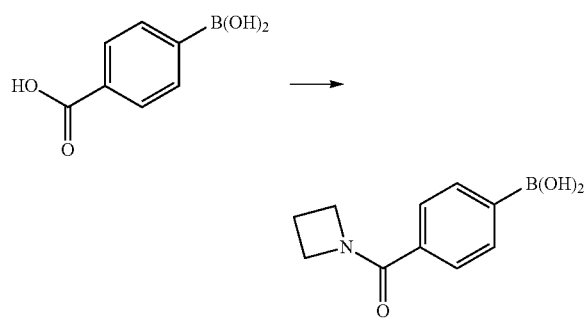 | Chloroform-d: 8.89 (s, 1 H), 7.82-7.92 (m, 2 H), 7.62-7.67 (m, 1 H), 7.47-7.59 (m, 3 H), 7.02 (d, J = 7.55 Hz, 1 H), 4.57 (s, 1 H), 3.77-3.91 (m, 4 H), 3.69 (br s, 2 H), 3.41 (br s, 2 H), 2.57 (s, 3 H), 1.25 (s, 3 H), 1.24 (s, 3 H) | 3.49 | 575 |

Synthesis of 4-(azetidine-1-carbonyl)phenylboronic acid

A solution of 4-boronobenzoic acid (527.4 mg, 3.18 mmol), O-(7-azabenzotriazol-1-yl)-N,N,N',N'-tetramethyluronium hexafluorophosphate (1.61 g, 4.23 mmol) and N,N-diisopropylethylamine (1.665 mL, 9.53 mmol) in CH₃CN (40 mL) was stirred at room temperature for 30 min. Azetidine (0.321 mL, 4.76 mmol) was added. After stirring for 3 days, the mixture was concentrated and purified by reverse phase HPLC (Sunfire S10 30×250 mm column, 10-40% solvent B gradient) to give the expected product as white solid (361 mg, 55% yield). ¹H NMR (500 MHz, methanol-d4) δ ppm 7.68 (2H, d, J=7.70 Hz), 7.60 (2H, d, J=7.97 Hz), 4.37 (2H, t, J=7.56 Hz), 4.19 (2H, t, J=7.84 Hz), 2.36 (2H, quin); MS (ES+) m/z: 206 (M+H); LC retention time: 2.01 min (analytical HPLC Method A).

Synthesis of 4-(3,3-difluoropyrrolidine-1-carbonyl)-3-fluorophenylboronic acid

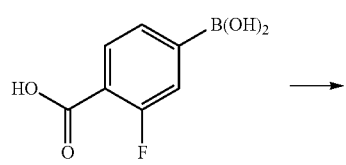

A solution of 4-borono-2-fluorobenzoic acid (1.00 g, 5.44 mmol), N,N-diisopropylethylamine (2.85 mL, 16.31 mmol), O-(7-azabenzotriazol-1-yl)-N,N,N',N'-tetramethyluronium hexafluorophosphate (2.163 g, 5.69 mmol) and 3,3-difluoropyrrolidine hydrochloride (1.00 g, 6.97 mmol) in DMF (6 mL) was stirred at room temperature for 22 h. Following addition of 1 N HCl (16 mL), the mixture was extracted with ethyl acetate (40 mL). HPLC analysis showed that the aqueous phase still contained product. The aqueous phase was neutralized to pH 7 with solid NaOH and K₂CO₃ and extracted with ethyl acetate. The combined extracts were dried (MgSO₄) and concentrated to give a thick brown oil. This residue was treated with equal volume of water. The white crystalline solid formed from the mixture was collected by filtration and washed with small amount of ether to give the desired product (0.7811 g). The filtrate was purified by reverse phase HPLC (Sunfire S10 30×250 mm column, 30-50% solvent B gradient) to give additional product (0.5632 g). The combined yield of the product was 1.344 g (91% yield). MS (ES+) m/z: 274 (M+H); LC retention time: 2.68 min (analytical HPLC Method A).

Synthesis of 4-(3,3-difluoropyrrolidine-1-carbonyl) phenylboronic acid

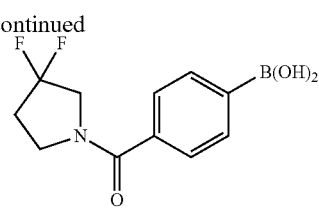

A mixture of 4-boronobenzoic acid (500 mg, 3.01 mmol), N-(3-dimethylaminopropyl)-N'-ethylcarbodiimide hydrochloride (866 mg, 4.52 mmol) and 1-hydroxybenzotriazole (554 mg, 3.62 mmol) in acetonitrile (25 mL) was sonicated until it became a solution. N,N-Diisopropylethylamine (1.579 mL, 9.04 mmol) and 3,3-difluoropyrrolidine (484 mg, 4.52 mmol) were added. After 30 min at room temperature, the mixture was quenched with saturated $NH_4Cl$ (50 mL) and extracted with EtOAc (3×). The combined extracts were washed with brine, water, dried ($Na_2SO_4$) and concentrated. Reverse phase HPLC purification gave the expected product (0.250 mg, 33% yield). MS (ES+) m/z: 256 (M+H); LC retention time: 1.87 min (analytical HPLC Method A).

4-(cyclopropyl(methyl)carbamoyl)phenylboronic acid

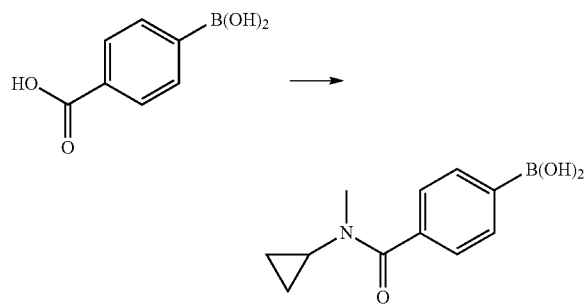

N,N-Diisopropylethylamine (1.693 mL, 9.69 mmol) was added to a suspension of 4-boronobenzoic acid (321.7 mg, 1.939 mmol) and O-(7-azabenzotriazol-1-yl)-N,N,N',N'-tetramethyluronium hexafluorophosphate (806.4 mg, 2.121 mmol) in $CH_3CN$ (20 mL). After 50 min at room temperature, N-methylcyclopropanamine oxalic acid salt (315.8 mg, 1.960 mmol) was added. After 1.25 h at room temperature, the mixture was purified by reverse phase HPLC (Sunfire S10 30×250 mm column, 30-50% solvent B gradient) to give the expected product (303.6 mg, 72% yield). MS (ES+) m/z: 220 (M+H); LC retention time: 2.40 min (analytical HPLC Method A).

3-fluoro-4-(morpholine-4-carbonyl)phenylboronic acid

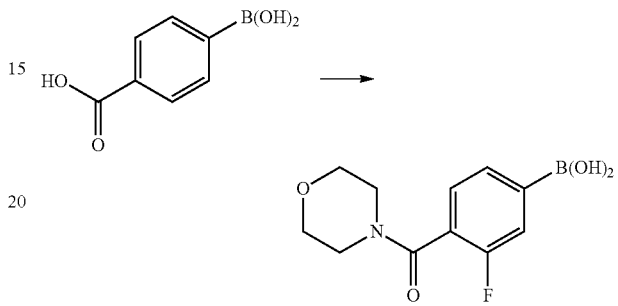

A solution of 4-borono-2-fluorobenzoic acid (1.000 g, 5.44 mmol), morpholine (0.951 mL, 10.87 mmol) and O-(7-azabenzotriazol-1-yl)-N,N,N',N'-tetramethyluronium hexafluorophosphate (2.103 g, 5.53 mmol) in DMF (10 mL) was stirred at room temperature for 16 h and quenched with 1 N HCl (20 mL). Attempted extraction with EtOAc did not remove all of the product from aqueous phase. The two phases were combined, concentrated and purified by reverse phase HPLC (Sunfire S10 30×250 mm column, 30-45% solvent B gradient) to give the expected product as white solid (1.2385 g, 90% yield). MS (ES+) m/z: 254 (M+H); LC retention time: 2.06 min (analytical HPLC Method A).

Examples 43-48

Examples 43-48 were prepared using the S-enantiomer from Step 7 of Example 14 in the manner described above for the preparation of the title compound of Example 14. Synthesis for most of the prerequisite aminothiazoles were described below the table. The amino thiadiazole for Examples 43 and 44 were described below the table of Examples 4-7.

| Ex # | Structure | $^1$H NMR (400 MHz) δ ppm | RT (min) | Obs. MS Ion |
|---|---|---|---|---|
| 43 | 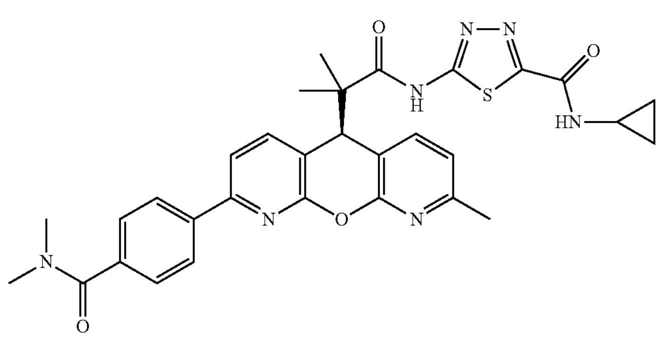 | Chloroform-d: 8.04 (d, J = 8.31 Hz, 2 H), 7.71-7.77 (m, 1 H), 7.62 (d, J = 7.81 Hz, 1 H), 7.47-7.58 (m, 4 H), 6.97 (d, J = 7.55 Hz, 1 H), 4.58 (s, 1 H), 3.19 (s, 3 H), 3.05 (s, 3 H), 2.94-3.03 (m, 1 H), 2.53 (s, 3 H), 1.26 (s, 3 H), 1.24 (s, 3 H), 0.93-0.98 (m, 2 H), 0.83-0.93 (m, 2 H) | 3.67 | 598 |

-continued

| Ex # | Structure | ¹H NMR (400 MHz) δ ppm | RT (min) | Obs. MS Ion |
|---|---|---|---|---|
| 44 | 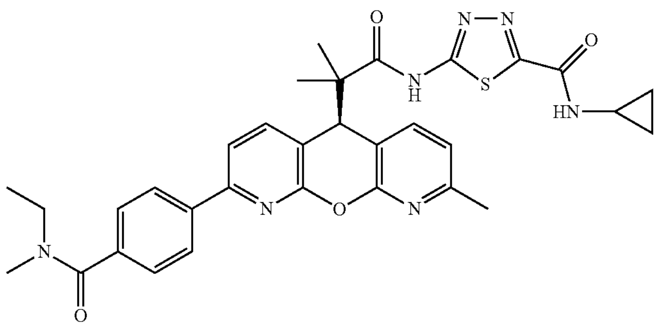 | Chloroform-d: 1:1 mixture of two tautomers 8.03 (d, J = 8.31 Hz, 4 H), 7.70 (d, J = 2.01 Hz, 2 H), 7.63 (d, J = 7.81 Hz, 2 H), 7.55 (d, J = 7.55 Hz, 4 H), 7.50 (t, J = 7.81 Hz, 4 H), 7.00 (d, J = 7.81 Hz, 2 H), 4.59 (s, 2 H), 3.65 (q, J = 7.05 Hz, 2 H), 3.34 (q, J = 6.63 Hz, 2 H), 3.15 (s, 3 H), 3.01 (s, 3 H), 2.94-3.00 (m, 2 H), 2.55 (s, 6 H), 1.30 (t, J = 7.05 Hz, 3 H), 1.26 (s, 6 H), 1.24 (s, 6 H), 1.18 (t, J = 7.05 Hz, 3 H), 0.91-0.99 (m, 4 H), 0.81-0.90 (m, 4 H). | 3.81 | 612 |
| 45 | 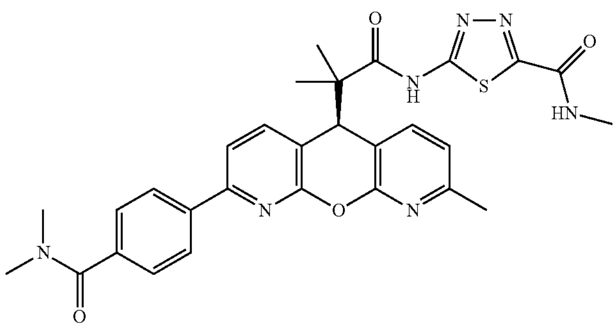 | Chloroform-d: 7.99 (d, J = 8.31 Hz, 2 H), 7.84 (q, J = 4.78 Hz, 1 H), 7.61 (d, J = 7.81 Hz, 1 H), 7.46-7.57 (m, 4 H), 6.99 (d, J = 7.55 Hz, 1 H), 4.61 (s, 1 H), 3.18 (s, 3 H), 3.13 (d, J = 4.78 Hz, 3 H), 3.05 (s, 3 H), 2.54 (s, 3 H), 1.26 (s, 6 H) | 3.54 | 572 |
| 46 | 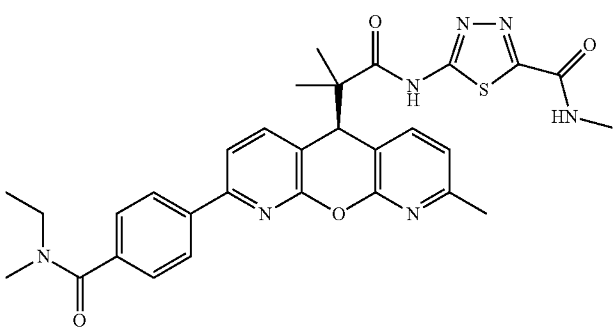 | Chloroform-d: 1:1 mixture of two tautomers 8.02 (d, J = 8.31 Hz, 4 H), 7.64 (dd, J = 7.68, 4.91 Hz, 4 H), 7.56 (d, J = 7.81 Hz, 2 H), 7.50 (t, J = 7.81 Hz, 6 H), 7.07 (d, J = 7.55 Hz, 2 H), 4.62 (s, 2 H), 3.66 (q, J = 7.05 Hz, 2 H), 3.35 (q, J = 7.30 Hz, 2 H), 3.15 (s, 3 H), 3.10 (d, J = 5.04 Hz, 6 H), 3.02 (s, 3 H), 2.60 (s, 6 H), 1.30 (t, J = 7.05 Hz, 3 H), 1.26 (s, 12 H), 1.19 (t, J = 7.05 Hz, 3 H) | 3.67 | 58 |
| 47 | 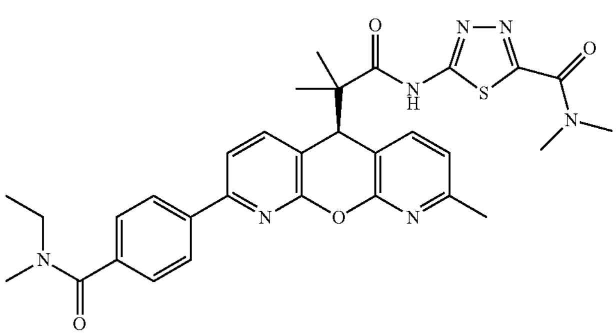 | Methanol-d: 8.08 (2 H, d, J = 8.25 Hz), 7.62-7.74 (2 H, m), 7.55 (1 H, d, J = 7.70 Hz), 7.44 (2 H, t, J = 8.94 Hz), 7.01 (1 H, d, J = 7.70 Hz), 4.61 (1 H, s), 3.47-3.63 (1 H, m), 3.45 (3 H, s), 3.26-3.36 (1 H, m), 3.10 (3 H, s), 2.89-3.05 (3 H, m), 2.35-2.50 (3 H, m), 1.13-1.30 (3 H, m), 1.07 (6 H, s). | 3.44 | 600 |

| Ex # | Structure | ¹H NMR (400 MHz) δ ppm | RT (min) | Obs. MS Ion |
|---|---|---|---|---|
| 48 | 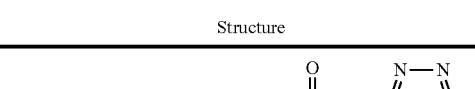 | Methanol-d: 8.10 (2 H, d, J = 7.97 Hz), 7.70 (2 H, s), 7.56 (1 H, d, J = 7.70 Hz), 7.46 (2 H, t, J = 9.07 Hz), 7.05 (1 H, d, J = 7.70 Hz), 4.59 (1 H, s), 3.49-3.64 (1 H, m), 3.34-3.46 (2 H, m), 3.27-3.36 (1 H, m), 3.00 (3 H, d), 2.45 (3 H, s), 1.15-1.33 (6 H, m), 1.08-1.16 (6 H, m). | 3.42 | 600 |

Synthesis of
5-amino-N-methyl-1,3,4-thiadiazole-2-carboxamide

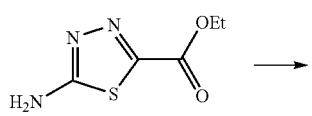

To a suspension of ethyl 5-amino-1,3,4-thiadiazole-2-carboxylate (106 mg, 0.612 mmol) in methanol (1.5 mL) was added 33 wt % ethanol solution of methylamine (0.5 mL, 4.00 mmol). The mixture was stirred at room temperature for 6 h, heated to 70° C. and cooled. The mixture was concentrated, mixed with water and lyophilized to give 5-amino-N-methyl-1,3,4-thiadiazole-2-carboxamide as a white solid (99 mg). ¹H NMR (400 MHz, DMSO-d6) δ ppm 8.69 (q, J=4.8 Hz, 1H), 7.70 (s, 2H) 2.73 (d, J=4.78 Hz, 3H); MS (ES+) m/z: 159 (M+H); LC retention time: 0.44 min (analytical HPLC Method A).

Synthesis of 5-amino-N,N-dimethyl-1,3,4-thiadiazole-2-carboxamide, TFA salt

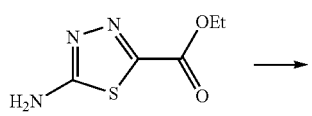

To a suspension of ethyl 5-amino-1,3,4-thiadiazole-2-carboxylate (200 mg, 1.155 mmol) in EtOH (3 mL) was added dimethylamine (1 mL, 7.90 mmol). The mixture was stirred at 90° C. for 2 h and concentrated. The residue was purified by reverse phase HPLC, using Sunfire S10 30×250 mm column and eluting with 0-40% solvent B (90% MeOH-10% H₂O-0.1% TFA) in solvent A (10% MeOH-90% H₂O-0.1% TFA) to provide the expected product as TFA salt (50 mg, 15% yield). MS (ES+) m/z: 173 (M+H); LC retention time: 0.66 min (analytical HPLC Method A).

Synthesis of
5-amino-N-ethyl-1,3,4-thiadiazole-2-carboxamide

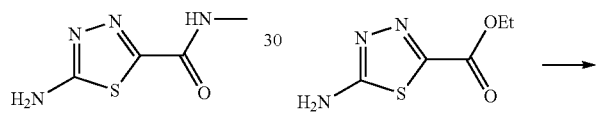

To a suspension of ethyl 5-amino-1,3,4-thiadiazole-2-carboxylate (200 mg, 1.155 mmol) in methanol (1.5 mL) was added a 70% aqueous solution of ethylamine (0.5 mL, 6.29 mmol). The mixture was stirred at room temperature overnight, concentrated, mixed with water and lyophilized to give 5-amino-N-ethyl-1,3,4-thiadiazole-2-carboxamide as a yellowish solid (200 mg). MS (ES+) m/z: 173 (M+H); LC retention time: 0.70 min (analytical HPLC Method A).

Example 49

N-cyclobutyl-5-((2-((5S)-2-(4-(ethyl(methyl)carbamoyl)phenyl)-8-methyl-5H-pyrido[3',2':5,6]pyrano[2,3-b]pyridin-5-yl)-2-methylpropanoyl)amino)-1,3,4-thiadiazole-2-carboxamide

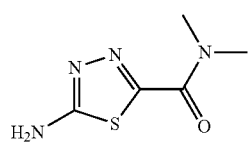

Cyclobutylamine (199 mg, 2.80 mmol) was added to a solution of Example 32 (20 mg, 0.028 mmol) in MeOH (1 mL). The mixture was stirred at room temperature for 15 h, at 60° C. for 5 h and concentrated. The residue was purified by reverse phase HPLC, using Sunfire S10 30×250 mm column and eluting with 40-100% solvent B (90% MeOH-10% $H_2O$-0.1% TFA) in solvent A (10% MeOH-90% $H_2O$-0.1% TFA). The product containing fractions were concentrated and diluted with ethyl acetate (60 mL), washed with saturated $NaHCO_3$ (2×5 mL), brine (5 mL), dried ($MgSO_4$) and concentrated to provide Example 49 as white solid (11 mg, 63% yield). $^1H$ NMR (500 MHz, methanol-d4) δ ppm 8.14 (2H, d, J=8.25 Hz), 7.74 (2H, s), 7.60 (1H, d, J=7.70 Hz), 7.41-7.55 (2H, m), 7.09 (1H, d, J=7.70 Hz), 4.63 (1H, s), 4.38-4.59 (1H, m), 3.50-3.73 (1H, m), 3.59 (1H, d, J=7.15 Hz), 3.31-3.46 (1H, m), 2.95-3.15 (3H, m), 2.49 (3H, s), 2.26-2.42 (2H, m), 2.09-2.27 (2H, m), 1.71-1.89 (2H, m), 1.20-1.45 (3H, m), 1.14-1.25 (6H, m); MS (ES+) m/z: 626 (M+H); LC retention time: 3.24 min (analytical HPLC Method A).

Example 50

4-((5S)-5-(1,1-dimethyl-2-((5-(4-morpholinylcarbonyl)-1,3,4-thiadiazol-2-yl)amino)-2-oxoethyl)-8-methyl-5H-pyrido[3',2':5,6]pyrano[2,3-b]pyridin-2-yl)-N-ethyl-N-methylbenzaide

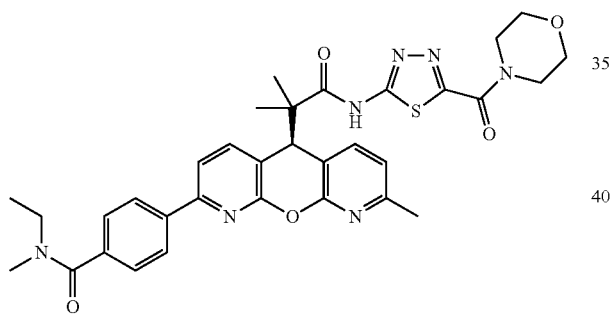

Morpholine (244 mg, 2.80 mmol) was added to a solution of Example 32 (20 mg, 0.028 mmol) in MeOH (1 mL). After 3 h at 60° C., additional morpholine (244 mg, 2.80 mmol) was added. The mixture was stirred at 70° C. for 24 h, cooled to room temperature and concentrated. The residue was purified by reverse phase HPLC, using Sunfire S10 30×250 mm column and eluting with 40 to 100% solvent B (90% MeOH-10% $H_2O$-0.1% TFA) in solvent A (10% MeOH-90% $H_2O$-0.1% TFA). The product containing fractions were concentrated and diluted with ethyl acetate (60 mL), washed with saturated $NaHCO_3$ (2×5 mL), brine (5 mL), dried ($MgSO_4$) and concentrated to provide Example 50 as white solid (9 mg, 50% yield). $^1H$ NMR (500 MHz, methanol-d4) δ ppm 8.15 (2H, d, J=8.80 Hz), 7.75 (2H, s), 7.61 (1H, d, J=7.70 Hz), 7.43-7.56 (2H, m), 7.10 (1H, d, J=7.70 Hz), 4.64 (1H, s), 4.20-4.40 (2H, m), 3.68-3.91 (6H, m), 3.51-3.66 (1H, m), 3.31-3.44 (1H, m), 2.96-3.15 (3H, m), 2.50 (3H, s), 1.21-1.40 (3H, m), 1.15-1.19 (6H, m); MS (ES+) m/z: 642 (M+H); LC retention time: 3.31 min (analytical HPLC Method A).

Example 51

2-((2-((5S)-2-(4-(dimethylcarbamoyl)phenyl)-8-methyl-5H-pyrido[3',2':5,6]pyrano[2,3-b]pyridin-5-yl)-2-methylpropanoyl)amino)-N-methyl-1,3-thiazole-5-carboxamide

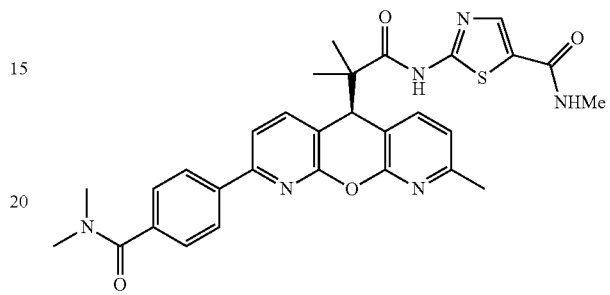

Step 1

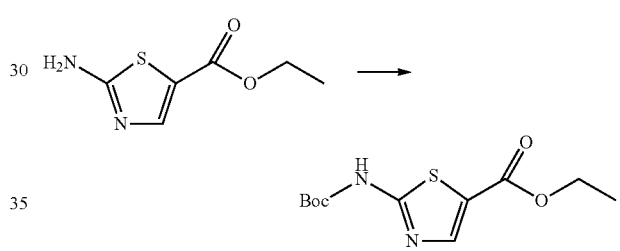

To a solution of ethyl 2-aminothiazole-5-carboxylate (3.1 g, 18 mmol) and $Boc_2O$ (5.0 mL, 22 mmol) in anhydrous THF (40 mL) was added DMAP (0.15 g, 1.3 mmol). The reaction mixture was stirred at room temperature under a nitrogen atmosphere for 19 h. Heptane (20 mL) was added slowly and the mixture was stirred at room temperature for 1 h. The solid that separated out was filtered and washed with a mixture of ethyl acetate and heptanes (1:1; 2×5 mL) to give the desired product (2.9 g) as a yellow solid. The mother liquor was concentrated and the solid residue was boiled with ethyl acetate (6 mL), cooled, filtered, and washed with cold ethyl acetate (1 mL) to give a second crop (1.3 g) of the desired compound as a yellow solid. Combined yield of ethyl 2-(tert-butoxycarbonylamino)thiazole-5-carboxylate was 4.2 g (85% yield). MS found: (M+H)+=273.

Step 2

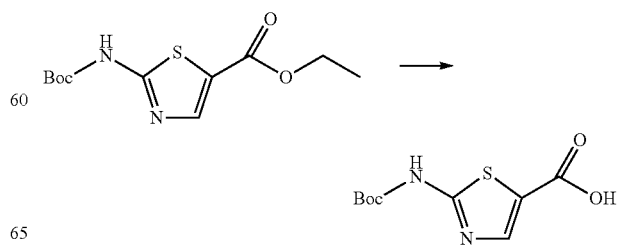

To a vigorously stirred suspension of ethyl 2-(tert-butoxycarbonylamino)thiazole-5-carboxylate (4.2 g, 15 mmol) in methanol (11 mL) was added 2 M aqueous solution of NaOH (22 mL, 44.0 mmol). The suspension was stirred at room temperature overnight. The mixture was concentrated in vacuo to remove methanol. The residual aqueous suspension was acidified with 6 N aqueous solution of HCl to pH ~1-2. The mixture was stirred and occasionally sonicated for 1 hr. The solid was filtered, washed with water, and dried to give 2-(tert-butoxycarbonylamino)thiazole-5-carboxylic acid (3.7 g, 100% yield) as a white solid. MS found: (M+H-Boc)+ =145.

Step 3

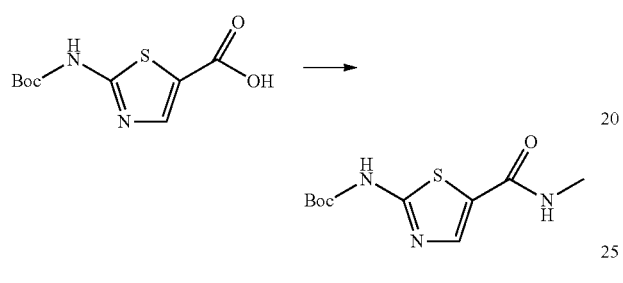

To a heterogeneous mixture of 2-(tert-butoxycarbonylamino)thiazole-5-carboxylic acid (1.0 g, 4.1 mmol), 1-hydroxybenzotriazole hydrate (0.63 g, 4.1 mmol), N,N-diisopropylethylamine (4.3 mL, 24 mmol), methylamine hydrochloride (0.83 g, 12 mmol) in anhydrous acetonitrile (20 mL), was added WSCDI (2.4 g, 12 mmol) at room temperature under a nitrogen atmosphere and stirred at room temperature overnight. The reaction mixture was concentrated in vacuo. To the residue was added saturated aqueous sodium bicarbonate solution (20 mL), ethyl acetate (6 mL), and heptane (2 mL). The solid that separates out was filtered, washed with water (2×2 mL) and diethyl ether (2×4 mL), and dried to give tert-butyl 5-(methylcarbamoyl)thiazol-2-ylcarbamate (0.77 g, 73% yield) as a white solid. MS found: (M+H)+=258; $^1$H NMR (400 MHz, methanol-d4) δ ppm 7.83 (s, 1H), 2.87 (s, 3H), 1.55 (s, 9H).

Step 4

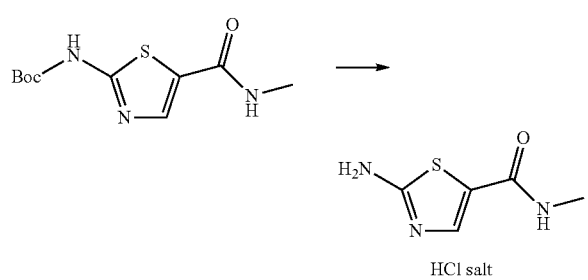

tert-Butyl 5-(methylcarbamoyl)thiazol-2-ylcarbamate (0.77 g, 3.0 mmol) was added to TFA (1.5 mL) that was cooled in a water bath. The solution obtained was stirred at room temperature for 1.5 h. A second batch of TFA (1.5 mL) was added and the reaction mixture was stirred at 40° C. for 30 min and then concentrated in vacuo. To the residue was added 1 M aqueous solution of HCl (3.0 mL, 3.0 mmol) and deionized water (2.0 mL) and the solution concentrated under reduced pressure. Lyophilization gave 2-amino-N-methylthiazole-5-carboxamide (HCl salt, 750 mg) as a white powder.

MS found: (M+H)+=158. The crude product was used as such in the next step without further purification.

Step 5

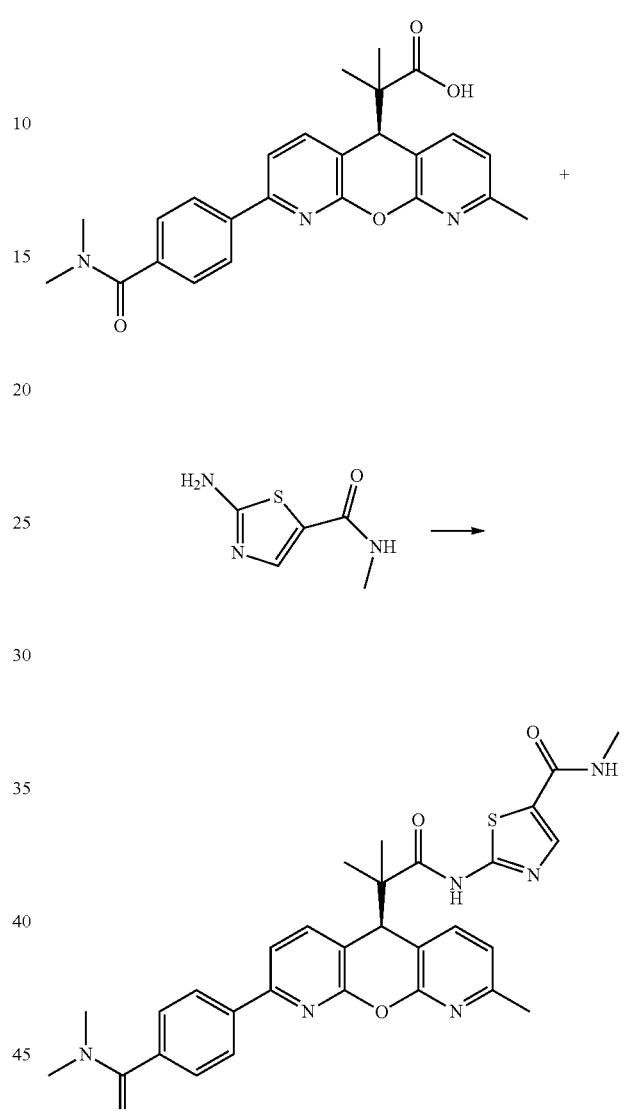

A mixture of the S-acid from Step 9 of Example 10 (20 mg, 0.046 mmol), 2-amino-N-methylthiazole-5-carboxamide (HCl salt, 35 mg, 0.14 mmol), O-(7-azabenzotriazol-1-yl)-N, N,N',N'-tetramethyluronium hexafluorophosphate (35 mg, 0.093 mmol), N,N-diisopropylethylamine (0.040 mL, 0.23 mmol), and anhydrous acetonitrile (0.5 mL) was stirred under a nitrogen atmosphere at room temperature for 10 min, at 60° C. for 4 h, and at 80° C. for 1.5 h. The mixture was filtered and dissolved in methanol (0.5 mL). Purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave Example 51 as a TFA salt (11 mg, 30% yield). $^1$H NMR (400 MHz, methanol-d4) δ ppm 8.16 (d, J=8.31 Hz, 2H), 7.97 (s, 1H), 7.77 (s, 2H), 7.66 (d, J=7.55 Hz, 1H), 7.54 (d, J=8.31 Hz, 2H), 7.13 (d, J=7.55 Hz, 1H), 4.65 (s, 1H), 3.13 (s, 3H), 3.05 (s, 3H), 2.90 (s, 3H), 2.52 (s, 3H), 1.17 (s, 6H); MS found: (M+H)+=571.

Example 52

4-((5S)-5-(1,1-dimethyl-2-((5-(4-morpholinylcarbonyl)-1,3-thiazol-2-yl)amino)-2-oxoethyl)-8-methyl-5H-pyrido[3',2':5,6]pyrano[2,3-b]pyridin-2-yl)-N,N-dimethylbenzamide

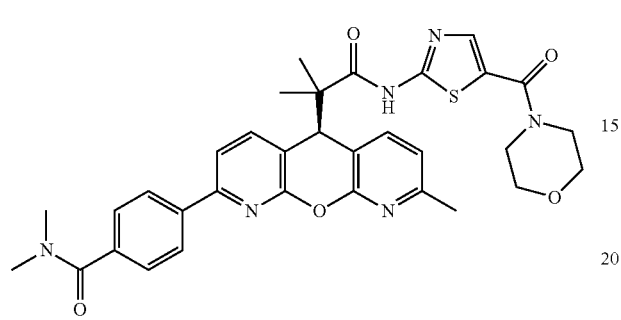

Following procedures described for synthesis of Example 51, Example 52 was prepared. $^1$H NMR (400 MHz, methanol-d4) δ ppm 8.16 (d, J=8.31 Hz, 2H), 7.80 (s, 1H), 7.77 (s, 2H), 7.64 (d, J=7.55 Hz, 1H), 7.55 (d, J=8.31 Hz, 2H), 7.12 (d, J=7.55 Hz, 1H), 4.65 (s, 1H), 3.72-3.82 (m, 8H), 3.13 (s, 3H), 3.05 (s, 3H), 2.51 (s, 3H), 1.17 (s, 6H); MS found: (M+H)+ =627.

Example 53

N-cyclopropyl-2-((2-((5S)-2-(4-(dimethylcarbamoyl)phenyl)-8-methyl-5H-pyrido[3',2':5,6]pyrano[2,3-b]pyridin-5-yl)-2-methylpropanoyl)amino)-1,3-thiazole-5-carboxamide

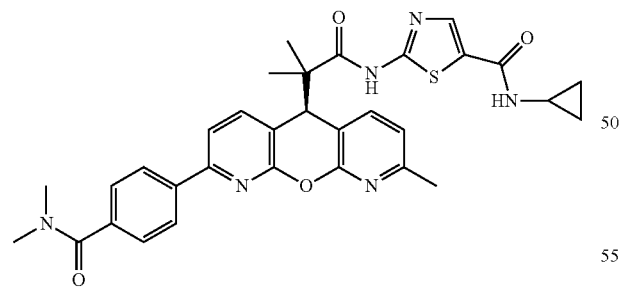

Following procedures described for synthesis of Example 51, Example 53 was prepared. $^1$H NMR (500 MHz, methanol-d4) δ ppm 8.16 (d, J=8.25 Hz, 2H), 7.98 (s, 1H), 7.76 (s, 2H), 7.63 (d, J=7.70 Hz, 1H), 7.54 (d, J=8.25 Hz, 2H), 7.11 (d, J=7.70 Hz, 1H), 4.65 (s, 1H), 3.13 (s, 3H), 3.05 (s, 3H), 2.79-2.85 (m, 1H), 2.51 (s, 3H), 1.16 (s, 6H), 0.78-0.83 (m, 2H), 0.62-0.66 (m, 2H); MS found: (M+H)+=597.

Example 54

4-(8-chloro-5-(1,1-dimethyl-2-oxo-2-(1,3,4-thiadiazol-2-ylamino)ethyl)-5H-pyrido[3',2':5,6]pyrano[2,3-b]pyridin-2-yl)-N,N-dimethylbenzamide

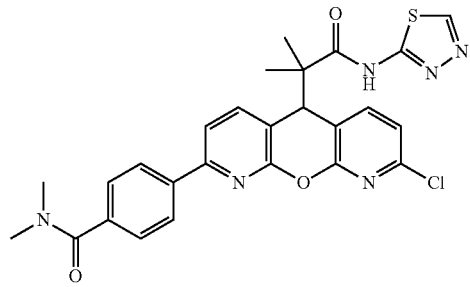

Stp 1

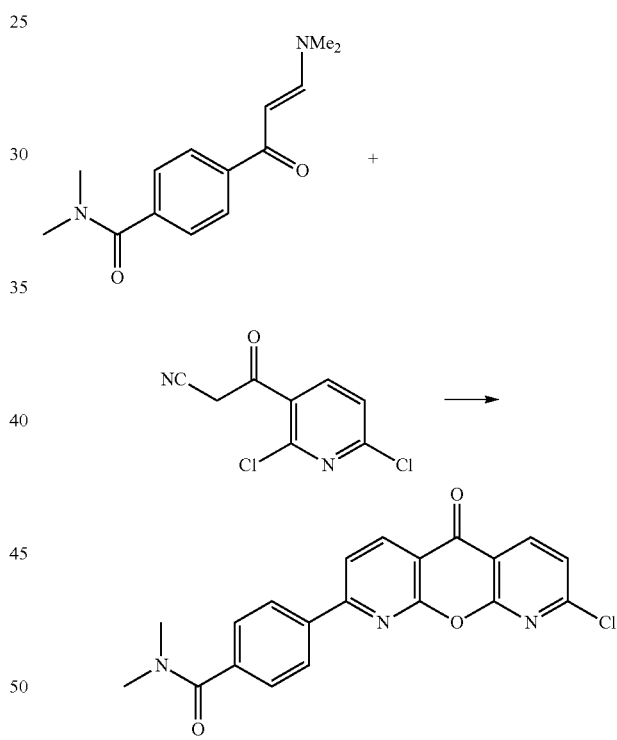

A solution of (E)-4-(3-(dimethylamino)acryloyl)-N,N-dimethylbenzamide (1.1 g, 4.47 mmol), 3-(2,6-dichloropyridin-3-yl)-3-oxopropanenitrile (1.344 g, 6.25 mmol) and acetic acid (1.278 mL, 22.33 mmol) in N,N-dimethylacetamide (10 mL) was stirred under $N_2$ at 120° C. for 6.5 h and cooled to room temperature. Following addition of water (120 mL), the precipitate was collected by filtration and purified by silica gel chromatography, eluting with 50-100% EtOAc in hexanes, to give a yellow solid. The impure material was stirred with MeOH (10 mL). The solid residue was collected by filtration to give the expected product as off-white solid (0.551 g, 33% yield). MS (ES+) m/z: 380 (M+H); LC retention time: 3.68 min (analytical HPLC Method A).

Step 2

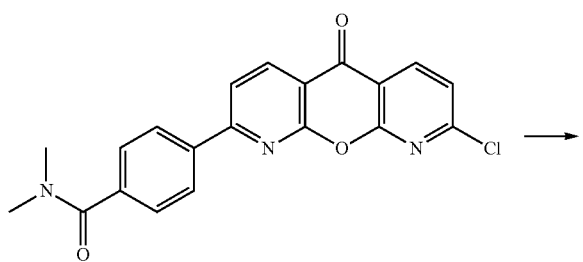

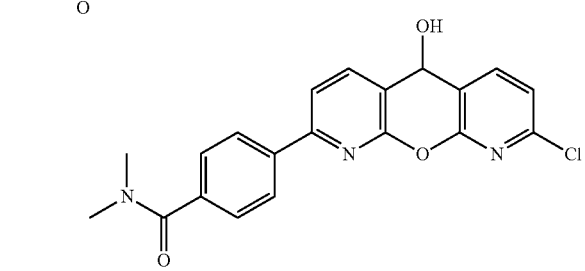

Sodium borohydride (226.3 mg, 5.98 mmol) was added to a solution of the ketone from Step 1 (503.4 mg, 1.325 mmol) in CH$_2$Cl$_2$ (22 mL) and MeOH (33 mL) at 0° C. After 1 h, the mixture was quenched with saturated NH$_4$Cl (10 mL) and water (10 mL). The organic solvents were evaporated in vacuo. EtOAc (50 mL) was added. The mixture was sonicated until all precipitate dissolved. The two phases were separated and the aqueous phase extracted with EtOAc (3×50 mL). The combined EtOAc extracts were washed with brine (5 mL), dried (MgSO$_4$) and concentrated to give the expected product as an off-white solid (0.45 g, 89% yield). The crude material was used in the next reaction without further purification.

Step 3

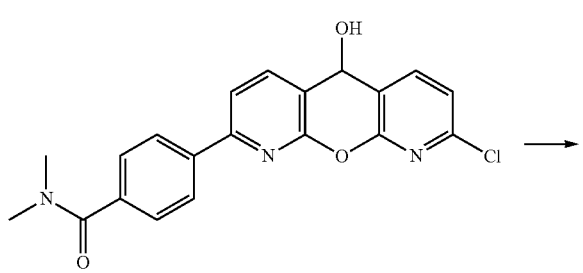

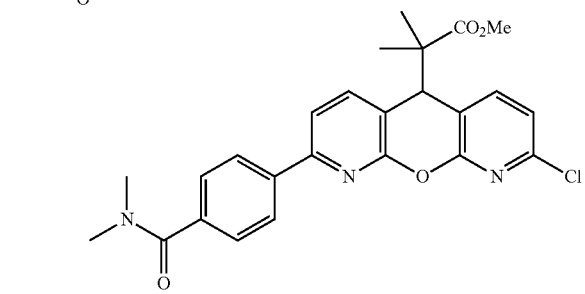

A 1.0 M CH$_2$Cl$_2$ solution of titanium(IV) chloride (2.95 mL, 2.95 mmol) was added to a suspension of the alcohol from Step 2 (450 mg, 1.179 mmol) in CH$_2$Cl$_2$ (100 mL) at 0° C. After 30 min at 0° C., methyl trimethylsilyl dimethylketene acetal (1.197 mL, 5.89 mmol) was added at 0° C. The mixture was stirred for 1 h, quenched with saturated NaHCO$_3$ (75 mL) at 0° C., and stirred at room temperature overnight. The two phases were separated. The aqueous phase was extracted with CH$_2$Cl$_2$ (25 mL). The combined organic extracts were concentrated and purified by silica gel chromatography, eluting with 50-100% EtOAc in hexanes, to give the desired product as light yellow solid (0.5079 g, 92% yield). MS (ES+) m/z: 466 (M+H); LC retention time: 3.68min (analytical HPLC Method A).

Step 4

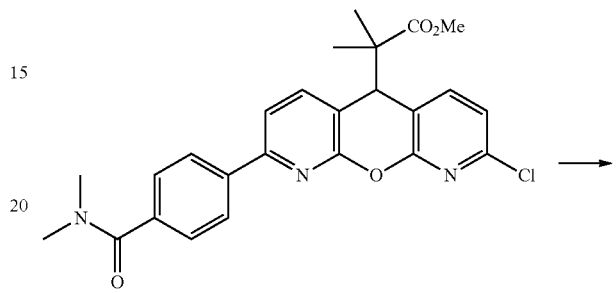

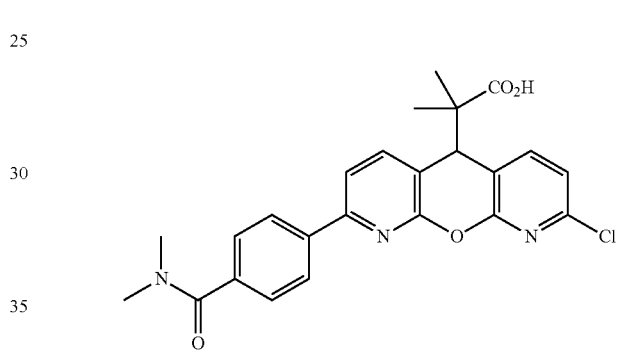

A suspension of the ester from Step 3 (207.6 mg, 0.446 mmol) and lithium chloride (953 mg, 22.48 mmol) in DMF (5 mL) was heat under microwave at 220° C. for 30 min. The mixture was poured into saturated NH$_4$Cl (50 mL), acidified to pH 4-5 with 1 N HCl (~0.5 mL) and extracted with EtOAc (1×50 mL, 2×20 mL). The combined extracts were washed with brine (5 mL), dried (MgSO$_4$), and concentrated. The residue was treated with water (10 mL). The precipitate formed was collected by filtration, washed with EtOAc to give the expected product as off-white powder (0.1291 g, 64% yield). MS (ES+) m/z: 452 (M+H); LC retention time: 3.55 min (analytical HPLC Method A).

Step 5

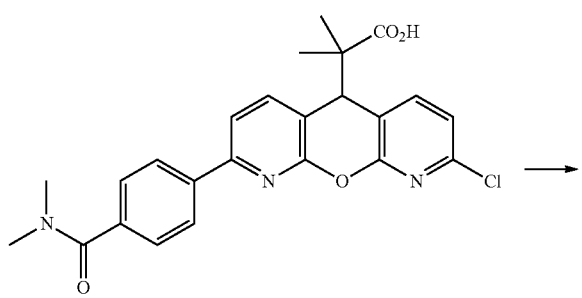

111

-continued

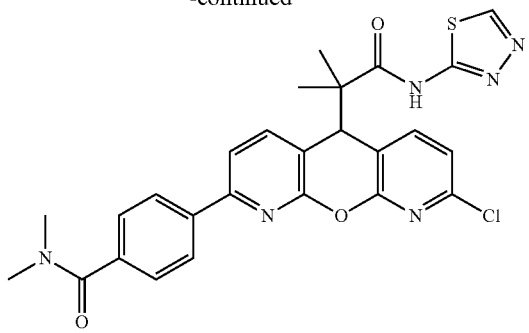

A solution of the acid from Step 4 (15.3 mg, 0.034 mmol), 1,3,4-thiadiazol-2-amine (6.9 mg, 0.068 mmol), O-(7-azabenzotriazol-1-yl)-N,N,N',N'-tetramethyluronium hexafluorophosphate (22.5 mg, 0.059 mmol) and N,N-diisopropylethylamine (5.91 μL, 0.034 mmol) in CH$_3$CN (1 mL) was stirred at 60° C. for 18 h. The crude material was purified by reverse phase HPLC (Sunfire S10 30×250 mm column, 55 to 75% solvent B gradient) to give Example 54 as white solid, assumed as bis-TFA salt (13 mg, 44% yield). $^1$H NMR (400 MHz, chloroform-d) δ ppm 8.90 (1H, s), 8.09 (2H, d, J=8.31 Hz), 7.57-7.65 (2H, m), 7.53 (3H, m), 7.16 (1H, d, J=7.81 Hz), 4.62 (1H, s), 3.19 (3H, s), 3.06 (3H, s), 1.25 (6H, s); MS (ES+) m/z: 535 (M+H); LC retention time: 3.56 min (analytical HPLC Method A).

Example 55

4-(8-chloro-5-(1,1-dimethyl-2-oxo-2-(1,3,4-thiadiazol-2-ylamino)ethyl)-5H-pyrido[3',2':5,6]pyrano[2,3-b]pyridin-2-yl)-N,N-dimethylbenzamide

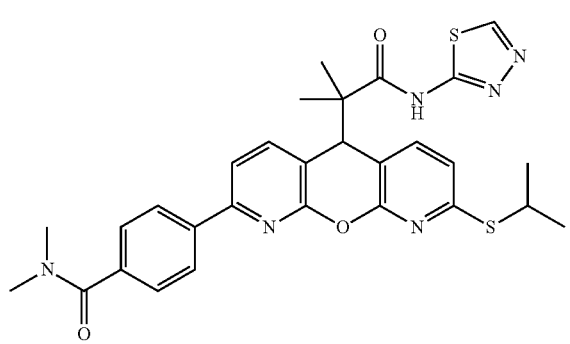

Step 1

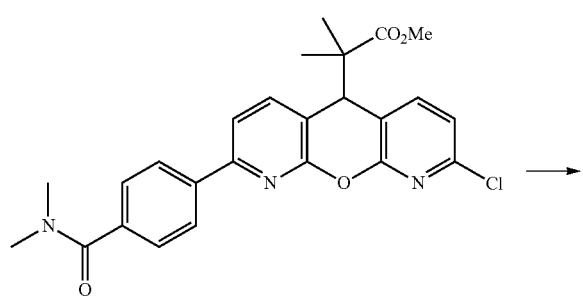

112

-continued

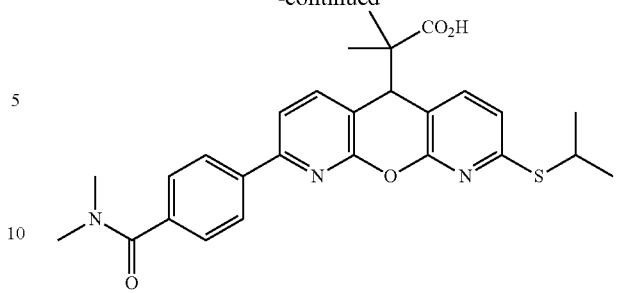

A solution of the ester from Step 3 of Example 54 (87 mg, 0.187 mmol) and sodium 2-propanethiolate (167.7 mg, 1.709 mmol) in DMF (3.5 mL) was heated at 50° C. for 1 h. After cooling to room temperature, the mixture was acidified with 1 N HCl (35 mL) and extracted with ethyl acetate (20 mL). The organic extract was washed with brine, dried (MgSO$_4$), and purified by silica gel chromatography, eluting with 40-90% EtOAc in hexanes, to give the expected product as light yellow powder (54.2 mg, 55% yield). MS (ES+) m/z: 492 (M+H); LC retention time: 4.11 min (analytical HPLC Method A).

Step 2

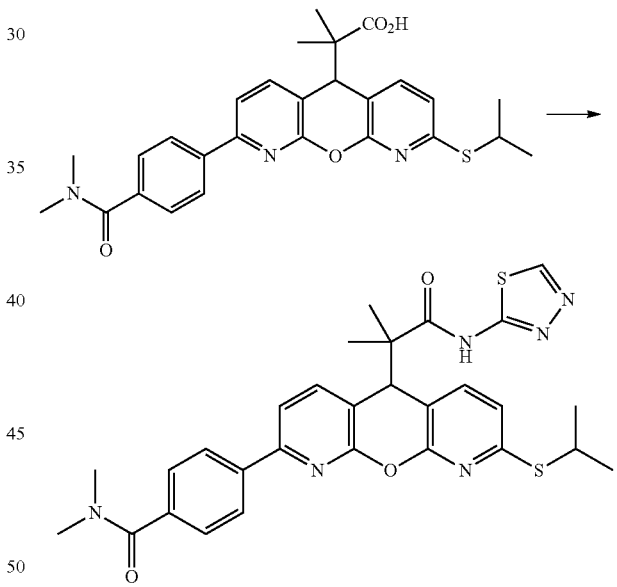

Following conditions similar to Step 5 of Example 54, Example 55 was prepared using the acid from Step 2. $^1$H NMR (400 MHz, chloroform-d) δ ppm 8.88 (1H, s), 8.07-8.13 (2H, m), 7.50-7.64 (4H, m), 7.32 (1H, d, J=7.81 Hz), 6.95 (1H, d, J=8.06 Hz), 4.52 (1H, s), 4.06-4.19 (1H, m), 3.19 (3H, s), 3.05 (3H, s), 1.42 (6H, t, J=6.67 Hz), 1.25 (6H, s); MS (ES+) m/z: 575 (M+H); LC retention time: 4.10 min (analytical HPLC Method A).

Examples 56-57

Examples 56-57 were prepared using the conditions from Step 5 of Example 54, substituting the 1,3,4-thiadiazol-2-amine with appropriate amines.

| Ex # | Structure | ¹H NMR (400 MHz) δ ppm | RT (min) | Obs. MS Ion |
|---|---|---|---|---|
| 56 | 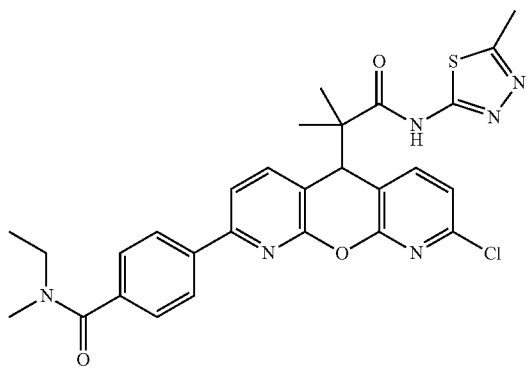 | Chloroform-d 8.09 (d, J = 8.31 Hz, 2 H), 7.39-7.84 (m, 5 H), 7.16 (d, J = 8.06 Hz, 1 H), 4.63 (s, 1 H), 3.18 (s, 3 H), 3.05 (s, 3 H), 2.77 (s, 3 H), 1.23 (s, 6 H) | 3.72 | 549 |
| 57 | 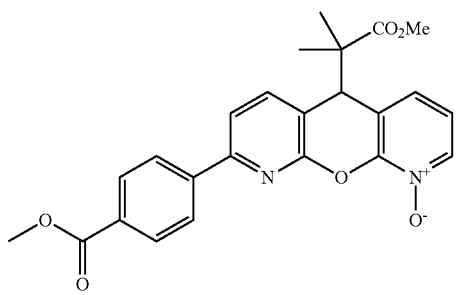 | Chloroform-d 8.10 (d, J = 8.31 Hz, 2 H), 7.45-7.68 (m, 5 H), 7.15 (d, J = 7.81 Hz, 1 H), 4.61 (s, 1 H), 3.17 (s, 3 H), 3.04 (s, 3 H), 2.55-2.62 (m, 3 H), 1.24 (s, 3 H), 1.23 (s, 3 H) | 3.85 | 549 |

Example 58

4-(8-chloro-5-(1,1-dimethyl-2-((5-methyl-1,3,4-thiadiazol-2-yl)amino)-2-oxoethyl)-5H-pyrido[3',2':5,6]pyrano[2,3-b]pyridin-2-yl)-N-ethyl-N-methylbenzamide

Step 1

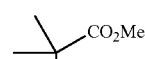

m-CPBA (8.00 g, 46.4 mmol) was added to a suspension of the ester from Step 4 of Example 3 (9.7 g, 23.18 mmol) in CHCl₃ (200 mL). After 15 h at room temperature, another portion of m-CPBA (8.0 g) was added. After another 56 h, the mixture was quenched with saturated Na$_2$SO$_3$ solution (150 mL) and stirred for 1 h. The organic layer was separated, washed with saturated Na$_2$CO$_3$ (4×100 mL), saturated NaHCO$_3$ (100 mL), brine (100 mL), dried (MgSO$_4$) and concentrated to provide the expected product as 93% pure material (9.20 g, 85% yield). $^1$H NMR (400 MHz, chloroform-d) δ ppm 8.30 (1H, dd, J=6.42, 1.38 Hz), 8.16-8.26 (2H, m), 8.08-8.17 (2H, m), 7.67-7.80 (2H, m), 6.98-7.19 (2H, m), 4.52 (1H, s), 3.94 (3H, s), 3.66-3.77 (3H, m), 0.87-1.17 (6H, m); MS (ES+) m/z: 435 (M+H); LC rention time: 3.28 min (analytical HPLC Method A).

Step 2

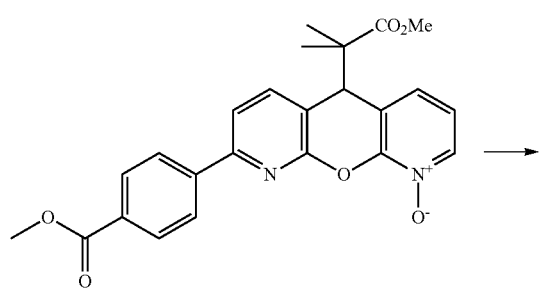

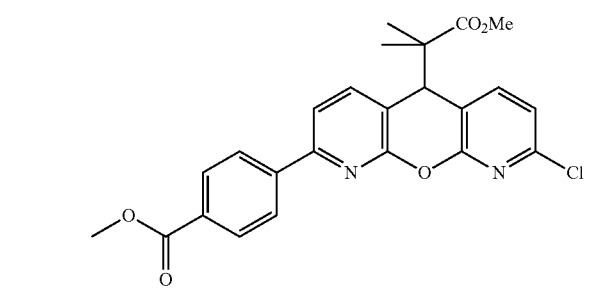

A suspension of the pyridine oxide from Step 1 (8.56 g, 19.70 mmol) in POCl$_3$ (100 mL) was heated to 110° C. for 2 h, cooled to room temperature, poured into ice-water and filtered. The solid was treated with CH$_2$Cl$_2$ (1.2 L) and saturated Na$_2$CO$_3$ (400 mL). The resultant suspension was stirred at room temperature for 1 h. The organic suspension was separated and washed with H$_2$O (2×200 mL) and filtered. The solid was dried under vacuum to give brown solid (4.5 g). The filtrate was concentrated to give another batch of brown solid (4.0 g). Both batches contained impure product, were combined, dissolved in DMSO (400 mL), diluted with CH2Cl2 (1200 mL), and washed with H$_2$O (3×300 mL), brine (300 mL), dried (MgSO$_4$) and concentrated to approximately 100 mL in volume. The precipitate was filtered and washed with CH$_2$Cl$_2$ to provide the expected product as brown solid (1.8 g, ~85% pure). The combined aqueous phase was concentrated to ~100 mL in volume. The precipitate was filtered and dried under vacuum to provide second batch of product (3.0 g, ~60% pure).

Step 3

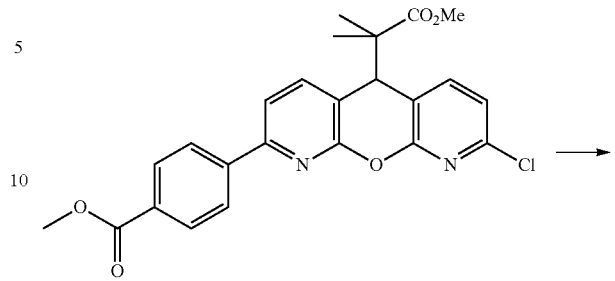

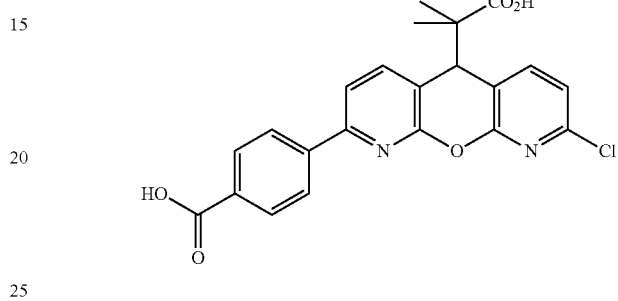

A 1.0 N aqueous NaOH (10 mL, 10.00 mmol) was added to a suspension of the product from Steps 2 (1.00 g, ~85% pure) in MeOH (20 mL) at room temperature. After 6 h at 80° C., the organic solvent was evaporated in vacuo. The aqueous residue was adjusted with 1 N HCl to pH 1-2. The solid was collected by filtration and purified by reverse phase HPLC (Sunfire S10 30×250 mm column, 20 to 100% solvent B gradient) to give the expected product, assumed as bis-TFA salt (250 mg, 21% yield). $^1$H NMR (400 MHz, DMSO-d6) δ ppm 8.24 (2H, d, J=8.31 Hz), 8.06 (2H, d, J=8.56 Hz), 8.01 (1H, d), 7.91-7.98 (1H, m), 7.88 (1H, d, J=7.81 Hz), 7.44 (1H, d, J=7.81 Hz), 4.52 (1H, s), 0.93 (6H, s), MS (ES+) m/z: 425 (M+H); LC retention time: 3.38 min (analytical HPLC Method A).

Step 4

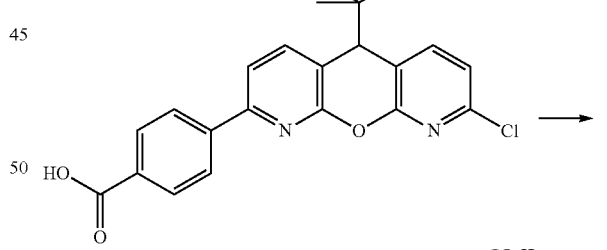

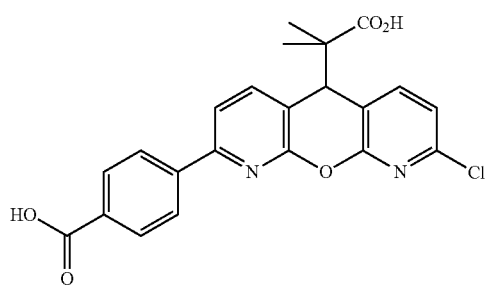

homochiral
(first peak off ChiralPak AD column)

Using a procedure similar to Step 3, a second batch of the ester from Step 2 (2.0 g, 60% pure) was converted to the diacid. The two enantiomers were separated using Chiralpak AD column. The first peak off the column was collected to give the desired enantiomer (0.354 g, 41% yield). $^1$H NMR (400 MHz, methanol-d4) δ ppm 8.09-8.21 (m, 4H), 7.94 (d, J=8.06 Hz, 1H), 7.86 (dd, J=7.93, 1.89 Hz, 2H), 7.31 (d, J=7.81 Hz, 1H), 4.55 (s, 1H), 1.04 (s, 3H), 1.02 (s, 3H); MS (ES+) m/z: 425 (M+H); LC retention time: 3.71 min (analytical HPLC Method A).

Step 5

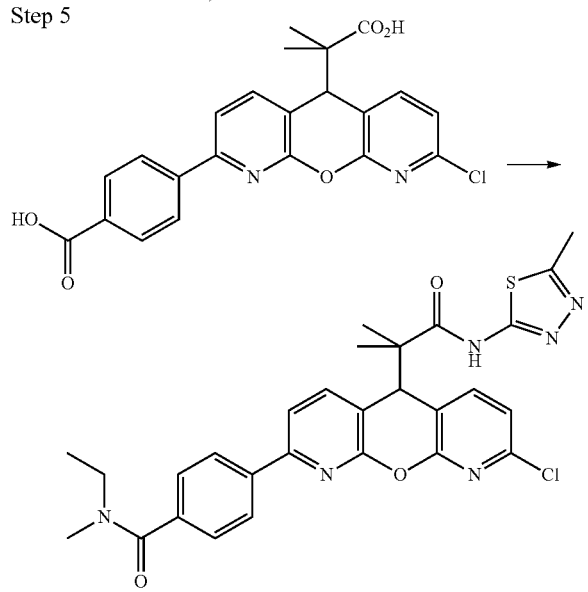

Hunig's base (0.107 mL, 0.613 mmol) was added to a suspension of O-(7-azabenzotriazol-1-yl)-N,N,N',N'-tetramethyluronium hexafluorophosphate (69.9 mg, 0.184 mmol) and the acid from Step 3 (40 mg, 0.061 mmol) in acetonitrile (2 mL). The resultant solution was stirred at room temperature for 30 minutes then cooled to 0° C. A 0.5 M THF solution of N-ethylmethylamine (0.123 mL, 0.061 mmol) was added. After 1.5 h at 0° C., 5-methyl-1,3,4-thiadiazol-2-amine (21.17 mg, 0.184 mmol) was added. The mixture was stirred at 55° C. for 15 h, concentrated and purified by reverse phase HPLC (Sunfire S10 30×250 mm column, 20 to 100% solvent B gradient) to give Example 58, assumed as bis-TFA salt (20 mg, 41% yield). $^1$H NMR (400 MHz, methanol-d4) δ ppm 8.11 (2H, d, J=8.56 Hz), 7.75 (2H, s), 7.70 (1H, d, J=7.81 Hz), 7.49 (2H, t, J=8.18 Hz), 7.26 (1H, d, J=7.81 Hz), 4.64 (1H, s), 3.32-3.67 (2H, m), 2.95-3.20 (3H, m), 2.70 (3H, s), 1.03-1.43 (9H, m); MS (ES+) m/z: 563 (M+H); LC retention time: 3.52 min (analytical HPLC Method A).

Examples 59-63

Examples 59-61 were prepared using the conditions from Step 5 of Example 58, using amines that are commercially available or prepared before. Examples 62-63 were prepared using the conditions from Step 5 of Example 58, using the homochiral acid from Step 4 of Example 58 and amines that are commercially available or prepared before.

| Ex # | Structure | $^1$H NMR (400 MHz) δ ppm | RT (min) | Obs. MS Ion |
|---|---|---|---|---|
| 59 | 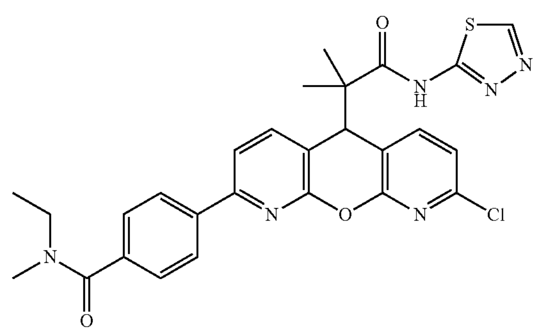 | Chloroform-d: 8.91 (s, 1 H), 8.08 (d, J = 8.52 Hz, 2 H), 7.61-7.67 (m, 1 H), 7.54-7.61 (m, 2 H), 7.50 (t, J = 8.94 Hz, 2 H), 7.12-7.18 (m, 1 H), 4.65 (s, 1 H), 3.60-3.71 (m, 1 H), 3.29-3.40 (m, 1 H), 3.14 (s, 2 H), 3.01 (s, 1 H), 1.29 (t, J = 7.01 Hz, 1 H), 1.25 (s, 6 H), 1.18 (t, J = 7.01 Hz, 2 H) | 3.71 | 549 |
| 60 | 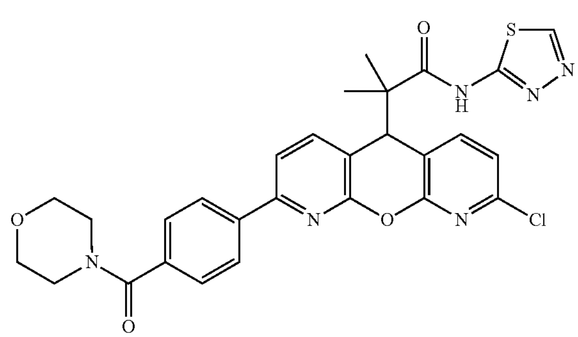 | methanol-d4: 9.12 (1 H, s), 8.12 (2 H, d, J = 8.31 Hz), 7.61-7.92 (3 H, m), 7.52 (2 H, d, J = 8.56 Hz), 7.26 (1 H, d, J = 7.81 Hz), 4.66 (1 H, s), 3.37-3.91 (8 H, m), 1.18 (6 H, s). | 3.33 | 577 |

| Ex # | Structure | ¹H NMR (400 MHz) δ ppm | RT (min) | Obs. MS Ion |
|---|---|---|---|---|
| 61 | 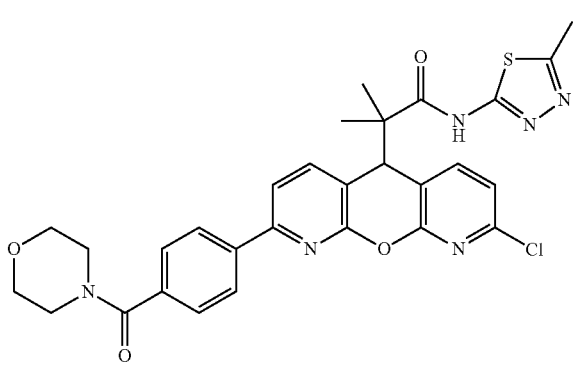 | methanol-d4: 8.09 (2 H, d, J = 8.56 Hz), 7.57-7.90 (3 H, m), 7.49 (2 H, d, J = 8.31 Hz), 7.23 (1 H, d, J = 7.81 Hz), 4.61 (1 H, s), 3.36-4.04 (8 H, m), 2.66 (3 H, s), 1.13 (6 H, s). | 3.48 | 591 |
| 62 | 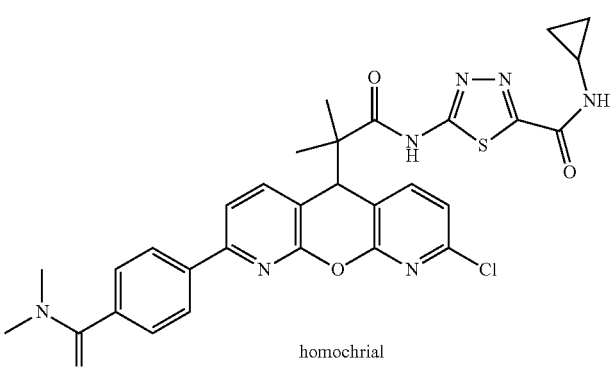 homochrial | Chloroform-d: 8.09 (d, J = 8.31 Hz, 2 H), 7.92 (br. s, 1 H), 7.66-7.73 (m, 1 H), 7.60-7.65 (m, 1 H), 7.54 (d, J = 8.31 Hz, 2 H), 7.46 (d, J = 8.06 Hz, 1 H), 7.05 (d, J = 7.81 Hz, 1 H), 4.58 (s, 1 H), 3.20 (s, 3 H), 3.07 (s, 4 H), 1.30 (s, 3 H) 1.23 (s, 3 H), 0.98 (m, 4 H). | 3.80 | 618 |
| 63 | 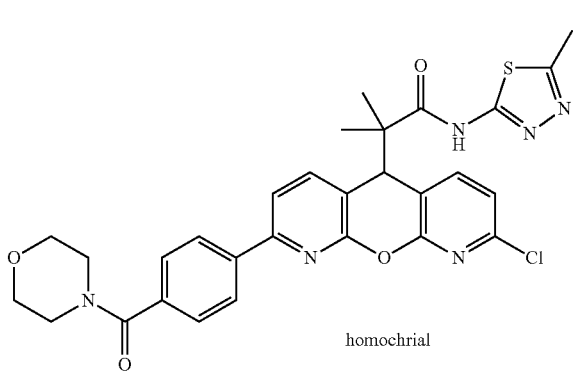 homochrial | Chloroform-d: 8.11 (2 H, d, J = 8.25 Hz), 7.73 (1 H, d, J = 7.97 Hz), 7.67 (1 H, d, J = 7.97 Hz), 7.58 (1 H, d, J = 7.97 Hz), 7.51 (2 H, d, J = 8.25 Hz), 7.13 (1 H, d, J = 7.97 Hz), 4.84 (1 H, s), 3.80 (4 H, br. s), 3.65 (2 H, br. s), 3.48 (2 H, br. s), 2.77 (3 H, s), 1.25 (6 H, s) | 3.69 | 591 |

Example 64

4-(5-(1,1-dimethyl-2-oxo-2-(1,3,4-thiadiazol-2-ylamino)ethyl)-8-vinyl-5H-pyrido[3',2':5,6]pyrano[2,3-b]pyridin-2-yl)-N,N-dimethylbenzamide

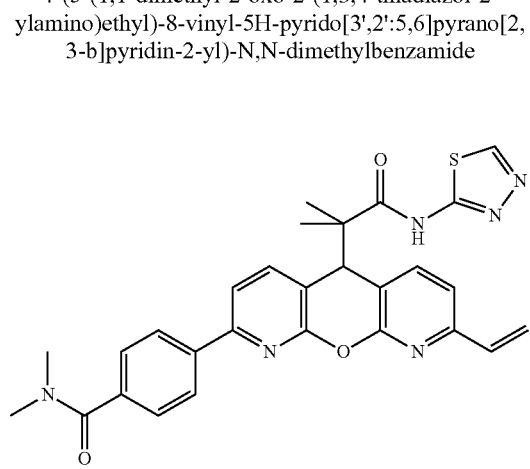

Step 1

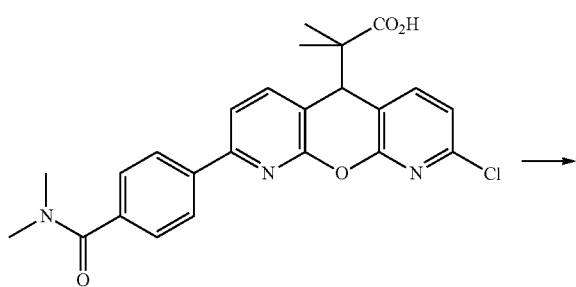

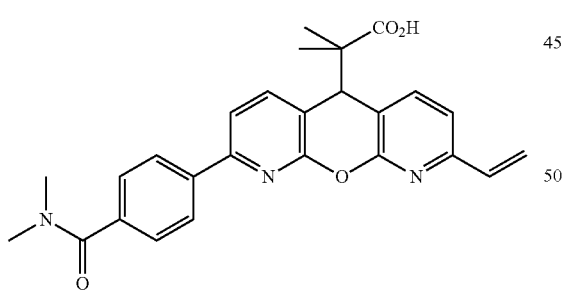

A solution of the acid from Step 4 of Example 54 (22 mg, 0.049 mmol), Pd(Ph$_3$P)$_4$ (6.8 mg, 5.88 μmol) and 2 M aqueous solution of potassium phosphate (0.024 mL, 0.049 mmol) in DMF (1.5 mL) was pumped and backfilled with N$_2$ twice. After 11 h at 90° C., the mixture was poured into saturated NH$_4$Cl (10 mL) and extracted with EtOAc (3×10 mL). The combined extracts were washed with brine (2 mL), dried (Na$_2$SO$_4$) and concentrated to give a brown oil. The crude material was used in the next reaction without further purification.

Step 2

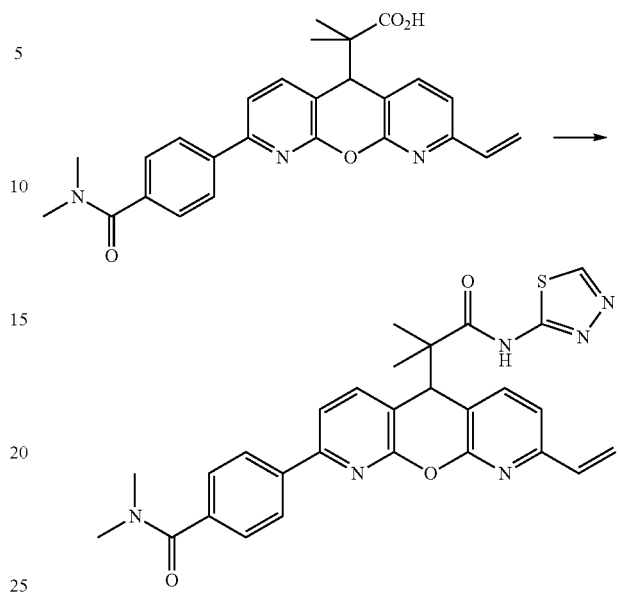

A solution of the crude acid from Step 1, 1,3,4-thiadiazol-2-amine (7.7 mg, 0.076 mmol), O-(7-azabenzotriazol-1-yl)-N,N,N',N'-tetramethyluronium hexafluorophosphate (19 mg, 0.050 mmol) and N,N-diisopropylethylamine (30 μL, 0.172 mmol) in CH$_3$CN (1 mL) was stirred at 60° C. for 15 h, cooled to room temperature and purified by reverse phase HPLC (Sunfire S10 30×250 mm column, 60 to 85% solvent B gradient) to give Example 64 as white powder (12.4 mg, 34% yield over 2 steps). $^1$H NMR (400 MHz, chloroform-d) δ ppm 8.89 (1H, s), 8.11 (2H, d, J=8.31 Hz), 7.53-7.64 (5H, m), 7.14 (1H, d, J=7.81 Hz), 6.77 (1H, dd, J=17.37, 10.58 Hz), 6.34 (1H, dd, J=17.37, 1.01 Hz), 5.56 (1H, d, J=11.58 Hz), 4.58 (1H, s), 3.19 (3H, s), 3.05 (3H, s), 1.25 (6H, s); MS (ES+) m/z: 527 (M+H); LC retention time: 3.59 min (analytical HPLC Method A).

Example 65

4-(5-(1,1-dimethyl-2-oxo-2-(1,3,4-thiadiazol-2-ylamino)ethyl)-8-phenyl-5H-pyrido[3',2':5,6]pyrano[2,3-b]pyridin-2-yl)-N,N-dimethylbenzamide

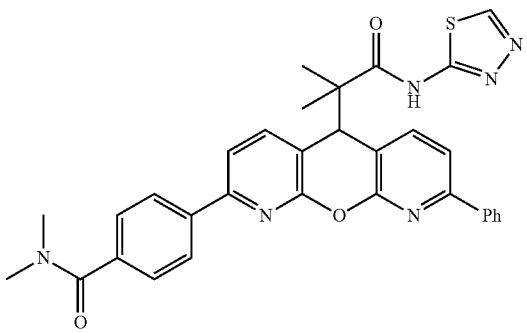

Using a two-step sequence for the synthesis of Example 64, Example 65 was synthesized from the acid from Step 4 of Example 54 and phenylboronic acid. $^1$H NMR (400 MHz, chloroform-d) δ ppm 8.90 (1H, s), 8.13 (2H, d, J=8.31 Hz), 8.08 (2H, d, J=6.80 Hz), 7.43-7.67 (9H, m), 4.64 (1H, s), 3.18

(3H, s), 3.05 (3H, s), 1.29 (3H, br. s), 1.28 (3H, br. s); MS (ES+) m/z: 577 (M+H); LC retention time: 3.96 min (analytical HPLC Method A).

Example 66

4-(8-cyano-5-(1,1-dimethyl-2-oxo-2-(1,3,4-thiadiazol-2-ylamino)ethyl)-5H-pyrido[3',2':5,6]pyrano[2,3-b]pyridin-2-yl)-N,N-dimethylbenzamide

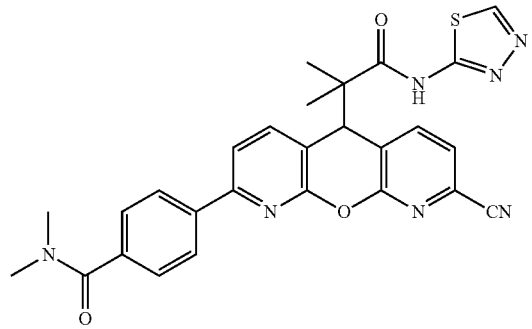

Step 1

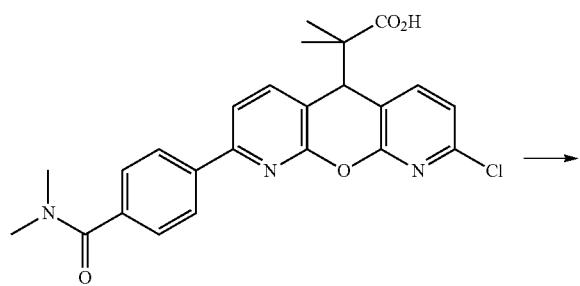

A suspension of the acid from Step 4 of Example 54 (24.8 mg, 0.055 mmol), zinc cyanide (16.7 mg, 0.142 mmol) and Pd(Ph₃P)₄ (14.5 mg, 0.013 mmol) in DMF (1 mL) was pumped and backfilled with $N_2$ twice. After 2.5 h at 100° C., the mixture was purified by reverse phase HPLC (Sunfire S10 30×250 mm column, 50 to 80% solvent B gradient) to give the expected product as white powder (16.6 mg, 45% yield). MS (ES+) m/z: 443 (M+H); LC retention time: 3.13 min (analytical HPLC Method A).

Step 2

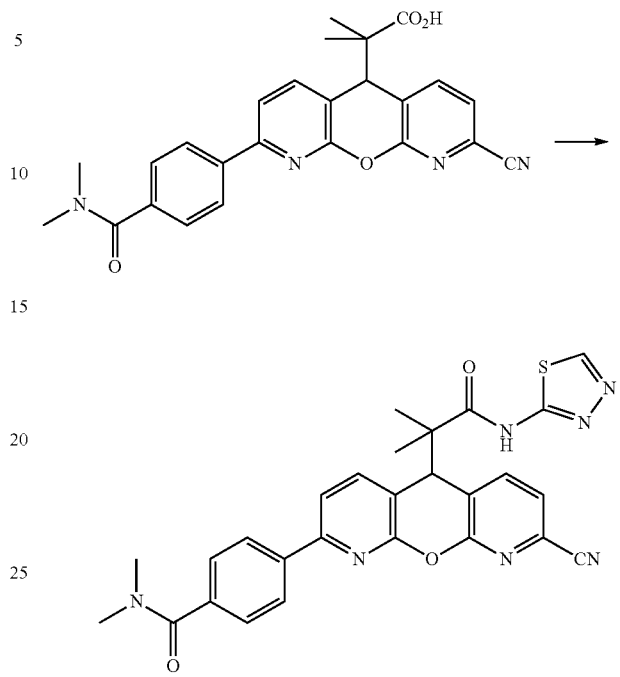

Using conditions described for Step 2 of Example 64, Example 66 was synthesized using the acid from Step 1. ¹H NMR (400 MHz, chloroform-d) δ ppm 8.92 (1H, s), 8.10 (2H, d, J=8.31 Hz), 7.77 (1H, d, J=7.81 Hz), 7.64 (2H, q, J=7.89 Hz), 7.51-7.57 (3H, m), 4.75 (1H, s), 3.19 (3H, s), 3.05 (3H, s), 1.27 (3H, br. s), 1.26 (3H, br. s); MS (ES+) m/z: 526 (M+H); LC retention time: 3.34 min (analytical HPLC Method A).

Example 67

4-(8-(dimethylamino)-5-(1,1-dimethyl-2-oxo-2-(1,3,4-thiadiazol-2-ylamino)ethyl)-5H-pyrido[3',2':5,6]pyrano[2,3-b]pyridin-2-yl)-N,N-dimethylbenzamide

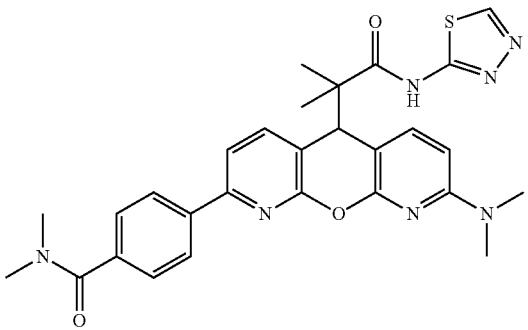

Step 1

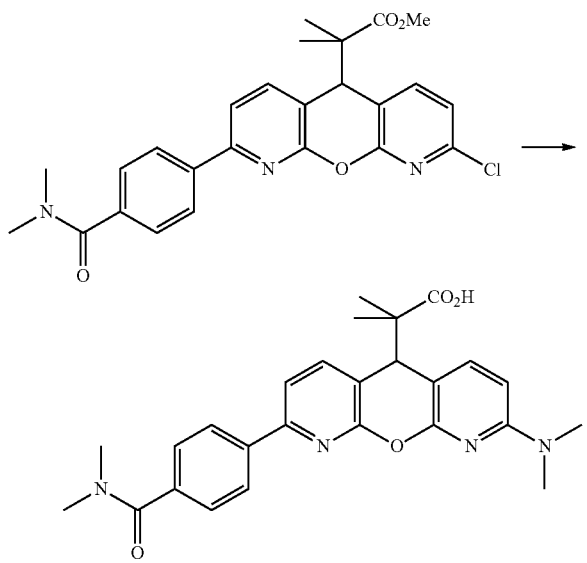

A solution of the ester from Step 3 of Example 54 (39 mg, 0.084 mmol), 40% aqueous dimethylamine (1 mL, 7.90 mmol) in MeOH (0.5 mL) was attempted to heat to 220° C. under microwave, but stopped due to high pressure (>19 psi). The mixture was then heated to ~150° C. under microwave for 1 h. Purification by reverse phase HPLC (Sunfire S10 30×250 mm column, 55 to 85% solvent B gradient) gave the expected product (47.3 mg, 70% yield). MS (ES+) m/z: 461 (M+H); LC retention time: 3.67 min (analytical HPLC Method A).

Step 2

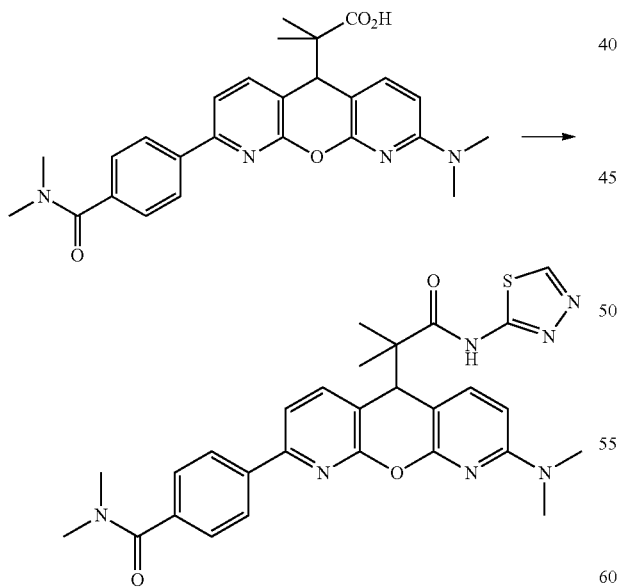

Using conditions described for Step 2 of Example 64, Example 67 was synthesized using the acid from Step 1. $^1$H NMR (400 MHz, chloroform-d) δ ppm 8.88 (1H, s), 8.10 (2H, d, J=8.31 Hz), 7.47-7.62 (4H, m), 7.28 (1H, d, J=8.56 Hz), 6.29 (1H, d, J=8.31 Hz), 4.41 (1H, s), 3.19 (3H, s), 3.11 (6H, s), 3.05 (3H, s), 1.24 (6H, s); MS (ES+) m/z: 544 (M+H); LC retention time: 3.69 min (analytical HPLC Method A).

Example 68

4-(8-(dimethylamino)-5-(1,1-dimethyl-2-((5-methyl-1,3,4-thiadiazol-2-yl)amino)-2-oxoethyl)-5H-pyrido[3′,2′:5,6]pyrano[2,3-b]pyridin-2-yl)-N,N-dimethylbenzamide

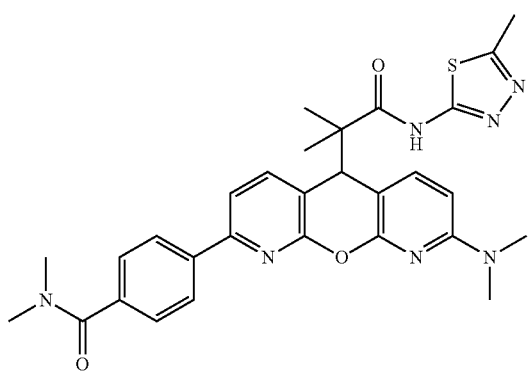

Using conditions described for Step 2 of Example 64, Example 68 was synthesized using the acid from Step 1 of Example 67. $^1$H NMR (400 MHz, chloroform-d) δ ppm 8.11 (2H, d, J=8.56 Hz), 7.45-7.61 (4H, m), 7.24-7.28 (1H, m), 6.27 (1H, d, J=8.31 Hz), 4.40 (1H, s), 3.17 (3H, s), 3.10 (6H, s), 3.04 (3H, s), 2.76 (3H, s), 1.22 (6H, s); MS (ES+) m/z: 558 (M+H); LC retention time: 3.84 min (analytical HPLC Method A).

Example 69

4-(5-(1,1-dimethyl-2-oxo-2-(1,3,4-thiadiazol-2-ylamino)ethyl)-8-(4-morpholinyl)-5H-pyrido[3′,2′:5,6]pyrano[2,3-b]pyridin-2-yl)-N,N-dimethylbenzamide

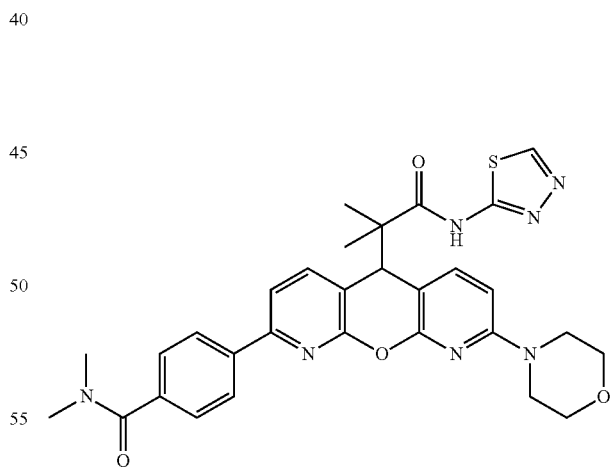

Using conditions described for synthesis of Example 67, the ester from Step 3 of Example 54 was reacted with morpholine and converted Example 69. $^1$H NMR (400 MHz, chloroform-d) δ ppm 8.88 (1H, s), 8.10 (2H, d, J=8.31 Hz), 7.56-7.61 (1H, m), 7.48-7.56 (3H, m), 7.32 (1H, d, J=8.31 Hz), 6.38 (1H, d, J=8.31 Hz), 4.44 (1H, s), 3.82 (4H, t, J=4.78 Hz), 3.47-3.63 (4H, m), 3.19 (3H, s), 3.05 (3H, s), 1.25 (6H, s); MS (ES+) m/z: 586 (M+H); LC retention time: 3.62 min (analytical HPLC Method A).

Example 70

4-(5-(1,1-dimethyl-2-oxo-2-(1,3,4-thiadiazol-2-ylamino)ethyl)-8-(1-pyrrolidinyl)-5H-pyrido[3',2':5,6]pyrano[2,3-b]pyridin-2-yl)-N,N-dimethylbenzamide

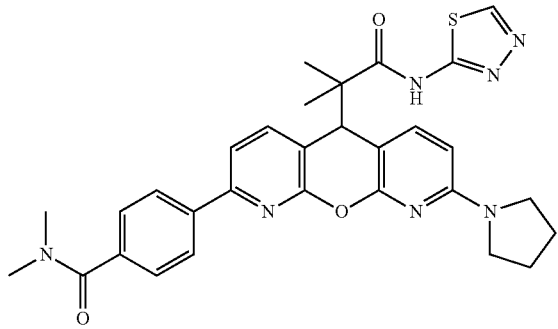

Using conditions described for synthesis of Example 67, the acid from Step 4 of Example 54 was reacted with pyrrolidine and converted Example 70. $^1$H NMR (400 MHz, chloroform-d) δ ppm 8.90 (1H, s), 8.06 (2H, d, J=8.31 Hz), 7.56 (2H, s), 7.51 (2H, d, J=8.31 Hz), 7.42 (1H, d, J=8.81 Hz), 6.27 (1H, d, J=8.56 Hz), 4.43 (1H, s), 3.53-3.64 (4H, m), 3.19 (3H, s), 3.06 (3H, s), 2.00-2.16 (4H, m), 1.25 (3H, s), 1.23 (3H, s); MS (ES+) m/z: 570 (M+H); LC retention time: 3.88 min (analytical HPLC Method A).

Example 71-72

Using the acid from Step 4 of Example 58, Examples 71-72 were synthesized following conditions for Step 1 of Example 67 and Step 5 of Example 58.

| Ex # | Structure | $^1$H NMR (400 MHz) δ ppm | RT (min) | Obs. MS Ion |
|---|---|---|---|---|
| 71 | 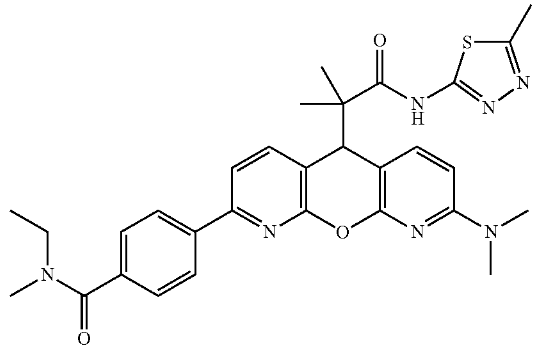 | Chloroform-d: 8.01-8.32 (2 H, m), 7.58-7.76 (1 H, m), 7.44-7.51 (3 H, m), 7.35-7.45 (1 H, m), 6.24 (1 H, d, J = 8.52 Hz), 4.69 (1 H, s), 3.50-3.68 (1 H, m), 3.22-3.37 (1 H, m), 3.10 (6 H, s), 2.89-3.20 (3 H, m), 2.78 (3 H, s), 1.25 (6 H, s), 1.05-1.37 (3 H, m). | 3.64 | 572 |
| 72 | 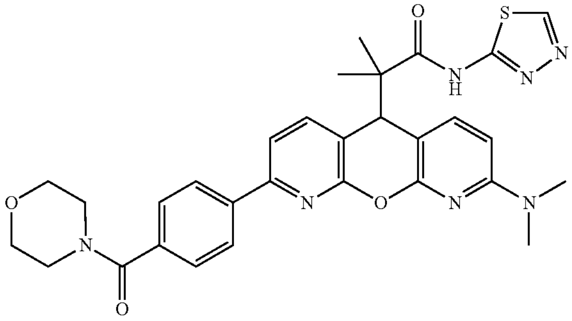 | Chloroform-d: 11.53 (1 H, s), 8.90 (1 H, s), 8.07 (2 H, d, J = 8.31 Hz), 7.58 (1 H, d, J = 7.81 Hz), 7.36-7.52 (3 H, m), 7.31 (1 H, d, J = 8.56 Hz), 6.12-6.28 (1 H, m), 4.60 (1 H, s), 3.25-4.06 (8 H, m), 3.08 (6 H, s), 1.22 (6 H, s). | 3.46 | 586 |

Example 73

4-(8-(dimethylamino)-5-(1,1-dimethyl-2-oxo-2-(1,3,4-thiadiazol-2-ylamino)ethyl)-5H-pyrido[3',2':5,6]pyrano[2,3-b]pyridin-2-yl)-2-fluoro-N,N-dimethyl-benzamide

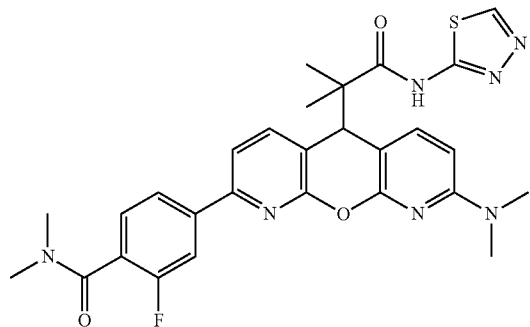

Step 1

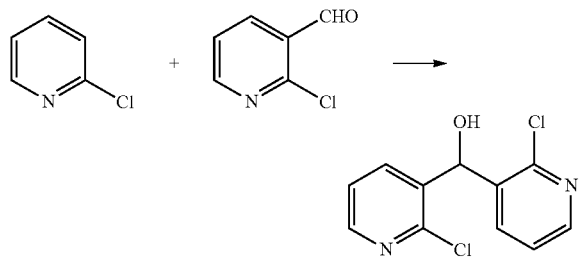

A 2.5 M hexane solution of BuLi (12.33 mL, 30.8 mmol) was added dropwise to a solution of diisopropylamine (4.39 mL, 30.8 mmol) in THF (100 mL) at −78° C. The mixture was stirred at 0° C. for 15 min and cooled to −78° C. A THF (15 mL) solution of 2-chloropyridine (3.5 g, 30.8 mmol) was added dropwise. The solution gradually turned to bright yellow. After 1 h at −78° C., a suspension of 2-chloronicotinaldehyde (4.80 g, 33.9 mmol) in THF (80 mL) was added dropwise. The flask was rinsed with THF (5 mL) and added. After 2 h at −78° C., the mixture was quenched with saturated NH$_4$Cl (200 mL), acidified to pH 4 with concentrated HCl, and extracted with ether (150 mL, 2×50 mL). The combined extracts were washed with brine (10 mL), dried (MgSO$_4$) and concentrated. Silica gel chromatography, eluting with 10-100% EtOAc in hexanes, gave the expected product as light brown powder (2.48 g, 26% yield). MS (ES+) m/z: 255 (M+H); LC retention time: 2.38 min (analytical HPLC Method A).

Step 2

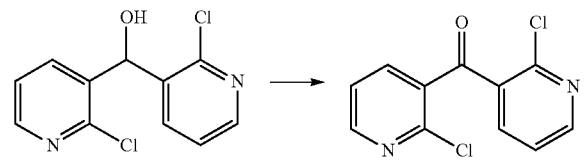

Dess-Martin Periodinane (5.18 g, 12.21 mmol) was added to a solution of bis(2-chloropyridin-3-yl)methanol (1.88 g, 7.37 mmol) in dichloromethane (100 mL) and THF (20 mL). After 1.5 h at room temperature, 1.4 M NaHSO$_3$ (50 mL) was added and the mixture was stirred at room temperature for 20 min. After removal of solid by filtration, the two phases of the filtrate were separated. The aqueous phase was basified to pH 8 with saturated NaHCO$_3$ (200 mL) and extracted with CH$_2$Cl$_2$ (100 mL). The combined CH$_2$Cl$_2$ phase was dried (MgSO$_4$) and concentrated. Silica gel chromatography, eluting with 0-100% EtOAc in hexanes, gave the expected product as light brown powder (1.87 g, 91% yield). MS (ES+) m/z: 253 (M+H); LC retention time: 2.79 min (analytical HPLC Method A).

Step 3

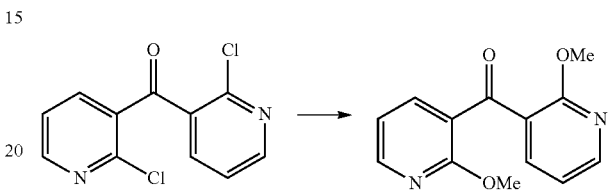

A suspension of bis(2-chloropyridin-3-yl)methanone (1.87 g, 7.39 mmol) in MeOH (18 mL) was added to a suspension of sodium methoxide (1.36 g, 25.2 mmol) in MeOH (7 mL). The mixture was heated to reflux under nitrogen for 7 h. Additional NaOMe (2.91 g) was added. After additional 14 h at reflux, the solvent was evaporated in vacuo. The resulting was dissolved in water (50 mL) and extracted with EtOAc (2×50 mL). The combined extracts were washed with pH 7 buffer (10 mL), brine (10 mL), dried (MgSO$_4$), and concentrated to give the expected product as white solid (1.7669 g, 98% yield). MS (ES+) m/z: 245 (M+H).

Step 4

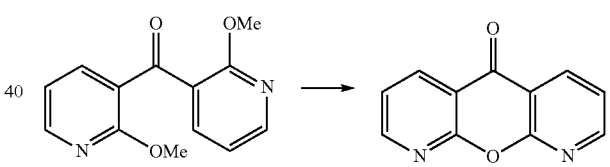

A solid mixture of bis(2-methoxypyridin-3-yl)methanone (1.7549 g, 7.18 mmol) and pyridine hydrochloride (7.3 g, 63.2 mmol) was divided into two microwave vials and microwaved at 220° C. for 10 min for each. The mixture was combined and dissolved in CHCl$_3$ (200 mL) and water (100 mL) with sonication. After separation of the two phases, the aqueous phase was extracted with CHCl$_3$ (2×100 mL). The combined CHCl$_3$ phase was dried over MgSO$_4$ and concentrated to give the expected product as a tan crystalline solid (1.07 g, 75% yield). MS (ES+) m/z: 199 (M+H); LC retention time: 2.35 min (analytical HPLC Method A).

Step 5

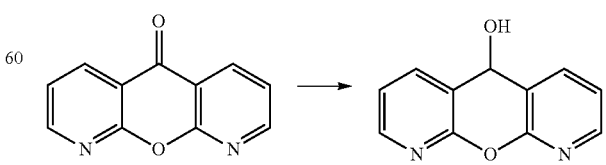

Sodium borohydride (1.021 g, 27.0 mmol) was added to a suspension of the ketone from Step 4 (1.07 g, 5.40 mmol) in CH$_2$Cl$_2$ (5 mL) and MeOH (25 mL). Additional sodium borohydride (0.5 g and 0.3 g) was added at 1 h and 2 h time points and the mixture was stirred overnight. Dichloromethane (100 mL), saturated NH$_4$Cl (50 mL) and water (50 mL) were added. The two phases were separated. The aqueous phase was extracted with CH$_2$Cl$_2$ (3×100 mL) and EtOAc (1×100 mL). All organic phase was combined, washed with brine (10 mL), dried (MgSO$_4$) and concentrated to give the expected product as light yellow solid (1.11 g, 89% yield). MS (ES+) m/z: 201 (M+H); LC retention time: 1.93 min (analytical HPLC Method A).

Step 6

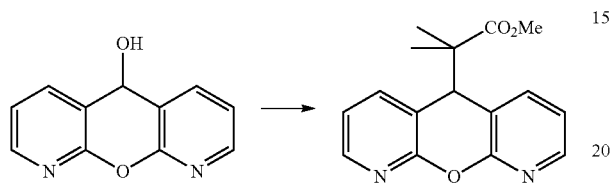

A 1.0 M CH$_2$Cl$_2$ solution of titanium(IV) chloride (12.06 mL, 12.06 mmol) was added to a suspension of the alcohol from Step 5 (1.11 g, 4.82 mmol) in CH$_2$Cl$_2$ (200 mL) at 0° C. After 1 h at 0° C., methyl trimethylsilyl dimethylketene acetal (4.90 mL, 24.12 mmol) was added. After 1 h at 0° C., the mixture was quenched with saturated NaHCO$_3$ (75 mL), stirred at room temperature for 30 min and filtered. The two phases of the filtrate were separated. The aqueous phase was extracted with CH$_2$Cl$_2$ (1×100 mL). The combined CH$_2$Cl$_2$ phase was washed with brine (5 mL), dried (MgSO$_4$) and concentrated. Silica gel chromatography, eluting with 0-100% EtOAc in hexanes, gave the expected product as white solid (1.08 g, 79% yield). MS (ES+) m/z: 285 (M+H); LC retention time: 2.91 min (analytical HPLC Method A).

Step 7

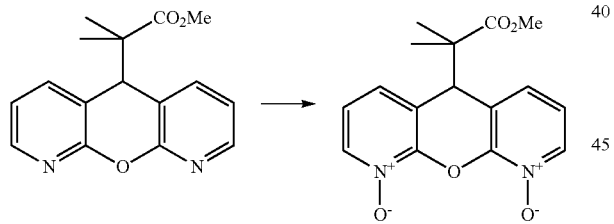

A 30% aqueous hydrogen peroxide (22.31 mL, 218 mmol) and methyltrioxorhenium(VII) (0.392 g, 1.573 mmol) were added to a solution of the ester from Step 6 (1.035 g, 3.64 mmol) in CH$_2$Cl$_2$ (40 mL). One hour later, additional methyltrioxorhenium(VII) (0.5461 g) was added. After another 2 h, additional methyltrioxorhenium(VII) (0.5372 g) and hydrogen peroxide (22 mL) were added. Another portion of methyltrioxorhenium(VII) (1.89 g) and hydrogen peroxide (22 mL) were added 3 h later. After a total of 24 h, a water suspension of MnO$_2$ (0.5 g) was slowly added to induce decomposition of H$_2$O$_2$. The biphasic mixture was stirred for 1 h and separated. The aqueous phase was found to contain most of the desired product, was washed with CH$_2$Cl$_2$ (3×50 mL) and concentrated. Silica gel chromatography, eluting with 10% methanol in CH$_2$Cl$_2$, gave impure product as off-white solid (3.68 g). A portion of the material (2.08 g) was purified by reverse phase HPLC (Sunfire S10 30×250 mm column, 0-21% solvent B gradient) to give the expected product as white solid (355 mg). MS (ES+) m/z: 317 (M+H); LC retention time: 1.60 min (analytical HPLC Method A).

Step 8

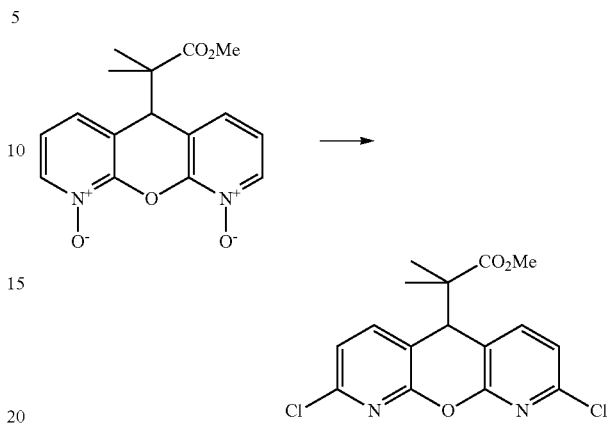

A mixture of the product from Step 7 (313.6 mg, 0.991 mmol) and POCl$_3$ (4 mL, 42.9 mmol) was heated to 100° C. for 20 h, cooled to room temperature and poured into ~100 mL of water-ice mixture. With stirring, the mixture was neutralized to pH 5 with solid NaHCO$_3$ and extracted with EtOAc (2×50 mL). The combined extracts were concentrated and purified by silica gel chromatography, eluting with 0-30% EtOAc in CH$_2$Cl$_2$, to give the expected product as white solid (0.1358 g, 34% yield). MS (ES+) m/z: 353 (M+H); LC retention time: 3.55 min (analytical HPLC Method A).

Step 9

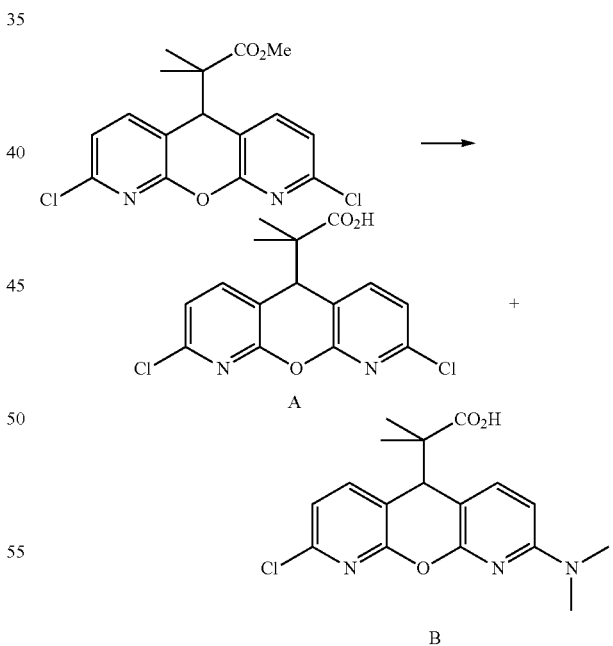

A suspension of the product from Step 8 (127.6 mg, 0.361 mmol) and lithium chloride (220 mg, 5.19 mmol) in DMF (3 mL) was microwaved at 220° C. for 30 min. The mixture was purified by reverse phase HPLC (YMC 30×250 mm ODS-A column, 45-90% solvent B gradient) to give product A (26 mg) and product B (19 mg). Characterization of A: MS (ES+) m/z: 339 (M+H); LC retention time: 3.38 min (analytical HPLC Method A). Characterization of B: MS (ES+) m/z: 348 (M+H); LC retention time: 3.58 min (analytical HPLC Method A).

Step 10-11

Following conditions similar to Steps 8 and 9 of Example 14, Example 73 was prepared. ¹H NMR (400 MHz, methanol-d3) δ ppm 9.07 (1H, s), 7.86-7.97 (2H, m), 7.69 (2H, s), 7.45 (1H, t, J=7.43 Hz), 7.37 (1H, d, J=8.56 Hz), 6.40 (1H, d, J=8.56 Hz), 4.47 (1H, s), 3.11 (3H, s), 3.06 (6H, s), 2.96 (3H, s), 1.14 (3H, s), 1.13 (3H, s); MS (ES+) m/z: 562 (M+H); LC retention time: 3.76 min (analytical HPLC Method A).

Examples 74-80

Examples 74-80 were prepared using the S-enantiomer from Step 7 of Example 14 in the manner described above for the preparation of the title compound of Example 14, using commercially available boronic acids and amines

| Ex # | Structure | ¹H NMR (400 MHz) δ ppm | RT (min) | Obs. MS Ion |
|---|---|---|---|---|
| 74 | 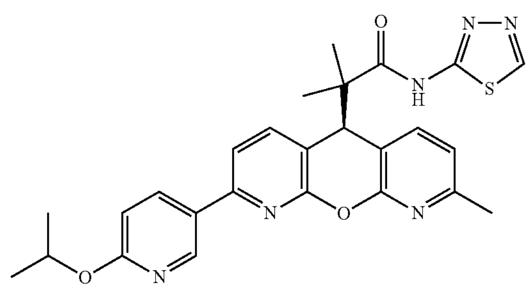 | Chloroform-d (500 MHz): 11.67 (1 H, br. s.), 9.03 (1 H, s), 8.93 (1 H, dd, J = 9.21, 1.79 Hz), 8.91 (1 H, s), 7.68 (2 H, s), 7.62 (1 H, d, J = 7.70 Hz), 7.18 (1 H, d, J = 9.07 Hz), 7.08 (1 H, d, J = 7.70 Hz), 5.13 (1 H, spt, J = 6.05 Hz), 4.65 (1 H, s), 2.60 (3 H, s), 1.51 (6 H, d, J = 6.05 Hz), 1.27 (3 H, s), 1.25 (3 H, s). | 3.99 | 503 |
| 75 | 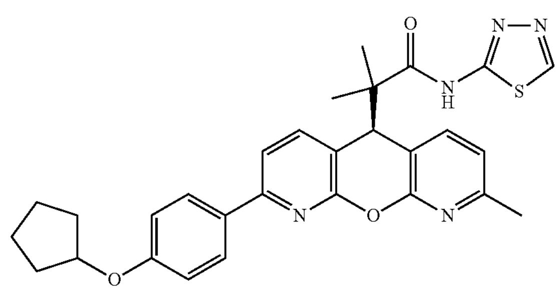 | Chloroform-d (500 MHz): 8.90 (1 H, s), 7.91 (2 H, d, J = 8.80 Hz), 7.65 (1 H, d, J = 7.70 Hz), 7.59 (1 H, d, J = 7.97 Hz), 7.51 (1 H, d, J = 7.97 Hz), 7.08 (1 H, d, J = 7.97 Hz), 6.95 (2 H, d, J = 8.52 Hz), 4.78-4.88 (1 H, m), 4.58 (1 H, s), 2.63 (3 H, s), 1.74-2.02 (6 H, m), 1.57-1.72 (2 H, m), 1.26 (3 H, s), 1.24 (3 H, s). | 4.39 | 528 |
| 76 | 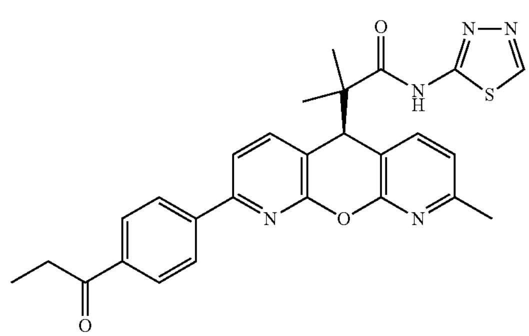 | Chloroform-d (500 MHz): 11.90 (1 H, br. s.), 8.92 (1 H, s), 8.09-8.15 (2 H, m), 8.03-8.09 (2 H, m), 7.62-7.70 (3 H, m), 7.09 (1 H, d, J = 7.97 Hz), 4.62 (1 H, s), 3.06 (2 H, q, J = 7.33 Hz), 2.62 (3 H, s), 1.18-1.32 (9 H, m). | 3.86 | 500 |
| 77 | 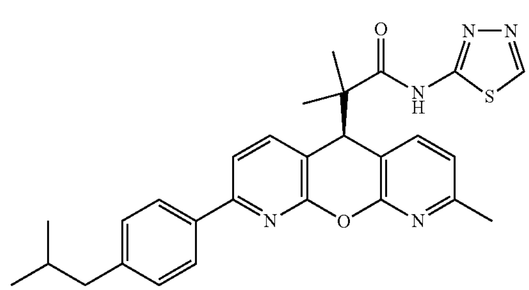 | Chloroform-d (500 MHz): 12.87 (1 H, br. s.), 8.90 (1 H, s), 7.91 (2 H, d, J = 8.25 Hz), 7.61 (2 H, d, J = 7.70 Hz), 7.56 (1 H, d), 7.24 (2 H, d, J = 8.25 Hz), 7.05 (1 H, d, J = 7.70 Hz), 4.60 (1 H, s), 2.61 (3 H, s), 2.52 (2 H, d, J = 7.15 Hz), 1.84-1.97 (1 H, m), 1.25 (6 H, d, J = 8.52 Hz), 0.92 (3 H, s), 0.91 (3 H, s). | 4.49 | 500 |

| Ex # | Structure | ¹H NMR (400 MHz) δ ppm | RT (min) | Obs. MS Ion |
|---|---|---|---|---|
| 78 | 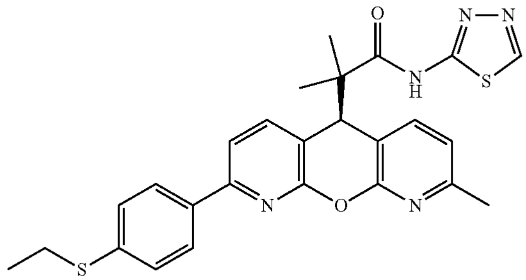 | Chloroform-d (500 MHz): 12.74 (3 H, br. s.), 8.90 (1 H, s), 7.94 (2 H, d, J = 8.52 Hz), 7.56-7.62 (2 H, m), 7.52-7.56 (1 H, m), 7.37 (2 H, d, J = 8.25 Hz), 7.04 (1 H, d, J = 7.70 Hz), 4.57 (1 H, s), 3.02 (2 H, q, J = 7.33 Hz), 2.60 (3 H, s), 1.36 (3 H, t, J = 7.42 Hz), 1.25 (3 H, s), 1.23 (3 H, s). | 4.21 | 504 |
| 79 | 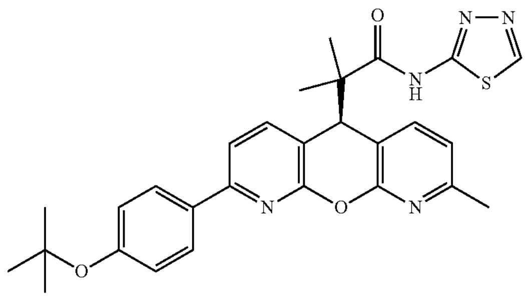 | Chloroform-d (500 MHz): 11.86 (1 H, br. s.), 8.92 (1 H, s), 7.88 (2 H, d, J = 8.52 Hz), 7.76 (1 H, d, J = 7.70 Hz), 7.61-7.65 (1H, m), 7.56 (1 H, d, J = 7.97 Hz), 7.16 (1 H, d, J = 7.97 Hz), 7.09 (2 H, d, J = 8.52 Hz), 4.61 (1 H, s), 2.67 (3 H, s), 1.40 (9 H, s), 1.26 (6 H, s). | 4.16 | 516 |
| 80 | 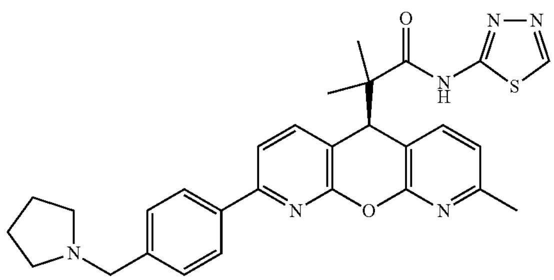 | Methano-d4: 9.11 (1 H, s), 8.18 (2 H, d, J = 8.28 Hz), 7.73-7.80 (2 H, m), 7.64 (3 H, t, J = 8.16 Hz), 7.12 (1 H, d, J = 8.03 Hz), 4.65 (1 H, s), 4.44 (2 H, s), 3.47-3.60 (2 H, m), 3.16-3.28 (2 H, m), 2.52 (3 H, s), 2.15-2.27 (2 H, m), 1.99-2.08 (2 H, m), 1.20 (3 H, s), 1.18 (3 H, s). | 2.96 | 527 |

Example 81

2-((5S)-2-(4-(ethylsulfinyl)phenyl)-8-methyl-5H-pyrido[3',2':5,6]pyrano[2,3-b]pyridin-5-yl)-2-methyl-N-1,3,4-thiadiazol-2-ylpropanamide

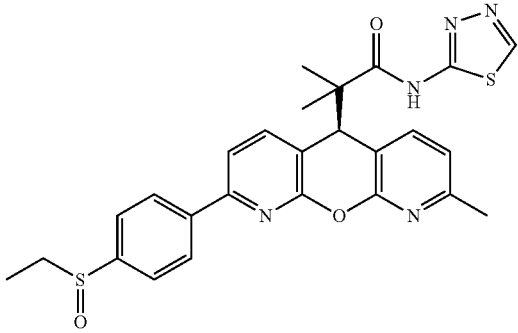

A solution of oxone (17.2 mg, 0.028 mmol) in water (0.5 mL) was added dropwise to a solution of Example 78, bis-TFA salt (30 mg, 0.061 mmol) in MeOH (0.5 mL) at 0° C. After 1.5 h, the mixture was quench with 1 M solution of Na₂SO₃ (1 mL), and stirred overnight. The mixture was concentrated, taken up in CH2Cl2 and loaded on a prep silica gel plate (150 A, 1000 um thickness, 20×20 cm), and developed using 5% MeOH in CH2Cl2. The major band was collected to give Example 81 as white solid (7.0 mg, 47% yield). ¹H NMR (500 MHz, chloroform-d) d ppm 8.92 (1H, s), 8.23 (2H, dd, J=8.52, 1.65 Hz), 7.76 (1H, d, J=7.70 Hz), 7.70 (2H, d, J=8.25 Hz), 7.58 (1H, dd, J=7.97, 2.20 Hz), 7.54 (1H, d, J=7.70 Hz), 6.95 (1H, d, J=7.42 Hz), 4.84 (1H, s), 2.91-3.03 (1H, m), 2.75-2.87 (1H, m), 2.54 (3H, s), 1.30 (3H, s), 1.27 (3H, s), 1.22 (3H, t, J=7.42 Hz); MS (ES+) m/z: 520 (M+H); LC retention time: 3.46 min (analytical HPLC Method A).

Example 82

2-((5S)-2-(4-(isopropylsulfinyl)phenyl)-8-methyl-5H-pyrido[3',2':5,6]pyrano[2,3-b]pyridin-5-yl)-2-methyl-N-1,3,4-thiadiazol-2-ylpropanamide

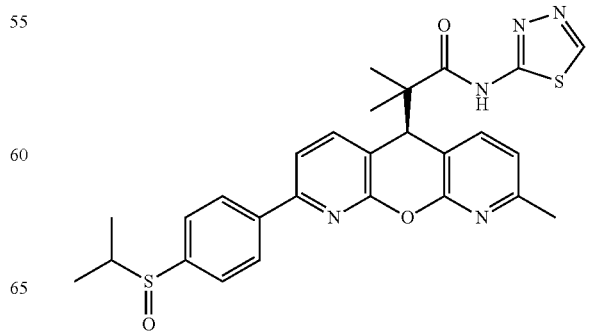

Following conditions described for Steps 8 and 9 of Example 14 and Example 81, the S-enantiomer from Step 7 of Example 14 was converted to Example 82. $^1$H NMR (500 MHz, chloroform-d) d ppm 8.92 (1H, s), 8.22 (2H, dd, J=8.52, 1.65 Hz), 7.76 (1H, d, J=7.42 Hz), 7.68 (2H, d, J=8.52 Hz), 7.59 (1H, dd, J=7.70, 2.20 Hz), 7.54 (1H, d, J=7.42 Hz), 6.95 (1H, d, J=7.70 Hz), 4.83 (1H, s), 2.83-2.96 (1H, m), 2.54 (3H, s), 1.29 (3H, d, J=6.87 Hz), 1.27 (3H, s), 1.26 (3H, s), 1.16 (3H, d, J=6.87 Hz); MS (ES+) m/z: 534 (M+H); LC retention time: 3.59 min (analytical HPLC Method A).

Example 83

2-((5S)-2-(4-(isopropylsulfonyl)phenyl)-8-methyl-5H-pyrido[3',2':5,6]pyrano[2,3-b]pyridin-5-yl)-2-methyl-N-1,3,4-thiadiazol-2-ylpropanamide

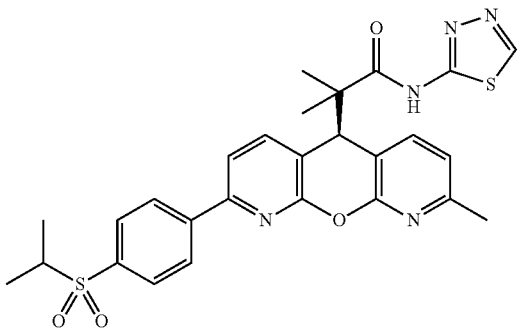

Following conditions described for Example 81, Example 82 was converted to Example 83. $^1$H NMR (500 MHz, chloroform-d) d ppm 8.91 (1H, s), 8.26 (2H, d, J=8.52 Hz), 7.97 (2H, d, J=8.52 Hz), 7.75 (1H, d, J=7.97 Hz), 7.60 (1H, d, J=7.70 Hz), 7.52 (1H, d, J=7.70 Hz), 6.96 (1H, d, J=7.70 Hz), 4.77 (1H, s), 3.18-3.29 (1H, m), 2.54 (3H, s), 1.32 (6H, d, J=6.87 Hz), 1.28 (3H, s), 1.26 (3H, s); MS (ES+) m/z: 550 (M+H); LC retention time: 3.59 min (analytical HPLC Method A).

Example 84

4-(5-(1,1-dimethyl-2-oxo-2-(1,3,4-thiadiazol-2-ylamino)ethyl)-9-oxido-5H-pyrido[3',2':5,6]pyrano[2,3-b]pyridin-2-yl)-N-ethyl-N-methylbenzamide

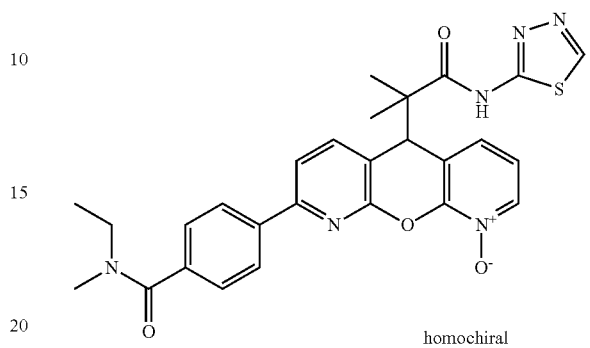

homochiral

A 30% aqueous hydrogen peroxide (0.5 mL, 4.89 mmol) and methyltrioxorhenium(VII) (11 mg, 0.044 mmol) were added to a solution of Example 9 (36.6 mg, 0.071 mmol) in dichloromethane (1 mL). After 4 h at rt, the mixture was concentrated and purified by preparative RP-HPLC (45-75% solvent B in 30 min, 40 mL/min, Sunfire 30×250 mm) to give Example 84 as TFA salt (11.8 mg, 25% yield). $^1$H NMR (500 MHz, methanol-d4) δ ppm 9.09 (2H, s), 8.42-8.47 (2H, m), 8.10-8.17 (4H, m), 7.82-7.89 (4H, m), 7.61 (2H, d, J=7.15 Hz), 7.51 (4H, t, J=8.39 Hz), 7.32 (2H, dd, J=7.70, 6.60 Hz), 4.87 (2H, s), 3.61 (2H, q, J=7.06 Hz), 3.35 (2H, q, J=7.06 Hz), 3.10 (3H, s), 3.01 (3H, s), 1.27 (3H, t, J=7.15 Hz), 1.25 (6H, s), 1.23 (6H, s), 1.17 (3H, t, J=7.15 Hz), 1:1 mixture of two amide rotamers; MS (ES+) m/z: 531 (M+H); LC retention time: 3.04 min (analytical HPLC Method A).

Examples 85-87

Examples 85-87 were prepared from Example 32 following conditions similar to the synthesis of Example 50, using appropriate amines.

| Ex # | Structure | $^1$H NMR (400 MHz) δ ppm | RT (min) | Obs. MS Ion |
|---|---|---|---|---|
| 85 | 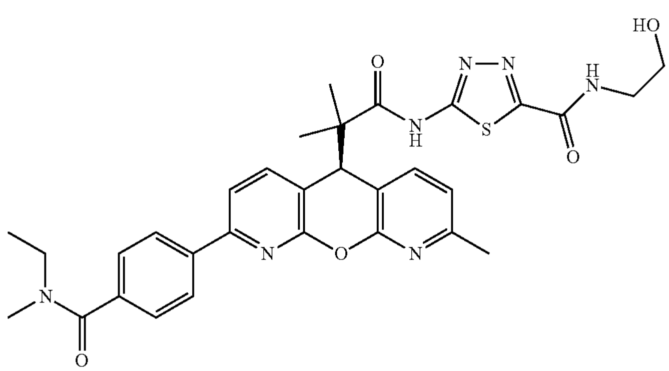 | Chloroform-d (500 MHz): 8.50 (2 H, br. s.), 7.83 (4 H, t, J = 7.29 Hz), 7.57-7.63 (2 H, m), 7.46-7.54 (6 H, m), 7.31 (2 H, t, J = 8.94 Hz), 6.91 (2 H, d, J = 7.70 Hz), 4.50 (2 H, s), 4.28-4.41 (2 H, m), 4.18 (2 H, m), 3.89-4.03 (2 H, m), 3.73-3.86 (2 H, m), 3.65 (2 H, q, J = 6.87 Hz), 3.35 (2 H, q, J = 6.87 Hz), 3.15 (3 H, s), 3.01 (3 H, s), 2.46 (6 H, s), 1.33 (6 H, s), 1.26-1.32 (9 H, m), 1.19 (3 H, t), a mixture of 2 amide rotamers. | 3.55 | 616 |

| Ex # | Structure | ¹H NMR (400 MHz) δ ppm | RT (min) | Obs. MS Ion |
|---|---|---|---|---|
| 86 | 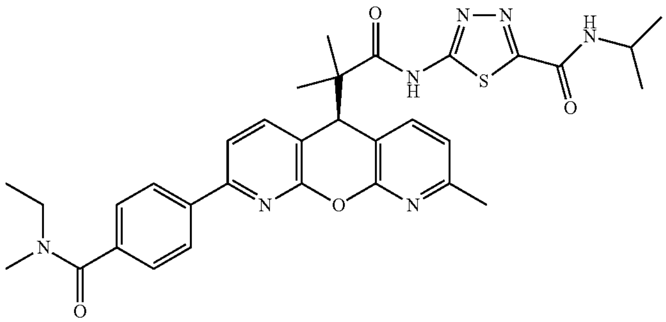 | Chloroform-d (500 MHz): 8.05 (4 H, d, J = 8.25 Hz), 7.61-7.66 (2 H, m), 7.57 (4 H, dd, J = 7.70, 3.30 Hz), 7.50 (4 H, t, J = 8.94 Hz), 7.24 (2 H, d, J = 8.25 Hz), 7.02 (2 H, d, J = 7.70 Hz), 4.60 (2 H, s), 4.24-4.36 (2 H, m), 3.66 (2 H, q, J = 6.97 Hz), 3.35 (2 H, q, J = 6.96 Hz), 3.15 (3 H, s), 3.01 (3 H, s), 2.57 (6 H, s), 1.34 (12 H, dd, J = 6.60, 3.57 Hz), 1.30 (3 H, t, J = 7.15 Hz), 1.26 (6 H, s), 1.24 (6 H, s), 1.18 (3 H, t, J = 7.15 Hz), a mixture of 2 amide rotamers. | 3.89 | 614 |
| 87 | 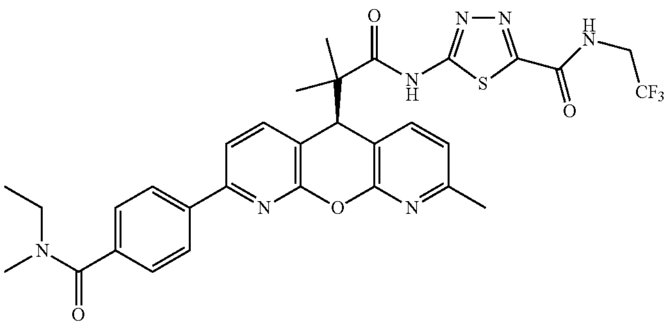 | Chloroform-d: 8.06 (4 H, d, J = 8.28 Hz), 7.82 (2 H, br. s.), 7.61-7.68 (2 H, m), 7.55-7.60 (2 H, m), 7.46-7.55 (6 H, m), 6.99 (2 H, d, J = 7.78 Hz), 4.58 (2 H, s), 4.09-4.29 (4 H, m), 3.65 (2 H, q, J = 7.03 Hz), 3.34 (2 H, q, J = 7.03 Hz), 3.15 (3 H, s), 3.01 (3 H, s), 2.55 (6 H, s), 1.23-1.35 (15 H, m), 1.18 (3 H, t, J = 7.03 Hz), a mixture of 2 amide rotamers. | 3.95 | 654 |

Example 88

5-((2-methyl-2-((5S)-2-methyl-8-(4-(4-morpholinylcarbonyl)phenyl)-5H-pyrano[2,3-b:6,5-b']dipyridin-5-yl)propanoyl)amino)-N-(tetrahydro-2H-pyran-4-yl)-1,3,4-thiadiazole-2-carboxamide

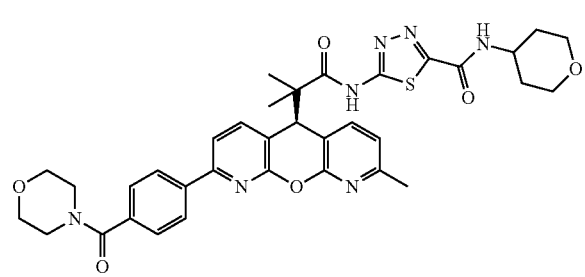

Steps 1-2

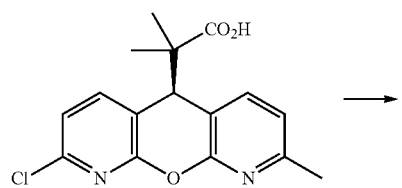

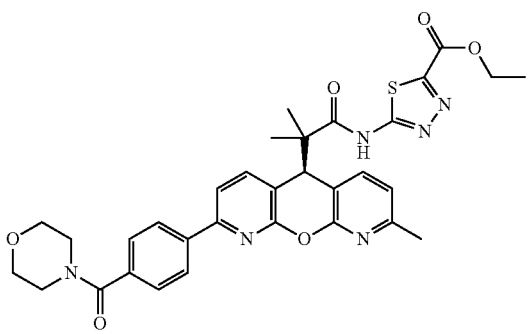

Following the reaction procedures from Example 14, steps 8 and 9, the acid from Step 7 of Example 14 was coupled with the appropriate boronic acid and aminothiadiazole to give the expected product. ¹H NMR (400 MHz, chloroform-d) δ ppm 8.09-8.17 (2H, m), 7.79 (1H, t, J=7.69 Hz), 7.45-7.63 (4H, m), 6.91-7.02 (1H, m), 4.73 (1H, s), 4.56 (2H, q, J=7.03 Hz), 3.38-3.91 (8H, m), 2.54 (3H, s), 1.48 (3H, t, J=7.14 Hz), 1.19-1.33 (6H, m); MS (ES+) m/z: 629 (M+H); LC retention time: 3.75 min (analytical HPLC Method B).

Steps 3

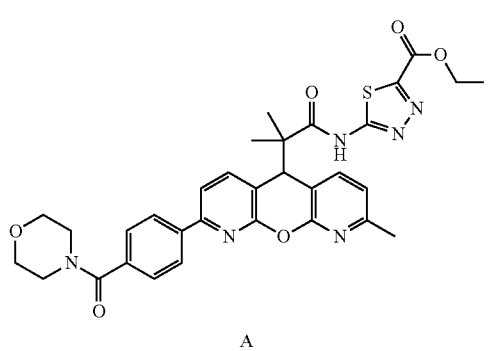

A

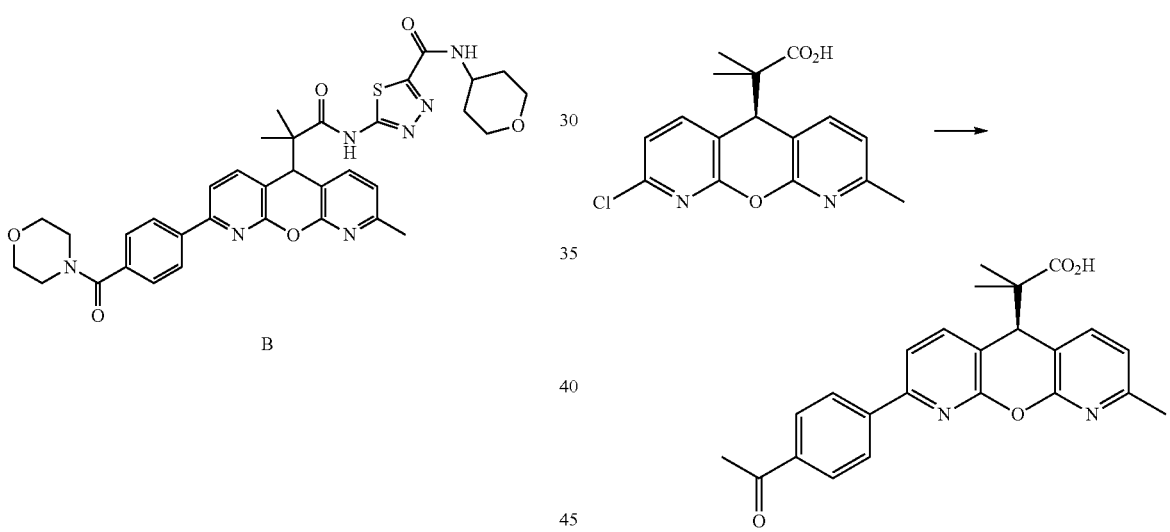

B

The compound from Step 2 (40 mg, 0.064 mmol) in THF (2 mL) was added water (0.6 mL) and LiOH—H2O (6.7 mg, 0.16 mmol). The mixture was stirred at rt overnight and concentrated under vacuo. The residue was taken in isopropanol and concentrated to dryness to give a lithium salt. A mixture of the lithium salt (20 mg, 0.033 mmol) and tetrahydro-2H-pyran-4-amine (16.7 mg, 0.17 mmol) in DMF (3 mL) was added BOP (29.2 mg, 0.066 mmol) and DIEA (42.6 mg, 0.33 mmol). The mixture was stirred at rt for 2 h and taken in ethyl acetate (50 mL), which was washed with saturated NH4Cl (20 mL) and NaHCO3 (20 mL), dried over Na2SO4 and concentrated under vacuo. The crude product was purified with preparative HPLC to give the desired product as TFA salt. (13 mg, 49.2% yield). $^1$H NMR (400 MHz, methanol-$d_4$) δ ppm 8.07 (2H, d, J=8.35 Hz), 7.67 (2H, s), 7.54 (1H, d, J=7.69 Hz), 7.45 (2H, d, J=8.35 Hz), 7.02 (1H, d, J=7.69 Hz), 4.55 (1H, s), 3.97-4.12 (1H, m), 3.83-3.96 (2H, m), 3.68 (6H, br. s.), 3.35-3.51 (4H, m), 2.41 (3H, s), 1.82 (2H, dd, J=12.63, 2.31 Hz), 1.56-1.74 (2H, m), 1.09 (6H, s). MS (ES+) m/z: 684 (M+H); LC retention time: 3.59 min (analytical HPLC Method B).

Example 89

2-((5S)-2-(4-(1-hydroxy-1-methylethyl)phenyl)-8-methyl-5H-pyrido[3',2':5,6]pyrano[2,3-b]pyridin-5-yl)-2-methyl-N-1,3,4-thiadiazol-2-ylpropanamide

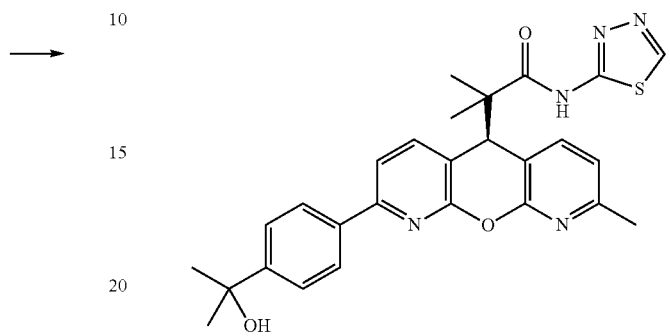

Step 1

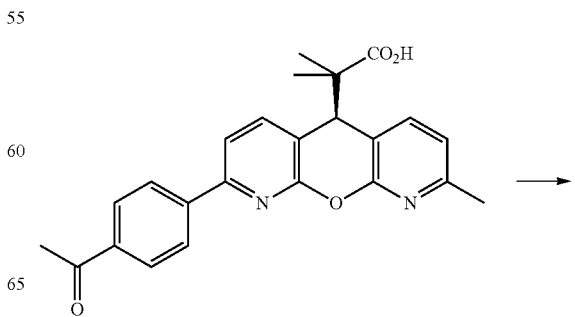

Following the reaction procedure from Step 8 of Example 14, the acid from Step 7 of Example 14 was coupled with 4-acetylphenylboronic acid to give the expected product. MS (ES+) m/z: 403 (M+H); LC retention time: 2.85 min (analytical HPLC Method B).

Step 2

-continued

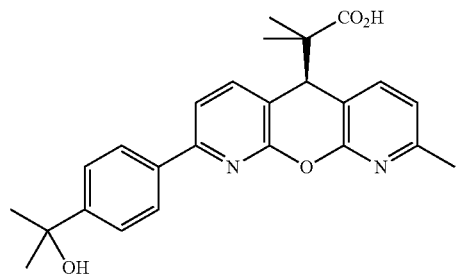

To a solution of the ketone from Step 1 (60 mg, 0.15 mmol) in anhydrous THF (2 mL) was added methylmagnesium bromide solution (3 M in diethyl ether, 0.50 mL, 1.5 mmol) at −78° C. under nitrogen. After 30 min at rt, 10% aqueous citric acid solution was added to adjust the PH to 6. The mixture was extracted with ethyl acetate (3×1 mL). The combined extracts were dried (Na2SO4), concentrated and purified by RP-HPLC to give the expected product (31 mg, 50% yield). MS (ES+) m/z: 419 (M+H); LC retention time: 2.92 min (analytical HPLC Method B).

Step 3

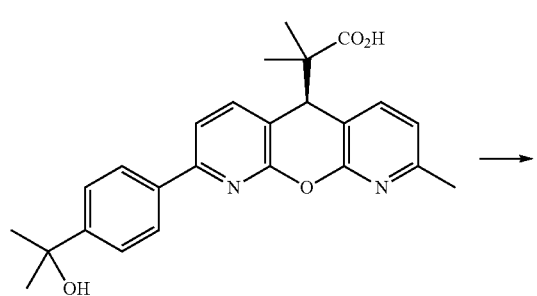

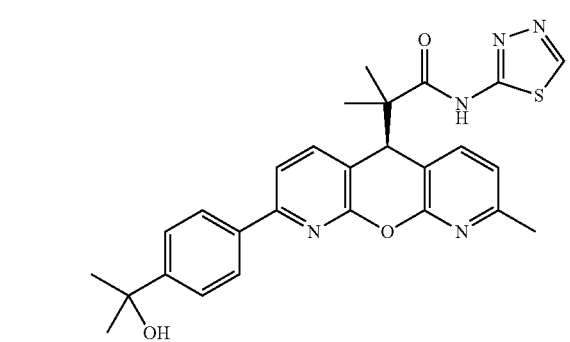

Following conditions described for Step 9 of Example 14, the acid from Step 2 was coupled with aminothiadiazole to give Example 89. $^1$H NMR (400 MHz, chloroform-d) δ ppm 1.13-1.20 (m, 6H) 1.55 (s, 6H) 2.49 (s, 3H) 4.52 (s, 1H) 6.91 (d, J=7.78 Hz, 1H) 7.39-7.55 (m, 5H) 7.94 (d, J=8.28 Hz, 2H) 8.83 (s, 1H); MS (ES+) m/z: 502 (M+H); LC retention time: 2.96 min (analytical HPLC Method B).

Example 90

1-(4-((5S)-5-(1,1-dimethyl-2-oxo-2-(1,3,4-thiadiazol-2-ylamino)ethyl)-8-methyl-5H-pyrido[3',2':5,6]pyrano[2,3-b]pyridin-2-yl)benzoyl)-D-prolinamide

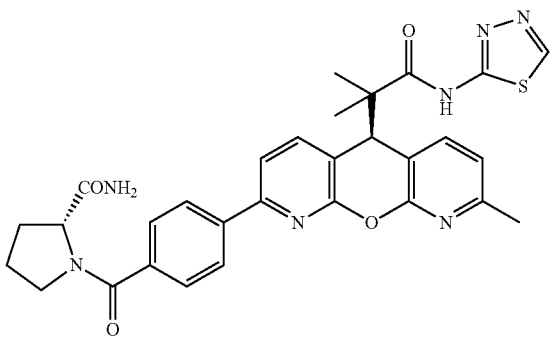

Following conditions for Steps 8 and 9 of Example 14, the acid from Step 7 of Example 14 was coupled with (R)-4-(2-carbamoylpyrrolidine-1-carbonyl)phenylboronic acid and 2-amino-1,3,4-thiadiazole to give Example 90. 1H NMR (400 MHz, chloroform-d) δ ppm 0.79-0.84 (m, 4H) 0.99 (d, J=10.54 Hz, 6H) 2.29 (s, 2H) 2.33 (s, 3H) 4.15 (s, 1H) 4.36 (s, 1H) 6.77 (dd, J=12.92, 7.65 Hz, 1H) 6.86-6.92 (m, 1H) 7.25 (d, J=7.78 Hz, 1H) 7.31-7.42 (m, 4H) 7.86 (d, J=8.28 Hz, 2H) 8.67 (s, 1H); MS (ES+) m/z: 584 (M+H); LC retention time: 2.52 min (analytical HPLC Method B).

Example 91

1-(4-((5S)-5-(1,1-dimethyl-2-((5-methyl-1,3,4-thiadiazol-2-yl)amino)-2-oxoethyl)-8-methyl-5H-pyrido[3',2':5,6]pyrano[2,3-b]pyridin-2-yl)benzoyl)-D-prolinamide

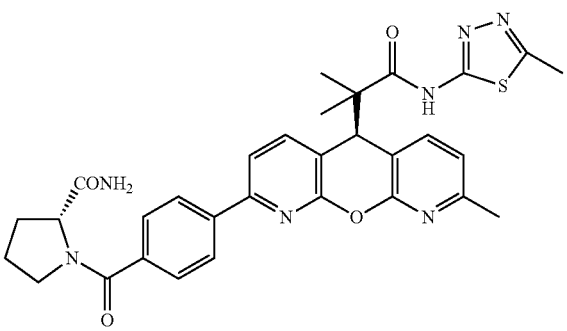

Following conditions for Steps 8 and 9 of Example 14, the acid from Step 7 of Example 14 was coupled with (R)-4-(2-carbamoylpyrrolidine-1-carbonyl)phenylboronic acid and 2-amino-5-methyl-1,3,4-thiadiazole to give Example 91. 1H NMR (400 MHz, chloroform-d) δ ppm 1.13 (d, J=14.31 Hz, 6H) 1.84 (d, J=6.78 Hz, 1H) 1.98-2.07 (m, 1H) 2.07-2.18 (m, 1H) 2.25-2.37 (m, 1H) 2.49 (s, 3H) 2.69 (s, 3H) 3.42-3.62 (m, 2H) 4.54 (s, 1H) 4.75 (dd, J=7.78, 5.52 Hz, 1H) 6.93 (d, J=7.53 Hz, 1H) 7.40-7.59 (m, 5H) 8.00 (d, J=8.28 Hz, 2H); MS (ES+) m/z: 598 (M+H); LC retention time: 2.73 min (analytical HPLC Method B).

Example 92

2-methyl-2-((5S)-2-methyl-8-(4-(4-morpholinylcarbonyl)phenyl)-5H-pyrido[3',2':5,6]pyrano[2,3-b]pyridin-5-yl)-N-(2-methyl-2H-tetrazol-5-yl)propanamide

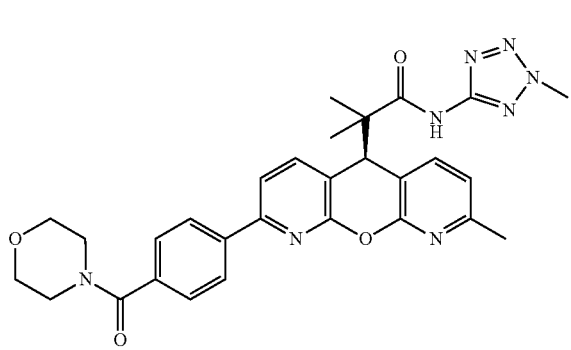

Step 1

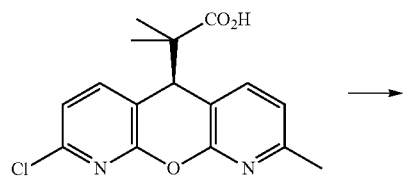

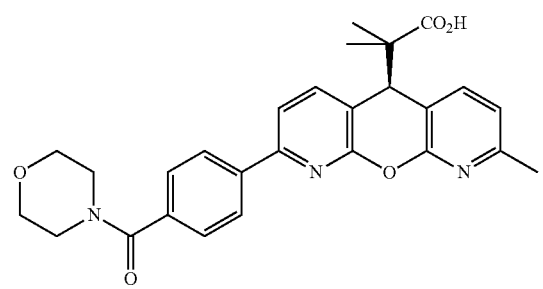

Following the reaction procedure from Step 8 of Example 14, the acid from Step 7 of Example 14 was coupled with morpholino(4-(4,4,5,5-tetramethyl-1,3,2-dioxaborolan-2-yl)phenyl)methanone to give the expected product. MS (ES+) m/z: 474 (M+H); LC retention time: 2.62 min (analytical HPLC Method B).

Step 2

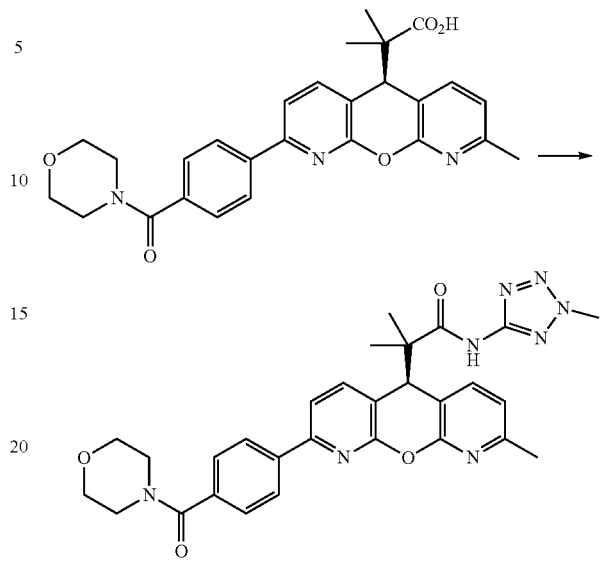

To a solution of the acid from Step 1 (30 mg, 0.063 mmol) in THF (5 mL) was added methanesulfonyl chloride (9.87 µL, 0.127 mmol) and DIEA (0.033 mL, 0.190 mmol), respectively. After 5 h at rt, 1-methyl-1H-tetrazol-5-amine (25.1 mg, 0.253 mmol) was added. The mixture was stirred at rt for 24 h, diluted with MeOH (1 mL) and purified by reverse phase-HPLC to give Example 92 as bis TFA salt (27 mg, 55% yield). 1H NMR (400 MHz, chloroform-d) δ ppm 1.08 (d, J=4.27 Hz, 6H) 2.48 (s, 3H) 3.35-3.81 (m, 8H) 4.29 (s, 3H) 4.59 (s, 1H) 7.13 (d, J=7.78 Hz, 1H) 7.45-7.51 (m, 2H) 7.70-7.77 (m, 2H) 7.80-7.85 (m, 1H) 8.09 (d, 2H); MS (ES+) m/z: 555 (M+H); LC retention time: 2.45 min (analytical HPLC Method B).

Example 93

N-(5-cyclopropyl-1,3,4-thiadiazol-2-yl)-2-methyl-2-((5 S)-2-methyl-8-(4-(4-morpholinylcarbonyl)phenyl)-5H-pyrido[3',2':5,6]pyrano[2,3-b]pyridin-5-yl)propanamide

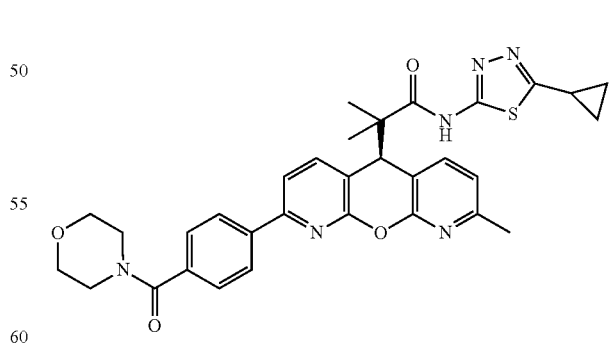

Following conditions described for Step 9 of Example 14, the acid from Step 1 of Example 92 was coupled with 2-amino-5-cyclopropylthiadiazole to give Example 93. 1H NMR (400 MHz, chloroform-d) δ ppm 1.16-1.41 (m, 10H) 2.27-2.38 (m, 1H) 2.57 (s, 3H) 3.43-3.93 (m, 8H) 4.59 (s, 1H) 7.01 (d, J=7.78 Hz, 1H) 7.51 (t, J=8.53 Hz, 3H) 7.56-7.67 (m, 2H) 8.12 (d, 2H); MS (ES+) m/z: 597 (M+H); LC retention time: 3.08 min (analytical HPLC Method B).

Example 94

4-((5S)-5-(1,1-dimethyl-2-((2-methyl-2H-tetrazol-5-yl)amino)-2-oxoethyl)-8-methyl-5H-pyrido[3',2':5,6]pyrano[2,3-b]pyridin-2-yl)-N,N-dimethylbenzamide

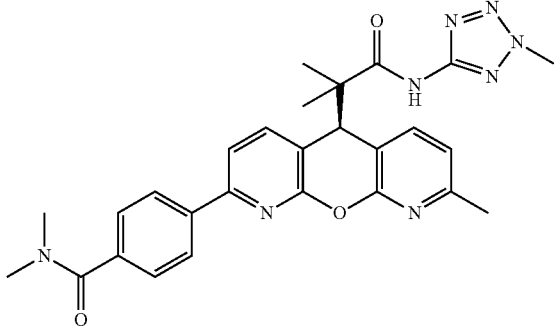

Following conditions described for Step 2 of Example 92, the S-acid from Step 9 of Example 10 was coupled with 1-methyl-1H-tetrazol-5-amine to give Example 94. 1H NMR (400 MHz, chloroform-d) δ ppm 1.21 (d, J=7.53 Hz, 6H) 2.58 (s, 3H) 3.05 (s, 3H) 3.19 (s, 3H) 4.38 (s, 3H) 4.68 (s, 1H) 7.03 (d, J=7.78 Hz, 1H) 7.52 (d, J=8.28 Hz, 2H) 7.58 (d, J=7.78 Hz, 1H) 7.67 (d, J=7.78 Hz, 1H) 7.74 (d, J=8.03 Hz, 1H) 8.09 (d, J=8.28 Hz, 2H) 8.58 (s, 1H); MS (ES+) m/z: 513 (M+H); LC retention time: 2.48 min (analytical HPLC Method B).

Biological Activity Data

The AP-1 activity of Examples ("Exp") 1 to 94 is given where the AP-1 $EC_{50}$ is less than 1 uM. Accompanying AP-1 maximum inhibition values are also given. Where the AP-1 $EC_{50}$ is greater than 1 uM and/or the maximal inhibition is less than 20%, the glucocorticoid receptor (GR) binding affinity (Ki) is given. The data presented below were obtained using the assays referred to in the table below and described herein in the ASSAY section supra.

| Exp # | GR ($K_i$, nM) (measured in GR binding Assay II) | AP-1 ($EC_{50}$, nM) (measured in cellular transrepression assay) | AP-1 Max % inhibition (measured in cellular transrepression assay) |
|---|---|---|---|
| 1 | | 255.10 | 29.30 |
| 2 | 199.00 | | |
| 3 | | 188.60 | 38.60 |
| 4 | | 197.00 | 46.64 |
| 5 | | 142.10 | 33.86 |
| 6 | 59.02 | | |
| 7 | 65.59 | | |
| 8 | | 194.20 | 45.16 |
| 9 | | 66.17 | 55.41 |
| 10 | | 188.80 | 39.03 |
| 11 | | 90.12 | 45.18 |
| 12 | | 296.60 | 26.64 |
| 13 | | 233.30 | 38.08 |
| 14 | | 97.19 | 57.97 |
| 15 | | 459.70 | 47.44 |
| 16 | | 541.40 | 40.24 |
| 17 | | 72.77 | 42.42 |
| 18 | | 51.99 | 47.77 |
| 19 | 269.20 | | |
| 20 | | 198.10 | 27.87 |
| 21 | | 166.00 | 49.73 |
| 22 | | 81.86 | 59.26 |
| 23 | 4.59 | | |
| 24 | 2.66 | | |
| 25 | 172.00 | | |
| 26 | 590.90 | | |
| 27 | | 41.85 | 32.38 |
| 28 | 14.18 | | |
| 29 | 18.85 | | |
| 30 | | 41.56 | 34.62 |
| 31 | | 375.50 | 49.28 |
| 32 | | 176.50 | 74.28 |
| 33 | | 449.30 | 50.76 |
| 34 | | 14.58 | 64.93 |
| 35 | | 175.30 | 45.02 |
| 36 | | 525.70 | 26.94 |
| 37 | 78.91 | | |
| 38 | | 470.10 | 41.89 |
| 39 | 38.16 | | |
| 40 | | 539.40 | 43.32 |
| 41 | | 359.20 | 39.16 |
| 42 | | 228.40 | 43.62 |
| 43 | 11.55 | | |
| 44 | | 589.30 | 60.84 |
| 45 | 134.50 | | |
| 46 | | 759.40 | 36.04 |
| 47 | 149.00 | | |
| 48 | | 341.30 | 59.36 |
| 49 | | 98.02 | 66.34 |
| 50 | | 908.50 | 35.43 |
| 51 | 422.80 | | |
| 52 | 411.50 | | |
| 53 | 105.70 | | |
| 54 | | 33.78 | 59.16 |
| 55 | | 353.90 | 30.46 |
| 56 | | 70.64 | 45.88 |
| 57 | | 68.49 | 31.42 |
| 58 | | 58.11 | 57.68 |
| 59 | | 15.82 | 62.26 |
| 60 | | 10.68 | 57.45 |
| 61 | | 47.51 | 49.84 |
| 62 | | 351.70 | 59.46 |
| 63 | | 86.95 | 54.57 |
| 64 | 80.79 | | |
| 65 | 656.70 | | |
| 66 | | 334.80 | 38.87 |
| 67 | | 53.00 | 57.86 |
| 68 | | 95.28 | 46.34 |
| 69 | 68.91 | | |
| 70 | 384.70 | | |
| 71 | | 67.21 | 48.56 |
| 72 | | 17.99 | 48.66 |
| 73 | | 194.50 | 43.40 |
| 74 | 27.62 | | |
| 75 | 13.53 | | |
| 76 | | 119.10 | 48.45 |
| 77 | 2.53 | | |
| 78 | 2.15 | | |
| 79 | 40.52 | | |
| 80 | 1154.00 | | |
| 81 | | 367.60 | 28.68 |
| 82 | | 180.80 | 34.44 |
| 83 | 25.19 | | |
| 84 | 1154.00 | | |
| 85 | 67.25 | | |
| 86 | | 183.40 | 61.64 |
| 87 | | 574.30 | 51.70 |
| 88 | | 56.89 | 32.90 |
| 89 | | 21.04 | 46.92 |
| 90 | 103.20 | | |
| 91 | 122.30 | | |
| 92 | 152.90 | | |

| Exp # | GR ($K_i$, nM) (measured in GR binding Assay II) | AP-1 ($EC_{50}$, nM) (measured in cellular transrepression assay) | AP-1 Max % inhibition (measured in cellular transrepression assay) |
|---|---|---|---|
| 93 | | 166.60 | 44.34 |
| 94 | | 789.80 | 35.94 |

What is claimed is:

1. A compound according to formula I

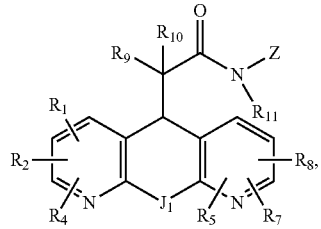

I an enantiomer, diastereomer, tautomer, or a pharmaceutically-acceptable salt thereof, wherein:

Z is selected from heterocyclo, heteroaryl, and cyano;

$J_1$ is an O, S, SO or $SO_2$;

$R_1$, $R_2$, $R_4$, $R_5$, $R_7$, and $R_8$ are the same or different and at each occurrence are independently selected from (i) hydrogen, halogen, alkyl, substituted alkyl, alkenyl, substituted alkenyl, alkynyl, substituted alkynyl, alkoxy, substituted alkoxy, nitro, cyano, $OR_{12}$, —$NR_{12}R_{13}$, —C(=O)$R_{12}$, —$CO_2R_{12}$, —C(=O)$NR_{12}R_{13}$, —OC(=O)$NR_{12}R_{13}$,

I

—OC(=O)$R_{12}$, —$NR_{12}$C(=O)$R_{13}$, —$NR_{12}$C(O)$OR_{13}$, —$NR_{12}$C(S)$OR_{13}$, —S(O)$_p R_{16}$, $NR_{12}SO_2R_{16}$, dialkylaminoalkoxy, alkoxyalkyloxyalkyloxy, $SO_2NR_{12}R_{13}$, cycloalkyl, cycloalkenyl, cycloalkynyl, heterocyclo, aryl, and heteroaryl; and/or (ii) where possible, together with the atoms to which they are attached, each one of $R_1$, $R_2$, $R_4$, $R_5$, $R_7$, and $R_8$ is taken together with any one of $R_1$, $R_2$, $R_4$, $R_5$, $R_7$, and $R_8$ located on an adjacent atom to form a fused ring;

$R_9$ and $R_{10}$ are the same or different and at each occurrence are independently selected from (i) hydrogen, halogen, alkyl, substituted alkyl, alkenyl, substituted alkenyl, alkynyl, substituted alkynyl, nitro, cyano, $OR_{14}$, $NR_{14}R_{15}$, C(=O)$R_{14}$, $CO_2R_{14}$, C(=O)$NR_{14}R_{15}$, —O—C(=O)$R_{14}$, $NR_{14}$C(=O)$R_{15}$, $NR_{14}$C(=O)$OR_{15}$, $NR_{14}$C(=S)$OR_{15}$, S(O)$_p R_{17}$, $NR_{14}SO_2R_{17}$, $SO_2NR_{14}R_{15}$, cycloalkyl, cycloalkenyl, heterocyclo, aryl, and heteroaryl; or (ii) together with the atom to which they are attached, $R_9$ and $R_{10}$ are taken together to form a carbonyl, alkenyl, substituted alkenyl, cycloalkyl, cycloalkenyl, or heterocyclo group;

$R_{11}$ at each occurrence is independently selected from hydrogen, alkyl, substituted alkyl, aryl, heteroaryl, heterocyclo, and cycloalkyl;

$R_{12}$, $R_{13}$, $R_{14}$, and $R_{15}$ are the same or different and at each occurrence are independently selected from (i) hydrogen, alkyl, substituted alkyl, alkenyl, substituted alkenyl, alkynyl, substituted alkynyl, cycloalkyl, cycloalkenyl, aryl, heteroaryl, and heterocyclo; or (ii) where possible $R_{12}$ is taken together with $R_{13}$, and/or where possible $R_{14}$ is taken together with $R_{15}$ to form a heteroaryl or heterocyclo ring;

$R_{16}$ and $R_{17}$ are the same or different and at each occurrence are independently selected from alkyl, substituted alkyl, alkenyl, substituted alkenyl, alkynyl, substituted alkynyl, cycloalkyl, cycloalkenyl, aryl, heteroaryl, and heterocyclo; and p is 0, 1 or 2.

2. A compound as defined in claim 1, or an enantiomer, diastereomer, tautomer, or a pharmaceutically-acceptable salt thereof, wherein the tricyclic moiety:

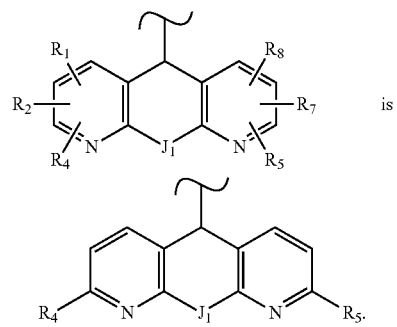

is

3. A compound of claim 1, or an enantiomer, diastereomer, tautomer, or a pharmaceutically-acceptable salt thereof, wherein $R_4$ is selected from hydrogen, alkyl, alkenyl, alkylthio, substituted alkylthio, aryl, substituted aryl, cyano, $CF_3$, alkoxy, halogen, hydroxyl, dialkylamino, monoalkylamino, dialkylaminoalkoxy, alkoxyalkoxyalkoxy, and a 4- to 7-membered heterocyclo having one to three heteroatoms selected from O, S and N.

4. A compound of claim 1, or an enantiomer, diastereomer, tautomer, or a pharmaceutically-acceptable salt thereof, wherein $R_1$, $R_2$, $R_7$ and $R_8$ are each hydrogen.

5. A compound of claim 1, or an enantiomer, diastereomer, tautomer, or a pharmaceutically-acceptable salt thereof, wherein $R_5$ is selected from hydrogen, haloalkyl, alkoxy, haloalkoxy, halogen, amino, dialkylamino, heterocyclo, phenyl, halophenyl, alkyl(halo)$_{0-1}$aryl, heterocyclocarbonyl(halo)$_{0-1}$aryl, alkoxy(halo)$_{0-1}$aryl, carboxy(halo)$_{0-1}$aryl, alkylaminocarbonyl(halo)$_{0-1}$aryl, dialkylaminocarbonyl(halo)$_{0-1}$aryl, alkylamino, hydroxyl, dialkylaminoalkoxy, arylalkylamino, alkoxyarylalkylamino, alkylheterocyclo, arylalkyl, heterocycloalkoxy, arylheterocyclo, arylalkyl(alkyl)amino, haloaryl, dialkylamino(halo)$_{0-1}$aryl, alkoxyalkoxyalkoxyl, alkylcarbonylamino, heteroaryl, dialkyl(halo)$_{0-1}$aryl, alkyl(halo)$_{0-1}$aryl, hydroxy(halo)$_{0-1}$aryl, alkoxycarbonyl(halo)$_{0-1}$aryl, alkylcarbonylamino(halo)$_{0-1}$aryl, dialkylaminosulfonyl(halo)$_{0-1}$aryl, alkylsulfonylamino(halo)$_{0-1}$aryl, alkylthio(halo)$_{0-1}$aryl, amino(halo)$_{0-1}$aryl, alkylcarbonylaryl, alkylcarbonyl(halo)aryl, aryloxy(halo)$_{0-}$ 1aryl, alkylsulfonylaryl, alkylsulfinylaryl, thioxyaryl, cycloalkoxyaryl, cycloalkylaminocarbonyl, and cyano(halo)$_{0-1}$aryl.

6. A compound of claim 1, or an enantiomer, diastereomer, tautomer, or a pharmaceutically-acceptable salt thereof, wherein:
$R_9$ and $R_{10}$ are (i) the same or different and independently selected from hydrogen, alkyl, and substituted alkyl; or (ii) $R_9$ and $R_{10}$ taken together with the atom to which they are attached combined to form $C_{3-6}$cycloalkyl; and
$R_{11}$ is hydrogen.

7. A compound of claim 1, or an enantiomer, diastereomer, tautomer, or a pharmaceutically-acceptable salt thereof, wherein $R_9$ and $R_{10}$ are each independently selected from methyl or taken together with the carbon they are attached to to form cyclopropyl, cyclobutyl, and cyclopentyl.

8. A compound of claim 1, or an enantiomer, diastereomer, tautomer, or a pharmaceutically-acceptable salt thereof, wherein:
Z is a 5- to 6-membered heteroaryl or heterocyclo group, each group substituted with one, two or three groups, $R^m$, $R^n$, and/or $R^o$, which are the same or different and are independently selected from hydrogen, halogen, alkyl, substituted alkyl, alkenyl, substituted alkenyl, alkynyl, substituted alkynyl, nitro, cyano, OR NR$^a$R$^b$, C(=O)R$^a$, CO$_2$R$^a$, C(=O)NR$^a$R$^b$, —O—C(=O)R$^a$, NR$^a$C(=O)R$^b$, NR$^a$C(=O)OR$^b$, NR$^a$C(=S)OR$^b$, S(O)$_p$R$^c$, NR$^a$SO$_2$R$^c$, SO$_2$NR$^a$R$^b$, cycloalkyl, cycloalkenyl, heterocyclo, aryl, and heteroaryl, wherein p is 0, 1 or 2;
$R^a$ and $R^b$ are the same or different and at each occurrence are independently selected from (i) hydrogen, alkyl, substituted alkyl, alkenyl, substituted alkenyl, alkynyl, substituted alkynyl, cycloalkyl, cycloalkenyl, aryl, heteroaryl, and heterocyclo; or (ii) where possible together with the atoms to which they are attached R$^a$ is taken together with R$^b$ to form a heteroaryl or heterocyclo ring; and
$R^c$ at each occurrence is independently selected from alkyl, substituted alkyl, alkenyl, substituted alkenyl, alkynyl, substituted alkynyl, cycloalkyl, cycloalkenyl, aryl, heteroaryl, and heterocyclo.

9. A compound of claim 1, or an enantiomer, diastereomer, tautomer, or a pharmaceutically-acceptable salt thereof, wherein
Z is

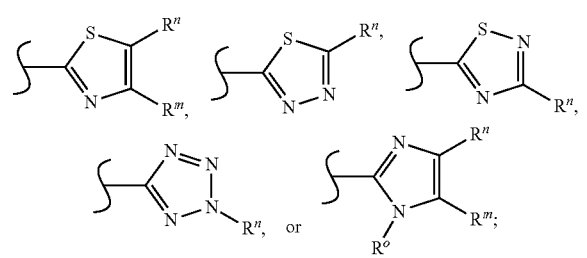

$R^m$ and $R^n$ are the same or different and at each occurrence are independently selected from hydrogen, —CO$_{1-2}$R$^a$, —C(O)NR$^a$R$^b$, C$_{1-6}$alkyl, —CF$_3$, —CH$_2$OH, —SR$^c$, —NR$^a$R$^b$, —CH$_2$F, cyano, and C$_{3-6}$cycloalkyl;
$R^o$ is hydrogen or C$_{1-6}$alkyl;
$R^a$ and $R^b$ are (i) the same or different and at each occurrence are independently selected from hydrogen, C$_{1-6}$alkyl, substituted C$_{1-6}$alkyl, 4- to 7-membered heterocyclo having 1-3 heteroatoms selected from O, S, or N, and C$_{3-6}$cycloalkyl; or (ii) R$^a$ is taken together with R$^b$ to form a 4- to 7-membered heterocyclo having 1-3 heteroatoms selected from O, S, or N; and
$R^c$ is selected from C$_{1-6}$alkyl, and C$_{3-6}$cycloalkyl.

10. A compound as defined in any one of claim 1, or an enantiomer, diastereomer, tautomer, or a pharmaceutically-acceptable salt thereof, wherein:
Z is

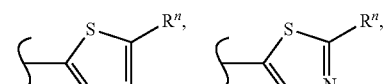

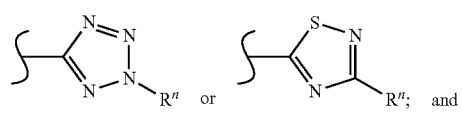

$R^n$ is hydrogen, —C(O)NH(cyclopropyl), —C(O)NH(Me), —C(O)N(Me)$_2$, —C(O)NH(Et), methyl, —C(O)OEt, —C(O)NH(cyclobutyl), —C(O)NH(CH$_2$)$_2$OH, —C(O)NH(iPr)-C(O)NHCH$_2$(CF$_3$),

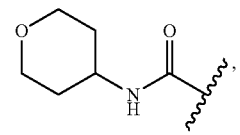

cyclopropyl, or

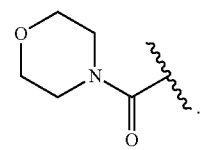

11. A compound of claim 1, or an enantiomer, diastereomer, tautomer, or a pharmaceutically-acceptable salt thereof, having the structure:

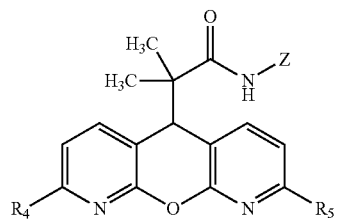

wherein:
$R_4$ is hydrogen, methyl, chloro, iso-propylthio, ethenyl, phenyl, cyano, dimethylamino, N-pyrrolidinyl, or N-morpholinyl;

R$_5$ is chloro, dimethylamino,

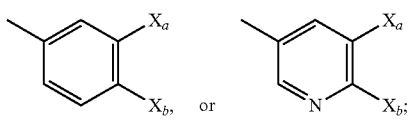

X$_a$ is hydrogen or fluoro; and
X$_b$ is selected from (Me)$_2$NC(O)—,

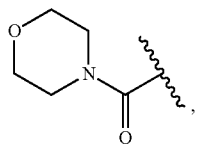

(Et)(Me)NC(O)—,

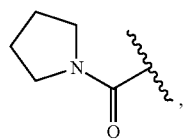

MeC(O)—, —O(phenyl), —OCF$_3$, —SO$_2$N(Me)$_2$, (t-Bu)NHC(O)—, —S(iPr), —S(Me), —O(iPr), —S(O)Me, —S(O)$_2$Me,

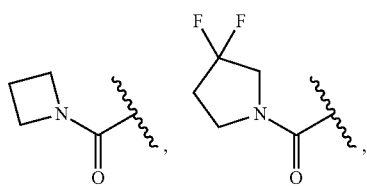

S(O)(iPr), S(O)$_2$(iPr), S(O)Et, iBu, —)(t-Bu), —S(Et), iBu, iPr, —O(cyclopentyl), EtC(O)—,

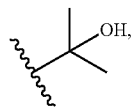

and —C(O)N(Me)(cyclopropyl).

12. A pharmaceutical composition comprising a compound of claim 1 and a pharmaceutically acceptable carrier therefor.

13. A pharmaceutical combination comprising a compound of claim 1 and an immunosuppressant, an anticancer agent, an anti-viral agent, an anti-inflammatory agent, an anti-fungal agent, an anti-biotic, an anti-vascular hyperproliferation agent, an anti-depressant agent, a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the lipid lowering agent is an MTP inhibitor, an HMG CoA reductase inhibitor, a squalene synthetase inhibitor, a fibric acid derivative, an upregulator of LDL receptor activity, a lipoxygenase inhibitor, or an ACAT inhibitor, wherein the antihypertensive agent is an ACE inhibitor, angiotensin II receptor antagonist, NEP/ACE inhibitor, calcium channel blocker and/or β-adrenergic blocker.

14. A compound according to claim 1, or an enantiomer, diastereomer, tautomer, or a pharmaceutically-acceptable salt thereof, wherein J$_1$ is O.

15. A compound according to claim 1, or an enantiomer, diastereomer, tautomer, or a pharmaceutically-acceptable salt thereof, wherein R$_4$ is selected from hydrogen, alkyl, alkenyl, alkylthio, substituted alkylthio, aryl, substituted aryl, cyano, CF$_3$, alkoxy, halogen, hydroxyl, dialkylamino, monoalkylamino, dialkylaminoalkoxy, alkoxyalkoxyalkoxy, and a 4- to 7-membered heterocyclo having one to three heteroatoms selected from O, S and N.

16. A compound according to claim 6 wherein R$_9$ and R$_{10}$ are each selected from methyl, or combined with the carbon they are attached to form cyclopropyl, cyclobutyl, and cyclopentyl.

17. A compound according to claim 5, or an enantiomer, diastereomer, tautomer, or a pharmaceutically-acceptable salt thereof, wherein R$_5$ is chloro, dimethylamino,

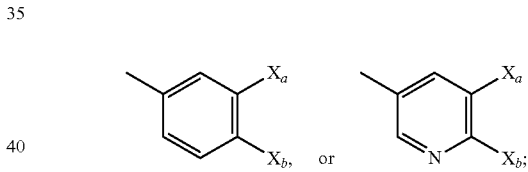

X$_a$ is hydrogen or fluoro; and
X$_b$ is selected from (Me)$_2$NC(O)—,

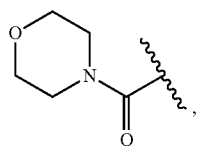

(Et)(Me)NC(O)—,

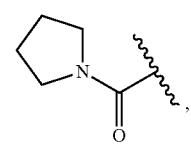

MeC(O)—, —O(phenyl), —OCF$_3$, —SO$_2$N(Me)$_2$, (t-Bu)NHC(O)—, —S(iPr), —S(Me), —O(iPr), —S(O)Me, —S(O)$_2$Me,

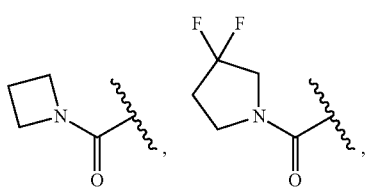
S(O)(iPr), S(O)₂(iPr), S(O)Et, iBu, —O(t-Bu), —S(Et), iBu, iPr, —O(cyclopentyl), EtC(O)—,
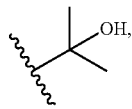
and —C(O)N(Me)(cyclopropyl).
18. A compound according to claim 2, or an enantiomer, diastereomer, tautomer, or a pharmaceutically-acceptable salt thereof, wherein
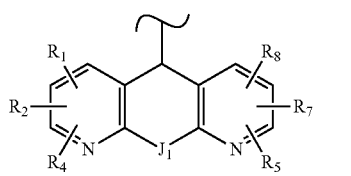    is
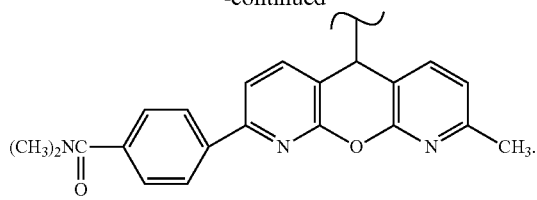
19. A compound according to claim 1, or an enantiomer, diastereomer, tautomer, or a pharmaceutically-acceptable salt thereof having the formula
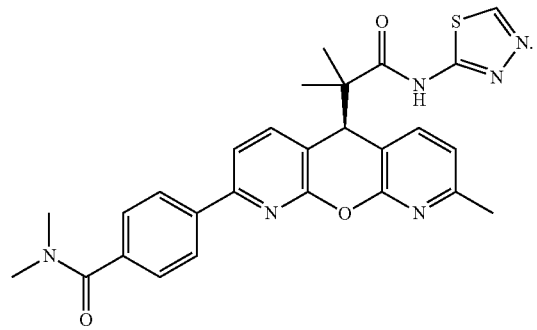
* * * * *

UNITED STATES PATENT AND TRADEMARK OFFICE
CERTIFICATE OF CORRECTION

PATENT NO. : 8,304,539 B2
APPLICATION NO. : 12/866270
DATED : November 6, 2012
INVENTOR(S) : Jingwu Duan et al.

It is certified that error appears in the above-identified patent and that said Letters Patent is hereby corrected as shown below:

On the Title Page:

Item (57), ABSTRACT:

Column 2, line 6 (Abstract), change "tautomer" to -- tautomer --.

Column 2, line 8 (Abstract), change "S-" to -- 5- --.

Column 2, line 9 (Abstract), change "S-" to -- 5- --.

Column 2, line 16 (Abstract), change "$R_3$" to -- $R_8$, --.

In the Claims:

Claim 1:

Column 149, lines 35 and 36, change "—OC(=O)NR$_{12}$,R$_{13}$," to -- —OC(=O)NR$_{12}$R$_{13}$, --.

Column 149, line 36, after "—OC(=O)NR$_{12}$,R$_{13}$," insert --
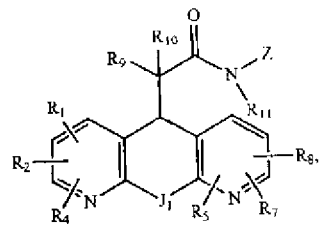
--.

Column 149, lines 39 to 48, delete " ".

Claim 5:

Column 150, line 67, change "alkylcarbonyl(halo)aryl," to -- alkylcarbonyl(halo)$_{0-1}$aryl, --.

Signed and Sealed this
Twenty-first Day of May, 2013

Teresa Stanek Rea
*Acting Director of the United States Patent and Trademark Office*

CERTIFICATE OF CORRECTION (continued)
U.S. Pat. No. 8,304,539 B2

In the Claims:

Claim 7:

Column 151, line 16, before "form", delete "to".

Claim 8:

Column 151, line 25, change "OR" to -- OR$^c$, --.

Claim 10:

Column 152, line 6, after "compound", delete "as defined in any one".

Column 152, line 28, after "—C(O)NH(iPr)", insert -- , --.

Claim 11:

Column 153, line 44, change "—)(t-Bu)," to -- —O(t-Bu), --.

Claim 13:

Column 153, line 60, after "anti-biotic", insert -- agent --.